(12) United States Patent
Ge et al.

(10) Patent No.: US 9,890,374 B2
(45) Date of Patent: Feb. 13, 2018

(54) THERMOSTABLE CARBONIC ANHYDRASES AND METHODS OF USE THEREOF

(71) Applicant: DANISCO US INC, Palo Alto, CA (US)

(72) Inventors: Jing Ge, Palo Alto, CA (US); Ling Hua, Hockessin, DE (US); Ayrookaran J. Poulose, Belmont, CA (US)

(73) Assignee: DANISCO US INC CA (US)

( * ) Notice: Subject to any disclaimer, the term of this patent is extended or adjusted under 35 U.S.C. 154(b) by 0 days.

(21) Appl. No.: 15/215,844

(22) Filed: Jul. 21, 2016

(65) Prior Publication Data

US 2017/0081653 A1 Mar. 23, 2017

Related U.S. Application Data

(62) Division of application No. 14/113,775, filed as application No. PCT/US2012/036932 on May 8, 2012, now Pat. No. 9,410,140.
(Continued)

(30) Foreign Application Priority Data

| May 10, 2011 | (WO) | PCT/CN2011/073871 |
| May 10, 2011 | (WO) | PCT/CN2011/073873 |
| May 10, 2011 | (WO) | PCT/CN2011/073876 |
| May 10, 2011 | (WO) | PCT/CN2011/073886 |
| Dec. 21, 2011 | (WO) | PCT/CN2011/084363 |

(Continued)

(51) Int. Cl.
*C12N 9/88* (2006.01)
*C02F 3/34* (2006.01)
(Continued)

(52) U.S. Cl.
CPC ............... *C12N 9/88* (2013.01); *B01D 53/84* (2013.01); *C02F 3/342* (2013.01); *C12N 11/14* (2013.01);
(Continued)

(58) Field of Classification Search
CPC .......... C12N 9/88; C12N 11/14; B01D 53/84; B01D 2258/0283; B01D 2251/95; B01D 53/62; C02F 3/342; C12Y 402/01001
See application file for complete search history.

(56) References Cited

U.S. PATENT DOCUMENTS

| 5,776,741 A | 6/1998 | Pedersen |
| 6,524,843 B1 | 2/2003 | Blais |

(Continued)

FOREIGN PATENT DOCUMENTS

| WO | WO2004/007058 | 1/2004 |
| WO | WO2004/104160 | 12/2004 |

(Continued)

OTHER PUBLICATIONS

Supplementary European Search Report for European Patent Application No. EP12782314 dated Apr. 2, 2015.
(Continued)

*Primary Examiner* — Alexander D Kim

(57) ABSTRACT

The present compositions and methods relate to a thermostable carbonic anhydrases, polynucleotides encoding the carbonic anhydrase, and methods of make and/or use thereof. Formulations containing the carbonic anhydrase are suitable for use in extracting carbon dioxide.

18 Claims, 35 Drawing Sheets

Related U.S. Application Data

(60) Provisional application No. 61/578,408, filed on Dec. 21, 2011, provisional application No. 61/578,416, filed on Dec. 21, 2011, provisional application No. 61/578,421, filed on Dec. 21, 2011, provisional application No. 61/578,429, filed on Dec. 21, 2011.

(30) Foreign Application Priority Data

| Dec. 21, 2011 | (WO) | ............... | PCT/CN2011/084366 |
|---|---|---|---|
| Dec. 21, 2011 | (WO) | ............... | PCT/CN2011/084371 |
| Dec. 21, 2011 | (WO) | ............... | PCT/CN2011/084384 |

(51) Int. Cl.
- *B01D 53/84* (2006.01)
- *C12N 11/14* (2006.01)
- *B01D 53/62* (2006.01)

(52) U.S. Cl.
CPC ...... *C12Y 402/01001* (2013.01); *B01D 53/62* (2013.01); *B01D 2251/95* (2013.01); *B01D 2258/0283* (2013.01); *Y02E 50/343* (2013.01)

(56) References Cited

U.S. PATENT DOCUMENTS

| 6,566,112 | B2 | 5/2003 | Jones |
|---|---|---|---|
| 7,132,090 | B2 | 10/2006 | Dziedzic |
| 7,596,952 | B2 | 9/2009 | Fradette |
| 2006/0154843 | A1 | 7/2006 | Wang |
| 2010/0209968 | A1 | 8/2010 | Akers |
| 2011/0020899 | A1 | 1/2011 | Aehle |

FOREIGN PATENT DOCUMENTS

| WO | WO2005/114417 | 12/2005 |
|---|---|---|
| WO | WO2007/19859 | 2/2007 |
| WO | WO2007/036235 | 4/2007 |
| WO | WO2008/095057 | 8/2008 |
| WO | WO2010/014774 | 2/2010 |
| WO | WO2010/037109 | 4/2010 |
| WO | WO2010/138792 | 12/2010 |
| WO | WO2010/151787 | 12/2010 |
| WO | WO2011/01457 | 1/2011 |
| WO | WO2011/014956 | 2/2011 |

OTHER PUBLICATIONS

Altschul et al., "Dasic Local Alignment Search Tool," J. Mol. Biol. 215:403-410, 1990.

Bhattacharya et al., "CO2 hydration by immobilized carbonic anhydrase," Biotechnol. Appl. Biochem. 38:2, pp. 111-117, 2003.

Chang et al., "High frequency transformation of Bacillus subtilis protoplasts by plasmid DNA," Mol. Gen. Genet. 68 1 115, 1979.

Cowan et al., "CO2 capture by means of an enzyme-based reactor," Ann. NY Acad. Sci. 984:1, pp. 453-469, 2003.

Emanuelsson et al., "Locating proteins in the cell using TargetP, SignalP and related tools," Nature Protocols, 2.953-971, 2007.

Ferrari et al., "Genetics," in Harwood, Bacillus, Plenum Publishing Corporation, pp. 57-72, 1989.

Freire, "Differential Scanning Calorimetry," Methods Mol. Biol., 41:191-218, 1995.

Henikoff et al., "Amino acid substitution matrices from protein blocks," Proc. Natl. Acad. Sci. USA 89:10915-10919, 1992 (Date listed on specification as 1989).

Higgins et al., "CLUSTAL: a package for performing multiple sequence alignment on a microcomputer," Gene 73:237-244, 1988.

PCT International Search Report and Written Opinion of the International Searching Authority dated Dec. 14, 2012.

Karlin et al., "Applications and statistics for multiple high-scoring segments in molecular sequences," Proc. Natl. Acad. Sci USA 90:5873, 1993 (Author spelled "Karin" in specification.).

Majumdar et al., "A new liquid membrane technique for gas separation," AIChE Journal 34.10, pp. 1135-1145, 1988.

McKenzie et al., "The nucleotide sequence of pUB110: some salient features in relation to replication and its regulation," Plasmid, 15:93-103, 1986.

NCBI GenBank Accession No. ZP_02194086.1, Nov. 9, 2010. http://www.ncbi.nlm.nih.gov/protein/ZP_02194066.1?report=genpept.

NCBI GenBank Accession No. ZP_04921370.1, Sep. 22, 2011. http://www.ncbi.nlm.nih.gov/protein/ZP_04921370.1, ?report=genpept.

NCBI GenBank Accession No. ZP_04922188.1, Sep. 22, 2011. http://www.ncbi.nlm.nih.gov/protein/ZP_04922188.1, ?report=genpept.

NCBI GenBank Accession No. ZP_06907409.1, Oct. 25, 2010. http://www.ncbi.nlm.nih.gov/protein/ZP_06907409.1 , ?report=genpept.

NCBI GenBank Reference Sequence: NZ_DS267810.1, May 29, 2013, http://www.ncbi.nlm.nih.gov/nuccore/NZ_DS267810.1.

NCBI GenBank Accession No. XP_001210252.1, Mar. 31, 2008. http://www.ncbi.nlm.nih.gov/protein/XP_001210252.1.

Pearson et al., "Improved tools for biological sequence comparison," Proc. Natl. Acad. Sci. USA 85:2444-2448, 1988.

Penttila et al, A versatile transformation system for the celluolytic filamentous fungus Trichoderma reesei, Gene, 81:155-164, 1987.

Smith et al., "Protoplast transformation in coryneform bacteria and introduction of an α-amylase gene from Bacillus amyloliquefadens into Brevibacterium lactofermentum," Appl. Env. Microbiol. 51:2, pp634-639, 1986.

Tamura K. et al., "MEGA5: molecular evolutionary genetics analysis using maximum likelihood, evolutionary distance, and maximum parsimony methods," Mel Biol Evol 28(10): 2731-2739, 2011.

Wilbur, K. et al., Electrometric and colorimetric determination of carbonic anhydrase, J. Biol. Chem. 176:147-154, 1948.

```
YP_176677_Bacillus_clausii         ------------------------------------------------------------MKRSHLFTSITLASVVTLATAPAASAA
BgiCA1                             ---------------------------------------------------------------AHGNHVSSSSLIHS---------
YP_003868697_Paenibacillus_polymyxa ---------------------------------------------MKKNWKGCLFSIFAILLVVSVTGCNSQPAISSTPSTSSSSA
YP_003944556_Paenibacillus_polymyxa ---------------------------------------------MKKHWRGCLFSIFSIILALSVTGCTPSATSSTTSATSSSSA
ZP_04209878_Bacillus_cereus        ------------------------------------------------------MKGLKFVYKTPLILTMSVVLMGCNTAKQE----
ZP_04248491_Bacillus_cereus        ------------------------------------------------------MKGLKFVYKTPLILTMSVVLMGCNTAKQE----
ZP_03428428_Bacillus_pseudofirmus  ---------------------------------------------MKRKSIYLLVAASLALAACAEQTETAPVETPPITDSTEPSD
NP_241226_Bacillus_halodurans      ----------------------------------------------MKKYLWGKTCLVVSLSVMVTACSSAPSTEPVDEPSET----
NP_946147_Rhodopseudomonas_palustris ---------------------------------------------------MDRRNILKAFAGLALCPLC-----------------
YP_488219_Rhodopseudomonas_palustris --------------------------------------------------MEPILIPEHRPMDRRAILKAFAGLALCPLC---------
NP_767777_Bradyrhizobium_japonicum MGRKDRVGEPINSTRDGHCDSPRLSPRLRAHRRSNSSWGNMMNRRHALKALAGLALCPVC YP_176677_Bacillus_clausii         SFLSPLQALKASWSYEGETGPEFWGDLDEAFAACSNGKEQSPINLFYDR---EQTSKWNWA
BgiCA1                             PYDRLTANASHDWSYSGPTGPEFWGELDSEFKACSNGTQQSPIALDPTD--VGDEKWSLD
YP_003868697_Paenibacillus_polymyxa TNAHAAVQKGPHWSYEGDQGPEHWGELEKDFVACGNGHEQSPVNIEHTHLEASQTRQPLQ
YP_003944556_Paenibacillus_polymyxa NNVHAVVQKSPHWSYEGDEGPEHWGELEKDFVACGNGQEQSPINIEHSHLEASHTQQPLQ
ZP_04209878_Bacillus_cereus        APHKQSTKENTQWSYEGTTGPEHWGELKPEYKICLNGQEQSPIDIKTEQIKSTVDNNLLQ
ZP_04248491_Bacillus_cereus        APQKQSTKENTQWSYKGTTGPEHWGELKPEYNMCLNGQEQSPIDIKTEQIKSTVDNNLLQ
ZP_03428428_Bacillus_pseudofirmus  ETQEESTEELTEWSYEGESGPEHWGHLHASYSACVDGSEQSPINIDLAEMEANQQIEEID
NP_241226_Bacillus_halodurans      HEETSGGAHEVHWSYTGDTGPEHWAELDSEYGACAQEEGQSPINLDKAE--AVDTDTEIQ
NP_946147_Rhodopseudomonas_palustris ATAGAAAEGAHHWGYEGEGGPAKWGEIDPANQICSIGVQQSPVDIRSTV---SANLFPLQ
YP_488219_Rhodopseudomonas_palustris ASAGVAGEGGHHWGYEGDGGPAKWGELDPANQFCSVGVQQSPIDIGTTI----GANLYPIE
NP_767777_Bradyrhizobium_japonicum KPAFAEA---GVHWSYEGAGAPAKWGDLDAANKACAVGLQQSPIDIEATI----KSQLPTLK
                                                                                                *  *****:

YP_176677_Bacillus_clausii         FSYSEAAFSVENNGHTIQANV----ENEDAGGLEINGEAYQLIQFHFHTPSEHTIEETSFP
BgiCA1                             LDYAKTEFSIENNGHTIQANVVEKKGQPSNQLTLGDSTYELVQFHFHSPSEHTLAGESYE
YP_003868697_Paenibacillus_polymyxa VHYTNTKASILNNGHTVQINV----ADASNNIMLDGTKFTLKQFHFHHPSEHQIDGKNAE
YP_003944556_Paenibacillus_polymyxa VHYSTTKVSILNNGHTVQVNA----ASPSNDIVVDGTKFTLKQFHFHHPSEHQIDGKNAE
ZP_04209878_Bacillus_cereus        INYQPISFSIKNNGHSIEGKA----NSSDNYLTLGENRYTLKQFHFHTPSEHQFEGKHAD
ZP_04248491_Bacillus_cereus        INYQPISFSIKNNGHSIEGKA----NSSDDYLTLGENRYTLKQFHFHTPSEHQFEGKHAD
ZP_03428428_Bacillus_pseudofirmus  IQYEPASFSLVNNGHTIQKNA----VDENNAITLDGQEYQLVQFHFHTPSEHQFNGEHYD
NP_241226_Bacillus_halodurans      VHYEPSAFTIKNNGHTIQAET----TSDGNTIEIDGKEYTLVQFHFHIPSEHEMEGKNLD
NP_946147_Rhodopseudomonas_palustris VQWADTADTIINNGHTIQLNV----AEGSTLKLGGATFKLVQFHFHRPSEHQIDGKSFP
YP_488219_Rhodopseudomonas_palustris IRWADTADTIVNNGHTIQLNV----AEGSHLKLGGVTFKLVQFHFHRPSEHLIDGKNFP
NP_767777_Bradyrhizobium_japonicum LNWGKSADTIVNNGHTIQLNF----AEGSTLTLGDVKYKLLQVHFHRPSEHMIGGKNFP
```

*FIG. 4A*

```
YP_176677_Bacillus_clausii            MELHLVHANHAGDLAVLGVLMEMGNDHEGIEAVWEVMPEEEG--TAAYSISLDPNLFLPE
BgiCA1                                MEVHLVHKDEQDNLAVLGVLMEEGEKNKALKDMWKKMPTSVG--TSTKTIKLNPSELVPT
YP_003868697_Paenibacillus_polymyxa   MELHFVHQSDNGSTAVLGVLIQSGKENKAFNRIWSKLPKDNSQEAAALDKEINLAALLPK
YP_003944556_Paenibacillus_polymyxa   MELHFVHQSDTGSTAVLGVLIQSGKENKAFNRIWSKLPKDISQEAV-LDEDVNLAALLPK
ZP_04209878_Bacillus_cereus           MELHLVHQNDQGQLVVVGIMIKEGQKNEGFAAMWQNLPHRKN--IKADVQHTIDIKQILPS
ZP_04248491_Bacillus_cereus           MELHLVHQNDQGQLVVVGIMIKEGQKNEGFAAMWQNLPHRKN--IKADVQHTIDIKQILPS
YP_003428428_Bacillus_pseudofirmus    MELHLVHQDINGNLAVLGVMIEEGAENEELAPAWGELPEEETENEVALEEPINLQNLLPD
NP_241226_Bacillus_halodurans         MELHFVHKNENDELAVLGVLMKAGEENEELAKLWSKLPAEETEENISLDESIDLNALLPE
NP_946147_Rhodopseudomonas_palustris  MEVHFVHRMDSGTLGVVGVLMQEGAANAAFAKIVATMPQSEG-PAVKADAGINPNALLPA
YP_488219_Rhodopseudomonas_palustris  MEVHFVHRADSGTLGVVGVLMQPGKANAAFSKIVATMPQSEG-PAKKADPAIDPNALLPE
NP_767777_Bradyrhizobium_japonicum    MEAHFVHRNDAGGLAVVGVLMAEGKPNPAFGKIVKTMPAADG-PAVKADASIDPLAMLPT
                                      **  **:**      .             :                  :      ::

YP_176677_Bacillus_clausii            SVTAYQYDGSLTTPPCSEGVKWTVLNDTISISETQLDAFRDIYPQNYRPVQELGDREIGF
BgiCA1                                DLSTFQYDGSLTTPPCSEGVKWSVSDSSITLSSEQLQAFQDLYPNNYRPIQDLGDREVGF
YP_003868697_Paenibacillus_polymyxa   DLHSVRYNGSLTTPPCTEHVNWTVLEQPIEMSADQINQFAAIFPDNHRPVQQLGTRELTA
YP_003944556_Paenibacillus_polymyxa   DLHSVRYNGSLTTPPCTEHVNWTVLEQPIEMSADQIKQFAAIFPDNHRPVQQLGTRELKA
ZP_04209878_Bacillus_cereus           DYSSFRYMGSLTTPPCTENVQWIVMKQTIEMSKKQIKVFHKLFPTNNRPVQPINGRAVL-
ZP_04248491_Bacillus_cereus           DYSSFRYMGSLTTPPCTENVQWIVMKQTIEMSKKQIKVFHKLFPTNNRPVQPINGRAVL-
YP_003428428_Bacillus_pseudofirmus    DHSSFRYMGSLTTPPCTEENVQWIVMKQTIEMSKKQIKVFHKLFPTNNRPVQPINGRAVL-
NP_241226_Bacillus_halodurans         DQSSFHYNGSLTTPPCSEGVKWTVLSEPITVSQEQIDAFAEIFPDNHRPVQPLNERG---
NP_946147_Rhodopseudomonas_palustris  SKEGFHYNGSLTTPPCSEGVKWTVLSEPITVSQEQIDAFAEIFPDNHRPVQPLNERG---
YP_488219_Rhodopseudomonas_palustris  KLGYYRYEGSLTTPPCSEVVDWMVLTDPITVAAEDVAAFAKLYPMNARPVQKDNRRFVLQ
NP_767777_Bradyrhizobium_japonicum    TRNYYRYEGSLTTPPCSEIVDWMVLASPITVAADDIAAFAKLYPMNARPVQKDNRRFVLQ
                                      RLSYFRYPGSLTTPPCSEVVEWLLLTTPIQVSAADVAAFAKLYPMNARPVQKDNRRYVLR
                                      :  * .***:********:*     *..*       *   :*::* **:: .

YP_176677_Bacillus_clausii            HYH---
BgiCA1                                HY----
YP_003868697_Paenibacillus_polymyxa   DK----
YP_003944556_Paenibacillus_polymyxa   DK----
ZP_04209878_Bacillus_cereus           ------
ZP_04248491_Bacillus_cereus           ------
YP_003428428_Bacillus_pseudofirmus    ------
NP_241226_Bacillus_halodurans         VITE--
NP_946147_Rhodopseudomonas_palustris  SN----
YP_488219_Rhodopseudomonas_palustris  SN----
NP_767777_Bradyrhizobium_japonicum    ST----
```

*FIG. 4B*

| | |
|---|---|
| YP_003868697_Paenibacillus_polymyxa | ----------------------------------MKKNWKGCLFSIFAILLVVSVTGCNSQPAISS |
| YP_003944556_Paenibacillus_polymyxa | ----------------------------------MKKHWRGCLFSIFSIFSIILALSVTGCTPSATSST |
| NP_241226_Bacillus_halodurans | ----------------------------------MKKYLWGKTCLVVSLSVMVTACSSAPST |
| YP_003166850_Candidatus_accumulibacter | ------------------------------MIVTTTDGTPSMHPVIRLSSAFLVLSLLP |
| YP_287120_Dechloromonas_aromatica | -----------------------------------------MRHLIIASLLAALPWA |
| YP_05029585_Microcoleus_chthonoplastes | --------------------------------------------MKNSTFTFIVFVLLA |
| YP_419944_Magnetospirillum_magnetotacticum | ----------------------------------MDRRSFLKGATGAACLCG |
| ZP_00056365_Magnetospirillum_magnetotacticum | ------------------------------------------------------ |
| YP_003610599_Enterobacter_cloacae | ------------------------------------------------MKHILTA |
| ZP_08017465_Lautropia_mirabilis | ------------------------------------------------------ |
| PviCA1 | MIHIPNLRKAIMHVKQLLVPLLLSGLFLSSAAMAETAQPAADAAGASPGQ |

| | |
|---|---|
| YP_003868697_Paenibacillus_polymyxa | TPSTSSSSATNAH---------------------------------- |
| YP_003944556_Paenibacillus_polymyxa | TSATSSSSANNVH---------------------------------- |
| NP_241226_Bacillus_halodurans | EPVDEPSETHEET---------------------------------- |
| YP_003166850_Candidatus_accumulibacter | PGVGAAWQVISAEPGKRVEIDRASIRKDETGKSVAQGRIVLEKPIVDPKT |
| YP_287120_Dechloromonas_aromatica | ASAAPTWQTISSEPGKRIEIDRTSLKR-EGSTVQAGRIVLEKELTDAKS |
| YP_05029585_Microcoleus_chthonoplastes | SCLIIAPNVKSS----------------------------------- |
| YP_419944_Magnetospirillum_magnetotacticum | TCGGSIAEAVAAE---------------------------------- |
| ZP_00056365_Magnetospirillum_magnetotacticum | ------MASE------------------------------------- |
| YP_003610599_Enterobacter_cloacae | SLFALSASVFAGS---------------------------------- |
| ZP_08017465_Lautropia_mirabilis | VPAASSDSKPADK---------------------------------- |
| PviCA1 | ETSAPPPATD-------------------------------------- |

| | |
|---|---|
| YP_003868697_Paenibacillus_polymyxa | ---------------------------------------------- |
| YP_003944556_Paenibacillus_polymyxa | ---------------------------------------------- |
| NP_241226_Bacillus_halodurans | ---------------------------------------------- |
| YP_003166850_Candidatus_accumulibacter | ---------------------------------------------- |
| YP_287120_Dechloromonas_aromatica | ---------------------------------------------- |
| YP_05029585_Microcoleus_chthonoplastes | ---------------------------------------------- |
| YP_419944_Magnetospirillum_magnetotacticum | SSSYRIVEAVNRYDCASRSYSTLKRSYFKDEGDLLREEEVKVQIEMPVRT |
| ZP_00056365_Magnetospirillum_magnetotacticum | GAGYRVIEAITRYDCNTRNANTIKRIFKKNENEVIREEEIKGS-DLPVRT |
| YP_003610599_Enterobacter_cloacae | ---------------------------------------------- |
| ZP_08017465_Lautropia_mirabilis | ---------------------------------------------- |
| PviCA1 | ---------------------------------------------- |

FIG. 9A

```
YP_003868697_Paenibacillus_polymyxa            ------------------------------------------------------
YP_003944556_Paenibacillus_polymyxa            ------------------------------------------------------
NP_241226_Bacillus_halodurans                  ------------------------------------------------------
YP_003166850_Candidatus_accumulibacter         GMLDDKLLREVCRPKPGPDAATAASKVADKVNQAAGELRKANEALVQKEV
YP_287120_Dechloromonas_aromatica              GTLDDKVLREVCRPPKESPA-------ELAKKANEAAGELKAANDALLKKEM
ZP_05029585_Microcoleus_chthonoplastes         ------------------------------------------------------
YP_419944_Magnetospirillum_magnetotacticum     ------------------------------------------------------
ZP_00056365_Magnetospirillum_magnetotacticum   ------------------------------------------------------
YP_003610599_Enterobacter_cloacae              ------------------------------------------------------
ZP_08017465_Lautropia_mirabilis                ------------------------------------------------------
PviCA1                                         ------------------------------------------------------

YP_003868697_Paenibacillus_polymyxa            ------------------------------------------------------
YP_003944556_Paenibacillus_polymyxa            ------------------------------------------------------
NP_241226_Bacillus_halodurans                  ------------------------------------------------------
YP_003166850_Candidatus_accumulibacter         KRANLQTPNVDKAEAEPRSSPAAKPTAAAAMPARVHSARPAAPRPGE----
YP_287120_Dechloromonas_aromatica              AKAEKPATIKASDVPDKEAEHGAIPSIRPNLKAATESAKETAPAPTPAAA
ZP_05029585_Microcoleus_chthonoplastes         ------------------------------------------------------
YP_419944_Magnetospirillum_magnetotacticum     ------------------------------------------------------
ZP_00056365_Magnetospirillum_magnetotacticum   ------------------------------------------------------
YP_003610599_Enterobacter_cloacae              ------------------------------------------------------
ZP_08017465_Lautropia_mirabilis                ------------------------------------------------------
PviCA1                                         ------------------------------------------------------

YP_003868697_Paenibacillus_polymyxa            -----------------------------------------AAVQKGP
YP_003944556_Paenibacillus_polymyxa            -----------------------------------------AVVQKSP
NP_241226_Bacillus_halodurans                  -----------------------------------------SGGAHEV
YP_003166850_Candidatus_accumulibacter         ----------------------------------TSPAIAHAHG
YP_287120_Dechloromonas_aromatica              PAKAVAPAKAATVVVHTTPAPAPKARKPARSEGYMLELTHSEPAAQHAQI
ZP_05029585_Microcoleus_chthonoplastes         -----------------------------------------NTHSV
YP_419944_Magnetospirillum_magnetotacticum     -----------------------------------------GA
ZP_00056365_Magnetospirillum_magnetotacticum   -----------------------------------------GA
YP_003610599_Enterobacter_cloacae              -----------------------------------------AP
ZP_08017465_Lautropia_mirabilis                -----------------------------------------PA
PviCA1                                         -----------------------------------------EV
```

FIG. 9B

```
YP_003868697_Paenibacillus_polymyxa         HWSYEGDQGPEHWGELEKDFVACGNGHEQSPVNIEHTHLEASQTRQPLQV
YP_003944556_Paenibacillus_polymyxa         HWSYEGDEGPEHWGELEKDFVACGNGQEQSPINIEHSHLEASHTQQPLQV
NP_241226_Bacillus_halodurans               HWSYTGDTGPEHWAELDSEYGACAQGEEQSPINLDKA--EAVDTDTEIQV
YP_003166850_Candidatus_accumulibacter      HWAYEGEGGPDNWGKLKPEYATCATGKRQSPIDIR----DGFRVDLEPIQF
YP_287120_Dechloromonas_aromatica           HWAYDGAGAPENWPNLDPKNKVCAIGERQSPIDIK----DGIKVDLEPIKF
ZP_05029585_Microcoleus_chthonoplastes      DWGYSGDESPEKWGDLSPEFETCKLGKTQSPIDLN----DMSASSADSLEF
YP_419944_Magnetospirillum_magnetotacticum  HWAYEGHGGPKEWGMLSPEYAACSMGREQSPVDLT----RPIAAIIGDPMA
ZP_00056365_Magnetospirillum_magnetotacticum HWAYEGHGGPKEWGMLSPEYAACSMGREQSPVDLS----KPIAAIIGDPLT
YP_003610599_Enterobacter_cloacae           HWTYEGKSGPENWGELSDEFATCKTGKFQSPIDIR----NAYNATLPPLEM
ZP_08017465_Lautropia_mirabilis             HWSYGGSEGPAYWGELSADYSQCSIGRNQSPVDLNQD-DAIRSNKDAVQV
PviCA1                                      HWSYEGDTGPDNWGQLSDEFVECSIGEAQSPVDLPDH--ADETTEPPTV
                                             *  *     *   *      *  . *  **:::  *       .

YP_003868697_Paenibacillus_polymyxa         HYTNTKASILNNGHTVQINVADASNNIMLDGTKFTLKQFHFHHPSEHQID
YP_003944556_Paenibacillus_polymyxa         HYSTTKVSILNNGHTVQVNAASPSNDIVVDGTKFTLKQFHFHHPSEHQID
NP_241226_Bacillus_halodurans               HYEPSAFTIKNNGHTIQAETTSDGNTIEIDGKEYTLVQFHFHFHIPSEHEME
YP_003166850_Candidatus_accumulibacter      VYRPSQFRVVDNGHTVQVEV-SGSSISLLG-RSYDLTQFHFHFHRPSEERVN
YP_287120_Dechloromonas_aromatica           KYQPSTFRIVDNGHTVQVEV-GDGSISLTG-KTYELVQFHFHFHRPSEEKVN
ZP_05029585_Microcoleus_chthonoplastes      TYKYTPYKVINNGHAIEVAYKAGSSIKIEG-KRYELLQFHFHAPSEHTIK
YP_419944_Magnetospirillum_magnetotacticum  AWRPVPLRVQNNGHTIQVDCSGGGTLMLDG-KSYDLLQFHFHHPSEHTVD
ZP_00056365_Magnetospirillum_magnetotacticum AWRPIPLRVQNNGHTIQVDCAGGGSLMLDG-KSYDLLQFHFHHPSEHTVD
YP_003610599_Enterobacter_cloacae           NFHTAAEKLVNNGHTLQVT-ASDEDEFRLDDQIFTLRQYHFHTPSENRIN
ZP_08017465_Lautropia_mirabilis             DYQPMGYELVNNGHTLQATPAGSQPPLQIGSRFTFTLKQFHFHDPSEHTFK
PviCA1                                      TTWPTVGESVDTGHTIQLVPDGDASEVEWQDTTFDLAQVHFHMPSEHTIE
                                             :.**.::   :                    *. **  ***. :

YP_003868697_Paenibacillus_polymyxa         GKNAEMELHFVHQSDNGSTAVLIGVLIQSGKENKAFNRIWSKLPKDNSQEA
YP_003944556_Paenibacillus_polymyxa         GKNAEMELHFVHQSDTGSTAVLIGVLIQSGKENKAFNRIWSKLPKDISQEA
NP_241226_Bacillus_halodurans               GKNLDMELHFVHKNENDELAVLGVLMKAGEENEELAKLWSKLPAEETEEN
YP_003166850_Candidatus_accumulibacter      GKAFDMVAHLVHRAEDGRIAVVAVLLEKGLENPVIQSVWNNLPLEKNEYV
YP_287120_Dechloromonas_aromatica           GQRFDMVVHLVHKSDDGQLAVVAVLLERGTENPFIQTLWNNMPLEKNMAV
ZP_05029585_Microcoleus_chthonoplastes      GGDYPMEAHLVHKSQDGQLAVIGVFLKEGQYNPFIETLWANIPTQKGERI
YP_419944_Magnetospirillum_magnetotacticum  GAFFDMECHFVHKAADGGLAVLGVMIAKGAANPALEAIWQVMPAKAGEAA
ZP_00056365_Magnetospirillum_magnetotacticum GAFFDMECHFVHKAADGGLAVLGVMIAKGAANPALEAIWQVMPAKGGETA
YP_003610599_Enterobacter_cloacae           GKSFPLEAHFVHASKEGDVAVLAVMFEVGPENSALNPLLARLPKEKDHEI
ZP_08017465_Lautropia_mirabilis             GRHFPLELHLVHGAEDGALAVLAVVFQEGEENPALAPLVAE-SLSKGQTR
PviCA1                                      GEALDAEFHFVHTTEEGQALVIGVLARESSTENEAWQPFIDGAAEPGTED
                                             *          .    .  *:.*:   .  * .            .
```

FIG. 9C

```
YP_003868697_Paenibacillus_polymyxa        AALDKEINLAALLPKDLHSVRYNGSLTTPPCTEHVNWTVLEQPIEMSADQ
YP_003944556_Paenibacillus_polymyxa        V-LDEDVNLAALLPKDLHSVRYNGSLTTPPCTEHVNWTVLEQPIEMSADQ
NP_241226_Bacillus_halodurans              ISLDESIDLNALLPESKEGFHYNGSLTTPPCSEGVKWTVLSEPITVSQEQ
YP_003166850_Candidatus_accumulibacter     TPPELSIDVSQLLPQDHSYTTYMGSLTTPPCSEGVLWLVLRQPQQISPEQ
YP_287120_Dechloromonas_aromatica          APPTTTIDLNTLLPATRNYYTYMGSLTTPPCSEGVLWLVMKQPVQVSQDQ
ZP_05029585_Microcoleus_chthonoplastes     VRG-VTVNASALPPKDKSFYHYTGSLTTPPCTEGVNWYVLKQPIEISSQQ
YP_419944_Magnetospirillum_magnetotacticum TAT-SMLDASMLLPKDPVTFRYAGSLTTPPCTEVVQWVVYRQAITASAEQ
ZP_00056365_Magnetospirillum_magnetotacticum TGT-SMLDASMLLPKDPVTFRYAGSLTTPPCSEVVQWVVYRQAVTASAEQ
YP_003610599_Enterobacter_cloacae          SID-KHLDLRPLFPADLHYYRFSGSLTTPPCTEGLRWLVMKNTVTLSEKQ
ZP_08017465_Lautropia_mirabilis            KLA-EPLDIRPLLPKKLSYFRLNGSLTTPPCSEGVTWVFSSPVKASKAQ
PviCA1                                     LPL----DVAAMLPTDPTFEEYTGSLTTPPCTEGVEWVVYHEPIELSAEQ
                                                            *********:*  *  *

YP_003868697_Paenibacillus_polymyxa        INQFAAIFPD-NHRPVQQLGTRELTADK----------
YP_003944556_Paenibacillus_polymyxa        IKQFAAIFPD-NHRPVQQLGTRELKADK----------
NP_241226_Bacillus_halodurans              IDAFAEIFPD-NHRPVQPWNDRDVYDVITE--------
YP_003166850_Candidatus_accumulibacter     LAIFSRLYRN-NARPVQPNFARMIKESR----------
YP_287120_Dechloromonas_aromatica          INIFSRLYKN-NARPIQPSGGRLIKEGR----------
ZP_05029585_Microcoleus_chthonoplastes     LAKFQSVYSG-NARPVQPLNKRVIKTKEM---------
YP_419944_Magnetospirillum_magnetotacticum LAAFAKLFPN-NARPVQPLNRRKLLLDVM---------
ZP_00056365_Magnetospirillum_magnetotacticum LAAFAKLFPN-NARPVQPLNRRKLLLDVM---------
YP_003610599_Enterobacter_cloacae          LEMFKQALEHSNNRPLQPLNGRVIVQ------------
ZP_08017465_Lautropia_mirabilis            IEALGQIMGGPNNRPVQPLNARILVDDDR---------
PviCA1                                     IAVLRDAYDN-TARPTQLLGDRVVYEGTIDVEAEEAH
                                            :      .    ** * *  :
```

FIG. 9D

```
XP_001827551_Aspergillus oryza     ------------------------MKFATTLLPLLAGASAFCIHSPVMRRAAGGLDD
XP_002384772_Aspergillus flavus    MWLPCFQPIFFRCSSVMKFATTLLPLLAGASAFCIHSPVMRRAAGGLDD
XP_001210252_AteCA1                ------------------------MKLTAAVLSLAVAASASCIRHARRADGVVE
XP_002152231_Penicillium marneffei ------------------------MDFALAFVSLITAASASCIYGTSLMPRAAEGVVD
XP_002148277_Penicillium marneffei ------------------------MMKLSSLLFFALPAAAAHIHARAAHGVID
                                                           *   *:*  .

XP_001827551_Aspergillus oryza     ANKFNYTGLGGPLNWYGLD-EANEACAKGKHQSPIVIDSAAIDYAASGSL
XP_002384772_Aspergillus flavus    ANKFNYTGLGGPLNWYGLD-EANEACAKGKHQSPIVIDSAAIDYAASGSL
XP_001210252_AteCA1                TNSYNYTEMGGPLNWYGLDPEANSACATGKHQSPIVIHSEDIDYVSPGSL
XP_002152231_Penicillium marneffei ILSFNYTATGGPLNWHLLNTTANNACATGKNQSPVDIVMEGITYAIPGSV
XP_002148277_Penicillium marneffei TNPFNYTGLGGPLNWYGLNKTANEACAKGMRQSPINIDTHTIEYAATGSV
                                   :*** ***** ***  :  *  ***.*  .****: * .* . .**:

XP_001827551_Aspergillus oryza     KLDLPLADGSKLENLGFGLQVTLTNGSLTANSKTYTLAQFHFHTPSEHHV
XP_002384772_Aspergillus flavus    KLDLPLADGSKLENLGFGLQVTLTNGSLTANSKTYTLAQFHFHTPSEHHV
XP_001210252_AteCA1                KFDIPKADYAKFENLGSGLEVVLTNGSLTVGNKSLPLAQFHFHTPSEHRV
XP_002152231_Penicillium marneffei KLDIPCAGGVELENLNNVEVVEVVANNGTLTTPESIYKLAQFHFHTPSEHRV
XP_002148277_Penicillium marneffei NFNISNVASAKFENSGFGLEVLMTNGSLVVNNITYYLDNFHFHTPSEHRV
                                   : :: .   .    ** . .: *   . .  *  .*   : :********.*
```

*FIG. 14A*

```
XP_001827551_Aspergillus_oryza         NEEHFPMEVHFVFQTAAKETAVVGFFFQLSEVGDSVPLFDSVFAPIDNIP
XP_002384772_Aspergillus_flavus        NEEHFPMEVHFVFQTAAKETAVVGFFFQLSEVGDSVPLFDSVFAPIDNIP
XP_001210252_AteCA1                    NDEYYPMEVHFVFQNKAKDTAVVGFFFQLSELGYSVPLFDTIFDHVLEIE
XP_002152231_Penicillium_marneffei     NEEYFPMEAHFVFENEASQIAVAAFLFQLSESGASNPLFDSVFAHLDDIT
XP_002148277_Penicillium_marneffei     DEEYFPMECHFGFVSDDYKIAVVGFFMEISRFGYTTPLLDSVFARLDDIT
                                       :.*::****  **.*     .**..*::::*.  .*   ::******::

XP_001827551_Aspergillus_oryza         DAGTSTTTGQLDFGGLLDHFNRHGVYQYTGSLTTPPCTEEVMWNLSTEPL
XP_002384772_Aspergillus_flavus        DAGTSTTTGQLDFGGLLDHFNRHGVYQYTGSLTTPPCTEEVMWNLSTEPL
XP_001210252_AteCA1                    EPGAFTHTGEMDFAGLTHHLYMHGIYQYSGSLTTPPCSEDVAWYLSTEPL
XP_002152231_Penicillium_marneffei     TPGTFTFKTGPLDFTTVNQHFSNHGIFQYSGSLTTPPCSEGLSWYISTEPM
XP_002148277_Penicillium_marneffei     KPGTFTKTGPLDFSGLISHFNKYGVYTYSGSLTTPPCTEGVSWFISTEPL
                                       .*  *  ** :** :. *:    *::   * ************ . : *****:

XP_001827551_Aspergillus_oryza         PLTVQGYNKVKKIIKYNARYTQNALGQDNLLEVAAQKLNSIR---------
XP_002384772_Aspergillus_flavus        PLTVQGYNKVKKIIKYNARYTQNALGQDNLLEVAAQKLNSIR---------
XP_001210252_AteCA1                    PLTVQDYNKVKKVLKYNARYTQNALGEDNLLEVAAKSLN------------
XP_002152231_Penicillium_marneffei     PLNVQTYNKVKKVVKFNARYTQNTLGQNNLLELAATPSG------------
XP_002148277_Penicillium_marneffei     WINVQQSQAVKKVIRYNARYTQNNLGEPNLLVVAAKAFDCNVSSSMWS
                                       :.** : ***:**::::**:**:*** *** ::**  :**     .

| | |
|---|---|
| ZP_07308563_Streptomyces_viridochromogene | GEVLDEAVLGSVAYGVLELAIPLVVLGHQSCGAVRAAVQAEQSGERLPA |
| ZP_04996739_Streptomyces_sp._Mg1 | GEVLDEAVVGSVAYGVLELGIPLVVVLGHQACGAVAAAVHAETGHGELPG |
| ZP_05006186_Streptomyces_clavuligerus | GQVLDEAVLGSVAYGVLELDIPLVVVLGHQSCGAVAAAVHADETGAELPA |
| YP_003487983_Streptomyces_scabiei | GEVLDQSVLGSVKYGVLELNIPLVVVLGHQSCGAVKAAVAVDESGEELPS |
| ZP_06588467_Streptomyces_roseosporus | GEVLDEAVLGSIGYGVLELGIPLVVVLGHQSCGAV----HAEETGESLPA |
| ZP_04697556_Streptomyces_roseosporus | GEVLDEAVLGSIGYGVLELDIPLVMVLGHQSCGAV----HAEETGESLPA |
| ZP_06907409_SprCA1 | GEVLDEAVLGSVAYGVLELDIPLVMVLGHQSCGAVTAAVHAEETGEELPA |
| ZP_07290742_Streptomyces_sp. | GEVLDEAVLGSIAYGVLELKIPLVLVLGHQSCGAVGAAVHADETGERLPA |
| ZP_06769567_Streptomyces_clavuligerus | GQVLDESVIGSVEYGVVALRIPLVVVLGHQSCGAVKSAIEIEQTGEQLPG |
| | *:*:::*:. **: *.***:.:*** |
| | |
| ZP_07308563_Streptomyces_viridochromogene | HMQYLVDQIGPAIDHGVDGDARIDATVSANVRLVRSRLAAEPELAARVAD |
| ZP_04996739_Streptomyces_sp._Mg1 | PLRYLAGQIRPSIDRTLRGDACVDAAVTANVRRVAARLAAQAEMAGRIAA |
| ZP_05006186_Streptomyces_clavuligerus | HIQYIAAEIRPAIDRSVQGDARIDATVSAQVRRVRSRLAAEPDLAPRIAA |
| YP_003487983_Streptomyces_scabiei | GIQYIADEIAPAIDHSVTGDARVAATIDANVRLVRSKVVADPDVAARLKA |
| ZP_06588467_Streptomyces_roseosporus | HIQYVAEQIRPAIVHGQHGDARVDATVSAQVRLVRSRLARETDLASKVAA |
| ZP_04697556_Streptomyces_roseosporus | HIQYVAEQIRPAIVHGQHGDARVDATVSAQVRLVRSRLARETDLASKVAA |
| ZP_06907409_SprCA1 | HIQYIADRIRPAIDHSQEGAARVDSTITRNVQMVTRLLAQEPDLAARIAA |
| ZP_07290742_Streptomyces_sp. | HIQYIADQINPAIDRTRHGDARVRATIDAHARSTRDRLAAEPDLARAVSA |
| ZP_06769567_Streptomyces_clavuligerus | SIQYIAERIWPAIDQTQQGDARLNATTDANALMIRDQLAALPTLATRIAA |
| | *:* . .. . *** :. * :: .: : ** |
| | |
| ZP_07308563_Streptomyces_viridochromogene | GRLAIVGARYELTTQTVHRVA |
| ZP_04996739_Streptomyces_sp._Mg1 | GKLAVVGARYELAGQWHQVG |
| ZP_05006186_Streptomyces_clavuligerus | GRLAITGARYELTSQLVHQLA |
| YP_003487983_Streptomyces_scabiei | GKVAVVGARYDLTTQRVHLLK |
| ZP_06588467_Streptomyces_roseosporus | GELAIVGARYELSTELVHRVG |
| ZP_04697556_Streptomyces_roseosporus | GELAIVGARYELSTELVHRVG |
| ZP_06907409_SprCA1 | GKLAVVGARYELSSQLVHTVA |
| ZP_07290742_Streptomyces_sp. | GKLAVAAARYDLHDQRVSTLN |
| ZP_06769567_Streptomyces_clavuligerus | GQLSVVSARYELTDQSVRLLP |
| | *.::::.***::: : * |

```
NP_241226_Bacillus_halodurans          EMEGKNLDMELHFVHKNENDELAVLGVLMKAGEENEELAKLWSKLPAEET
BagCA1_mature                          QKNGEHLDMELHFVHQNQEGELAVLGVLMEEGEVNDALAELWAEMPQEEM
YP_419944_Magnetospirillum_magneticum  TVDGAFFDMECHFVHKAADGGLAVLGVMIAKGAANPALEAIWQVMPAKAG
ZP_08403178_Rubrivivax_benzoatilyticus RIDGRQSEMVAHLVHRDPEGRLAVVAVLLQRGEEQPVVQSVWNNLPLEKH
ZP_004645315_Paenibacillus_mucilaginosus QINGKNFEMEGHLVHKNKDGGLAVGFLMTAGKENKPLAEMWSKLPKQET
YP_003944556.1_Paenibacillus_polymyxa  QIDGKNAEMELHFVHQSDTGSTAVLGVLIQSGKENKAFNRIWSKLPKDIS
ZP_04248491_Bacillus_cereus_Rock1-3    QFEGKHADMELHLVHQNDQGQLAVVGIMIKEGQKNEGFAAMWQNLPHRKN
ZP_04209878_Bacillus_cereus_Rock4-18   QFEGKHADMELHLVHQNDQGQLVVVGIMIKEGQKNEGFAAMWQNLPHRKN
YP_003428428_Bacillus_pseudofirmus     QFNGEHYDMELHLVHQDINGNLAVLGVMIEEGAENEELAPAWGELPEEET
BAK17997_Solibacillus_silvestris       QFNGQNYDMELHLVHSDKDGKLAVIGLMIQEGNENKQFASMWNELPTDKT
YP_176677_Bacillus_clausii             TIEETSFPMELHLVHANHAGDLAVLGVLMEMGNDHEGIEAVWEVMPEEEG
                                         *  *:**           . .*:..::     *      . *:   *

NP_241226_Bacillus_halodurans          EENISLDESIDLNALLPESKEGFHYNGSLTTPPCSEGVKWTVLSEPITVS
BagCA1_mature                          DETIELTDAIDLNALLPSSHEGFHYGGSLTTPPCTEGVKWVVLEKTISVS
YP_419944_Magnetospirillum_magneticum  EAATA--TSMLDASMLLPKDPVTFRYAGSLTTPPCTEVVQWVVYRQAITAS
ZP_08403178_Rubrivivax_benzoatilyticus DEARA--SGAIDLAQLLPADRGYYTYMGSLTTPPCTEGVLIWIVMRQPVAVS
ZP_004645315_Paenibacillus_mucilaginosus KEDVKLEQPVDLPGLVPSTAHAFRYEGSLTTPPCSEHVKWIVLADPIEVS
YP_003944556.1_Paenibacillus_polymyxa  QEAV-LDEDVNLAALLPKDLHSVRYNGSLTTPPCTEHVNWTVLEQPIEMS
ZP_04248491_Bacillus_cereus_Rock1-3    IKADV-QHTIDIKQILPSDHSSFRYMGSLTTPPCTENVQWIVMKQTIEMS
ZP_04209878_Bacillus_cereus_Rock4-18   IKADV-QHTIDIKQILPSDYSSFRYMGSLTTPPCTENVQWIVMKQTIEMS
YP_003428428_Bacillus_pseudofirmus     ENEVALEEPINLQNLLPDDQSSFHYNGSLTTPPCTEEVKWIVFKEPIQKS
BAK17997_Solibacillus_silvestris       AKGNSEKHIIDLQALLPENETTFQYAGSLTTPPCTEEVQWIVFEQPIEMS
YP_176677_Bacillus_clausii             TAAYS---ISLDPNLFLPESVTAYQYDGSLTTPPCSEGVKWTVLNDTISIS
                                            .:     :   **        ********:*  *    .:  *

NP_241226_Bacillus_halodurans          QEQIDAFAEIFPDNHRPVQPWNDRDVYDVITE
BagCA1_mature                          QEQIDTFAEIFPTNNRPVQPWNDRHVYEVAID
YP_419944_Magnetospirillum_magneticum  AEQLAAFAKLFPNNARPVQPLNRRKLLLDVM-
ZP_08403178_Rubrivivax_benzoatilyticus QEQIDIFARLYPMNARPVQPSSGRLIKQSR--
ZP_004645315_Paenibacillus_mucilaginosus KEQIEAFAAIFPDNHRPVQPLNQRTVVSN----
YP_003944556.1_Paenibacillus_polymyxa  ADQIKQFAAIFPDNHRPVQQLGTRELKADK--
ZP_04248491_Bacillus_cereus_Rock1-3    KKQIKVFHKLFPTNNRPVQPINGRAVL-----
ZP_04209878_Bacillus_cereus_Rock4-18   KKQIKVFHKLFPTNNRPVQPINGRAVL-----
YP_003428428_Bacillus_pseudofirmus     AEQIQAFQEIYEENHRPVQPLNERG-------
BAK17997_Solibacillus_silvestris       KAQIKAFQKIFPDNHRPVQPINEREINKSGE-
YP_176677_Bacillus_clausii             ETQLDAFRDIYPQNYRPVQELGDREIGFHYH-
                                        **  *     :  * ****

FIG. 24B
```

THERMOSTABLE CARBONIC ANHYDRASES AND METHODS OF USE THEREOF

CROSS-REFERENCE

This application is a divisional of U.S. application Ser. No. 14/113,775, filed Dec. 12, 2013 (now U.S. Pat. No. 9,410,140), which is a 371 National Stage application of PCT/US2012/036932, filed on May 8, 2012, which claims the benefit of Chinese PCT application number PCT/CN2011/073886 filed May 10, 2011; Chinese PCT application number PCT/CN2011/073876 filed May 10, 2011; Chinese PCT application number PCT/CN2011/073873 filed May 10, 2011; Chinese PCT application number PCT/CN2011/073871 filed May 10, 2011; Chinese PCT application number PCT/CN2011/084371 filed Dec. 21, 2011; Chinese PCT application number PCT/CN2011/084366 filed Dec. 21, 2011; Chinese PCT application number PCT/CN2011/084363 filed Dec. 21, 2011; Chinese PCT application number PCT/CN2011/084384 filed Dec. 21, 2011; U.S. provisional application No. 61/578,408 filed on Dec. 21, 2011; U.S. provisional application No. 61/578,429 filed on Dec. 21, 2011; U.S. provisional application No. 61/578,416 filed on Dec. 21, 2011; and U.S. provisional application No. 61/578,421 filed on Dec. 21, 2011. All these prior applications are incorporated herein by reference in their entirety.

BACKGROUND

Much of the world's electrical power is generated from the combustion of fossil-fuels such as coal, natural gas and fuel oil. Carbon dioxide ($CO_2$) is a by-product of combustion and is the principal greenhouse gas. As such, $CO_2$ emissions are believed to be a major contributor to the phenomenon of global warming, which could lead to drastic climate changes (e.g., violent weather patterns, changes in precipitation, rising ocean levels, and increases in temperature). Additionally, because $CO_2$ is an acidic gas, it forms the corrosive product carbonic acid in the presence of water.

Several approaches for extraction $CO_2$ have been suggested, including transformation by algae, sequestration in oceans, storage in depleted oil and natural gas wells, dissolution in deep water tables, and transformation into carbonates. However, many of these approaches have significant draw backs, and are often economically or ecologically unviable.

Carbonic anhydrases (EC 4.2.1.1; and CAS No. 9001-03-0) catalyze the inter-conversion between carbon dioxide and bicarbonate [$CO_2+H_2O \leftrightarrow HCO_3^-+H^+$]. The active site of most carbonic anhydrases contains a zinc ion, therefore; these enzymes are also classified as metalloenzymes. Carbonic anhydrases may serve as biological catalysts to accelerate the capture of $CO_2$. Naturally occurring carbonic anhydrases typically function at low temperatures and are poorly suited to extraction of $CO_2$ from hot combustion gases. Accordingly, the need exists for carbonic anhydrases that can effectively hydrate $CO_2$ under inhospitable conditions (e.g., elevated temperatures, alkaline pH, and/or in the presence of high concentrations of bicarbonate).

SUMMARY

The present disclosure provides compositions and methods that relate to recombinant carbonic anhydrases from *Bacillus gibsonii*, *Promicromonospora vindobonensis*, *Aspergillus terreus*, *Streptomyces pristinaespiralis*, *Bacillus agaradhaerens*, *Vibrio* sp. AND4, *Vibrio* sp. Ex25, polynucleotides encoding the carbonic anhydrases, and methods of make and/or use thereof. Formulations containing the recombinant carbonic anhydrases are suitable for use in extracting carbon dioxide.

In some embodiments, the present compositions and methods relate to a recombinant carbonic anhydrase 1 from *Bacillus gibsonii* (Bgi CA1). In some embodiments, the present compositions and methods relate to a recombinant carbonic anhydrase 1 from *Promicromonospora vindobonensis* (Pvi CA1). In some embodiments, the present compositions and methods relate to a recombinant carbonic anhydrase 1 cloned from *Aspergillus terreus* (Ate CA1). In some embodiments, the present compositions and methods relate to a recombinant carbonic anhydrase 1 from *Streptomyces pristinaespiralis* (Spr CA1). In some embodiments, the present compositions and methods relate to a recombinant carbonic anhydrase 1 from *Bacillus agaradhaerens* (Bag CA1). In some embodiments, the present compositions and methods relate to a recombinant carbonic anhydrase 1 from *Vibrio* sp. AND4 (Vsp CA1). In some embodiments, the present compositions and methods relate to a recombinant carbonic anhydrase I from *Vibrio* sp. Ex25 (VspE CA1). In some embodiments, the present compositions and methods relate to a recombinant carbonic anhydrase II from *Vibrio* sp. Ex25 (VspE CA2). Formulations containing one or more of the recombinant carbonic anhydrases are suitable for use in extracting carbon dioxide from a carbon dioxide-containing medium, such as combustion exhaust and flue gas streams.

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136, wherein the polypeptide has carbonic anhydrase activity. In some embodiments, the recombinant polypeptide is contained in a basic, high ionic strength solution.

In some embodiments, the invention provides a recombinant polypeptide comprising an amino acid sequence, where the amino acid sequence has carbonic anhydrase activity, where the amino acid sequence has a higher thermostability and/or melting temperature at a higher ionic strength, and where the amino acid sequence is at least 70% identical to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136.

In some embodiments, the invention provides a recombinant polypeptide comprising an amino acid sequence, where the amino acid sequence has carbonic anhydrase activity greater than 25% of the carbonic anhydrase activity when incubated for 30 minutes or longer at a pH of from about 8 to about 10.5, and where the amino acid sequence is at least 70% identical to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136.

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence of SEQ ID NO: 3, wherein the polypeptide has carbonic anhydrase activity. In some embodiments, the recombinant polypeptide is contained in a basic, high ionic strength solution. In some embodiments, the polypeptide retains greater than 70% (e.g., greater than 70%, greater than 75%, greater than 80%, greater than 85%, greater than 90%, greater than 95%, greater than 96%, greater than 97%, greater than 98%, greater than 99%, or 100%) of the carbonic anhydrase activity when incubated for 5 or more hours at a pH of from 8.5 to 10.5, which, in some embodiments, takes place at a temperature of from 25° C. to 40° C. In some embodiments, the polypeptide retains at least 90% (e.g., at least 90%, at least 91%, at least 92%, at least 93%, at least 94%, at least 95%, at least 96%, at least 97%, at least 98%, at least 99% or 100%) of the carbonic anhydrase activity when incubated for about 24 hours at a temperature of about 25° C., which, in some embodiments, is at a pH of from 8.5 to 10.5. In some embodiments, the polypeptide retains at least 90% (e.g., at least 90%, at least 91%, at least 92%, at least 93%, at least 94%, at least 95%, at least 96%, at least 97%, at least 98%, at least 99% or 100%) of the carbonic anhydrase activity when incubated for about 24 hours at a temperature of about 40° C., which, in some embodiments, is at a pH of from 8.5 to 10.5. In some embodiments, the polypeptide retains at least 50% (e.g., at least 50%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 3 hours at a temperature of about 50° C., which, in some embodiments, is at a pH of from 8.5 to 9.5. In some embodiments, the polypeptide retains at least 25% (e.g., at least 25%, at least 35%, at least 45%, at least 55%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 3 hours at a temperature of about 50° C., which, in some embodiments, is at a pH of 10.5. In some embodiments, the polypeptide retains at least 50% (e.g., at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for 1 to 3 hours at a temperature of from 20° C. to 50° C. under high ionic strength conditions. In some embodiments, the high ionic strength conditions comprise 1 M bicarbonate. In some embodiments, the polypeptide has a melting temperature that is elevated in the presence of 1-2 M bicarbonate.

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence of SEQ ID NO: 28, wherein the polypeptide has carbonic anhydrase activity. In some embodiments, the recombinant polypeptide is contained in a basic, high ionic strength solution. In some embodiments, the polypeptide retains greater than 70% (e.g., greater than 70%, greater than 75%, greater than 80%, greater than 85%, greater than 90%, greater than 95%, greater than 96%, greater than 97%, greater than 98%, greater than 99%, or 100%) of the carbonic anhydrase activity when incubated for 5 or more hours at a pH of from 8.5 to 9.5, which, in some embodiments, takes place at a temperature of from 25° C. to 40° C. In some embodiments, the polypeptide retains at least 80% (e.g., at least 80%, at least 85%, at least 90%, at least 91%, at least 92%, at least 93%, at least 94%, at least 95%, at least 96%, at least 97%, at least 98%, at least 99% or 100%) of the carbonic anhydrase activity when incubated for about 24 hours at a temperature of about 25° C., which, in some embodiments, is at a pH of from 8.5 to 9.5. In some embodiments, the polypeptide retains at least 80% (e.g., at least 80%, at least 85%, at least 90%, at least 91%, at least 92%, at least 93%, at least 94%, at least 95%, at least 96%, at least 97%, at least 98%, at least 99% or 100%) of the carbonic anhydrase activity when incubated for about 24 hours at a temperature of about 40° C., which, in some embodiments, is at a pH of from 8.5 to 9.5. In some embodiments, the polypeptide retains at least 40% (e.g., at least 40%, at least 50%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 3 hours at a temperature of about 50° C., which, in some embodiments, is at a pH of from 8.5 to 9.5. In some embodiments, the polypeptide retains at least 25% (e.g., at least 25%, at least 35%, at least 45%, at least 55%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 3 hours at a temperature of about 40° C., which, in some embodiments, is at a pH of 10.5. In some embodiments, the polypeptide retains at least 50% (e.g., at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for 1 to 3 hours at a temperature of from 20° C. to 50° C. under high ionic strength conditions. In some embodiments, the high ionic strength conditions comprise 1 M bicarbonate. In some embodiments, the polypeptide has a melting temperature that is elevated in the presence of 1-2 M bicarbonate.

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence of SEQ ID NO: 43, wherein the polypeptide has carbonic anhydrase activity. In some embodiments, the recombinant polypeptide is contained in a basic, high ionic strength solution. In some embodiments, the polypeptide retains greater than 70% (e.g., greater than 70%, greater than 75%, greater than 80%, greater than 85%, greater than 90%, greater than 95%, greater than 96%, greater than 97%, greater than 98%, greater than 99%, or 100%) of the carbonic anhydrase activity when incubated for 5 or more hours at a pH of from 8.0 to 11 (e.g., from 8.0 to 10.5, from 8.5 to 10.5, from 8.5 to 11, from 8.5 to 10, from 8.0 to 10, from 9.0 to 11, etc), which, in some embodiments, takes place at a temperature of from 25° C. to 40° C. In some embodiments, the polypeptide retains at least 90% (e.g., at least 90%, at least 91%, at least 92%, at least 93%, at least 94%, at least 95%, at least 96%, at least 97%, at least 98%, at least 99% or 100%) of the carbonic anhydrase activity when incubated for about 24 hours at a temperature of about 25° C., which, in some embodiments, is at a pH of from 8.5 to 10.5. In some embodiments, the polypeptide retains at least 80% (e.g., at least 80%, at least 82%, at least 84%, at least 86%, at least 88%, at least 90%, at least 91%, at least 92%, at least 93%, at least 94%, at least 95%, at least 96%, at least 97%, at least 98%, at least 99% or 100%) of the carbonic anhydrase activity when incubated for about 24 hours at a temperature of about 40° C., which, in some embodiments, is at a pH of from 8.5 to 10.5. In some embodiments, the polypeptide retains at least 40% (e.g., at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 3 hours at a temperature of about 50° C., which, in some embodiments, is at a pH of from 8.5 to 10 (e.g., 8.5 to 9.5, 8.5 to 10, 9 to 10, etc). In some embodiments, the polypeptide retains at least 25% (e.g., at least 25%, at least 35%, at least 45%, at least 55%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 3 hours at a temperature of about 50° C., which, in some embodiments, is at a pH of 10.5. In some embodiments, the polypeptide retains at least 50% (e.g., at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for 1 to 3 hours at a temperature of from 20° C. to 50° C. under high ionic strength conditions. In some embodiments, the high ionic strength conditions comprise 1 M bicarbonate. In some embodiments, the polypeptide has a melting temperature that is elevated in the presence of 1-2 M bicarbonate. In related embodiments, the polypeptide has increased thermostability at higher ionic strength conditions. For example, the polypeptide has a higher melting temperature at a higher ionic strength condition (e.g., at 1 M bicarbonate) as compared to at a lower ionic strength condition (e.g., at 0.8, 0.6, 0.4, 0.2, or 0.1 M bicarbonate).

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence of SEQ ID NO: 53, wherein the polypeptide has carbonic anhydrase activity. In some embodiments, the recombinant polypeptide is contained in a basic, high ionic strength solution. In some embodiments, the polypeptide retains greater than 50% (e.g., greater than 50%, greater than 60%, greater than 70%, greater than 75%, greater than 80%, greater than 85%, greater than 90%, greater than 95%, greater than 96%, greater than 97%, greater than 98%, greater than 99%, or 100%) of the carbonic anhydrase activity when incubated for 5 or more hours at a pH of from 8 to 10 (e.g., 8 to 9.5, 8.5 to 9.5, 8.5 to 10, 8 to 10, etc), which, in some embodiments, takes place at a temperature of from 25° C. to 40° C. In some embodiments, the polypeptide retains at least 70% (e.g., at least 70%, at least 80%, at least 90%, at least 91%, at least 92%, at least 93%, at least 94%, at least 95%, at least 96%, at least 97%, at least 98%, at least 99% or 100%) of the carbonic anhydrase activity when incubated for about 24 hours at a temperature of about 25° C., which, in some embodiments, is at a pH of from 8 to 11 (e.g., 8 to 10.5, 8.5 to 10.5, 8.5 to 11, 8.5 to 10, etc). In some embodiments, the polypeptide retains at least 50% (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100%) of the carbonic anhydrase activity when incubated for about 24 hours at a temperature of about 40° C., which, in some embodiments, is at a pH of from 8.5 to 10.5 (e.g., 8.5 to 10, 8.5 to 10.5, 8.5 to 9.5, 8 to 10, 8 to 9.5, etc). In some embodiments, the polypeptide retains at least 30% (e.g., at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 2 hours at a temperature of about 50° C., which, in some embodiments, is at a pH of from 8 to 11 (e.g., 8 to 10.5, 8.5 to 10.5, 8.5 to 11, 8.5 to 10, 9 to 10.5, etc). In some embodiments, the polypeptide retains at least 15% (e.g., at least 15%, at least 20%, at least 25%, at least 35%, at least 45%, at least 55%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 2 hours at a temperature of about 50° C., which, in some embodiments, is at a pH of 8, 8.5, 9.0, 9.5, 10, 10.5, or 11. In some embodiments, the polypeptide retains at least 50% (e.g., at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for 1 to 3 hours at a temperature of from 20° C. to 50° C. under high ionic strength conditions. In some embodiments, the high ionic strength conditions comprise 1 M bicarbonate. In some embodiments, the polypeptide has a melting temperature that is elevated in the presence of 1-2 M bicarbonate.

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence SEQ ID NO: 64, wherein the polypeptide has carbonic anhydrase activity. In some embodiments, the recombinant polypeptide is contained in a basic, high ionic strength solution. In some embodiments, the polypeptide retains greater than 70% (e.g., greater than 70%, greater than 75%, greater than 80%, greater than 85%, greater than 90%, greater than 95%, greater than 96%, greater than 97%, greater than 98%, greater than 99%, or 100%) of the carbonic anhydrase activity when incubated for 5 or more hours at a pH of from about 8.0 to about 11 (e.g., about 8.5 to about 10.5, about 8.5 to about 9.5, about 9.5 to about 10.5, about 8.5 to about 10, about 9 to about 10.5, etc), which, in some embodiments, takes place at a temperature of from about 20° C. to about 55° C. (e.g., about 25° C. to about 50° C., about 30° C. to about 45° C., about 35° C. to 40° C., etc). In some embodiments, the polypeptide retains at least 90% (e.g., at least 90%, at least 91%, at least 92%, at least 93%, at least 94%, at least 95%, at least 96%, at least 97%, at least 98%, at least 99% or 100%) of the carbonic anhydrase activity when incubated for about 3, about 5, about 10, about 24 hours or longer at a temperature of about 25° C., which, in some embodiments, is at a pH of from 8.0 to 11 (e.g., 8.5 to 10.5, 8.5 to 9.5, 9.5 to 10.5, 8.5 to 10, 9 to 10, 9 to 10.5, etc). In some embodiments, the polypeptide retains at least 90% (e.g., at least 90%, at least 91%, at least 92%, at least 93%, at least 94%, at least 95%, at least 96%, at least 97%, at least 98%, at least 99% or 100%) of the carbonic anhydrase activity when incubated for about 3, about 5, about 10, about 24 hours at a temperature of about 40° C., which, in some embodiments, is at a pH of from 8.0 to 11 (e.g., 8.5 to 10.5, 8.5 to 9.5, 9.5 to 10.5, 8.5 to 10, 9 to 10, 9 to 10.5, etc). In some embodiments, the polypeptide retains at least 50% (e.g., at least 50%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 3 hours at a temperature of about 50° C., which, in some embodiments, is at a pH of from about 8 to about 10 (e.g., about 8.5 to about 9.5, etc). In some embodiments, the polypeptide retains at least 25% (e.g., at least 25%, at least 35%, at least 45%, at least 55%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 3 hours at a temperature of about 50° C., which, in some embodiments, is at a pH of about 9.5 to 11 (e.g., about 10 to about 10.5, etc). In some embodiments, the polypeptide retains at least 50% (e.g., at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for as long as 10 hours (e.g., for 1 to 3 hours, for 1 to 5 hours, for 1 to 7 hours, for 1 to 9 hours, etc) at a temperature of from about 20° C. to about 55° C. (e.g., about 25° C. to about 50° C., about 20° C. to about 50° C., about 30° C. to about 50° C., etc) under high ionic strength conditions. In some embodiments, the high ionic strength conditions comprise 1 M bicarbonate. In some embodiments, the polypeptide has a melting temperature that is elevated in the presence of 1 to 2 M bicarbonate.

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence of SEQ ID NO: 80, wherein the polypeptide has carbonic anhydrase activity. In some embodiments, the recombinant polypeptide is contained in a basic, high ionic strength solution. In some embodiments, the polypeptide retains greater than 50% (e.g., greater than 50%, greater than 55%, greater than 60%, greater than 65%, greater than 70%, greater than 75%, greater than 80%, greater than 85%, greater than 90%, greater than 95%, greater than 96%, greater than 97%, greater than 98%, greater than 99%, or 100%) of the carbonic anhydrase activity when incubated for 3 or more hours at a pH of from about 8 to about 11 (e.g., from about 8 to about 10.5, from about 8.5 to about 9.5, from about 8.2 to about 10.6, from about 8.5 to about 10.5, from about 8.4 to about 10.2, from about 8.6 to about 10, or from 9.5 to about 10.5, etc), which, in some embodiments, takes place at a temperature of from 20° C. to 55° C. (e.g., from 25° C. to 50° C., 30° C. to 45° C., 35° C. to 40° C., etc). In some embodiments, the polypeptide retains at least 60% (e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%) of the carbonic anhydrase activity when incubated for at least about 1 hour, at least about 5 hours, at least about 10 hours, at least about 24 hours, or longer at a temperature of about 25° C., which, in some embodiments, is at a pH of from about 8 to about 11 (e.g., about 8 to about 10.8, about 8.2 to about 10.6, about 8.5 to about 10.5, about 8.5 to about 9.5, about 9.5 to about 10.5, about 8.6 to about 10.2, about 8.8 to about 10, etc). In some embodiments, the polypeptide retains at least 50% (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%) of the carbonic anhydrase activity when incubated for longer than about 1 hour, about 3 hours, about 5 hours, about 10 hours, about 24 hours, or longer, at a temperature of about 40° C., which, in some embodiments, is at a pH of from about 8 to about 10 (e.g., about 8 to about 10.8, about 8.5 to about 9.5, about 9.5 to about 10.5, about 8.2 to about 10.6, about 8.5 to about 10.5, about 8.6 to about 10.2, about 8.8 to about 10, etc). In some embodiments, the polypeptide retains at least 50% (e.g., at least 50%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 1 hour, about 3 hours, about 5 hours, about 10 hours, or at least 24 hours, at a temperature of about 50° C., which, in some embodiments, is at a pH of about 8.5. In some embodiments, the polypeptide retains at least 20% (e.g., at least 20%, at least 25%, at least 35%, at least 45%, at least 55%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 1 hour, about 2 hours, or about 3 hours at a temperature of about 50° C., which, in some embodiments, is at a pH of about 9.5 to about 10.5. In some embodiments, the polypeptide retains at least 30% (e.g., at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for 1 to 3 hours at a temperature of about 20° C. under high ionic strength conditions. In some embodiments, the polypeptide retains at least about 30% (e.g., at least 30%, at least 35%, at least 40%, at least 45%, at least 50%, at least 55%, at least 60%, at least 65% or at least 70%) of the carbonic anhydrase activity when incubated for 10 minutes to 40 minutes, under high ionic strength conditions. In some embodiments, the high ionic strength conditions comprise 1 M bicarbonate. In some embodiments, the polypeptide has a melting temperature that is elevated in the presence of 1-2 M bicarbonate. In related embodiments, the polypeptide has an increased thermostability at a higher ionic strength. For example, the polypeptide can suitably have an increased melting temperature at a higher ionic strength (e.g., at 1 M bicarbonate) than at a lower ionic strength (e.g., at 0.8 M bicarbonate, at 0.6 M bicarbonate, at 0.4 M bicarbonate, at 0.2 M bicarbonate, or at 0.1 M bicarbonate, etc).

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence of SEQ ID NO:130, wherein the polypeptide has carbonic anhydrase activity. In some embodiments, the recombinant polypeptide is contained in a basic, high ionic strength solution. In some embodiments, the polypeptide retains greater than 50% (e.g., greater than 50%, greater than 55%, greater than 60%, greater than 65%, greater than 70%, greater than 75%, greater than 80%, greater than 85%, greater than 90%, greater than 95%, greater than 96%, greater than 97%, greater than 98%, greater than 99%, or 100%) of the carbonic anhydrase activity when incubated for 1 or more, 2 or more, 3 or more, 4 or more, or 5 or more hours at a pH of from about 8 to about 11 (e.g., about 8.5 to about 10.5, about 8.5 to about 9.5, about 9.5 to about 10.5, about 8 to about 10.5, etc), which, in some embodiments, takes place at a temperature of from about 20° C. to about 55° C. (e.g., about 25° C. to about 50° C., about 25° C. to about 40° C., about 40° C. to about 55° C., etc). In some embodiments, the polypeptide retains at least 60% (e.g., at least 60%, at least 65%, at least 70%, at least 75%, at least 80%, at least at least 90%, at least 91%, at least 92%, at least 93%, at least 94%, at least 95%, at least 96%, at least 97%, at least 98%, at least 99%, or 100%) of the carbonic anhydrase activity when incubated for about 30 minutes or longer, 1 hour or longer, 2 hours or longer, 3 hours or longer, 5 hours or longer, 10 hours or longer, 15 hours or longer, or even 24 hours or longer, at a temperature of about 25° C., which, in some embodiments, is at a pH of from about 8 to about 11 (e.g., about 8.5 to about 10.5, about 9.5 to about 10.5, about 8.5 to about 9.5). In some embodiments, the polypeptide retains at least 70% (e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100%) of the carbonic anhydrase activity when incubated for about 30 minutes, about 1 hour, about 2 hours, about 3 hours, about 5 hours, about 10 hours, about 15 hours, or about 24 hours at a temperature of about 40° C., which, in some embodiments, is at a pH of from about 8 to about 11 (e.g., about 8.5 to about 10.5, about 8.5 to about 9.5, about 9.5 to about 10.5, about 8 to about 10.5, etc). In some embodiments, the polypeptide retains at least 30% (e.g., at least 30%, at least 35%, at least 40%, at least 45%, at least 50%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 30 minutes, about 1 hour, about 2 hours, about 3 hours, or longer at a temperature of about 50° C., which, in some embodiments, is at a pH of from about 8 to about 11 (e.g., about 8.5 to about 10.5, about 8.5 to about 9.5, about 9.5 to about 10.5, about 8 to about 10.5, etc). In some embodiments, the polypeptide retains at least 15% (e.g., at least 15%, at least 20%, at least 25%, at least 35%, at least 45%, at least 55%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 30 minutes, 1 hour, 2 hours, or 3 hours or longer, at a temperature of about 50° C., which, in some embodiments, is at a pH of between about 8.5 to about 11 (e.g., about 8.5 to about 10.5, about 8.5 to about 9.5, about 9.5 to about 10.5, about 8 to about 10.5, or at individual pH values of about 8, about 8.5, about 9.0, about 9.5, about 10, about 10.5, or about 11). In some embodiments, the polypeptide retains at least 30% (e.g., at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 30 minutes, about 1 hour, about 2 hours, about 3 hours, or longer, at a temperature of from 20° C. to 50° C. under high ionic strength conditions. In some embodiments, the high ionic strength conditions comprise 1 M bicarbonate. In some embodiments, the polypeptide has a melting temperature that is elevated in the presence of 1-2 M bicarbonate. In related embodiments, the polypeptide has improved or higher thermostability at higher ionic strength conditions. For example, the polypeptide has a higher melting temperature at a higher ionic strength (e.g., 1 M bicarbonate) as compared to its melting temperature at a lower ionic strength (e.g., 0.8 M bicarbonate, 0.6 M bicarbonate, 0.4 M bicarbonate, 0.2 M bicarbonate, 0.1 M bicarbonate, etc).

In one aspect, recombinant polypeptides are provided, comprising an amino acid sequence that is at least 55% (e.g., 55%, 60%, 65%, 70%, 75%, 80%, 85%, 90%, 95%, 96%, 97%, 98%, 99%, or 100%) identical to the amino acid sequence of SEQ ID NO: 136, wherein the polypeptide has carbonic anhydrase activity. In some embodiments, the recombinant polypeptide is contained in a basic, high ionic strength solution. In some embodiments, the polypeptide retains greater than 25% (e.g., greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or 100%) of the carbonic anhydrase activity when incubated for 30 minutes or longer, 1 hour, 2 hours, 3 hours, 5 hours, 10 hours, or longer at a pH of from about 8 to about 11 (e.g., about 8.5 to about 10.5, about 8.5 to about 9.5, about 9.5 to about 10.5, about 8 to about 10, etc), which, in some embodiments, takes place at a temperature of from 20° C. to 55° C. (e.g., 25° C. to 40° C., 40° C. to 55° C., 20° C. to 50° C., etc). In some embodiments, the polypeptide retains at least 40% (e.g., at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for at least about 30 minutes, at least about 1 hour, at least about 2 hours, at least about 3 hours, at least about 5 hours, at least about 10 hours, at least about 24 hours, or longer at a temperature of about 25° C., which, in some embodiments, is at a pH of from about 8 to about 11 (e.g., about 8.5 to about 10.5, about 8.5 to about 9.5, about 9.5 to about 10.5, about 8 to about 10, etc). In some embodiments, the polypeptide retains at least 60% (e.g., at least 60%, at least 65%, at least 70%, at least 75%, at least 80%, at least 85%, at least 90%, at least 95%, at least 96%, at least 97%, at least 98%, at least 99% or 100%) of the carbonic anhydrase activity when incubated for at least 30 minutes, at least 1 hour, at least 2 hours, at least 5 hours, at least 10 hours, or at least 24 hours, or longer at a temperature of about 40° C., which, in some embodiments, is at a pH of from about 8 to about 11 (e.g., about 8.5 to about 10.5, about 8.5 to about 9.5, about 9.5 to about 10.5, about 8 to about 10, etc). In some embodiments, the polypeptide retains at least 25% (e.g., at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 30 minutes, about 1 hour, about 2 hours, about 3 hours, or longer, at a temperature of about 50° C., which, in some embodiments, is at a pH of from about 8 to about 11 (e.g., about 8.5 to about 9.5, about 8.5 to about 10.5, about 8 to about 10, about 9.5 to about 10.5, etc.). In some embodiments, the polypeptide retains at least 25% (e.g., at least 25%, at least 35%, at least 45%, at least 55%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for about 30 minutes, about 1 hour, about 2 hours, about 3 hours, or longer, at a temperature of about 50° C., which, in some embodiments, is at a pH of 10.5. In some embodiments, the polypeptide retains at least 40% (e.g., at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%) of the carbonic anhydrase activity when incubated for 1 to 3 hours at a temperature of from 20° C. to 50° C. under high ionic strength conditions. In some embodiments, the high ionic strength conditions comprise 1 M bicarbonate. In some embodiments, the polypeptide has a melting temperature that is elevated in the presence of 1-2 M bicarbonate. In related embodiments, the polypeptide has an increased or higher thermostability at a higher ionic strength conditions.

For example, the polypeptide has a higher melting temperature at a higher ionic strength (e.g., 1 M bicarbonate) as compared to at a lower ionic strength (e.g., 0.8 M bicarbonate, 0.6 M bicarbonate, 0.4 M bicarbonate, 0.2 M bicarbonate, or 0.1 M bicarbonate, etc).

In some embodiments, the polypeptide comprises an amino acid sequence that is at least 70% (e.g., at least 75%, at least 80%, at least 85%, at least 90%, at least 91%, at least 92%, at least 93%, at least 94%, at least 95%, at least 96%, at least 97%, at least 98%, at least 99%, or 100%) identical to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136, at least 80% (e.g., at least 80%, at least 85%, at least 90%, at least 91%, at least 92%, at least 93%, at least 94%, at least 95%, at least 96%, at least 97%, at least 98%, at least 99%, or 100%) identical to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136, at least 90% (e.g., at least 90%, at least 91%, at least 92%, at least 93%, at least 94%, at least 95%, at least 96%, at least 97%, at least 98%, at least 99%, or 100%) identical to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136, or at least 95% (e.g., at least 95%, at least 96%, at least 97%, at least 98%, at least 99%, or 100%) identical to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136. Also provided are compositions comprising the recombinant polypeptide and a carbon dioxide-containing medium. In some embodiments, the recombinant polypeptide is immobilized. In some embodiments, the recombinant polypeptide is immobilized on a polymer, a membrane, a matrix, a micellar material, a wafer, a solid support, or a micro-particle.

In certain aspect, an isolated nucleic acid is provided, which encodes a recombinant polypeptide of any of the preceding paragraph. In some embodiments, the polypeptide further comprises a signal peptide sequence. In some embodiments, the signal peptide and the carbonic anhydrase polypeptide are derived from different microorganisms. In certain embodiments, the signal peptide sequence is selected from the group consisting of SEQ ID NOs: 10-15, 69-73, 81-83, and 131-132. Also provided is an expression vector comprising the isolated nucleic acid in operable combination with a regulatory sequence. Additionally, a host cell is provided comprising the expression vector. In some embodiments, the host cell is a bacterial cell or a fungal cell. In still further embodiments, a composition is provided, which comprises the host cell and a culture medium.

In certain aspect, methods of producing a carbonic anhydrase are provided, comprising: culturing a host cell of the preceding paragraph in a culture medium, under suitable conditions to produce the carbonic anhydrase. Also provided are compositions that comprise the carbonic anhydrase produced in accordance with the methods provided herein in supernatant of the culture medium.

In a further aspect, methods for extracting carbon dioxide from a carbon dioxide-containing medium are provided, comprising: contacting the carbon dioxide-containing medium with the polypeptide of one of the preceding paragraphs to yield a medium reduced in carbon dioxide. In some embodiments, the carbon dioxide-containing medium is selected from the group consisting of a gas, a liquid, and a multi-phase mixture. In some embodiments, the carbon dioxide-containing medium is a gas selected from the group consisting of a flue gas, a raw natural gas, a syngas, a hydrogen gas, and a biogas. In some embodiments, the carbon dioxide-containing medium is a by-product of combustion or fermentation.

In certain aspect, methods for regulating pH of a medium containing one or both of $CO_2$ and bicarbonate are provided, comprising: contacting the medium with the polypeptide of one of the preceding paragraphs to yield a medium with an altered pH.

Also provided herein is a carbonic anhydrase or a suitable variant thereof, which has been engineered to achieve improved thermostability, improved activity/stability at certain alkaline pH, and/or in the presence of a high concentration of bicarbonate. In some embodiments, the carbonic anhydrase is a recombinant carbonic anhydrase derived from a *Bacillus gibsonii* carbonic anhydrase.

In certain embodiments, the recombinant carbonic anhydrase comprises an amino acid sequence that is at least 55% identical to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136, or is one that is encoded by a polynucleotide sequence that is at least 50% (e.g., 55%, 60%, 65%, 70%, 75%, 80%, 85%, 90%, 91%, 92%, 93%, 94%, 95%, 96%, 97%, 98%, 99%) identical to SEQ ID NO: 1, SEQ ID NO: 26, SEQ ID NO: 41 SEQ ID NO: 51, SEQ ID NO: 62, SEQ ID NO: 77, SEQ ID NO:127, or SEQ ID NO: 133 or is capable of hybridizing under intermediate, high, or maximum stringency to a complement of SEQ ID NO: 1, SEQ ID NO: 26, SEQ ID NO: 41 SEQ ID NO: 51, SEQ ID NO: 62, SEQ ID NO: 77, SEQ ID NO:127, or SEQ ID NO: 133. In certain embodiments, the recombinant carbonic anhydrase is expressed and/or produced in a suitable host organism as described herein.

In some embodiments, the improved thermostability is manifested or evidenced by the retention of at least about 30% (e.g., at least about 40%, at least about 50%, at least about 60%, at least about 70%, at least about 80%, at least about 85%, at least about 90%, at least about 95%, or a higher percentage) of enzymatic activity when incubated under a temperature of between about 30° C. and about 85° C. (e.g., between about 30° C. and about 80° C., between about 40° C. and about 70° C., between about 45° C. and about 65° C., between about 40° C. and about 60° C.). In some embodiments, the improved activity/stability at certain alkaline pH is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity under a pH that is between about 8.0 and about 10.0 (e.g., between about 8.0 and about 9.8, between about 8.2 and about 9.6, between about 8.4 and about 9.4, between about 8.6 and about 9.5, etc).

In some embodiments, the improved activity/stability in the presence of a high concentration of bicarbonate is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity when the enzyme is incubated in the presence of about 0.1 M, 0.2 M, 0.5 M, 0.7 M, 0.9 M, 1.0 M, 1.2 M, 1.5 M, 2.0 M or a higher concentration of $HCO_3^-$ for an extended period of time, for example, for at least 1 hour, 2 hours, 3 hours, 5 hours, 10 hours, 12 hours, 24 hours, several days, a week, several weeks, a month, or longer. In related embodiments, the polypeptide has increased melting temperature at higher ionic strength conditions. The polypeptide can thus be said to have improved or increased thermostability at higher ionic strength conditions. For example, the melting temperature of the polypeptide is higher at a higher ionic strength condition (e.g., at 1 M bicarbonate) as compared to at a lower ionic strength condition (e.g., at 0.8 M, 0.6 M, 0.4 M, 0.2 M, or 0.1 M bicarbonate). In certain embodiments, the recombinant carbonic anhydrase comprises an amino acid sequence that is at least 55% identical to the amino acid sequence of SEQ ID NO: 3.

In some embodiments, the improved thermostability is manifested or evidenced by the retention of at least about 30% (e.g., at least about 40%, at least about 50%, at least about 60%, at least about 70%, at least about 80%, at least about 85%, at least about 90%, at least about 95%, or a higher percentage) of enzymatic activity when incubated under a temperature of between about 20° C. and about 75° C. (e.g., between about 25° C. and about 60° C., between about 30° C. and about 50° C., between about 25° C. and about 55° C., between about 35° C. and about 65° C.). In some embodiments, the improved activity/stability at certain alkaline pH is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity under a pH that is between about 8.0 and about 11.0 (e.g., between about 8.0 and about 9.8, between about 8.2 and about 9.6, between about 8.4 and about 9.4, between about 8.6 and about 9.5, between about 8.5 and about 10.8, between about 9.0 and about 10.5, etc). In some embodiments, the improved activity/stability in the presence of a high concentration of bicarbonate is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity when the enzyme is incubated in the presence of about 0.1 M, 0.2 M, 0.5 M, 0.7 M, 0.9 M, 1.0 M, 1.2 M, 1.5 M, 2.0 M or a higher concentration of $HCO_3^-$ for an extended period of time, for example, for at least 1 hour, 2 hours, 3 hours, 5 hours, 10 hours, 12 hours, 24 hours, several days, a week, several weeks, a month, or longer. In certain related embodiments, an improved and/or increased thermostability is observed as the ironic strength increases. For example, the melting temperature of the polypeptide is higher at a higher ionic strength (e.g., at 1 M bicarbonate) as compared to at a lower ionic strength (e.g., at 0.8, 0.6, 0.4, 0.2, or 0.1 M bicarbonate). In certain embodiments, the recombinant carbonic anhydrase comprises an amino acid sequence that is at least 55% identical to the amino acid sequence of SEQ ID NO: 28.

In some embodiments, the improved thermostability is manifested or evidenced by the retention of at least about 30% (e.g., at least about 40%, at least about 50%, at least about 60%, at least about 70%, at least about 80%, at least about 85%, at least about 90%, at least about 95%, or a higher percentage) of enzymatic activity when incubated under a temperature of between about 30° C. and about 85° C. (e.g., between about 30° C. and about 80° C., between about 40° C. and about 70° C., between about 45° C. and about 65° C., between about 40° C. and about 60° C.). In some embodiments, the improved activity/stability at certain alkaline pH is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity under a pH that is between about 8.0 and about 11.0 (e.g., between about 8.0 and about 10.5, between about 8.5 and about 11, between about 8.5 and about 10.5, between about 8.5 and about 10, between about 8.0 and about 9.5, between about 8.2 and about 10, between about 8.6 and about 10.8, etc). In some embodiments, the improved activity/stability in the presence of a high concentration of bicarbonate is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity when the enzyme is incubated in the presence of about 0.1 M, 0.2 M, 0.5 M, 0.7 M, 0.9 M, 1.0 M, 1.2 M, 1.5 M, 2.0 M or a higher concentration of $HCO_3^-$ for an extended period of time, for example, for at least 1 hour, 2 hours, 3 hours, 5 hours, 10 hours, 12 hours, 24 hours, several days, a week, several weeks, a month, or longer. In related embodiments, the polypeptide provided herein has an improved thermostability under higher ionic strength conditions. For example, the polypeptide can suitably have a higher melting temperature at a higher ionic strength condition (e.g., at 1 M bicarbonate) as compared to at a lower ionic strength condition (e.g., at 0.8, 0.6, 0.4, 0.2, or 0.1 M bicarbonate). In certain embodiments, the recombinant carbonic anhydrase comprises an amino acid sequence that is at least 55% identical to the amino acid sequence of SEQ ID NO: 43.

In some embodiments, the improved thermostability is manifested or evidenced by the retention of at least about 30% (e.g., at least about 40%, at least about 50%, at least about 60%, at least about 70%, at least about 80%, at least about 85%, at least about 90%, at least about 95%, or a higher percentage) of enzymatic activity when incubated under a temperature of between about 30° C. and about 85° C. (e.g., between about 30° C. and about 80° C., between about 40° C. and about 70° C., between about 45° C. and about 65° C., between about 40° C. and about 60° C.). In some embodiments, the improved activity/stability at certain alkaline pH is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity under a pH that is between about 8.0 and about 11.0 (e.g., between about 8.0 and about 11, between about 8 and about 10.5, between about 8.5 and about 10, between about 8.5 and about 9.8, between about 8.2 and about 9.6, between about 8.4 and about 9.4, between about 8.6 and about 9.5, etc) In some embodiments, the improved activity/stability in the presence of a high concentration of bicarbonate is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity when the enzyme is incubated in the presence of about 0.1 M, 0.2 M, 0.5 M, 0.7 M, 0.9 M, 1.0 M, 1.2 M, 1.5 M, 2.0 M or a higher concentration of $HCO_3^-$ for an extended period of time, for example, for at least 1 hour, 2 hours, 3 hours, 5 hours, 10 hours, 12 hours, 24 hours, several days, a week, several weeks, a month, or longer. In certain embodiments, the recombinant carbonic anhydrase comprises an amino acid sequence that is at least 55% identical to the amino acid sequence of SEQ ID NO: 53.

In some embodiments, the improved thermostability is manifested or evidenced by the retention of at least about 30% (e.g., at least about 40%, at least about 50%, at least about 60%, at least about 70%, at least about 80%, at least about 85%, at least about 90%, at least about 95%, or a higher percentage) of enzymatic activity when incubated under a temperature of between about 20° C. and about 85° C. (e.g., between about 25° C. and about 80° C., between about 30° C. and about 70° C., between about 35° C. and about 65° C., between about 40° C. and about 60° C., etc). In some embodiments, the improved activity/stability at certain alkaline pH is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity under a pH that is between about 8.0 and about 11 (e.g., between about 8.0 and about 10.5, between about 8.5 to about 9.5, between about 8.2 and about 10.2, between about 8.4 and about 10, between about 8.6 and about 9.8, between about 8.5 to about 10.5, between about 9.5 to about 10.5, etc.). In some embodiments, the improved activity/stability in the presence of a high concentration of bicarbonate is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity when the enzyme is incubated in the presence of about 0.1 M, 0.2 M, 0.5 M, 0.7 M, 0.9 M, 1.0 M, 1.2 M, 1.5 M, 2.0 M or a higher concentration of $HCO_3^-$ for an extended period of time, for example, for at least 1 hour, 2 hours, 3 hours, 5 hours, 10 hours, 12 hours, 24 hours, several days, a week, several weeks, a month, or longer. In related embodiments, the carbonic anhydrase enzyme has higher or increased thermostability and/or melting temperature under higher ionic strength conditions. For example, a carbonic anhydrase polypeptide suitably has a higher melting temperature at a higher concentration of bicarbonate (e.g., at 1 M bicarbonate) as compared to its melting temperature at a lower concentration of bicarbonate (e.g., at 0.8, 0.6, 0.4, 0.2, or 0.1 M bicarbonate). In certain embodiments, the recombinant carbonic anhydrase comprises an amino acid sequence that is at least 55% identical to the amino acid sequence of SEQ ID NO: 64.

In some embodiments, the improved thermostability is manifested or evidenced by the retention of at least about 25% (e.g., at least about 25%, at least about 30%, at least about 35%, at least about 40%, at least about 45%, at least about 50%, at least about 60%, at least about 70%, at least about 80%, at least about 85%, at least about 90%, at least about 95%, or a higher percentage) of enzymatic activity when incubated under a temperature of between about 20° C. and about 55° C. (e.g., between about 20° C. and about 50° C., between about 25° C. and about 50° C., between about 25° C. and about 40° C., between about 40° C. and about 55° C., etc.). In some embodiments, the improved activity/stability at certain alkaline pH is manifest or evidenced by the retention of at least about 20% (e.g., at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity under a pH that is about 8.0 and about 11 (e.g., about 8.0 and about 10.8, about 8.2 and about 10.6, about 8.5 and about 10.5, about 8.2 and about 10, about 8.4 and about 9.8, about 8.5 to about 9.5, about 9.5 to about 10.5, etc), for a time period of at least about 0.5, about 1.0, about 2.0, about 3.0, about 4.0, or about 5.0 hours, or longer. In some embodiments, the improved activity/stability in the presence of a high concentration of bicarbonate is manifest or evidenced by the retention of at least about 20% (e.g., at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity when the enzyme is incubated in the presence of about 0.1 M, 0.2 M, 0.5 M, 0.7 M, 0.9 M, 1.0 M, 1.2 M, 1.5 M, 2.0 M or a higher concentration of $HCO_3^-$ for an extended period of time, for example, for at least 1 hour, 2 hours, 3 hours, 5 hours, 10 hours, 12 hours, 24 hours, several days, a week, several weeks, a month, or longer. In related embodiments, the carbonic anhydrase polypeptide has an increased thermostability at a higher ionic strength. For example, the carbonic anhydrase polypeptide can suitably have a higher melting temperature at a higher ionic strength condition (e.g., at 1 M bicarbonate) as compared to at a lower ionic strength condition (e.g., at 0.8 M bicarbonate, at 0.6 M bicarbonate, at 0.4 M bicarbonate, at 0.2 M bicarbonate, or at 0.1 M bicarbonate, etc). In certain embodiments, the recombinant carbonic anhydrase comprises an amino acid sequence that is at least 55% identical to the amino acid sequence of SEQ ID NO: 80.

In some embodiments, the improved thermostability is manifested or evidenced by the retention of at least about 25% (e.g., at least about 25%, at least about 30%, at least about 35%, at least about 40%, at least about 50%, at least about 60%, at least about 70%, at least about 80%, at least about 85%, at least about 90%, at least about 95%, or a higher percentage) of enzymatic activity when incubated under a temperature of between about 20° C. and about 55° C. (e.g., between about 20° C. and about 50° C., between about 25° C. and about 55° C., between about 25° C. and about 40° C., between about 30° C. and about 50° C.). In some embodiments, the improved activity/stability at certain alkaline pH is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity under a pH that is between about 8.0 and about 11 (e.g., between about 8.5 and about 10.5, between about 8.5 and about 9.5, between about 9.5 and about 10.5, between about 8 and about 10, etc). In some embodiments, the improved activity/stability in the presence of a high concentration of bicarbonate is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity when the enzyme is incubated in the presence of about 0.1 M, 0.2 M, 0.5 M, 0.7 M, 0.9 M, 1.0 M, 1.2 M, 1.5 M, 2.0 M or a higher concentration of $HCO_3^-$ for an extended period of time, for example, for at least 30 minutes, at least 1 hour, 2 hours, 3 hours, 5 hours, 10 hours, 12 hours, 24 hours, several days, a week, several weeks, a month, or longer. In related embodiments, the carbonic anhydrase polypeptide suitably has increased or improved thermostability under higher ionic strength conditions. For example, the polypeptide can suitably have a higher melting temperature at a higher ionic strength (e.g., at 1 M bicarbonate) than at a lower ionic strength (e.g., at 0.8 M bicarbonate, at 0.6 M bicarbonate, at 0.4 M bicarbonate, at 0.2 M bicarbonate, or at 0.1 M bicarbonate, etc). In certain embodiments, the recombinant carbonic anhydrase comprises an amino acid sequence that is at least 55% identical to the amino acid sequence of SEQ ID NO: 130.

In some embodiments, the improved thermostability is manifested or evidenced by the retention of at least about 25% (e.g., at least about 25%, at least about 30%, at least about 35%, at least about 40%, at least about 50%, at least about 60%, at least about 70%, at least about 80%, at least about 85%, at least about 90%, at least about 95%, or a higher percentage) of enzymatic activity when incubated under a temperature of between about 20° C. and about 85° C. (e.g., between about 20° C. and about 80° C., between about 20° C. and about 70° C., between about 30° C. and about 65° C., between about 40° C. and about 60° C.). In some embodiments, the improved activity/stability at certain alkaline pH is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity under a pH that is between about 8.0 and about 11 (e.g., between about 8.0 and about 10, between about 8.5 and about 10.5, between about 8.5 and about 9.5, between about 9.5 and about 10.5, etc). In some embodiments, the improved activity/stability in the presence of a high concentration of bicarbonate is manifest or evidenced by the retention of at least about 25% (e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more) activity when the enzyme is incubated in the presence of about 0.1 M, 0.2 M, 0.5 M, 0.7 M, 0.9 M, 1.0 M, 1.2 M, 1.5 M, 2.0 M or a higher concentration of $HCO^{3-}$ for an extended period of time, for example, for at least 1 hour, 2 hours, 3 hours, 5 hours, 10 hours, 12 hours, 24 hours, several days, a week, several weeks, a month, or longer. In related embodiments, the carbonic anhydrase polypeptide has increased or higher thermostability at a higher ionic strength conditions. For example, the carbonic anhydrase polypeptide has a higher melting temperature at a higher ionic strength (e.g., 1 M bicarbonate) as compared to at a lower ionic strength (e.g., 0.8 M bicarbonate, 0.6 M bicarbonate, 0.4 M bicarbonate, 0.2 M bicarbonate, 0.1 M bicarbonate, etc). In certain embodiments, the recombinant carbonic anhydrase comprises an amino acid sequence that is at least 55% identical to the amino acid sequence of SEQ ID NO: 136.

Carbon dioxide capture or sequestration processes that use carbonic anhydrase to convert $CO_2$ to bicarbonate typically involve the use of immobilized or soluble carbonic anhydrase in certain amine solvents or aqueous carbonate solutions. Thus, the Carbonic anhydrase polypeptides of the present disclosure in some aspects suitably have, in addition to good stability at high temperatures (e.g., at or above 40° C., 50° C., 60° C., 70° C., or 80° C.), and/or high activity/ stability or thermostability at high ionic strengths (e.g., at or about 0.5, 1.0, 1.5, 2.0, 2.5, or even 3.0 M bicarbonate), high stability when exposed to amine solvents (e.g., at or above concentrations of amine solvents typically used to immobilize or solublize carbonic anhydrase enzymes in industrial use to fix $CO_2$).

Furthermore, flue gases, which are the combustion exhaust gas produced at coal power plants typically can comprise, without limitation, oxygen, nitrogen, carbon dioxide, water vapor, along with small amounts of carbon monoxide, nitrogen oxides, sulfur oxides, and/or heavy metals, e.g., mercury. As such, the Carbonic anhydrase polypeptides of the present disclosure in certain aspects suitably have, in addition to good stability at high temperatures, and/or high activity/stability or thermostability at high ionic strengths, and/or high stability when exposed to amine solvents, also stability when exposed to oxides of sulfur, oxides of nitrogen, and/or to heavy metals, such as, e.g., mercury.

Moreover, natural gas compositions can vary depending on the sources from which the compositions have been extracted. For example, they may contain mostly methane and varying amounts of ethane, propane, butane, higher alkanes, nitrogen, carbon dioxide, and hydrogen sulfides. A number of previously known carbonic anhydrases can be destabilized when exposed to hydrogen sulfides. However, the Carbonic anhydrase polypeptides of the present disclosure, in some aspects, can suitably have, in addition to good stability at high temperatures, and/or high activity/stability or thermostability at high ionic strength, and/or high stability when exposed to amine solvents, and/or stability when exposed to oxides of sulfur, oxides of nitrogen, and/or to heavy metals, also good stability when exposed to hydrogen sulfides.

Also provided herein are an immobilized carbonic anhydrase enzyme or an immobilized variant thereof, and a method of preparing and/or using such an immobilized enzyme. In some embodiments, the carbonic anhydrase enzyme is immobilized using the various techniques provided herein. In certain embodiments, the carbonic anhydrase is a recombinant enzyme. In some embodiments, the stability and/or activity of carbonic anhydrase under a given condition (e.g., at a pH of between about 8.0 and about 10.0, at a temperature of between about 30° C. and 85° C., or at an ionic strength conferred by at least about 0.1 M (e.g., at least about 0.2 M, at least about 0.5 M, at least about 1 M, at least about 1.5 M, at least about 2.0 M, or a higher concentration of) $HCO_3^-$, is higher than that of a native (parent) carbonic anhydrase under the same condition.

These and other aspects of Carbonic anhydrase compositions and methods will be apparent from the following description.

DESCRIPTION OF THE DRAWINGS

FIGS. 4A-B provide an alignment of the amino acid sequence of the mature form of Bgi CA1 (SEQ ID NO: 3) with the sequences of other carbonic anhydrases (SEQ ID NOs: 16-25). Table 1G-1 lists the percent identity shared by the carbonic anhydrases of this alignment.

FIGS. 9A-D provide an alignment of the amino acid sequence of the mature form of Pvi CA1 (SEQ ID NO: 28) with the sequences of other carbonic anhydrases (SEQ ID NOs: 16, 20, 21, 32-38). Table 2G-1 lists the percent identity shared by the carbonic anhydrases of this alignment.

FIGS. 14A-B provide an alignment of the amino acid sequence of the mature form of Ate CA1 (SEQ ID NO: 43) with the sequences of other carbonic anhydrases (SEQ ID NOs: 45-48). Table 3G-1 lists the percent identity shared by the carbonic anhydrases of this alignment.

FIGS. 19A-B provide an alignment of the amino acid sequence of the mature form of Spr CA1 (SEQ ID NO: 53) with the sequences of other carbonic anhydrases (SEQ ID NOS: 54-61). Table 4G-1 lists the percent identity shared by the carbonic anhydrases of this alignment.

FIGS. 24A-B provide an alignment of the amino acid sequence of the mature form of Bag CA1 (SEQ ID NO: 64) with the sequences of other carbonic anhydrases (SEQ ID NOs: 16, 19, 21, 21, 22, 24, 25, 35, 74-76). Table 5G-1 lists the percent identity shared by the carbonic anhydrases of this alignment.

DETAILED DESCRIPTION

I. Introduction

Figure 1:
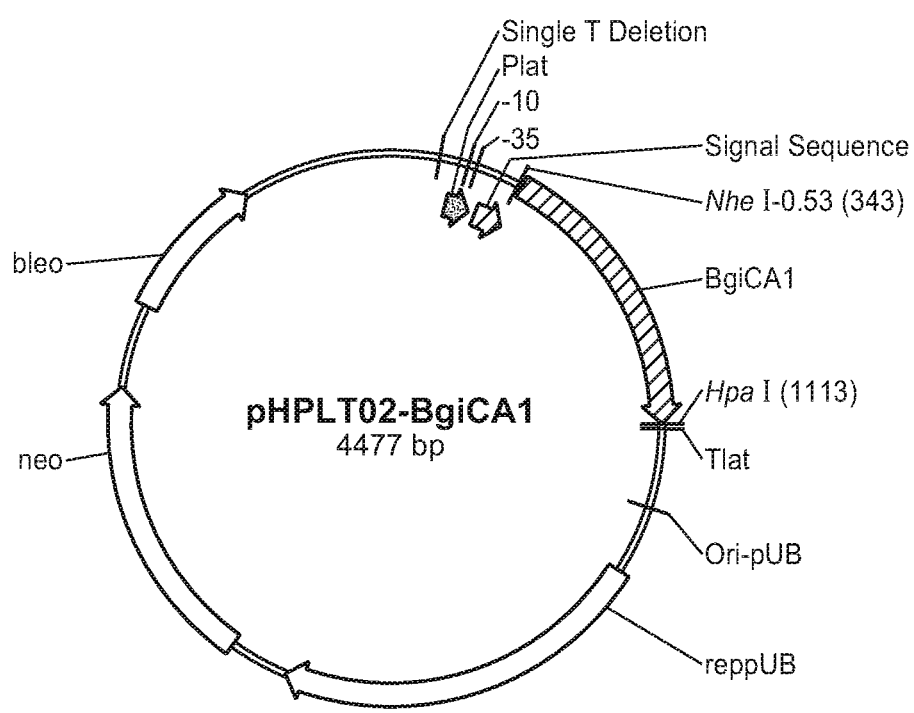
FIG. 1 provides a plasmid map of pHPLT02-BgiCA1.

The present disclosure provides compositions and methods that relate to recombinant carbonic anhydrases from *Bacillus gibsonii*, *Promicromonospora vindobonensis*, *Aspergillus terreus*, *Streptomyces pristinaespiralis*, *Bacillus agaradhaerens*, *Vibrio* sp. AND4, *Vibrio* sp. Ex25, polynucleotides encoding the carbonic anhydrases, and methods of make and/or use thereof.

In some embodiments, compositions and methods are described relating to a recombinant carbonic anhydrase from *Bacillus gibsonii* strain DSM 8722 (Bgi CA1). The compositions and methods are based, in part, on the observations that cloned and expressed Bgi CA1 is thermostable and/or retains carbonic anhydrase activity under high-ionic strength conditions and/or in the presence of high concentrations of bicarbonate. These features of Bgi CA1 make it suitable for use in processes for extracting or sequestering carbon dioxide ($CO_2$) from, for example, combustion exhaust and flue gas streams.

The recombinant Bgi CA1 carbonic anhydrase has shown thermostability at pH values ranging from about 8.5 to about 10.5. In particular, the recombinant Bgi CA1 retains about 90% of carbonic anhydrase activity when incubated for at least about 24 hours at 40° C. at a pH of from about 8.5 to about 10.5, and about 40% of carbonic anhydrase activity when incubated for about 5 hours at 50° C., at a pH of from about 8.5 to about 9.5. Moreover, the recombinant Bgi CA1 retains over 70% of activity in a bicarbonate solution for at least about 3 hours. Additionally, the recombinant Bgi CA1 has a melting temperature of at or above about 76° C. under high ionic strength conditions in a bicarbonate solution. These characteristics make the Bgi CA1 described herein suitable for use in $CO_2$ extraction.

In some embodiments, compositions and methods are described relating to a recombinant carbonic anhydrase from *Promicromonospora vindobonensis* strain YIM65009 (Pvi CA1). The compositions and methods are based, in part, on the observations that cloned and expressed Pvi CA1 is thermostable and/or retains carbonic anhydrase activity under high ionic strength conditions and/or in the presence of high concentrations of bicarbonate. These features of Pvi CA1 make it suitable for use in processes for extracting or sequestering carbon dioxide ($CO_2$) from, for example, combustion exhaust and flue gas streams.

The recombinant Pvi CA1 carbonic anhydrase has shown thermostability at pH values ranging from about 8.5 to about 10.5. In particular, the recombinant Pvi CA1 retains greater than 60% of carbonic anhydrase activity when incubated for at least 24 hours at 40° C. at a pH of about 8.5 to about 9.5. Moreover, the recombinant Pvi CA1 retains all of its carbon anhydrase activity in a bicarbonate solution for at least 3 hours at 50° C. Additionally, the recombinant Pvi CA1 has a melting temperature of at or above about 75° C. under high ionic strength conditions.

In some embodiments, compositions and methods are described relating to a recombinant carbonic anhydrase cloned from *Aspergillus terreus* NIH2624 (Ate CA1). The compositions and methods are based, in part, on the observations that cloned and expressed Ate CA1 is thermostable and/or retains carbonic anhydrase activity under high-ionic strength conditions and/or in the presence of high concentrations of bicarbonate. These features of Ate CA1 make it suitable for use in processes for extracting or sequestering carbon dioxide ($CO_2$) from, for example, combustion exhaust and flue gas streams.

The recombinant Ate CA1 carbonic anhydrase has shown thermostability at pH values ranging from about 8.5 to about 10.5. In particular, the recombinant Ate CA1 retains about 60% or more (e.g., about 65% or more, about 70% or more, about 75% or more, about 80% or more, about 85% or more) of carbonic anhydrase activity when incubated for at least 24 hours at 40° C. The recombinant AteCA1 also may also retain about 50% or more (e.g., about 55% or more, about 60% or more) of carbonic anhydrase activity when incubated for about 1 hour at 50° C., at a pH of from about 8.5 to about 9.5. Moreover, the recombinant Ate CA1 retains about 70% or more (e.g., about 75% or more, about 80% or more, about 85% or more) of activity in the presence of bicarbonate for over 3 hours. Additionally, the recombinant Ate CA1 has a melting point of over about 74° C. under high ionic strength conditions in a bicarbonate solution. Furthermore, the recombinant Ate CA1 can have a thermostability and/or melting temperature that is higher at a higher ionic strength condition (e.g., at 1 M bicarbonate) as compared to at a lower ionic strength condition (e.g., at 0.8, 0.6, 0.4, 0.2, or 0.1 M bicarbonate). These characteristics make the Ate CA1 described herein suitable for use in $CO_2$ extraction.

In some embodiments, compositions and methods are described relating to a recombinant carbonic anhydrase from *Streptomyces pristinaespiralis* strain ATCC 25486 (Spr CA1). The compositions and methods are based, in part, on the observations that cloned and expressed Spr CA1 is thermostable and/or retains carbonic anhydrase activity under high-ionic strength conditions and/or in the presence of high concentrations of bicarbonate. In some embodiments, the Spr CA1 polypeptides of the present disclosure have improved thermostability at higher ionic strength conditions. These features of Spr CA1 make it suitable for use in processes for extracting or sequestering carbon dioxide ($CO_2$) from, for example, combustion exhaust and flue gas streams.

The recombinant Spr CA1 carbonic anhydrase has shown thermostability at pH values ranging from about 8.5 to about 10.5. In particular, the recombinant Spr CA1 retains over 60% of carbonic anhydrase activity when incubated for at least 24 hours between 0° C. and 40° C. at a pH of between 8.5 and 9.5. Moreover, the recombinant Spr CA1 retains over 60% of activity in a bicarbonate solution at 50° C. for at least about 2 hours. These characteristics make Spr CA1 suitable for use in carbon dioxide extraction.

In some embodiments, compositions and methods are described relating to a recombinant carbonic anhydrase from *Bacillus agaradhaerens* (Bag CA1). The compositions and methods are based, in part, on the observations that cloned and expressed Bag CA1 is thermostable and/or retains carbonic anhydrase activity under high-ionic strength conditions and/or in the presence of high concentrations of bicarbonate. It is also observed that surprisingly the recombinant carbonic anhydrase has increased thermostability with increased ionic strength. These features of Bag CA1 make it suitable for use in processes for extracting or sequestering carbon dioxide ($CO_2$) from, for example, combustion exhaust and flue gas streams.

The recombinant Bag CA1 carbonic anhydrase has shown thermostability at pH values ranging from about 8.0 to about 11 (e.g., from about 8.5 to about 10.5, from about 8.5 to about 9.5, from about 9.5 to about 10.5, from about 8.5 to about 10.8, from about 8.6 to about 10.6, from about 8.4 to about 10.4, from about 8.2 to about 10.2, from about 8.0 to about 10, or from about 7.8 to about 9.8, etc). In particular, the recombinant Bag CA1 retains about 90% of carbonic anhydrase activity when incubated for at least about 3 hours, 5 hours, 10 hours, 24 hours or longer at about 25° C., and at a pH of from about 8.0 to about 11 (e.g., about 8.5 to about 10.5, about 8.5 to about 9.5, about 9.5 to about 10.5). The carbonic anhydrase activity decreased more markedly at higher pHs. However, at lower pHs (e.g., about 8 to about 9.5, about 8.5 to about 9.5, etc), Bag CA1 remains suitably stable over a long period of time at supra-physiological temperatures, at which enzymatic $CO_2$ extractions are conducted. Moreover, it has been observed that the recombinant Bag CA1 retained over 50% of activity in a bicarbonate solution for at least about 3 hours, at least about 5 hours, at least about 10 hours, at least about 24 hours, or longer. Additionally, the recombinant Bag CA1 has a melting temperature of at or above about 50° C. (e.g., at least about 55° C., at least about 60° C., at least about 70° C., etc) under high ionic strength conditions, for example, in a bicarbonate solution. Furthermore, the Bag CA1 polypeptides of the present disclosure can suitably have improved thermostability, carbonic anhydrase activity, and/or higher melting temperatures at a higher ionic strength condition (for example, at 1 M bicarbonate concentration) as compared to these parameters, alone or in combination, at a lower ionic strength condition (for example, at 0.9 M bicarbonate concentration, at 0.8 M bicarbonate concentration, at 0.6 M bicarbonate concentration, at 0.5 M bicarbonate concentration, at 0.4 M bicarbonate concentration, at 0.3 M bicarbonate concentration, at 0.2 M bicarbonate concentration, or at 0.1 M bicarbonate concentration, etc. These characteristics make the Bag CA1 described herein suitable for use in $CO_2$ extraction.

In some embodiments, compositions and methods are described relating to a recombinant carbonic anhydrase from *Vibrio* sp. AND4 (Vsp CA1). The compositions and methods are based, in part, on the observations that cloned and expressed Vsp CA1 is thermostable and/or retains carbonic anhydrase activity under high-ionic strength conditions and/or in the presence of high concentrations of bicarbonate. It has also been observed that the Vsp CA1 polypeptides of the present disclosure exhibit increased thermostability at higher ionic strength conditions, for example they suitably can have higher melting temperatures at higher ionic strength conditions, which is surprising. These features of Vsp CA1 make it suitable for use in processes for extracting or sequestering carbon dioxide ($CO_2$) from, for example, combustion exhaust and flue gas streams.

The recombinant Vsp CA1 carbonic anhydrase has shown thermostability at pH values ranging from about 8.0 to about 11 (e.g., about 8.5 to about 10.5, about 8.5 to about 9.5, about 9.5 to about 10.5, about 8.5 to about 10, etc). At the lower end of the basic pH, for example, at pH of about 8 to about 9.5 (e.g., about 8.5 to about 9.5, etc), the recombinant Vsp CA1 retains most of its carbonic anhydrase activity for an extended period of time, for example, for at least 1 hour, at least 2 hours, at least 3 hours, at least 5 hours, at least 10 hours, at least 24 hours, or even longer. For example, the recombinant Vsp CA1 suitably retains at least about 35% (e.g., at least about 35%, at least about 40%, at least about 45%, at least about 50%, at least about 55%, at least about 60%, at least about 65%, at least about 70% or a higher percentage) of carbonic anhydrase activity when incubated for at least about 1 hours, 3 hours, 5 hours, 10 hours, or 24 hours or longer at 25° C. at a pH of from about 8.5 to about 9.5. At the higher end of the basic pH, for example, at a pH of about 10.5 or higher, the recombinant enzymes loses its carbonic anhydrase activity much more rapidly. For example, the recombinant Vsp CA1 can suitably retain at least about 20%, at least about 25%, at least about 30%, at least about 35%, at least about 40%, at least about 45%, at least about 50%, at least about 55%, or at least about 60% of its carbonic anhydrase activity when incubated for at least 1 hour, 2 hours or 3 hours at a pH of about 10.5. Moreover, the recombinant Vsp CA1 retains over 35% (e.g., over 35%, over 40%, over 45%, over 50%, over 55%, over 60%, over 65%, or even over 70%) of activity in a bicarbonate solution for at least about 1 hour, at least about 2 hours, or at least about 3 hours at 20° C. Additionally, the recombinant Vsp CA1 has a melting temperature of at or above about 65° C. (e.g., at or above about 65° C., at or above about 66° C., at or above about 67%, or at or above about 68° C., etc) under high ionic strength conditions, for example, in a bicarbonate solution. In related embodiments the recombinant Vsp CA1 can suitably have a higher or increased thermostability at higher ionic strength conditions. For example, the recombinant Vsp CA1 suitably has a higher melting temperature at a higher ionic strength (e.g., at 1 M bicarbonate) as compared to its melting temperature at a lower ionic strength (e.g., at 0.8 M bicarbonate, at 0.6 M bicarbonate, at 0.4 M bicarbonate, at 0.2 M bicarbonate, or at 0.1 M bicarbonate, etc). These characteristics make the Vsp CA1 described herein suitable for use in CO$_2$ extraction.

In some embodiments, compositions and methods are described relating to a recombinant carbonic anhydrase from *Vibrio* sp. Ex25 (VspE CA1). The compositions and methods are based, in part, on the observations that cloned and expressed VspE CA1 is thermostable and/or retains carbonic anhydrase activity under high-ionic strength conditions and/or in the presence of high concentrations of bicarbonate. Moreover, the VspE CA1 polypeptides suitably have higher or improved thermostability at higher ionic strength conditions. These features of VspE CA1 make it suitable for use in processes for extracting or sequestering carbon dioxide (CO$_2$) from, for example, combustion exhaust and flue gas streams.

The recombinant VspE CA1 carbonic anhydrase has shown thermostability at pH values ranging from about 8 to about 11 (e.g., about 8.5 to about 10.5, about 8.5 to about 9.5, about 9.5 to about 10.5, about 8 to about 10, etc). In particular, the recombinant VspE CA1 retains at least about 55% (e.g., at least about 55%, at least about 60%, at least about 65%, at least about 70%, at least about 75%, at least about 80%, at least about 85%, at least about 90%, at least about 95%, at least about 97%, or 100%) of carbonic anhydrase activity when incubated for at least about 30 minutes, about 1 hour, about 2 hours, about 5 hours, about 10 hours, about 15 hours, or about 24 hours, or longer at about 25° C., or about 50° C., at a pH of from about 8 to about 11 (e.g., about 8.5 to about 10.5, about 8.5 to about 9.5, about 9.5 to about 10.5, about 8 to about 10, etc). Moreover, the recombinant VspE CA1 retains over 30% of activity in a bicarbonate solution for at least about 30 minutes, about 1 hour, about 2 hours, or about 3 hours or longer at about 20° C., about 25° C., or about 40° C. Additionally, the recombinant VspE CA1 has a melting temperature of at or above about 45° C. (e.g., at or above about 45° C., about 46° C., about 47° C., about 48° C., about 49° C., or about 50° C., or higher, under high ionic strength conditions in a bicarbonate solution. In some embodiments, the recombinant VspE CA1 has an increased or higher thermostability at higher ionic strength conditions. For example, the recombinant VspE CA1 suitably has a higher melting temperature at a higher ionic strength (e.g., 1 M bicarbonate) as compared to at a lower ionic strength (e.g., 0.8 M bicarbonate, 0.6 M bicarbonate, 0.4 M bicarbonate, 0.2 M bicarbonate, or 0.1 M bicarbonate, etc). These characteristics make the VspE CA1 described herein suitable for use in CO$_2$ extraction.

In some embodiments, compositions and methods are described relating to a recombinant carbonic anhydrase II from *Vibrio* sp. Ex25 (VspE CA2). The compositions and methods are based, in part, on the observations that cloned and expressed VspE CA2 is thermostable and/or retains carbonic anhydrase activity under high-ionic strength conditions and/or in the presence of high concentrations of bicarbonate. Moreover, the VspE CA2 also has higher thermostability at higher ionic strength conditions. These features of VspE CA2 make it suitable for use in processes for extracting or sequestering carbon dioxide (CO$_2$) from, for example, combustion exhaust and flue gas streams.

The recombinant VspE CA2 carbonic anhydrase has shown thermostability at pH values ranging from about 8 to about 11 (e.g., about 8.5 to about 10.5, about 8 to about 10, about 8.4 to about 9.5, about 9.5 to about 10.5, etc.). In particular, the recombinant VspE CA2 retains at least about 25% (e.g., at least about 25%, at least about 30%, at least about 35%, at least about 40%, at least about 45%, at least about 50%, at least about 55%, at least about 60%, at least about 65%, at least about 70%, or a higher percentage) of carbonic anhydrase activity when incubated for at least 30 minutes, at least 1 hour, at least 2 hours, at least 3 hours, at least 5 hours, at least 10 hours, at least 24 hours at 25° C. at a pH of from about 8 to about 11 (e.g., about 8.5 to about 10.5, about 8 to about 10, about 8.4 to about 9.5, about 9.5 to about 10.5, etc). Moreover, the recombinant VspE CA2 retains over 40% (e.g., over 40%, over 45%, over 50%, over 55%, over 60%, over 65%, over 70%, over 75%, over 80%, or a higher percentage) of activity in a bicarbonate solution for at least about 30 minutes, about 1 hour, about 2 hours, or about 3 hours at 20° C. Additionally, the recombinant VspE CA2 has a melting temperature of at or above about 45° C. (e.g., at or above 47° C., at or above 50° C., at or above 65° C., at or above 70° C., at or above 75° C., or higher temperature) under high ionic strength conditions in a bicarbonate solution. Importantly the recombinant VspE CA2 has an increased or higher thermostability at a higher ionic strength condition. For example, the recombinant VspE CA2 can suitably have a higher melting temperature at a higher ionic strength (e.g., 1 M bicarbonate) as compared to at a lower ionic strength (e.g., 0.8 M bicarbonate, 0.6 M bicarbonate, 0.4 M bicarbonate, 0.2 M bicarbonate, 0.1 M bicarbonate, etc.). These characteristics make the VspE CA2 described herein suitable for use in CO$_2$ extraction.

II. Definitions

Prior to describing the present compositions and methods in detail, the following terms are defined for clarity. Terms and abbreviations not defined should be accorded their ordinary meaning as used in the art:

As used herein, "carbonic anhydrase" or "CA" describes a polypeptide having EC 4.2.1.1 activity, which is capable of catalyzing the inter-conversion between carbon dioxide and bicarbonate [i.e., $CO_2 + H_2O \leftrightarrow HCO_3^- + H^+$].

The term "$CO_2$-containing medium," describes any material that may contain at least 0.001% $CO_2$, carbonic acid, bicarbonate, carbonate, or mixtures thereof, or at least 0.01%, at least 0.1%, at least 1%, at least 5%, at least 10%, at least 20%, at least 50%, or more $CO_2$, carbonic acid, bicarbonate, carbonate, or mixtures thereof. For brevity sake, references made to a $CO_2$-containing medium encompass a medium containing carbonic acid, bicarbonate, carbonate or mixtures thereof, in addition to or in the absence of $CO_2$. Carbon dioxide-containing media may be gaseous phases, liquids, or multiphase mixtures, but may also be solids. A $CO_2$-containing gaseous phase is, for example, raw natural gas obtainable from oil wells, gas wells, and condensate wells, syngas generated by the gasification of a carbon containing fuel (e.g., methane) to a gaseous product comprising CO and/or $H_2$, or emission streams from combustion processes, e.g., from carbon-based electricity generation power plants, from flue gas stacks from such plants, industrial furnaces, stoves, ovens, or fireplaces, or from airplane or car exhausts. A $CO_2$-containing gaseous phase may alternatively be from respiratory processes in mammals, living plants and other $CO_2$ emitting species, in particular that from greenhouses. A $CO_2$-containing gas phase may also be an off-gas, from aerobic or anaerobic fermentation, such as brewing, fermentation to produce useful products such as ethanol, or the production of biogas. Such fermentation processes can occur at elevated temperatures if they are facilitated by thermophilic microorganisms, which are, for example, seen in the production of biogas. A $CO_2$-containing gaseous phase may alternatively be a gaseous phase enriched in $CO_2$ for the purpose of use or storage. The above described gaseous phases may also occur as multiphase mixtures, where the gas co-exists with a certain degree of fluids (e.g., water or other solvents) and/or solid materials (e.g., ash or other particles). Carbon dioxide-containing liquids are any solutions or fluids, in particular aqueous liquids, containing measurable amounts of $CO_2$. Carbon dioxide-containing liquids may be obtained by passing a $CO_2$-containing gas or solid (e.g., dry ice or soluble carbonate containing salt) into the liquids. A carbon dioxide-containing fluid may also be a compressed $CO_2$ liquid (that contains contaminants, such as a dry-cleaning fluid), or a supercritical $CO_2$, or a $CO_2$ solvent liquid, such as an ionic liquid.

The term "carbon dioxide extraction" or "$CO_2$ extraction" describes a reduction or otherwise separation of $CO_2$ from a $CO_2$-containing medium. Such an extraction may be performed from one medium to another, e.g., gas to liquid, liquid to gas, gas to liquid to gas, liquid to liquid, or liquid to solid, but the extraction may also refer to the conversion of $CO_2$ to bicarbonate or carbonate, or the conversion of bicarbonate or carbonate to $CO_2$, within the same medium. The terms "$CO_2$ capture" and "$CO_2$ sequestration" are also used to indicate extraction of $CO_2$ from one medium to another, separating $CO_2$ from a $CO_2$-containing medium, conversion of $CO_2$ to bicarbonate or carbonate, or conversion of bicarbonate or carbonate to $CO_2$.

The term "syngas" or "synthesis gas," describes a gas mixture that contains varying amounts of carbon monoxide (CO) and hydrogen ($H_2$) generated by the gasification of a carbon-containing fuel (e.g., methane or natural gas) to a gaseous product with a heating value. Carbon dioxide is produced in the syngas reaction and is removed to increase the heating value.

As used herein, "ionic strength conditions," with reference to a protein, refers to incubation of the protein in a solution containing an ionic salt, such as, for example, sodium chloride, potassium chloride, calcium chloride, sodium bicarbonate, potassium bicarbonate, ammonium bicarbonate, sodium carbonate, potassium carbonate, ammonium carbonate, etc. When the salt is present at a high concentration (e.g., 0.1 M, 0.5 M, 1 M, 1.5 M, 2 M, etc.), then the protein is said to be incubated under high ionic strength conditions.

As used herein, "catalytic activity" or "activity" describes quantitatively the conversion of a given substrate under defined reaction conditions. The term "residual activity" is defined as the ratio of the catalytic activity of the enzyme under a certain set of conditions to the catalytic activity under a different set of conditions. The term "specific activity" describes quantitatively the catalytic activity per amount of enzyme under defined reaction conditions.

As used herein, "pH-stability," with reference to a protein, refers to the ability of a protein to withstand a limited exposure to pH values significantly deviating from the pH where its stability is optimal (e.g., more than one pH unit above or below the pH optimum, without significantly losing its activity measured under conditions where its activity is measurable).

The term "thermal stability" or "thermostable," when used in reference to a carbonic anhydrase, refers to a carbonic anhydrase that retain a specified amount of enzymatic activity after exposure to an identified altered temperature over a given period of time under conditions prevailing during the carbon dioxide hydration, bicarbonate dehydration, or other process disclosed herein. Altered temperatures include increased or decreased temperatures from a temperature under which the native enzyme typically operates. In some embodiments, the identified altered temperature is, for example, a temperature within the range of about 20° C. to about 80° C., for example, about 30° C. to about 70° C., or about 40° C. to about 65° C. In some embodiments, the carbonic anhydrase retains at least about 20%, about 30%, about 40%, about 50%, about 60%, about 70%, about 75%, about 80%, about 85%, about 90%, about 91%, about 92%, about 93%, about 94%, about 95%, about 96%, about 97%, about 98%, or about 99% of a carbonic anhydrase activity after exposure to an altered temperature over a given time period, for example, for at least about 15 minutes, about 30 minutes, about 60 minutes, about 120 minutes, about 180 minutes, about 240 minutes, about 300 minutes, a month, several months, a year, several years etc.

As used herein, the term "purified" or "isolated" refers to the physical separation of a subject molecule, such as Bgi CA1, from its native source (e.g., *Bacillus gibsonii*) or other molecules, such as proteins, nucleic acids, lipids, media components, and the like. Once purified or isolated, a subject molecule may represent at least 50%, at least 60%, at least 70%, at least 80%, at least 85%, at least 90%, at least 95%, or more, of the total amount of material in a sample (wt/wt).

As used herein, a "polypeptide" refers to a molecule comprising a plurality of amino acids linked through peptide bonds. The terms "polypeptide," "peptide," and "protein" are used interchangeably. Proteins may be optionally be modified (e.g., glycosylated, phosphorylated, acylated, farnesylated, prenylated, sulfonated, and the like) to add functionality. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

As used herein, an "immobilized polypeptide" refers to a polypeptide that is physically confined on an immobilization material while retaining its function or catalytic activity. Examples of immobilization materials include, without limitation, a polymer, a membrane including liquid membranes, a matrix, a wafer, a solid support, or a micro-particle. In some embodiments, an "immobilized polypeptide" describes a polypeptide that is physically confined, which has increased stability and/or catalytic activity.

The term "polynucleotide" encompasses DNA, RNA, heteroduplexes, and synthetic molecules capable of encoding a polypeptide. Nucleic acids may be single-stranded or double-stranded, and may have chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acid sequences are presented in a 5'-to-3' orientation.

As used herein, the term "wild-type" or "native" refers to polypeptides or polynucleotides that are found in nature.

The terms "wild-type," "parental," or "reference," with respect to a polypeptide, refer to a naturally-occurring polypeptide that does not include a man-made substitution, insertion, or deletion at one or more amino acid positions. Similarly, the term "wild-type," "parental," or "reference," with respect to a polynucleotide, refers to a naturally-occurring polynucleotide that does not include a man-made nucleoside change. However, a polynucleotide encoding a wild-type, parental, or reference polypeptide is not limited to a naturally-occurring polynucleotide, but rather encompasses any polynucleotide encoding the wild-type, parental, or reference polypeptide.

As used herein, a "variant polypeptide" refers to a polypeptide that is derived from a parent (or reference) polypeptide by the substitution, addition, or deletion, of one or more amino acids, typically by recombinant DNA techniques. Variant polypeptides may differ from a parent polypeptide by a small number of amino acid residues. They may be defined by their level of primary amino acid sequence homology/identity with a parent polypeptide. Suitably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity to a parent polypeptide.

Sequence identity may be determined using known programs such as BLAST, ALIGN, and CLUSTAL using standard parameters. (See, e.g., Altschul et al. *J. Mol. Biol.* 215:403-410, 1990; Henikoff et al. *Proc. Natl. Acad. Sci. USA* 89:10915, 1989; Karin et al. *Proc. Natl. Acad. Sci USA* 90:5873, 1993; and Higgins et al. *Gene* 73:237-244, 1988). Software for performing BLAST analyses is publicly available through the National Center for Biotechnology Information. Databases may also be searched using FASTA (Pearson et al. *Proc. Natl. Acad. Sci. USA* 85:2444-2448, 1988). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution.

As used herein, a "variant polynucleotide" encodes a variant polypeptide, has a specified degree of homology/identity with a parent polynucleotide, or hybridized under stringent conditions to a parent polynucleotide or the complement thereof. Suitably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity to a parent polynucleotide or to a complement of the parent polynucleotide. Methods for determining percent identity are known in the art and described above.

The term "derived from" encompasses the terms "originated from," "obtained from," "obtainable from," "isolated from," and "created from," and generally indicates that one specified material find its origin in another specified material or has features that can be described with reference to the another specified material.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm −5° C. (5° C. below the Tm of the probe); "high stringency" at about 5-10° C. below the Tm; "intermediate stringency" at about 10-20° C. below the Tm of the probe; and "low stringency" at about 20-25° C. below the Tm. Alternatively, or in addition, hybridization conditions can be based upon the salt or ionic strength conditions of hybridization, and/or upon one or more stringency washes, e.g.: 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used). As used herein, stringent conditions are defined as 50° C. and 0.2×SSC (1×SSC=0.15 M NaCl, 0.015 M sodium citrate, pH 7.0).

The phrase "substantially similar" or "substantially identical," in the context of at least two nucleic acids or polypeptides, means that a polynucleotide or polypeptide comprises a sequence that has at least about 90%, at least about 91%, at least about 92%, at least about 93%, at least about 94%, at least about 95%, at least about 96%, at least about 97%, at least about 98%, or even at least about 99% identical to a parent or reference sequence, or does not include amino acid substitutions, insertions, deletions, or modifications made only to circumvent the present description without adding functionality.

As used herein, an "expression vector" refers to a DNA construct containing a DNA sequence that encodes a specified polypeptide and is operably linked to a suitable control sequence capable of effecting the expression of the polypeptides in a suitable host. Such control sequences may include a promoter to effect transcription, an optional operator sequence to control such transcription, a sequence encoding suitable mRNA ribosome binding sites and/or sequences that control termination of transcription and translation. The vector may be a plasmid, a phage particle, or a potential genomic insert. Once transformed into a suitable host, the vector may replicate and function independently of the host genome, or may, in some instances, integrate into the host genome.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in a manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a polypeptide, and which facilitates the secretion of the mature form of the protein from the cell. The mature form of the extracellular protein lacks the signal sequence which is cleaved off during the secretion process.

The term "selective marker" or "selectable marker," refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "regulatory element," refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally cells of prokaryotic or eukaryotic hosts that are transformed or transfected with vectors constructed using recombinant DNA techniques known in the art. Transformed host cells are capable of either replicating vectors encoding the protein variants or expressing the desired protein variant. In the case of vectors, which encode the pre- or pro-form of the protein variant, such variants, when expressed, are typically secreted from the host cell into the host cell medium.

The term "introduced," in the context of inserting a nucleic acid sequence into a cell, means transformation, transduction, or transfection. Means of transformation include protoplast transformation, calcium chloride precipitation, electroporation, naked DNA, and the like as known in the art. (See, Chang and Cohen *Mol. Gen. Genet.* 168: 111-115, 1979; Smith et al. *Appl. Env. Microbiol.* 51:634, 1986; and the review article by Ferrari et al., in Harwood, *Bacillus*, Plenum Publishing Corporation, pp. 57-72, 1989).

Other technical and scientific terms have the same meaning as commonly understood by one of ordinary skill in the art to which this disclosure pertains (See, e.g., Singleton and Sainsbury, *Dictionary of Microbiology and Molecular Biology*, 2d Ed., John Wiley and Sons, NY 1994; and Hale and Marham, *The Harper Collins Dictionary of Biology*, Harper Perennial, N.Y. 1991).

The singular terms "a," "an," and "the" include the plural reference unless the context clearly indicates otherwise.

As used herein in connection with a numerical value, the term "about" refers to a range of −10% to +10% of the numerical value, unless the term is otherwise specifically defined in context. For instance, the phrase a "pH value of about 6" refers to pH values of from 5.4 to 6.6, unless the pH value is specifically defined otherwise.

Headings are provided for convenience and should not be construed as limitations. The description included under one heading may apply to the specification as a whole.

III. Carbonic Anhydrases Polypeptides, Polynucleotides, Vectors, and Host Cells

A. Carbonic Anhydrases Polypeptides

In one aspect, the present compositions and methods provide a recombinant Bgi CA1 carbonic anhydrase polypeptide, fragments thereof, or variants thereof having carbonic anhydrase activity. An example of a recombinant Bgi CA1 polypeptide was isolated from *Bacillus gibsonii* strain DSM 8722. The mature Bgi CA1 polypeptide has the amino acid sequence set forth as SEQ ID NO: 3. Similar, substantially similar Bgi CA1 polypeptides may occur in nature, e.g., in other strains or isolates of *B. gibsonii*. These and other recombinant Bgi CA1 polypeptides are encompassed by the present compositions and methods.

In one aspect, the present compositions and methods provide a recombinant Pvi CA1 carbonic anhydrase polypeptide, fragments thereof, or variants thereof having carbonic anhydrase activity. An example of a recombinant Pvi CA1 polypeptide was isolated from *Promicromonospora vindobonensis* strain YIM65009. The mature Pvi CA1 polypeptide has the amino acid sequence set forth as SEQ ID NO: 28. Similar, substantially similar Pvi CA1 polypeptides may occur in nature, e.g., in other strains or isolates of *P. vindobonensis*. These and other recombinant Pvi CA1 polypeptides are encompassed by the present compositions and methods.

In one aspect, the present compositions and methods provide a recombinant Ate CA1 carbonic anhydrase polypeptide, fragments thereof, or variants thereof having carbonic anhydrase activity. An example of a recombinant Ate CA1 polypeptide was isolated from *Aspergillus terreus* strain NIH2624. The mature Ate CA1 polypeptide has the amino acid sequence set forth as SEQ ID NO: 43. Similar, substantially similar Ate CA1 polypeptides may occur in nature, e.g., in other strains or isolates of *A. terreus*. These and other recombinant Ate CA1 polypeptides are encompassed by the present compositions and methods.

In one aspect, the present compositions and methods provide a recombinant Spr CA1 carbonic anhydrase polypeptide, fragments thereof, or variants thereof having carbonic anhydrase activity. An example of a recombinant Spr CA1 polypeptide was isolated from *Streptomyces pristinaespiralis* strain ATCC 25486. The mature Spr CA1 polypeptide has the amino acid sequence set forth as SEQ ID NO: 53. Similar, substantially similar Spr CA1 polypeptides may occur in nature, e.g., in other strains or isolates of *S. pristinaespiralis*. These and other recombinant Spr CA1 polypeptides are encompassed by the present compositions and methods.

In one aspect, the present compositions and methods provide a recombinant Bag CA1 carbonic anhydrase polypeptide, fragments thereof, or variants thereof having carbonic anhydrase activity. An example of a recombinant Bag CA1 polypeptide was isolated from *Bacillus agaradhaerens*. The mature Bag CA1 polypeptide has the amino acid sequence set forth as SEQ ID NO: 64. Similar, substantially similar Bag CA1 polypeptides may occur in nature, e.g., in other strains or isolates of *B. agaradhaerens*. These and other recombinant Bag CA1 polypeptides are encompassed by the present compositions and methods.

In one aspect, the present compositions and methods provide a recombinant Vsp CA1 carbonic anhydrase polypeptide, fragments thereof, or variants thereof having carbonic anhydrase activity. An example of a recombinant Vsp CA1 polypeptide was isolated from *Vibrio* sp. AND4. The mature Vsp CA1 polypeptide has the amino acid sequence set forth as SEQ ID NO: 80. Similar, substantially similar Vsp CA1 polypeptides may occur in nature, e.g., in other strains or isolates of *Vibrio* sp. AND4. These and other recombinant Vsp CA1 polypeptides are encompassed by the present compositions and methods.

In one aspect, the present compositions and methods provide a recombinant VspE CA1 carbonic anhydrase polypeptide, fragments thereof, or variants thereof having carbonic anhydrase activity. An example of a recombinant VspE CA1 polypeptide was isolated from *Vibrio* sp. Ex25. The mature VspE CA1 polypeptide has the amino acid sequence set forth as SEQ ID NO: 130. Similar, substantially similar VspE CA1 polypeptides may occur in nature, e.g., in other strains or isolates of *Vibrio* sp. Ex25. These and other recombinant VspE CA1 polypeptides are encompassed by the present compositions and methods.

In one aspect, the present compositions and methods provide a recombinant VspE CA2 carbonic anhydrase polypeptide, fragments thereof, or variants thereof having carbonic anhydrase activity. An example of a recombinant VspE CA2 polypeptide was isolated from *Vibrio* sp. Ex25. The mature VspE CA2 polypeptide has the amino acid sequence set forth as SEQ ID NO: 136. Similar, substantially similar VspE CA2 polypeptides may occur in nature, e.g., in other strains or isolates of *Vibrio* sp. Ex25. These and other recombinant VspE CA2 polypeptides are encompassed by the present compositions and methods.

In some embodiments, the recombinant polypeptide is a variant polypeptide having a specified degree of amino acid sequence identity to the exemplified parent polypeptide, e.g., at least 50%, at least 51%, at least 52%, at least 53%, at least 54%, at least 55%, at least 56%, at least 57%, at least 58%, at least 59%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or even at least 99% sequence identity to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136. Sequence identity can be determined by amino acid sequence alignment, e.g., using a program such as BLAST, ALIGN, or CLUSTAL, as described herein.

In certain embodiments, the recombinant polypeptides are produced recombinantly, while in others the polypeptides are produced synthetically, or are purified from a native source (e.g., *B. gibsonii, Promicromonospora vindobonensis, Aspergillus terreus, Streptomyces pristinaespiralis, Bacillus agaradhaerens, Vibrio* sp. AND4, or *Vibrio* sp. Ex25).

In certain embodiments, the recombinant polypeptides include substitutions that do not substantially affect the structure and/or function of the polypeptide. Examples of these substitutions are conservative mutations, as summarized in Table I.

TABLE I

Amino Acid Substitutions

| Original Residue | Code | Acceptable Substitutions |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, beta-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Substitutions involving naturally occurring amino acids are generally made by mutating a nucleic acid encoding a recombinant carbonic anhydrase polypeptide, and then expressing the variant polypeptide in an organism. Substitutions involving non-naturally occurring amino acids or chemical modifications to amino acids are generally made by chemically modifying a carbonic anhydrase polypeptide after it has been synthesized by an organism.

In some embodiments, variant recombinant polypeptides are substantially identical to SEQ ID NO: 3, SEQ ID NO: 28, SEQ ID NO: 43, SEQ ID NO: 53, SEQ ID NO: 64, SEQ ID NO: 80, SEQ ID NO: 130, or SEQ ID NO: 136, meaning that they do not include amino acid substitutions, insertions, or deletions that do not significantly affect the structure, function, or expression of the polypeptide. Such variant recombinant carbonic anhydrase polypeptides will include those designed to circumvent the present description. In some embodiments, variants recombinant polypeptides, compositions and methods comprising these variants are not substantially identical SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO:136, but rather include amino acid substitutions, insertions, or deletions that affect, in certain circumstances, substantially, the structure, function, or expression of the polypeptide herein such that improved characteristics, including, e.g., improved specific activity, improved thermostability, improved pH stability, and/or improved activity under high ionic strength conditions, as compared to that of a polypeptide of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136, can be achieved.

In some embodiments, the recombinant polypeptide (including a variant thereof) has carbonic anhydrase activity. Carbonic anhydrase activity can be determined and measured using the assays described herein, or by other assays known in the art. In some embodiments, the recombinant carbonic anhydrase polypeptide has activity in the presence of a composition used to extract or sequester carbon dioxide.

Recombinant polypeptides include fragments of the "full-length" polypeptides that retain carbonic anhydrase activity. Such fragments suitably retain the active site of the full-length polypeptides but may have deletions of non-critical amino acid residues. The activity of fragments can be readily determined using the assays described herein, or by other assays known in the art. In some embodiments, the fragments of the polypeptides retain carbonic anhydrase activity in the presence of a composition used to extract or sequester carbon dioxide.

In some embodiments, the amino acid sequences and derivatives are produced as an N- and/or C-terminal fusion protein, for example, to aid in extraction, detection and/or purification and/or to add functional properties to the polypeptides. Examples of fusion protein partners include, but are not limited to, glutathione-S-transferase (GST), 6×His, GAL4 (DNA binding and/or transcriptional activation domains), FLAG-, MYC-tags or other tags known to those skilled in the art. In some embodiments, a proteolytic cleavage site is provided between the fusion protein partner and the protein sequence of interest to allow removal of fusion protein sequences. Suitably, the fusion protein does not hinder the activity of the recombinant polypeptide. In some embodiments, the recombinant polypeptide is fused to a functional domain including a leader peptide, propeptide, binding domain and/or catalytic domain. Fusion proteins are optionally linked to the recombinant polypeptide through a linker sequence that joins the polypeptide and the fusion domain without significantly affecting the properties of either component. The linker optionally contributes functionally to the intended application.

In some embodiments, the recombinant polypeptide is expressed in a heterologous organism, i.e., an organism other than the native source. Examples of suitable heterologous organisms are Gram(+) bacteria such as *Bacillus subtilis*, *Bacillus licheniformis*, *Bacillus lentus*, *Bacillus brevis*, *Geobacillus* (formerly *Bacillus*) *stearothermophilus*, *Bacillus alkalophilus*, *Bacillus amyloliquefaciens*, *Bacillus coagulans*, *Bacillus circulars*, *Bacillus lautus*, *Bacillus megaterium*, *Bacillus thuringiensis*, *Streptomyces lividans*, or *Streptomyces murinus*; Gram(−) bacteria such as *Escherichia coli*; yeast such as *Saccharomyces* spp. or *Schizosaccharomyces* spp., e.g. *Saccharomyces cerevisiae*; and filamentous fungi such as *Aspergillus* spp., e.g., *Aspergillus oryzae* or *Aspergillus niger*, and *Trichoderma reesei*. Methods of transforming nucleic acids into these organisms are known in the art. For example, a suitable procedure for transforming *Aspergillus* host cells is described in EP 238 023.

In some embodiments, the recombinant polypeptide is fused to a signal peptide, for example, to facilitate extracellular secretion of the recombinant polypeptide. For example, in certain embodiments, the signal peptide is encoded by a sequence selected from SEQ ID NOs: 10, 11, 12, 13, 14, 15, 69, 70, 71, 72, 73, 81, 82, 83, 131 and 132. In particular embodiments, the recombinant polypeptide is expressed in a heterologous organism as a secreted polypeptide. The compositions and methods herein thus encompass methods for expressing a carbonic anhydrase polypeptide as a secreted polypeptide in a heterologous organism.

B. Carbonic Anhydrase Polynucleotides

Another aspect of the compositions and methods described herein is a polynucleotide that encodes a recombinant carbonic anhydrase polypeptide (including variants and fragments thereof) having carbonic anhydrase activity.

In some embodiments the polynucleotide is provided in the context of an expression vector for directing the expression of a carbonic anhydrase polypeptide in a heterologous organism, such as the ones identified herein. The polynucleotide that encodes a recombinant carbonic anhydrase polypeptide may be operably-linked to regulatory elements (e.g., a promoter, terminator, enhancer, and the like) to assist in expressing the encoded polypeptides.

Examples of polynucleotide sequences encoding recombinant carbonic anhydrase polypeptides are the nucleotide sequence of SEQ ID NO: 1, SEQ ID NO: 26, SEQ ID NO: 41 SEQ ID NO: 51, SEQ ID NO: 62, SEQ ID NO: 77, SEQ ID NO: 127, or SEQ ID NO: 133. Similar, including substantially identical, polynucleotides encoding recombinant carbonic anhydrase polypeptides and variants may occur in nature, e.g., in different strains or other isolates of the native source. In view of the degeneracy of the genetic code, it will be appreciated that polynucleotides having different nucleotide sequences may encode the same carbonic anhydrase polypeptides, variants, or fragments.

In some embodiments, polynucleotides encoding recombinant polypeptides have a specified degree of amino acid sequence identity to the exemplified polynucleotide encoding a parent polypeptide, e.g., at least 50%, at least 51%, at least 52%, at least 53%, at least 54%, at least 55%, at least 56%, at least 57%, at least 58%, at least 59%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or even at least 99% sequence identity to the amino acid sequence of SEQ ID NO: 3, SEQ ID NO: 28, SEQ ID NO: 43, SEQ ID NO: 53, SEQ ID NO: 64, SEQ ID NO: 80, SEQ ID NO:130, or SEQ ID NO: 136. Homology can be determined by amino acid sequence alignment, e.g., using a program such as BLAST, ALIGN, or CLUSTAL, as described herein.

In some embodiments, the polynucleotide that encodes a recombinant polypeptide is fused in frame behind (i.e., downstream of) a coding sequence for a signal peptide for directing the extracellular secretion of a recombinant polypeptide. Heterologous signal sequences include, for example, those from bacterial cellulase genes. Expression vectors may be provided in a heterologous host cell suitable for expressing a recombinant polypeptide, or suitable for propagating the expression vector prior to introducing it into a suitable host cell.

In some embodiments, polynucleotides encoding recombinant polypeptides hybridize to the polynucleotide of SEQ ID NO: 1, SEQ ID NO: 26, SEQ ID NO: 41 SEQ ID NO: 51, SEQ ID NO: 62, SEQ ID NO: 77, SEQ ID NO: 127, or SEQ ID NO: 133 (or to the complement thereof) under specified hybridization conditions. Examples of conditions are intermediate stringency, high stringency and extremely high stringency conditions, which are described, herein.

Carbonic Anhydrase polynucleotides may be naturally occurring or synthetic (i.e., man-made), and may be codon-optimized for expression in a different host, mutated to introduce cloning sites, or otherwise altered to add functionality.

C. Carbonic Anhydrase Vectors and Host Cells

In order to produce a disclosed recombinant polypeptide, the DNA encoding the polypeptide can be chemically synthesized from published sequences or can be obtained directly from host cells harboring the gene (e.g., by cDNA library screening or PCR amplification). In some embodiments, the carbonic anhydrase polynucleotide is included in an expression cassette and/or cloned into a suitable expression vector by standard molecular cloning techniques. Such expression cassettes or vectors contain sequences that assist initiation and termination of transcription (e.g., promoters and terminators), and typically can also contain one or more selectable markers.

The expression cassette or vector is introduced into a suitable expression host cell, which then expresses the corresponding carbonic anhydrase polynucleotide. Suitable expression hosts are bacterial expression host genera including *Escherichia* (e.g., *Escherichia coli*), *Pseudomonas* (e.g., *P. fluorescens* or *P. stutzerei*), *Proteus* (e.g., *Proteus mirabilis*), *Ralstonia* (e.g., *Ralstonia eutropha*), *Streptomyces*, *Staphylococcus* (e.g., *S. carnosus*), *Lactococcus* (e.g., *L. lactis*), or *Bacillus* (e.g., *Bacillus subtilis, Bacillus megaterium, Bacillus licheniformis*, etc.). Also suitable are yeast expression hosts such as *Saccharomyces cerevisiae, Schizosaccharomyces pombe, Yarrowia hpolytica, Hansenula polymorpha, Kluyveromyces lactis* or *Pichia pastoris*. Suitable fungal expression hosts include *Aspergillus niger, Chrysosporium lucknowense, Aspergillus* (e.g., *A. oryzae, A. niger, A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines. Other eukaryotic hosts such as insect cells or viral expression systems (e.g., bacteriophages such as M13, T7 phage or Lambda, or viruses such as Baculovirus) are also suitable for producing the carbonic anhydrase polypeptide.

Promoters and/or signal sequences associated with secreted proteins in a particular host of interest are candidates for use in the heterologous production and secretion of thermostable carbonic anhydrases in that host or in other hosts. As an example, promoters from thermostable proteins, such as the *Bacillus licheniformis* thermostable amylase LAT promoter (pLAT), may be used. Alternatively, in filamentous fungal systems, the promoters that drive the genes for cellobiohydrolase I (cbh1), glucoamylase A (glaA), TAKA-amylase (amyA), xylanase (exlA), the gpd-promoter cbh1, cbhll, endoglucanase genes eg1-eg5, Ce161B, Ce174A, gpd promoter, Pgk1, pki1, EF-1alpha, tef1, cDNA1 and hex1 are suitable and can be derived from a number of different organisms (e.g., *A. niger, T. reesei, A. oryzae, A. awamori, A. nidulans*).

In some embodiments, the carbonic anhydrase polynucleotide is recombinantly associated with a polynucleotide encoding a suitable homologous or heterologous signal sequence that leads to secretion of the recombinant carbonic anhydrase polypeptide into the extracellular (or periplasmic) space, thereby allowing direct detection of enzyme activity in the cell supernatant (or periplasmic space or lysate). Suitable signal sequences for *Escherichia coli*, other Gram negative bacteria and other organisms known in the art include those that drive expression of the HlyA, DsbA, Pbp, PhoA, PelB, OmpA, OmpT or M13 phage Gill genes. For *Bacillus subtilis*, Gram-positive organisms and other organisms known in the art, suitable signal sequences further include those that drive expression of the AprE, NprB, Mpr, AmyA, AmyE, Blac, SacB, and for *S. cerevisiae* or other yeast, including the killer toxin, Bar1, Suc2, Mating factor alpha, InulA or Ggplp signal sequence. Signal sequences can be cleaved by a number of signal peptidases, thus removing them from the rest of the expressed protein. Additionally, signal sequences from thermostable proteins, including but not limited to, the *Bacillus licheniformis* LytD, NucB, BglC, hypothetical protein BLi01309 (cell wall-binding), YhcJ, and hypothetical protein BLi03260 may be used.

In some embodiments, the recombinant carbonic anhydrase polypeptide is expressed alone or as a fusion with other peptides, tags or proteins located at the N- or C-terminus (e.g., 6×His, HA or FLAG tags). Suitable fusions include tags, peptides or proteins that facilitate affinity purification or detection (e.g., 6×His, HA, chitin binding protein, thioredoxin or FLAG tags), as well as those that facilitate expression, secretion or processing of the target carbonic anhydrase. Suitable processing sites include enterokinase, STE13, Kex2 or other protease cleavage sites for cleavage in vivo or in vitro.

Carbonic anhydrase polynucleotides are introduced into expression host cells by a number of transformation methods including, but not limited to, electroporation, lipid-assisted transformation or transfection ("lipofection"), chemically mediated transfection (e.g., CaCl and/or CaP), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

Alternatively, the recombinant carbonic anhydrase polypeptides are expressed intracellularly. Optionally, after intracellular expression of the enzyme variants, or secretion into the periplasmic space using signal sequences such as those mentioned above, a permeabilisation or lysis step can be used to release the recombinant carbonic anhydrase polypeptide into the supernatant. The disruption of the membrane barrier is effected by the use of mechanical means such as ultrasonic waves, pressure treatment (French press), cavitation, or by the use of membrane-digesting enzymes such as lysozyme or enzyme mixtures. As a further alternative, the polynucleotides encoding the recombinant carbonic anhydrase polypeptide are expressed using a suitable cell-free expression system. In cell-free systems, the polynucleotide of interest is typically transcribed with the assistance of a promoter, but ligation to form a circular expression vector is optional. In some embodiments, RNA is exogenously added or generated without transcription and translated in cell-free systems.

IV. Activities of Carbonic Anhydrases Polypeptides

The recombinant carbonic anhydrase polypeptides disclosed herein may have carbonic anhydrase activity over a broad range of pH conditions. In certain embodiments the disclosed recombinant carbonic anhydrase polypeptides have carbonic anhydrase activity when incubated for at least 1 hour, at least 2.5 hours, at least 5 hours, at least 10 hours, at least 12 hours, at least 18 hours, at least 24 hours, at least one week, one month, six months, 12 months, 18 months or longer, at a pH of from about 8.0 to about 11, about 8.5 to about 10.5, or about 9.0 to about 10.0. Suitably, the recombinant carbonic anhydrase polypeptides have carbonic anhydrase activity at a pH of from about 8.5 to about 10.5. In some embodiments, the recombinant carbonic anhydrase polypeptides have carbonic anhydrase activity when incubated for at least 5 hours, at least 10 hours, at least 12 hours, at least 18 hours, at least 24 hours, or longer at a pH of about 6.0, 7.0, 8.0, 8.5, 9.0, 9.5, 10.0, 10.5, or 11.0. In further embodiments, the recombinant carbonic anhydrase polypeptides retain at least 20%, at least 30%, at least 40%, at least 50%, at least 60%, at least 70%, at least 75%, at least 80%, at least 85%, at least 90%, at least 95%, at least 99%, or higher carbonic anhydrase activity when incubated at a pH of from about 8.5 to about 10.5. It should be noted that the pH values described herein may vary by ±0.2. For example, a pH value of about 8.0 could vary from pH 7.8 to pH 8.2.

The recombinant carbonic anhydrase polypeptides disclosed herein may have carbonic anhydrase activity over a wide range of temperatures, e.g., from about 0° C. to about 80° C. In certain embodiments, the recombinant carbonic anhydrase polypeptides have carbonic anhydrase activity when incubated for at least 1 hour, at least 2.5 hours, at least 5 hours, at least 10 hours, at least 12 hours, at least 18 hours, at least 24 hours, at least one week, one month, six months, 12 months, 18 months or longer at a temperature of from about 0° C. to about 80° C., about 0° C. to about 70° C., about 0° C. to about 60° C., about 0° C. to about 50° C., about 0° C. to about 45° C., about 0° C. to about 40° C., about 0° C. to about 35° C., about 0° C. to about 30° C., about 0° C. to about 25° C., about 0° C. to about 20° C., about 0° C. to about 15° C., about 0° C. to about 10° C., or about 0° C. to about 5° C. In some embodiments, the recombinant carbonic anhydrase polypeptides have carbonic anhydrase activity when incubated for at least 1 hour, at least 2.5 hours, at least 5 hours, at least 10 hours, at least 12 hours, at least 18 hours, at least 24 hours, at least one week, one month, six months, 12 months, 18 months or longer at a temperature of about 0° C., 10° C., 15° C., 20° C., 25° C. 30° C., 35° C., 40° C., 45° C., 50° C., 55° C., 60° C., 65° C., 70° C., 75° C. or 80° C. It should be noted that the temperature values described herein may vary by ±0.2° C. For example a temperature of about 50° C. could vary from 49.8° C. to 50.2° C.

In certain embodiments, the recombinant carbonic anhydrase polypeptides disclosed herein retain at least 10%, at least 20%, at least 30%, at least 40%, at least 50%, at least 60%, at least 70%, at least 75%, at least 80%, at least 85%, at least 90%, at least 95%, at least 99%, or more of carbonic anhydrase activity when incubated for at least 1 hour, at least 2.5 hours, at least 5 hours, at least 10 hours, at least 12 hours, at least 18 hours, at least 24 hours, at least one week, one month, six months, 12 months, 18 months or longer at a temperature of about 25° C. 30° C., 35° C., 40° C., 45° C., 50° C., 55° C., 60° C., 65° C., 70° C., 75° C. or 80° C. In some embodiments, the incubation temperature is from about 40° C. to about 80° C.

In further embodiments, the recombinant carbonic anhydrase polypeptides disclosed herein have carbonic anhydrase activity when incubated for at least 1 hour, at least 2 hours, at least 3 hours, at least 4 hours, at least 5 hours, at least 6 hours, at least 7 hours, at least 8 hours, at least 9 hours, at least 10 hours, at least 12 hours, at least 18 hours, at least 24 hours, at least one week, one month, six months, 12 months, 18 months or longer in the presence of bicarbonate ($HCO_3^-$). Suitably, the $HCO_3^-$ concentration is achieved with 0.1 M, 0.25 M, 0.5 M, 1 M, 1.5 M, 2 M or a higher concentration of sodium bicarbonate ($NaHCO_3$), potassium bicarbonate ($KHCO_3$), or ammonium bicarbonate ($NH_4CO_3$). In related embodiments, the recombinant carbonic anhydrase polypeptides disclosed herein have increased or improved thermostability at increased ionic strengths. For example, the recombinant carbonic anhydrase polypeptides have a higher melting temperature at higher ionic strength conditions (e.g., at 1 M bicarbonate) as compared to at lower ionic strength conditions (e.g., at 0.8 M, 0.6 M, 0.4 M, 0.2 M, or 0.1 M bicarbonate).

The recombinant carbonic anhydrase polypeptides disclosed herein may have a wide range of melting temperatures depending upon pH, ionic strength conditions, and the presence of bicarbonate. In some embodiments, the recombinant carbonic anhydrase polypeptides have a melting temperature of at least about 50° C. (e.g., at least about 56° C., 57° C., 58° C., 59° C., 60° C., 62° C., 64° C., 66° C., 68° C., 70° C., 72° C., 74° C., 76° C., 78° C., 80° C., 82° C., 84° C., 86° C., 88° C., 90° C., 92° C., 94° C., 96° C., 98° C., or even 100° C.) at a pH of about 7.5 to about 11 (e.g., about 7.5 to about 10.5, about 8.0 to about 10.5, about 8.5 to about 10, about 9.0 to about 10.5, etc.). In certain embodiments, the recombinant carbonic anhydrase polypeptides have a melting temperature of about 56° C., 56.5° C., 57° C., 57.5° C., 58° C., 58.5° C., 59° C., 59.5° C., 60° C., 60.5° C., 61° C., 61.5° C., 62° C., 62.5° C., 63° C., 63.5° C., 64° C., 64.5° C., 65° C., 65.5° C., 66° C., 66.5° C., 67° C., 67.5° C., 68° C., 69° C., 70° C., 71° C., 72° C., 75° C., 78° C., 80° C., 82° C., 85° C., 90° C., or higher, at a pH of about 8.0, 8.5, 9.0, 9.5, 10.0, or 10.5. In some embodiments, the recombinant carbonic anhydrase polypeptides have a melting temperature of about 65° C., 69° C., 70° C., 71° C., 71.5° C., 72° C., 72.5° C., 73° C. or higher, under high ionic strength conditions. Suitably, the high ionic strength condition is achieved by melting the recombinant carbonic anhydrase polypeptides in the presence of about 0.5 M, 1 M, 1.5 M, 2 M, or a higher concentration of sodium chloride (NaCl). In some embodiments, the recombinant carbonic anhydrase polypeptides have a melting temperature of about 65° C., 69° C., 70° C., 71° C., 71.5° C., 72° C., 72.5° C., 73° C. or higher, in the presence of $HCO_3^-$. Suitably, the $HCO_3^-$ concentration is achieved with 0.5 M, 1 M, 1.5 M, 2 M or a higher concentration of $NaHCO_3$ or $KHCO_3$. In some embodiments, the recombinant carbonic anhydrase polypeptides have a melting temperature of about 70° C., 70.5° C., 71° C., 71.5° C., 72° C., 72.5° C., 73° C., 73.5° C., 74° C., 74.5° C., 75° C., 75.5° C., 76° C., 76.5° C., 77° C., 77.5° C., 80° C., 80.5° C., 81° C., 82° C., 83° C., 84° C., 85° C., 88° C., 90° C., 92° C., 95° C., 97° C., 100° C. or higher, in the presence of $HCO_3^-$ and under high ionic strength conditions. Suitably, the high ionic strength conditions is achieved by melting the recombinant carbonic anhydrase polypeptides in the presence of about 0.5 M, 1 M, 1.5 M, 2 M, or a higher concentration of NaCl, and in the presence of $HCO_3^-$, achieved with 0.5 M, 1 M, 1.5 M, 2 M or a higher concentration of $NaHCO_3$ or $KHCO_3$. In related embodiments, the recombinant carbonic anhydrase polypeptides have increased thermostability with increased ionic strengths. For example, the recombinant carbonic anhydrase polypeptides have increased or a higher melting temperature at a higher ionic strength condition (e.g., at 1 M bicarbonate) as compared to at a lower ionic strength condition (e.g., at 0.8, 0.6, 0.4, 0.2, or 0.1 M bicarbonate).

Example 1C shows that the recombinant Bgi CA1 polypeptide had carbonic anhydrase activity in carbon dioxide saturated water. In particular, the Bgi CA1 polypeptide was shown to have a specific activity of 4,023±387 Wilbur-Anderson units/mg. Accordingly, in certain embodiments, any of the recombinant Bgi CA1 polypeptides disclosed herein convert carbon dioxide into a bicarbonate or carbonate product, or convert a biocarbonate or carbonate-containing material into $CO_2$. In certain embodiments, any of the recombinant Bgi CA1 polypeptides have improved specific activity and/or improved stability as compared to a native Bgi CA1.

Example 2C shows the recombinant Pvi CA1 polypeptide had carbonic anhydrase activity in carbon dioxide saturated water. In particular, the Pvi CA1 polypeptide was shown to have a specific activity of 937±65 Wilbur-Anderson units/ mg. Accordingly, in certain embodiments, any of the recombinant Pvi CA1 polypeptides disclosed herein converts carbon dioxide into a bicarbonate or carbonate product, or convert a biocarbonate or carbonate-containing material into $CO_2$. In certain embodiments, any of the recombinant Pvi CA1 polypeptides have improved specific activity and/or improved stability as compared to a native Pvi CA1.

Example 3C shows that the recombinant Ate CA1 polypeptide had carbonic anhydrase activity in carbon dioxide saturated water. In particular, the Ate CA1 polypeptide was shown to have a specific activity of 1,327±285 Wilbur-Anderson units/mg. Accordingly, in certain embodiments, any of the recombinant Ate CA1 polypeptides disclosed herein converts carbon dioxide into a bicarbonate or carbonate product, or converts a bicarbonate or a carbonate-containing material into $CO_2$. In certain embodiments, any of the recombinant Ate CA1 polypeptides have improved specific activity and/or improved stability as compared to a native Ate CA1.

Example 4C shows that the recombinant Spr CA1 polypeptide had carbonic anhydrase activity in carbon dioxide saturated water. In particular, the Spr CA1 polypeptide was shown to have a specific activity of 2,433±412 Wilbur-Anderson units/mg. Accordingly, in certain embodiments, any of the recombinant Spr CA1 polypeptides disclosed herein convert carbon dioxide into a bicarbonate or carbonate product, or convert a biocarbonate or carbonate-containing material into $CO_2$. In certain embodiments, any of the recombinant Spr CA1 polypeptides have improved specific activity and/or improved stability as compared to a native Spr CA1.

Example 5C shows the recombinant Bag CA1 polypeptide had carbonic anhydrase activity in carbon dioxide saturated water. In particular, the Bag CA1 polypeptide was shown to have a specific activity of 3715±274 Wilbur-Anderson units/mg. Accordingly, in certain embodiments, any of the recombinant Bag CA1 polypeptides disclosed herein convert carbon dioxide into a bicarbonate or carbonate product, or convert a biocarbonate or carbonate-containing material into $CO_2$. In certain embodiments, any of the recombinant Bag CA1 polypeptides have improved specific activity and/or improved stability as compared to a native Bag CA1.

Example 6B shows that the recombinant Vsp CA1 polypeptide had carbonic anhydrase activity in carbon dioxide saturated water. In particular, the Vsp CA1 polypeptide was shown to have a specific activity of 10,028±551 Wilbur-Anderson units/mg. Accordingly, in certain embodiments, any of the recombinant Vsp CA1 polypeptides disclosed herein convert carbon dioxide into a bicarbonate or carbonate product, or convert a biocarbonate or carbonate-containing material into $CO_2$. In certain embodiments, any of the recombinant Vsp CA1 polypeptides have improved specific activity and/or improved stability as compared to a native Vsp CA1.

Example 7B shows that the recombinant VspE CA1 polypeptide had carbonic anhydrase activity in carbon dioxide saturated water. In particular, the VspE CA1 polypeptide was shown to have a specific activity of 4621+431 Wilbur-Anderson units/mg. Accordingly, in certain embodiments, any of the recombinant VspE CA1 polypeptides disclosed herein convert carbon dioxide into a bicarbonate or carbonate product, or convert a biocarbonate or carbonate-containing material into $CO_2$. In certain embodiments, any of the recombinant VspE CA1 polypeptides have improved specific activity and/or improved stability as compared to a native VspE CA1.

Example 8B shows that the recombinant VspE CA2 polypeptide had carbonic anhydrase activity in carbon dioxide saturated water. In particular, the VspE CA2 polypeptide was shown to have a specific activity of 3189+112 Wilbur-Anderson units/mg. Accordingly, in certain embodiments, any of the recombinant VspE CA2 polypeptides disclosed herein convert carbon dioxide into a bicarbonate or carbonate product, or convert a biocarbonate or carbonate-containing material into $CO_2$. In certain embodiments, any of the recombinant VspE CA2 polypeptides have improved specific activity and/or improved stability as compared to a native VspE CA2.

V. Compositions Comprising a Recombinant Carbonic Anhydrase Polypeptide

In some embodiments, the present disclosure provides compositions comprising a recombinant carbonic anhydrase polypeptide (including variants or fragments, thereof) having carbonic anhydrase activity and methods for using such compositions in carbon dioxide extraction or sequestration applications. In some embodiments, the recombinant carbonic anhydrase polypeptide are selected from the group consisting of Bgi CA1, Pvi CA1, Ate CA1, Spr CA1, Bag CA1, Vsp CA1, VspE CA1, and VspE CA2.

Unless otherwise noted, all component or composition levels provided herein are made in reference to the active level of that component or composition, and are exclusive of impurities, for example, residual solvents or by-products, which may be present in commercially available sources.

In certain embodiments a recombinant carbonic anhydrase polypeptide of the present disclosure is the major component of the composition, e.g., a mono-component composition. Such compositions may further include an excipient, which, in the context of a mono-component composition, is to be understood as any auxiliary agent or compound used to formulate the composition and includes, without limitation, solvents (e.g., water, inorganic salts, fillers, pigments, waxes), carriers, stabilizers, cross-linking agents, adhesives, preservatives, and buffers.

In certain embodiments, the composition may further include one or more enzymes other than the recombinant carbonic anhydrase polypeptide, including, without limitation, endo peptidases, aminopeptidases, amylases, carbohydrases, carboxypeptidases, catalases, cellulases, chitinases, cutinases, cyclodextrin glycosyltransferases, decarboxylases, deoxyribonucleases, esterases, alpha-galactosidases, beta-galactosidases, glucoamylases, alpha-glucosidases, beta-glucosidases, haloperoxidases, invertases, laccases, lipases, mannosidases, monooxygenases, nitrilases, oxidases, pectinolytic enzymes, peptidoglutaminases, peroxidases, phytases, polyphenoloxidases, proteolytic enzymes, ribonucleases, transglutaminases, xylanases, or combinations thereof.

In addition to the recombinant carbonic anhydrase polypeptides provided herein, one or more other suitable carbonic anhydrases can be included in the compositions of the present disclosure. Suitable carbonic anhydrases include, without limitation, alpha-carbonic anhydrases, beta-carbonic anhydrases, gamma-carbonic anhydrases, delta-carbonic anhydrases, epsilon-carbonic anhydrases, cytosolic carbonic anhydrases, mitochondrial carbonic anhydrases, secreted carbonic anhydrases, and membrane-associated carbonic anhydrases. Additionally, suitable carbonic anhydrases include, without limitation, those of animal, plant, fungal, bacterial, cyanobacterial, and diatomic origin.

Chemically or genetically modified mutants are encompassed by the present disclosure.

In some embodiments, the polypeptides disclosed herein may comprise a modification. As used herein, "modification" describes various functional groups in a polypeptide that interact covalently, ionically, or by hydrophobic or hydrophilic association with various modifying agents. Covalent modifications to various polypeptides can be made by reaction of the enzyme with a hydrophobic agent, a hydrophilic agent, or an amphiphilic agent. These interactions add a hydrophobic, hydrophilic, or amphiphilic moiety to the enzyme. Various hydrophobic agents can be used, for example, a monoamine (e.g., alkyl amine), an aldehyde (e.g., pentanal, isobutanal, acetanal, hexanal, octanal, decanal), a quaternary ammonium salt, an alkyltrimethylammonium cation, an organic cation, a phosphonium cation, a pyridinium cation, an imidazolium cation, a viologen, a bis(triphenylphosphine)iminium metal complex, a bipyridyl metal complex, a phenanthroline-based metal complex, or a combination thereof. In various embodiments, the hydrophobic agent can be butyl amine, hexyl amine, octyl amine, decyl amine, dodecyl amine, pentanal, isobutanal, acetanal, hexanal, octanal, decanal, acetyltrimethylammonium bromide, sodium dodecyl sulfate, ammonium lauryl sulfate, triphenylphosphonium, hexadecylpyridinium, ethidium, methyl viologen, benzyl viologen, [Ru(bipyridine)$_3$]$^{2+}$, [Fe(phenanthroline)$_3$]$^{3+}$, or a combination thereof. In some embodiments, the hydrophobic agent can be butyl amine, hexyl amine, octyl amine, decyl amine, dodecyl amine, pentanal, isobutanal, acetanal, hexanal, octanal, decanal, acetyltrimethylammonium bromide, sodium dodecyl sulfate, ammonium lauryl sulfate, triphenylphosphonium, hexadecylpyridinium, ethidium, methyl viologen, benzyl viologen, or a combination thereof. In certain embodiments, the polypeptides disclosed herein may be covalently modified with an alkyl amine or a water soluble polymer, such as an unbranched or branched polyethylene glycol, an ethylene glycol/propylene glycol copolymer, carboxymethylcellulose, dextran, polyvinyl alcohol, and the like. Alkyl amines useful for covalent modification are butyl amine, hexyl amine, octyl amine, decyl amine, dodecyl amine, and the like. In some embodiments, the polypeptides disclosed herein may be modified by various surface active agents. For example, non-ionic surface active agents can be N,N-bis(3-D-gluconamidopropyl)cholamide (BigCHAP), N,N-bis(3-D-gluconamidopropyl)deoxycholamide (DeoxyBigCHAP), a polyoxyethylene alcohol (e.g., Brij35 and Brij 58 P), 2-cyclohexylmethyl-β-D-maltoside (Cymal-1), 2-cyclohexylethyl-β-D-maltoside (Cymal-2), cyclohexylpentyl-β-D-maltoside (Cymal-5), cyclohexylhexyl-β-D-maltoside (Cymal-6), decyl-β-D-maltopyranoside, n-dodecyl-β-D-maltoside, n-hexyadecyl-β-D-maltoside, undecyl-β-D-maltoside, decyl-β-D-1-thiomaltopyranoside, octyl-β-D-thioglucopyranoside, digitonin, dimethydecylphosphine oxide, dodecyldimethylphosphine oxide, (octylphenoxy) polyethoxyethanol (IGEPAL® CA630), N-octanoyl-N-methylglucamine (MEGA-8), N-nonanoyl-N-methylglucamine (MEGA-9), N-decanoyl-N-methylglucamine (MEGA-10), a polyoxy ethylene octyl phenol (Nonidet® P40-substitute), a polyoxyethylene-polyoxypropylene block co-polymer (Pluronic F-68), saponin, polyoxyethylene 9-lauryl ether (These), a polyoxy ethylene octyl phenol (e.g., Triton® X-100 and Triton® X-114), a polyoxyethylene derivative of sorbitan monolaurate (e.g., TWEEN® 20, TWEEN® 40, and TWEEN® 80), N,N-dimethyldodecylamine-N-oxide, an alcohol ethoxylate (Synperonic A7), amidosulfobetaine-14, amidosulfobetaine-16, C7BzO, 3-[(3-cholamidopropyldimethylammonio]-1-propanesulphonate (CHAPS), 3-[(3-cholamidopropyldimethylammonio]-2-hydroxy-1-propane sulphonate (CHAPSO), (dodecyldimethylammonio)acetate (EMPIGEN® BB), 3-(N,N-dimethyloctylammonio) propanesulfonate, 3-(dodecylammonio)propanesulfonate, 3-(N,N-dimethylmyristylammonio) propanesulfonate, 3-(N,N-dimethylpalmitylammonio) propanesulfonate, 3-(N5N-dimethyloctadecylammonio) propanesulfonate, or a combination thereof.

The polypeptides disclosed herein may be modified at random positions within the molecule, or at predetermined positions within the molecule and may include one, two, three, or more attached chemical moieties. Methods for modifying polypeptides are known in the art, for example, EP 0401384 and Malik et al., Exp. Hematol. 20:1028-1035, 1992 (reporting PEGylation of GM-CSF using tresyl chloride).

In certain embodiments, the polypeptides disclosed herein may be immobilized. In certain embodiments, methods of protein engineering can be applied to the carbonic anhydrase polypeptide herein such that one or more sites, which are not previously present in the polypeptide, can be engineered into the polypeptide to facilitate immobilization; or alternatively, protein engineering methods can be used to alter certain of the residues in the polypeptide such that the polypeptide becomes more amenable to or suitable for immobilization. An immobilized polypeptide can contain two types of functions: (1) non-catalytic functions that are designed to aid separation (e.g., isolation of polypeptide from the application environment, reuse of the polypeptide, or control of the process); and (2) catalytic functions that are designed to convert the target compounds (or substrates) within the time and space desired (Cao, Carrier-bound Immobilized Enzymes: Principles, *Applications and Design*, Wiley-VCH Verlag GmbH & Co. KGaA, Weinheim, Germany, 2005). When a polypeptide is immobilized, it is made insoluble to the target compounds (e.g., substrates) it aids in converting, and to the solvents used. An immobilized polypeptide product can be separated from the application environment in order to facilitate its reuse, or to reduce the amount of polypeptide needed, or to use the polypeptide in a process where substrate is continuously delivered and product is continuously removed from proximity to the polypeptide. This approach may, for example, contribute to a reduced cost of polypeptide expenditure. Furthermore, polypeptides are often stabilized by immobilization. A process involving immobilized polypeptide is often continuous, which facilitates easy process control. The immobilized polypeptide can be retained as a heterogeneous catalyst by mechanical means, or by inclusion in a definite space. The latter can be done by microencapsulation, e.g., in semi permeable membranes or by inclusion in UF systems using, e.g., hollow fiber modules, etc. Immobilization on porous carriers is also commonly used. This includes binding of the polypeptide to the carrier, e.g., by adsorption, complex/ionic/covalent binding, or by simple absorption of soluble polypeptide on the carrier and subsequent removal of solvent. Cross-linking of the polypeptide can also be used as a means of immobilization. Additionally, a polypeptide may be immobilized by inclusion into a carrier (Buchholz et al., *Biocatalysts and Enzyme Technology*, Wiley-VCH Verlag GmbH & Co. KGaA, Weinheim, Germany, 2005).

There are a variety of methods for polypeptide immobilization, including without limitation, carrier-binding, cross-linking, and entrapping. Carrier-binding is the binding of polypeptides to water-insoluble carriers. Cross-linking is the intermolecular cross-linking of polypeptides by bifunctional or multifunctional reagents. Entrapping is incorporating polypeptides into the lattices of a semipermeable material. Additional methods of immobilizing polypeptides include, without limitation, spraying of the polypeptide together with a liquid medium comprising a polyfunctional amine and a liquid medium comprising a cross-linking agent onto a particulate porous carrier as described in WO 2007/036235, linking of the polypeptide with a cross-linking agent (e.g., glutaraldehyde) to an ovalbumin layer, which in turn adheres to an adhesive layer on a polymeric support as described in WO 2005/114417, coupling of the polypeptide to a silica carrier as described in U.S. Pat. No. 5,776,741, or to a silane, or a CNBr activated carrier surface such as glass, or co-polymerization of the polypeptide with methacrylate on polymer beads as described in Bhattacharya et al., *Biotechnol. Appl. Biochem.* 38: 111-117, 2003. The particular method of polypeptide immobilization used in connection with the compositions and methods described herein is flexible, so long as the immobilization material (1) immobilizes the polypeptide, and/or in some embodiments, (2) stabilizes the polypeptide. In various embodiments, the immobilization material is also permeable to a compound smaller than the polypeptide. A polypeptide is adsorbed to an immobilization material when it adheres to the surface of the material by chemical or physical interactions. Further, a polypeptide is immobilized by entrapment when the polypeptide is contained within the immobilization material, whether or not within a pocket of the material.

In certain embodiments, the immobilization material is permeable to various compounds that are smaller than a polypeptide. Such permeability allows the movement of a substrate compound through the material, such that the substrate compound can contact the polypeptide. The immobilization material can be prepared in a manner such that it contains internal pores, micellar pockets, channels, openings or a combination thereof, which allow the movement of the substrate compound throughout the immobilization material, but which constrain the polypeptide to substantially the same space within the immobilization material. Such constraint allows the polypeptide to retain its function or catalytic activity, or even to increase its catalytic activity and/or stability. In various embodiments, the polypeptide is confined to a space that is substantially the same size and shape as the polypeptide, wherein the polypeptide retains substantially all of its function or catalytic activity. The pores, micellar pockets, channels, or openings have physical dimensions that satisfy the above requirements, depending on the size and shape of the specific polypeptide to be immobilized.

In certain embodiments, the immobilization material has a micellar or inverted micellar structure. Generally, the molecules making up a micelle are amphipathic, meaning they contain a polar, hydrophilic group and a nonpolar, hydrophobic group. The molecules can aggregate to form a micelle, where the polar groups are on the surface of the aggregate and the hydrocarbon, nonpolar groups are sequestered inside the aggregate. Inverted micelles have the opposite orientation of polar groups and nonpolar groups. The amphipathic molecules making up the aggregate can be arranged in a variety of ways so long as the polar groups are in proximity to each other and the nonpolar groups are in proximity to each other. Also, the molecules can form a bilayer with the nonpolar groups pointing toward each other and the polar groups pointing away from each other. Alternatively, a bilayer can form wherein the polar groups can point toward each other in the bilayer, while the nonpolar groups point away from each other. Examples of micellar or inverted micellar immobilization material include, without limitation, a modified perfluoro sulfonic acid-PTFE copolymer (or modified perfluorinated ion exchange polymer) (modified NAFION® or modified FLEMION®) membrane; hydrophobically modified polysaccharides, such as chitosan, cellulose, chitin, starch, amylose, alginate, glycogen, and combinations thereof; polycationic polymers, such as hdrophobically modified chitosan; and polycanionic polymers, such as hdrophobically modified alginate. Other examples of immobilization material include, without limitation, modified polysulfone, modified polycarbonate, modified poly (vinylbenzyl chloride), modified polysiloxanes, and modified polysulfone-graft-polyethylene glycol. The above immobilization materials are described in detail in WO 2010/037109 and U.S. Patent Application Publication No. US 2010/0209968.

Methods of encapsulating or immobilizing a polypeptide in any of the above immobilization materials are known in the art. For example, WO 2010/037109 describes methods of encapsulating a polypeptide in polysufone, and immobilizing a polypeptide in alginate, poly(vinylbenzyl chloride), and polysulfone-graft-polyethylene glycol.

In certain embodiments, the immobilization material may include, without limitation, a polymer, a membrane including liquid membranes, a matrix, a wafer, a solid support, or a micro-particle. In some embodiments, the immobilization material may be selected from beads, fabrics, fibers, hollow fibers, membranes, particulates, porous surfaces, rods, structured packing, and tubes. Further examples of suitable immobilization material include, without limitation, alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polypropylene, polymerhydrogels, sephadex, sepharose, silica gel, precipitated silica, and TEFLON®-brand PTFE.

Once a polypeptide has been immobilized within the immobilization material, the immobilized polypeptide can be deposited on a support. The substrate can be a material that provides the desired mechanical support necessary for the selected use. For example, the support may be a filter, a wire mesh, porous polymer, organic and inorganic membrane, and the like when the immobilized polypeptide is used as a catalyst for a chemical transformation.

In some embodiments, compositions comprising immobilized polypeptides can be core particles. A core particle is any particle that provides a support for the immobilized polypeptide layer. A core particle can be spray-dried. The core particle can be, for example, a polymer particle, a carbon particle, a zeolite particle, a metal particle, a ceramic particle, a metal oxide particle, a silica particle, or a combination thereof. In some embodiments, the core particle is an inert core particle. In some embodiments, the core particle is not a polymer particle. Suitably, core particles do not adversely affect the stability of the polypeptide or a chemical transformation involving the polypeptide. Methods for preparing core particles are known in the art. For example, WO 2010/037109 describes methods for coating a core particle with a mixture containing the polypeptide and immobilization material.

In some embodiments, the polypeptides disclosed herein may be stabilized by any method known in the art e.g., by stabilizing the polypeptide in the composition by adding and antioxidant or reducing agent to limit oxidation of the polypeptide or by adding compounds that trap/inactivate the compounds that damage the enzyme or it may be stabilized by adding polymers such as PVP, PVA, PEG, sugars, oligomers, polysaccharides or other suitable polymers known to be beneficial to the stability of polypeptides in solid or liquid compositions. A preservative, such as Proxel™, can also be added to extend shelf life or performance of the composition.

In certain embodiments, the compositions of the present disclosure can be used for capturing carbon dioxide.

The compositions of the present disclosure may be prepared in accordance with methods known in the art, which may be in the form of a liquid or a solid composition. For example, the composition may be formulated using methods known to the art of formulating technical enzymes and/or pharmaceutical products, e.g., into coated or uncoated granules or micro-granules. The recombinant carbonic anhydrase polypeptides of the present disclosure may thus be provided in the form of a granule, such as a non-dusting granule, a liquid, in particular a stabilized liquid, a slurry, or a protected polypeptide.

VI. Uses of Carbonic Anhydrase Polypeptides

The recombinant carbonic anhydrase polypeptides disclosed herein are thermostable and can catalyze the interconversion of carbon dioxide ($CO_2$) and bicarbonate. In certain embodiments, a recombinant carbonic anhydrase polypeptide of the present disclosure can be used to hydrate $CO_2$ in the form of bicarbonate and a proton, which in turn, may be converted to carbonate and/or a mixture of bicarbonate and carbonate at an elevated pH. In some embodiments, a recombinant carbonic anhydrase polypeptide of the present disclosure can be used to release CO2 from bicarbonate under conditions that favor the dehydration of bicarbonate. In some embodiments, the recombinant carbonic anhydrase polypeptide are selected from the group consisting of Bgi CA1, Pvi CA1, Ate CA1, Spr CA1, Bag CA1, Vsp CA1, VspE CA1, and VspE CA2.

Accordingly, in certain embodiments, the present disclosure provides methods for extracting $CO_2$ from a $CO_2$-containing medium, such as a gas, a liquid, or multiphase mixture, by contacting the $CO_2$-containing medium with any of the disclosed compositions comprising a recombinant carbonic anhydrase polypeptide to yield a medium reduced in $CO_2$. In some embodiments, the $CO_2$ is extracted to another medium such as a gas or liquid separated from the first medium, but the extraction may also be the conversion of $CO_2$ to bicarbonate or of bicarbonate to $CO_2$, within the same medium. The carbonic anhydrase polypeptides disclosed herein are useful where the temperature of the $CO_2$-containing medium is high (e.g., where commercially available carbonic anhydrases, such as CA-I or CA-II isolated from bovine erythrocytes are not stable).

In certain embodiments, the methods disclosed herein may be used for extracting $CO_2$ from $CO_2$ emission streams, e.g., from carbon-based or hydrocarbon-based combustion in electric generation power plants, or from flue gas stacks from such plants, industrial furnaces, stoves, ovens, or fireplaces or from airplane or car exhausts. The disclosed methods may also be used to remove $CO_2$ in the preparation of industrial gases, including, without limitation, acetylene ($C_2H_2$), carbon monoxide (CO), chlorine ($Cl_2$), hydrogen ($H_2$), methane ($CH_4$), nitrous oxide ($N_2O$), propane ($C_3H_8$), sulfur dioxide ($SO_2$), argon (Ar), nitrogen ($N_2$), and oxygen ($O_2$). The disclosed methods may also be used to remove $CO_2$ from a raw natural gas during the processing to natural gas. Removal of $CO_2$ from the raw natural gas will serve to enrich the methane ($CH_4$) content in the natural gas, thereby increasing the thermal units/$m^3$. Raw natural gas is generally obtained from oil wells, gas wells, and condensate wells. Natural gas contains between 3 and 10% $CO_2$ when obtained from geological natural gas reservoirs by conventional methods.

In resemblance to the methane enrichment of natural gases, the disclosed methods can also be used to enrich the methane content in biogases. Biogases contain a considerable degree of $CO_2$, since the bacteria used in the fermentation process produce methane (60-70%) and $CO_2$ (30-40%). Biogas production may be performed using mesophilic or thermophilic microorganisms. The process temperatures for mesophilic strains are approximately between 25° C. and 40° C. In this temperature range a carbonic anhydrase may be utilized that is of bovine origin since the enzyme is not required to be thermostable. However, a carbonic anhydrase that tolerates higher temperatures, such as the disclosed recombinant carbonic anhydrase polypeptides, will offer improved robustness and fidelity in actual use and storage related to biogas processes utilizing mesophilic strains. Thermophilic strains allow the fermentation to occur at elevated temperatures, e.g., from 40° C. to 75° C. In such processes a heat-stable carbonic anhydrase is particularly useful in methods for removing $CO_2$ from the methane. In certain embodiments, the methods of present disclosure may be used in the production of syngas by removing the $CO_2$ generated by the gasification of a carbon containing fuel (e.g., methane or natural gas) thereby enriching the CO and $H_2$ content of the syngas.

In certain aspects of the methods disclosed herein, the $CO_2$ extraction from a $CO_2$-containing medium can be performed in enzyme-based bioreactors. Before the $CO_2$-containing medium is processed in a bioreactor, it may be purified to free it from contaminants which may disturb the enzymatic reaction or interfere with bioreactor functionality in other ways, e.g., by clotting outlets or membranes. Gasses/multiphase mixtures emitted from combustion processes, e.g., flue gases or exhausts, may be cleared of ash, particles, $NO_x$ and/or $SO_2$, before the gas/multiphase mixture is passed into the bioreactor. The raw natural gas from different regions may have different compositions and separation requirements. Oil, condensate, water, and natural gas liquids, if present in the raw natural gas, may also be removed prior to the extraction of $CO_2$ in an enzyme based bioreactor. The $CO_2$ from the raw natural gas may be extracted in the same process as the sulfur removal, or it may be extracted in a completely separate process. If the gas at this point exceeds the thermostability range of the carbonic anhydrase polypeptides of the present disclosure, some degree of cooling may be needed. Additionally, the reaction temperature may be between 40° C. and 75° C. However, due to the thermostability of the disclosed Carbonic anhydrase polypeptides, the need for cooling can be at least 5° C. less than if a CA-I or CA-II isolated from bovine erythrocytes is applied in the bioreactor.

One example of a suitable type of bioreactor that may be used with any of the compositions or methods disclosed herein is based on a process in which a mixed gas stream (e.g., containing oxygen, nitrogen and carbon dioxide) contacts an enzyme such as a carbonic anhydrase, at a gas-liquid interface to catalyze the conversion of carbon dioxide contained in the gas to bicarbonate or carbonate. The gas-liquid interface in such a bioreactor can for example be provided by an enzyme based hollow fiber membrane bioreactor (HFMB). An example of HFMB is a hollow fiber contained liquid membrane (HFCLM) as described by Majumdar et al., AIChE 1135-1145, 1988. CLMs are made by sandwiching a core liquid between two polymer membranes. The core liquid is suitably continuously re-supplied through a reservoir of liquid membrane solvent. An alternative type of enzyme based CLM permeator useful in a bioreactor is described in Cowan et al., *Ann. NY Acad. Sci.* 984: 453-469, 2003. For example, the bioreactor may contain a liquid membrane constructed by sandwiching a carbonic anhydrase-containing phosphate buffered solution between two hydrophobic, microporous, polypropylene membranes (e.g., Celgard PP-2400). The liquid membrane fluid volume can be maintained by hydrostatic fluid addition from a reservoir, ensuring a constant liquid membrane thickness and prevents separation between the polymer membrane and the metal support. One side of the CLM (the feed membrane) may be contacted with a $CO_2$-containing feed gas stream, and the other side of the CLM (the sweep membrane) may be in contact with a $CO_2$-free sweep gas stream, for example argon. In this bioreactor $CO_2$ from the feed gas stream is converted to bicarbonate in the liquid phase and then returned as $CO_2$ to the sweep gas stream from where it can be stored in the form of compressed $CO_2$. The entire process is catalyzed by the carbonic anhydrase. Alternative CLM permators may be composed of hollow-fiber membrane mats, e.g., Celgard X40-200 or X30-240 instead of hydrophobic, microporous, polypropylene membranes. The hollow-fiber permeator can be arranged into different designs. In one design the permeator is arranged much like a heat exchanger and consists of multiple sets of hollow fiber feed fibers and hollow fiber sweep fibers arranged orthogonally while a carrier fluid fills the space between the feed and sweep fiber bundles (see for example Majumdar et al., AIChE 1135-1145, 1988). Another design is a spiral wound hollow fiber design that can operate in either co-current or counter-current mode. WO 04/104160 describes these and other hollow-fiber permator designs in more detail. WO 04/104160 also describes the use of a phosphate buffer as the membrane liquid. When carbonic anhydrase is added to the membrane liquid it was either dissolved in phosphate buffer or in 1 M $NaHCO_3$. The above type of bioreactor is described in detail in WO 2010/014774 and WO 2010/151787.

Another example of a suitable type of bioreactor that may be used with any of the compositions or methods disclosed herein is based on a process in which a gas phase or multiphase mixture, is contacted with a liquid phase under conditions where the $CO_2$ in the gas phase is absorbed by the liquid phase where it is converted into bicarbonate by a carbonic anhydrase. The bicarbonate enriched liquid is removed from the reactor by a continuous flow, to ensure that the equilibrium between $CO_2$ and bicarbonate is shifted towards continuous conversion of $CO_2$. The gas phase dissolution into the liquid phase is dependent on the surface contact area between the gas and liquid. A large contact area can either be achieved by passing liquid and $CO_2$-containing gas through a packed column or by bubbling the $CO_2$-containing gas through the liquid generating an elevated pressure in the reaction chamber. For example, packed columns can be composed of packings such as raschig rings, berl saddles, intalox metal, intalox saddles, pall rings. The packing materials may be a polymer such as nylon, polystyrene a polyethylene, a ceramic such as silica, or a metal such as aluminum. In both reactor types the liquid is continuously exchanged, hence carbonic anhydrase must be retained in the reactor by various means. In the packed columns the carbonic anhydrase can be immobilized on the packing material. In the "bubbling" reactors the carbonic anhydrase can be entrapped in a porous substrate, for example, an insoluble gel particle such as silica, alginate, alginate/chitosane, alginate/carboxymethylcellulose, or the carbonic anhydrase can be immobilized on a solid packing (as in the packed columns) in suspension in the liquid, or the carbonic anhydrase can be chemically linked in an albumin or PEG network. When the reactors are in operation an aqueous or organic solvent enters the reactor at one end, preferably the top, and flows to the other end, preferably the bottom, and the $CO_2$-containing gas stream (feed gas) enters the reactor at one end, preferably at the opposite end of the solvent (the bottom) and the gas passes through the liquid and exits through a gas outlet at the opposite end (preferably, the top of the reactor). The solvent/liquid that exits the reactor is enriched in bicarbonate and the exit gas is reduced in the $CO_2$ content compared to the feed gas. The bicarbonate containing solution may be processed in subsequent reactions for example to generate pure $CO_2$ or carbonate precipitates such as $CaCO_3$. The exit gas may also be subjected to further rounds of $CO_2$ extraction. The above type of bioreactor is described in detail in U.S. Pat. No. 6,524,843, WO 2004/007058, and WO 2010/151787.

Another suitable type of bioreactor that may be used with any of the compositions or methods disclosed herein utilizes a gas diffusion membrane, such that gaseous $CO_2$, or $CO_2$ from a multiphase mixture is diffused into a capturing liquid by allowing the gaseous $CO_2$ to pass through a gas diffusion membrane. The $CO_2$ may pass into the liquid by diffusion (pressure aided) or the transfer may be aided by a carbonic anhydrase, such as the carbonic anhydrase polypeptides disclosed herein, immobilized on the diffusion membrane, e.g., by cross-linking or by affixing a gel or polymer matrix containing the carbonic anhydrase onto the diffusion membrane. Since the carbonic anhydrase reacts specifically with dissolved $CO_2$, it favors the movement of gaseous $CO_2$ into the fluid by accelerating the reaction of the dissolved $CO_2$ and water to form carbonic acid, thereby removing $CO_2$ rapidly and allowing the dissolution of $CO_2$ from the gas from the feed stream into the water to a greater extent than it would otherwise. The gas diffusion membrane may have a high surface area to facilitate a large flow of the gaseous $CO_2$ through the membrane. Suitable membranes include, without limitation, a polypropylene gas exchange membrane, ePTFE (GORE-TEX®), NAFION® membranes, zeolites, chytosan, polyvinylpyrollindine, cellulose acetate, and immobilized liquid membranes. The $CO_2$/bicarbonate rich fluid that emerges from the gas diffusion membrane is passed by a matrix that contains carbonic anhydrase. The matrix may be contained in a chamber which is separate from the chamber containing the diffusion membrane. Examples of suitable matrixes include, without limitation, beads, fabrics, fibers, membranes, particulates, porous surfaces, rods, and tubes. Specific examples of suitable matrixes include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polypropylene, polymerhydrogels, sephadex, sepharose, silica gel, and TEFLON®-brand PTFE. The carbonic anhydrase may be immobilized to the matrix or entrapped within it Once the $CO_2$ is passed into the liquid, an equilibrium between carbonic acid, bicarbonate and carbonate ions will be established, which process is catalyzed by carbonic anhydrase. Base (e.g., $OH^-$ ions) can then be added to shift the equilibrium to favor the formation of carbonate ions. In the final step, a mineral ion is added to a solution to precipitate carbonate salts. Alternatively, no base is added, thereby predominantly generating bicarbonate ion which can be concentrated using an ion-exchange resin or membrane. The bicarbonate can then be precipitated using sodium, magnesium, or calcium ions. The above type of bioreactor is described in detail in U.S. Pat. No. 7,132,090.

A further suitable type of bioreactor that may be used with any of the compositions or methods disclosed herein includes a partition membrane and a phase-conversion membrane that selectively absorbs a desired component gas from a mixed stream and coverts it into a second phase thereby isolating and purifying the desired component. The partition membranes include, for example, hollow fibers. These hollow fibers can be functionalized to accept covalent or other types of bonding with materials that can act as a bridge to yet other materials, here, for example an enzyme such as a carbonic anhydrase. Additionally, the phase-conversion membrane can be composed of aqueous solvents, protic solvents, aprotic solvents, hydrocarbons, aromatic hydrocarbons, ionic liquids and supercritical fluids, such as supercritical carbon dioxide or supercritical water. Moreover, the phase-conversion membrane can chemically convert the gas to an ionic species soluble in an aqueous medium by way of a phase-conversion catalyst, suitably, an enzyme such as a carbonic anhydrase. The above type of bioreactor is described in detail in WO 2004/104160.

Still another suitable type of bioreactor that may be used with any of the compositions or methods disclosed herein includes a resin-wafer electrodeionization (RW-EDI) for removing the carbon dioxide. The reactor includes cathode and anode electrodes separated by a plurality of porous solid ion exchange resin wafers, which when in use are filled with an aqueous fluid. The plurality of wafers can include one or more basic wafers arranged in a stack between the cathode and the anode. The wafers, anode, and cathode can be interleaved with ion exchange membranes. The basic wafers may contain a porous basic ion exchange medium, and may be adapted to (a) introduce a $CO_2$-containing gas into an aqueous fluid within the basic ion exchange medium to convert $CO_2$ from the gas into bicarbonate ion, and (b) vent a $CO_2$-depleted gas therefrom. In use, $CO_2$ is converted to bicarbonate in the fluid within the wafer under the basic conditions of the basic ion exchange medium. The bicarbonate-containing fluid can then be transported out of the reactor as a concentrated bicarbonate ion solution. The basic ion exchange medium of each wafer may contain a carbonic anhydrase polypeptide to facilitate conversion of gaseous $CO_2$ into bicarbonate ion. Additionally, the carbonic anhydrase polypeptide can be chemically or biochemically bound to the basic ion exchange medium to facilitate conversion of gaseous $CO_2$ into bicarbonate ion. The basic pH value of the basic ion exchange medium can be maintained by applying an electric potential appropriate to achieve the desired current (e.g., commonly about 1 to 6 volts per cell pair) across the cathode and anode to provide a driving force for transport of protons ($H^+$) toward the cathode and hydroxyl ions ($OH^-$) toward the anode through the wafers and ion exchange membranes. The transport of protons and hydroxyl ions may be balanced with the flow of other cations and anions present in the fluid within the ion exchange media of the wafer to maintain the pH in each wafer or portion in its basic state. The above type of bioreactor is described in detail in WO 2010/138792.

The enzyme based bioreactors described above also find more unconventional applications such as in pilot cockpits, submarine vessels, aquatic gear, safety and firefighting gear and astronaut's space suits to keep breathing air free of toxic $CO_2$ levels. Other applications are to remove $CO_2$ from confined spaces, such as to reduce hazardous $CO_2$ levels from inside breweries and enclosed buildings carrying out fermentation, and from $CO_2$ sensitive environments like museums and libraries, to prevent excessive $CO_2$ from causing acid damage to books and artwork.

The recombinant carbonic anhydrase polypeptides of the present disclosure may be used as an independent $CO_2$ extraction catalyst or may alternatively be combined with conventional $CO_2$ extraction technologies such as chemical absorption via amine-based solvents or aqueous ammonia or physical solvents such as SELEXOL™ (Union Carbide) or polyethylene glycol ethers. Such combinations may either be applied in the bioreactors described above or may be applied to already existing $CO_2$ scrubbing facilities based on more conventional techniques.

The recombinant carbonic anhydrase polypeptides disclosed herein also find use in processes for recycling carbon dioxide emissions from a fossil-fuel power plant into useful carbonated species. For example, carbon dioxide emissions may be recycled from a power plant that utilizes either coal or natural gas. In the case of coal, the fuel is burned in a combustion chamber; the heat is used to produce steam from water in a heat recovery steam generator system. The steam propels turbines and alternators producing electric power. The flue gas exiting the combustion chamber is treated to remove ash, $NO_x$ and/or $SO_x$. Rather than exhausting the gas by a stack, the gas is sent to additional heat exchangers and energy recovery systems to cool it down to an adequate temperature for the biological process. Energy is produced by this step. The cooled gas is then treated in a gas treatment unit to remove additional contaminants that may be harmful to the biological process, and finally, $CO_2$ is removed by a bioreactor that contains a free and/or immobilized polypeptide, such as a carbonic anhydrase, that converts $CO_2$ to bicarbonate, and the low $CO_2$ gas is blown to the atmosphere. In the case of natural gas, the fuel is burned directly in the turbine, and the intermediary step of steam production is not present in the main power production stage, although it may be used in subsequent heat recovery stages. This process may also be integrated with a $SO_x$ treatment unit. The above process for recycling carbon dioxide emissions from a fossil-fuel power plant is described in detail in U.S. Pat. No. 7,596,952.

Additionally, the recombinant carbonic anhydrase polypeptides disclosed herein find use in processes for capturing carbon dioxide from a $CO_2$-containing gas using carbonates and biocatalysts or micro-particles containing biocatalysts. For example, this processes includes contacting a $CO_2$-containing gas with an absorption mixture that includes water, biocatalysts, such as carbonic anhydrases, and a carbonate compound to enable dissolution and transformation of $CO_2$ into bicarbonate and hydrogen ions, thereby producing a $CO_2$-depleted gas and an ion-rich solution; and subjecting the ion-rich solution to desorption where the carbonate compound promotes release of the bicarbonate ions from the ion-rich solution producing a $CO_2$ gas stream and an ion-depleted solution. In certain embodiments, the biocatalyst may be comprised in a micro-particle, which can be provided at a concentration sufficient for the absorption mixture flows through the packed bioreactor and are carried with a liquid solution to promote dissolution and transformation of $CO_2$ into bicarbonate and hydrogen ions. Additionally, the carbonate compound may be of a type and may be added in sufficient quantities to promote precipitation of a bicarbonate species during absorption. The precipitates may be part of the ion-rich solution that is sent for desorption or treated separately for conversion into $CO_2$ gas. Additionally, the carbonate compound may be chosen to allow the precipitation of bicarbonate species, such as $KHCO_3$, $NaHCO_3$, or $NH_4HCO_3$. As such, the carbonate compound may include, without limitation, potassium carbonate, sodium carbonate, ammonium carbonate, promoted potassium carbonate solutions and promoted sodium carbonate solutions or promoted ammonium carbonate or mixtures thereof. The above process for capturing carbon dioxide from a $CO_2$-containing gas is described in detail in WO 2011/014956 and WO 2011/01457.

The recombinant carbonic anhydrase polypeptides disclosed herein also find use in systems for accelerating the rate of absorption and reaction of $CO_2$ into the aqueous phase of a carbonate solution to form bicarbonate. In particular, the systems may be used to hydrate carbon dioxide gas in a gas stream to form bicarbonate ions. The systems may utilize a variety of bioreactors, including without limitation, a packed bed, a fluidized bed, a continuous stirred tank, or any other bioreactor disclosed herein. When a packed or fluidized bed bioreactor is used, the gas and liquid streams entering the bioreactor can be in a co-current or counter current configuration. For example, in a co-current system, the gas and liquid streams may enter the bioreactor in the form of microbubbles of gas in the liquid stream. Further, the packing of the bioreactors may be packing material containing an immobilized carbonic anhydrase. For example, the immobilized carbonic anhydrase may be coated on the packing material. In some embodiments, the packing material has a high surface area. Further, the configuration in the bioreactor may be similar to a tray style distillation column wherein the packing material includes a membrane comprising the immobilized carbonic anhydrase is oriented to maximize the surface contact with the gas and liquid streams (e.g., by folding the membrane back on itself in a serpentine configuration).

In one example of such a system, a two unit continuous flow system can be used to hydrate $CO_2$ gas to form bicarbonate ions in a $CO_2$ absorber and dehydrate the bicarbonate ions to $CO_2$, water, and carbonate ions in a $CO_2$ desorber. In some instances, the units may have a packed tower design. A $CO_2$ gas stream enters the bottom of the absorber, and a liquid stream enters the top portion of the absorber. The liquid stream may be distributed over the top of the packing in the middle portion of the absorber by a distributor. The liquid stream wets the surfaces of the packing and flows downward through the absorber while the $CO_2$ gas stream flows upward through the interstices in the packing countercurrent to the flow of the liquid. The packing can provide an area of contact between the liquid and gas phases, and includes a carbonic anhydrase immobilized on its outer surface. The $CO_2$ in the gas stream is absorbed by the liquid, and the treated gas stream leaves the top of the absorber. The liquid is enriched in $CO_2$ as it flows down the column, bicarbonate is formed, and the treated liquid stream leaves the bottom of the absorber. The treated liquid stream can then be pumped to a top portion of the desorber, and may be distributed by a distributor over packing having the immobilized carbonic anhydrase. The bicarbonate within the liquid stream can then be converted to carbon dioxide, water, and carbonate. Reaction rates of this reaction to produce $CO_2$ may be increased by adding heat and by increasing the rate of removal of $CO_2$ from the desorber by operating at below atmospheric pressure. The water and carbonate can be recycled and combined with the liquid stream entering the absorber, and the carbon dioxide may leave the top of the desorber as a gas stream and can be further processed as desired. Alternatively, the absorber may have a carbonic anhydrase immobilized on standard bioreactor packing materials (such as Berl saddle, Intalox saddle, Raschig ring or Pall ring packings commonly used in packed towers) and can be contacted with a microbubble $CO_2$ gas and an aqueous carbonate solution to allow for increased surface area between the gas and liquid for transport of the $CO_2$ gas into the aqueous carbonate solution.

In certain embodiments, the system may include a bioreactor having a membrane wherein a gas stream containing $CO_2$ is in contact with a first surface of the membrane and an aqueous carbonate stream is on a second surface of the membrane. The membrane may be permeable to at least the $CO_2$ gas, but is either impermeable to the aqueous carbonate stream or the first surface is impermeable to the stream. The membrane may also support an immobilized carbonic anhydrase. The $CO_2$ gas in the gas stream can interact with the immobilized carbonic anhydrase and the stream, and then be converted to bicarbonate. The bicarbonate can then be absorbed by the stream in contact with the immobilized enzyme. The membrane material may be a polysaccharide, an ion exchange resin, a treated silicon oxide, a porous metal structure, a carbon rod or tube, a graphite fiber, a silica bead, a cellulose membrane, or a gel matrix (e.g., a polyacrylamide gel, a poly(acryloyl morpholine) gel, a nylon mesh and the like). The desorber may also have a carbonic anhydrase immobilized on standard bioreactor packing materials and a feed of bicarbonate solution from the absorber.

Additionally, these system designs can be combined in different configurations depending on the specific application or gas stream to be treated. For example, the system specifications can be tailored to the $CO_2$ content of the feed stream and the overall purity, recovery, and contaminant levels required for the product streams along with the temperature and pressure requirements of both streams. Moreover, a packed tower may be used as the absorber in conjunction with a membrane bioreactor as the desorber. Alternatively, a membrane bioreactor may be used as the absorber and a packed tower can be used as the desorber. Also, the system design may further include a carbon capture process unit that comprises a standard absorption unit and a stripping (reactive distillation) unit. The core components of the carbon capture system include, for example, an absorbing unit operation, a stripping unit operation, and a heat exchange component between the two unit operations. The above systems for accelerating the rate of absorption and reaction of $CO_2$ are described in detail in WO 2010/037109.

Another aspect of the present disclosure relate to the use of any of the carbonic anhydrase polypeptide-containing compositions disclosed herein to regulate the pH of an aqueous solution. In certain embodiments, an effective amount of the composition is contacted with an aqueous solution under suitable conditions to regulate the pH of the solution to yield a solution having a desired pH value.

Other aspects and embodiments of the present compositions and methods will be apparent from the foregoing description and following examples.

EXAMPLES

The following examples are provided to demonstrate and illustrate certain preferred embodiments and aspects of the present disclosure and should not be construed as limiting.

In the experimental disclosure which follows, the following abbreviations apply: M (molar); mM (millimolar); μM (micromolar); nM (nanomolar); mol (moles); mmol (millimoles); (micromoles); nmol (nanomoles); g and gm (grams); mg (milligrams); μg (micrograms); ng (nanograms); pg (picograms); L (liters); ml and mL (milliliters); μl and μL (microliters); cm (centimeters); mm (millimeters); μm (micrometers); nm (nanometers); U (units); MW (molecular weight); sec (seconds); min(s) (minute/minutes); h(s) and hr(s) (hour/hours); ° C. (degrees Centigrade); QS (quantity sufficient); ND (not done); rpm (revolutions per minute); $H_2O$ (water); $dH_2O$ (deionized water); HCl (hydrochloric acid); aa (amino acid); by (base pair); kb (kilobase pair); kD (kilodaltons); $Na_2SO_4$ (sodium sulfate) $MgCl_2$ (magnesium chloride); NaCl (sodium chloride); Ca (calcium); Mg (magnesium); $SO_4$ (sulfate); $SO_x$ (oxides of sulfur), NO (oxides of nitrogen), $CO_2$ (carbon dioxide); $H_2SO_4$ (sulfuric acid); $NaHCO_3^-$ (sodium bicarbonate); $KHCO_3^-$ (potassium bicarbonate); HEPES (4-(2-hydroxyethyl)-1-piperazineethanesulfonic acid); CHES (N-cyclohexyl-2-aminoethanesulfonic acid); CAPS (N-cyclohexyl-3-aminopropanesulfonic acid); BSA (bovine serum albumin); w/v (weight to volume); v/v (volume to volume); ppm (parts per million); Bgi CA1 (*Bacillus gibsonii* carbonic anhydrase 1); Pvi CA1 (*Promicromonospora vindobonensis* carbonic anhydrase1); Ate CA1 (*Aspergillus terreus* carbonic anhydrase1); Spr CA1 (*Streptomyces pristinaespiralis* carbonic anhydrase1); Bag CA1 (*Bacillus agaradhaerens* carbonic anhydrase 1); Vsp CA1 (*Vibrio* sp. AND4 carbonic anhydrase 1); and VspE CA1 (*Vibrio* sp. EX25 carbonic anhydrase 1).

Example 1

A. Cloning of *Bacillus gibsonii* Carbonic Anhydrase Bgi CA1

A carbonic anhydrase gene, Bgi CA1, was identified from the genome of *Bacillus gibsonii* DSM 8722 strain. The sequence of this gene is depicted in SEQ ID NO: 1. The sequence of the protein encoded by the Bgi CA1 gene is depicted in SEQ ID NO: 2. The gene has an alternative start codon (TTG). At the N-terminus, the protein has a signal peptide of 29 amino acids in length as predicted by SignalP-NN (Emanuelsson et al., Nature Protocols, 2:953-971, 2007). The presence of a signal sequence suggests that Bgi CA1 is a secreted enzyme.

The nucleotide sequence of the Bgi CA1 gene isolated from *Bacillus gibsonii* is set forth as SEQ ID NO: 1:

```
TTGAAACGATCAAATCTACTTATTAAAACGACAGTAGCCGCTACCATT
CTATTAACTAGTACATCCTTTTTGACAGAAGCAATGCTTGCACATGGA
AATCACGTAAGTTCCTCTTCTTTAATTCATTCACCCTATGATCGTTTG
ACTGCGAACGCGTCCCATGATTGGTCATATTCTGGTCCAACAGGTCCT
GAGTTTTGGGGAGAGCTTGACTCTGAATTTAAAGCCTGCTCTAATGGC
ACGCAGCAATCCCCAATTGCACTAGACCCAACCGATGTTGGCGATGAA
AAATGGAGCTTGGACCTAGATTATGCCAAAACAGAGTTTTCCATTGAA
AACAATGGTCATACCATTCAAGCCAATGTGGTTGAAAAAAAAGGACAG
CCTTCCAATCAATTAACACTTGGCGACTCCACATATGAACTGGTTCAA
TTTCATTTTCACTCACCGAGTGAGCATACGCTAGCAGGAGAGTCTTAT
GAAATGGAAGTACACCTTGTTCATAAAGATGAGCAAGACAATCTTGCT
GTGTTAGGCGTATTAATGGAAGAAGGAGAAAAAAACAAAGCTTTAAAA
GATATGTGGAAGAAGATGCCGACTAGTGTCGGAACTTCAACTAAAACC
```

-continued
```
ATTAAGTTAAATCCTAGTGAGCTGGTTCCTACTGATCTATCAACTTTT
CAATATGACGGTTCGCTTACTACCCCGCCTTGCTCTGAAGGTGTGAAG
TGGAGTGTGAGTGACTCTTCAATTACACTCTCTTCGGAACAGCTTCAA
GCTTTTCAAGATTTGTACCCGAATAACTATCGCCCAATTCAAGATTTA
GGGGATCGTGAAGTTGGTTTTCATTAT
```

The amino acid sequence of the Bgi CA1 precursor protein is set forth as SEQ ID NO: 2. the predicted native signal peptide is shown in italics.

```
MKRSNLLIKTTVAATILLTSTSFLTEAMLAHGNHVSSSSLIHSPYDRL
TANASHDWSYSGPTGPEFWGELDSEFKACSNGTQQSPIALDPTDVGDE
KWSLDLDYAKTEFSIENNGHTIQANVVEKKGQPSNQLTLGDSTYELVQ
FHFHSPSEHTLAGESYEMEVHLVHKDEQDNLAVLGVLMEEGEKNKALK
DMWKKMPTSVGTSTKTIKLNPSELVPTDLSTFQYDGSLTTPPCSEGVK
WSVSDSSITLSSEQLQAFQDLYPNNYRPIQDLGDREVGFHY
```

The amino acid sequence of the mature form of Bgi CA1 is set forth as SEQ ID NO: 3:

```
AHGNHVSSSSLIHSPYDRLTANASHDWSYSGPTGPEFWGELDSEFKAC
SNGTQQSPIALDPTDVGDEKWSLDLDYAKTEFSIENNGHTIQANVVEK
KGQPSNQLTLGDSTYELVQFHFHSPSEHTLAGESYEMEVHLVHKDEQD
NLAVLGVLMEEGEKNKALKDMWKKMPTSVGTSTKTIKLNPSELVPTDL
STFQYDGSLTTPPCSEGVKWSVSDSSITLSSEQLQAFQDLYPNNYRPI
QDLGDREVGFHY
```

B. Expression of *Bacillus gibsonii* Carbonic Anhydrase (Bgi CA1)

The Bgi CA1 gene was amplified from genomic DNA of *Bacillus gibsonii* by PCR. PCR was performed using a thermocycler with KOD-plus polymerase (TOYOBA) according to the instructions of the manufacturer (annealing temperature of 59° C.). The primers used were: BgiCA1-Fw 5'-GCGGCTAGCG CAGCACATGG AAATCACGTA AGTT-3' (SEQ ID NO: 4), and BgiCA1-Rv 5'-GCGGT-TAACT CATTAATAAT GAAAACCAAC TTCACG-3' (SEQ ID NO: 5). In order to remove the internal NheI site within the Bgi CA1 gene, an overlap PCR was first carried out to introduce a point mutation in the Bgi CA1 gene (A387 to G387). The primers used to insert the mutation were: BgiCA1-mu-Fw 5'-AGCATACGCT GGCAGGAGAG TCTTATGAAA TGG-3' (SEQ ID NO: 6), and BgiCA1-mu-Rv 5'-CTCTCCTGCC AGCGTATGCT CACTCGGTGA-3' (SEQ ID NO: 7).

The resulting PCR fragment of mature Bgi CA1 DNA was digested with NheI and HpaI and ligated using T4 DNA ligase into pHPLT vector (see, U.S. Pat. No. 6,566,112, containing the *B. licheniformis* LAT promoter (Plat), and additional elements from pUB 110 (McKenzie et al., Plasmid, 15:93-103, 1986) including a replicase gene (reppUB), a neomycin/kanamycin resistance gene (neo) and a bleomycin resistance marker (bleo)) (50 ng/μL) digested with the same restriction enzymes to obtain the expression plasmid pHPLT02-Bgi CA1 (FIG. 1). The reaction conditions used for ligation were according to the instructions of the supplier (New England Biolabs, MA). The pHPLT02 vector contains the thermostable amylase LAT promoter (pLAT) and a signal peptide from *Bacillus licheniformis* strain DSM13 for expression of Bgi CA1. The vector can replicate in *B. subtilis*. The ligation mixture was amplified using a rolling circle kit (GE Healthcare Life Sciences, NJ). A multi-delete *B. subtilis* host strain, which includes the deletion of a number of protease genes (including, e.g., the genes nprE, aprE, nprB, vpr, etc), was transformed with the amplified ligation mixture. The transformed cells were plated on Luria Agar plates supplemented with 10 ppm kanamycin. About 50-100 colonies were obtained, 24 of which were picked and grown in 24-well plates. The sequence of Bgi CA1 gene was confirmed by DNA sequencing. Selected clones from the 24-well plates were further grown in a 7-L fermentor.

The nucleotide sequence of the Bgi CA1 gene of plasmid pHPLT02-Bgi CA1 is set forth as SEQ ID NO: 8. The signal sequence is shown in italics, and the NheI restriction site is shown in bold.

ATGAAAAACATCCGCAAAACGGTCATCTTTGCGGCAATCATCCTGCTG

GTCCATACAGCGGTTCCGGCAATCCCG*GCTAGC*GCAGCACATGGAAAT

CACGTAAGTTCCTCTTCTTTAATTCATTCACCCTATGATCGTTTGACT

GCGAACGCGTCCCATGATTGGTCATATTCTGGTCCAACAGGTCCTGAG

TTTTGGGGAGAGCTTGACTCTGAATTTAAAGCCTGCTCTAATGCACG

CAGCAATCCCCAATTGCACTAGACCCAACCGATGTTGGCGATGAAAAA

TGGAGCTTGGACCTAGATTATGCCAAAACAGAGTTTTCCATTGAAAAC

AATGGTCATACCATTCAAGCCAATGTGGTTGAAAAAAAAGGACAGCCT

TCCAATCAATTAACACTTGGCGACTCCACATATGAACTGGTTCAATTT

CATTTTCACTCACCGAGTGAGCATACGCTGGCAGGAGAGTCTTATGAA

ATGGAAGTACACCTTGTTCATAAAGATGAGCAAGACAATCTTGCTGTG

TTAGGCGTATTAATGGAAGAAGGAGAAAAAAACAAAGCTTTAAAAGAT

ATGTGGAAGAAGATGCCGACTAGTGTCGGAACTTCAACTAAAACCATT

AAGTTAAATCCTAGTGAGCTGGTTCCTACTGATCTATCAACTTTTCAA

TATGACGGTTCGCTTACTACCCCGCCTTGCTCTGAAGGTGTGAAGTGG

AGTGTGAGTGACTCTTCAATTACACTCTCTTCGGAACAGCTTCAAGCT

TTTCAAGATTTGTACCCGAATAACTATCGCCCAATTCAAGATTTAGGG

GATCGTGAAGTTGGTTTTCATTATTAA

The amino acid sequence of the Bgi CA1 precursor protein expressed from plasmid pHPLT02-Bgi CA1 is set forth as SEQ ID NO: 9:

MKNIRKTVIFAAIILLVHTAVPAIPASAAHGNHVSSSSLIL HSPYDR

LTANASHDWSYSGPTGPEFWGELDSEFKACSNGTQQSPIALDPTDVGD

EKWSLDLDYAKTEFSIENNGHTIQANVVEKKGPSNQLTLGDSTYELVQ

FHFHSPSEHTLAGESYEMEVHLVHKDEQDNLAVLGVLMEEGEKNKALK

DMWKKMPTSVGTSTKTIKLNPSELPTDLSTFQYDGSLTTPPCSEGVKW

SVSDSSITLSSEQLQAFQDLYPNNYRPIQDLGDREVGFHY

Several signal sequences were used to express Bgi CA1. These sequences are listed in Table 1B-1.

TABLE 1B-1

Signal sequences used to express Bgi CA1

| SEQ ID | Signal Sequence (SS) |
|---|---|
| NO: 10 | MKNIRKTVIFAAIILLVHTAVPAIPASA |
| NO: 11 | MIKKWAVHLLFSALVLLGLSGASA |
| NO: 12 | MAAEKVFSKNKIIGGKRMSYMKRSISVF IACFMVAALGISGIIAPKASA |
| NO: 13 | MKKTIMSLAAAAAMSATAFGATASA |
| NO: 14 | MKKFACVVIFLLLAAVIAGCAADASA |
| NO: 15 | MKKRLMSLLVCILVLVPAAGASA |

Protein Purification of Bgi CA1

Bgi CA1 protein was purified from concentrated broth from a 7-L fermentor run using three chromatography columns: 1) a phenyl sepharose column equilibrated with 20 mM Tris HCl buffer, pH 8.0, containing 1 M ammonium sulfate, from which the protein was eluted in the void volume; 2) an anion exchange Q sepharose column equilibrated with 20 mM Tris HCl buffer, pH 8.0, from which the protein was eluted using a linear gradient of equilibration/wash buffer to 20 mM Tris HCl, pH 8.0 buffer containing 0.5 M NaCl; 3) a Superdex 75 gel filtration column, from which the protein was eluted using 20 mM sodium phosphate, pH 7.0, containing 0.15 M NaCl. The purified protein fractions were pooled and concentrated using a 3K Amicon Ultra-15 device and the concentrated protein fraction was used in further studies.

C. Carbonic Anhydrase Activity of Bgi CA1

The carbonic anhydrase activity of purified Bgi CA1 was measured on ice in 20 mM Tris sulfate buffer (pH 8.3 at 25° C.) containing 20 mM $Na_2SO_4$. Briefly, 3 mL of chilled 20 mM Tris sulfate buffer (pH 8.3 at 25° C.) containing 20 mM $Na_2SO_4$ was added to a 50-mL polypropylene conical tube placed on ice. 20 µL of enzyme sample or buffer was added to the tubes followed by 2 mL of chilled $CO_2$ saturated water (purified and deionized using Milli-Q Integral system, Millipore). After the contents were mixed, a standardized pH meter probe was immediately inserted into the solution and the time required for the pH to drop from 8.3 to 6.3 was recorded using a stop watch. The test was repeated until at least three blank measurements (with buffer added) were within a 15-second time window and the average of three determinations ($T_{Blank,avg}$) was between 70 and 100 seconds. A standard curve was prepared using bovine carbonic anhydrase II (bCAII, Sigma C2522). The test measurements for determining activity were performed in triplicate, and $T_{enzyme,avg}$ was obtained.

One unit of activity (Wilbur-Anderson (W-A) unit, Wilbur and Anderson, *J. Biol. Chem.* 176, 147-154, 1948) is defined as the time required for the pH of a 0.02 M Trizma buffer to drop from 8.3 to 6.3 per min at 0° C.:

Units/mL enzyme=$(T_{Blank,avg}-T_{enzyme,avg})$*
DF/$(T_{enzyme,avg}*V)$ where DF=dilution factor of enzyme sample, V=volume (in mL) of enzyme used, $T_{Blank,avg}$=average time values of Blank measurements, and $T_{enzyme,avg}$=average time values of Test measurements.

Units/mg protein=(units/mL enzyme)/(mg protein/mL enzyme)

The specific activity of purified Bgi CA1 was determined to be 4023±387 units/mg using the above method. Carbonic anhydrase activity of Bgi CA1 is suitable for enzyme based $CO_2$ extraction.

D. Temperature Stability of Bgi CA1

Figure 2A:
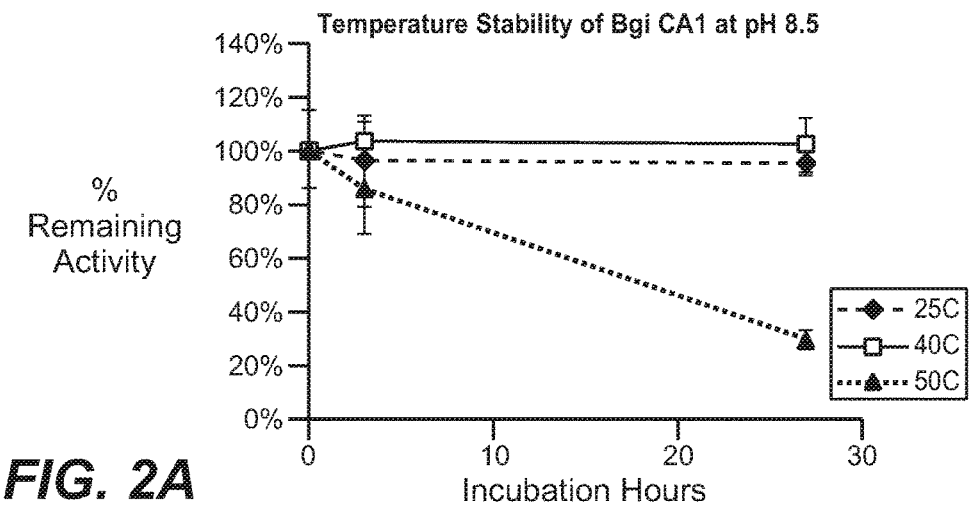
FIGS. 2A-C provide temperature stability profiles of Bgi CA1 at pH values of (A) 8.5, (B) 9.5 and (C) 10.5, respectively.
Figure 2B:
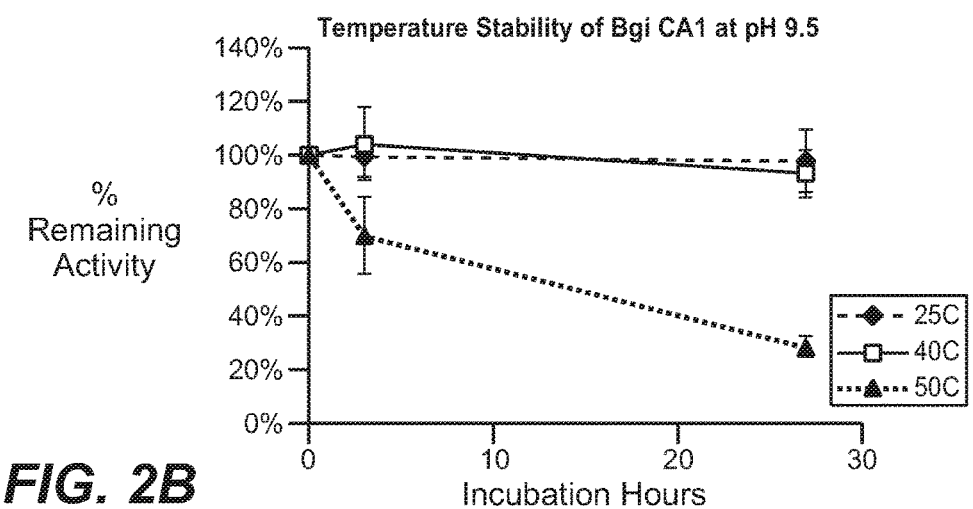
Figure 2C:
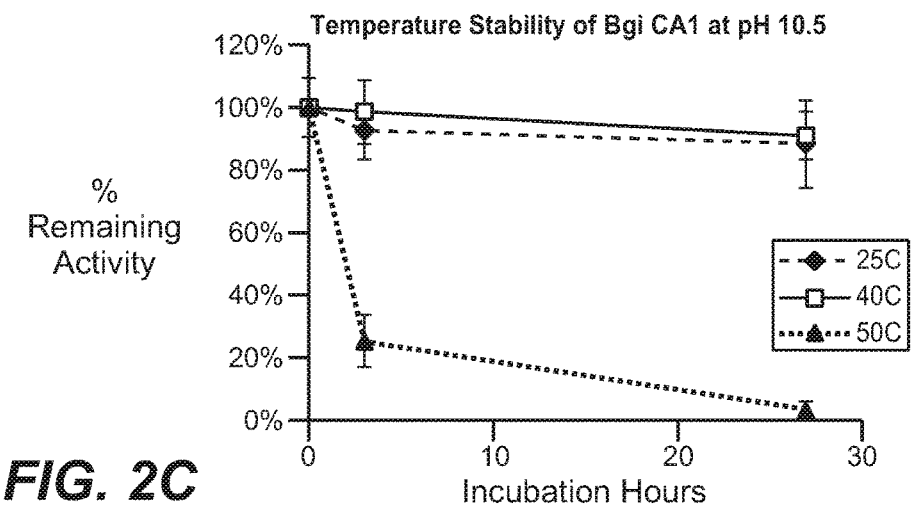

The temperature stability of Bgi CA1 was determined in 0.1 M Tris buffer, pH 8.5 (adjusted by $H_2SO_4$ at 25° C.), 0.1 M CHES buffer, pH 9.5 (adjusted by $H_2SO_4$ at 25° C.), and 0.1 M CAPS buffer, pH 10.5 (adjusted by $H_2SO_4$ at 25° C.). $Na_2SO_4$ was added to the buffer to a final concentration of 25 mM. 100 ppm Bgi CA1 in buffer, in 20 mL final volume, was incubated at room temperature (25° C.), or in a water bath at 40° C. and 50° C. At different time points (5 minutes to 24 hours), 0.5 mL of the enzyme sample from each tube was taken and placed on ice. The specific activity of each enzyme sample was measured as described in Example 1C. The specific activity measurements were performed in triplicates. The percent remaining activity was calculated at each time point and at each pH value. For each pH value, the activity of the sample at time 0 was defined as 100% activity. As shown in FIGS. 2A-C, Bgi CA1 retained more than 90% activity over a 24-hour incubation period at 25° C. and 40° C. At 50° C., at least 70% of the activity was retained after a 3-hour incubation period at pH 8.5 and pH 9.5, and 25% activity was retained at pH 10.5. Thus, Bgi CA1 is stable over different pH ranges typically used for enzymatic $CO_2$ extraction, and at supra-physiological temperatures.

E. Stability of Bgi CA1 in 1M $NaHCO_3$

Figure 3:
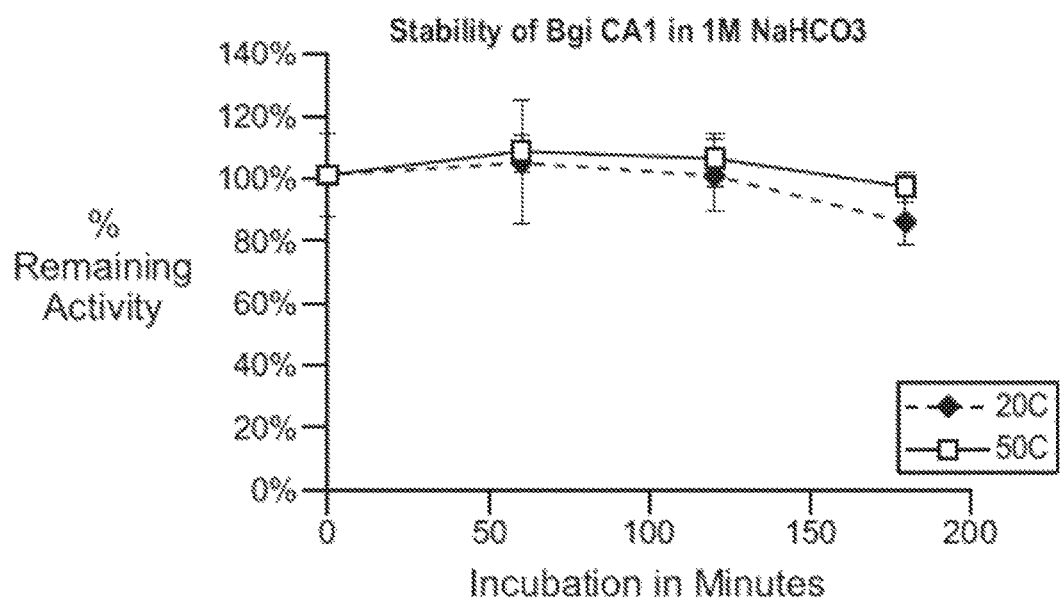
FIG. 3 provides a stability profile of Bgi CA1 in the presence of 1 M sodium bicarbonate ($NaHCO_3$).

The stability of Bgi CA1 under high ionic strength condition was determined in a 1 M $NaHCO_3$ solution. In a PCR machine, a 100 ppm solution of Bgi CA1 in 1 M $NaHCO_3$ was incubated at 20° C. and 50° C. The specific activities of the samples were measured as described in Example 1C. Prior to incubation and at varying time points (5 minutes to 3 hours), 100 µL samples were withdrawn, cooled on ice and their specific activity measured. The specific activity measurements were performed in triplicates. The percent remaining activity was calculated for each time point. The activity of the sample kept on ice at time 0 was defined as 100% activity. FIG. 3 shows stability of Bgi CA1 in 1 M $NaHCO_3$. Bgi CA1 retains most of the activity over a 3-hour incubation period at both 20° C. and 50° C. Thus, Bgi CA1 is stable in the presence of high concentrations of $NaHCO_3$ that are encountered in enzymatic $CO_2$ extraction.

F. Heat Capacity Measurement of Bgi CA1

Excessive heat capacity curves were measured for Bgi CA1 and bovine carbonic anhydrase II (bCA II) using an ultrasensitive scanning high-throughput microcalorimeter, VP-Cap DSC (MicroCal, Inc., Northampton, Mass.). The standard procedure for DSC measurements and the theory of the technique has been described previously (Freire, Differential Scanning calorimetry, *Methods Mol. Biol.*, 41:191-218, 1995). About 500 µL of a 0.5 mg/mL sample of each enzyme was studied. The proteins were scanned over a 35-100° C. temperature range. The same samples were then re-scanned (following cooling) to check the reversibility of the thermal unfolding process. For both carbonic anhydrases studied the thermal unfolding was irreversible. The proteins were studied in the following buffers: (1) 0.1 M Tris, pH 8.5, (2) 0.1 M CHES, pH 9.5, (3) 0.1 M CAPS, pH 10.5, and (4) 0.1 M CHES, pH 9.5+2 M NaCl. A 200° C./hr scan rate was used to minimize any artifacts that might have resulted from aggregation. The apparent thermal midpoint [$T_m$(app)] of the DSC curves was used as an indicator of the thermal stability and melting points for these carbonic anhydrase molecules. The melting temperature (Tm app) of each enzyme in various buffers is shown in Table 1F-1.

The $T_m$(app) values during thermal unfolding for both the carbonic anhydrase proteins showed a dependence on pH over the range 8.5-to-10.5. Bovine carbonic anhydrase II has highest $T_m$(app) values between pH 8.5 and 9.5, while Bgi CA1 has the highest $T_m$(app) values at pH 8.5. The buffer of 0.1 M CHES, pH 9.5, with 2 M NaCl decreased the $T_m$(app) for bovine CA II, and increased the $T_m$(app) for Bgi CA1. For Bgi CA1, the carbonate buffer increased the $T_m$(app) substantially, and the 0.1 M CHES, pH 9.5 with 2 M NaCl increased the $T_m$ by about 15° C. Thus, Bgi CA1 is suitable for enzymatic $CO_2$ extraction at higher temperatures because the $T_m$ of this enzyme increases in carbonate solution and under high ionic strength conditions typical of enzymatic $CO_2$ extraction.

TABLE 1F-1

Melting Temperature for Bgi CA1 and bCAII

| | Buffers | | | |
|---|---|---|---|---|
| | #1 | #2 | #3 | #4 |
| Protein | 0.1M Tris, pH 8.5 | 0.1M CHES, pH 9.5 | 0.1M CAPS, pH 10.5 | 0.1M CHES, pH 9.5 + 2M NaCl |
| Bovine CA II | 68.8 | 69.4 | 66.6 | 61.7 |
| Bgi CA1 | 59.9 | 56.9 | 56.6 | 71.9 |

$T_m$(app) was also determined for bCAII and Bgi CA1 in 1 M $KHCO_3$ with no added NaCl and at various concentrations of added NaCl, ranging from 0.1 M to 1 M (Table 1F-2). $T_m$(app) decreased for bCAII in bicarbonate solution as compared to $T_m$(app) in buffer, while $T_m$(app) increased for Bgi CA1 in bicarbonate solution, and with increased ionic strength. This increase in $T_m$(app) indicated the suitability of the enzyme Bgi CA1 in enzymatic $CO_2$ extractions, especially in the presence of high concentrations of carbonate solutions and at high ionic strength conditions. It was also noted that the Tm(app) of Bgi CA1 increases with increasing $KHCO_3$ concentration, which was unexpected.

TABLE 1F-2

$T_m$(app) [° C.] of Bgi CA1 in 1M $KHCO_3$

| [Salt] (M) | bCA II | Bgi CA1 |
|---|---|---|
| 0 | 62.1 | 70.9 |
| 0.1 | 62.8 | 71.4 |
| 0.5 | 62.5 | 74.1 |
| 1 | 62.7 | 76.6 |

G. Homology Identification

The Bgi CA1 mature protein sequence (252 residues) was subjected to a BLASTP search, and the top ten protein sequences were selected for sequence alignment (Vector NTI, Invitrogen) (see FIGS. 4A-B). Table 1G-1 shows the percent identities and NCBI Accession Nos. of the aligned sequences NP_241226 (SEQ ID NO:16), NP_767777 (SEQ ID NO:17), NP_946147 (SEQ ID NO:18), YP_003428428

Figure 5:
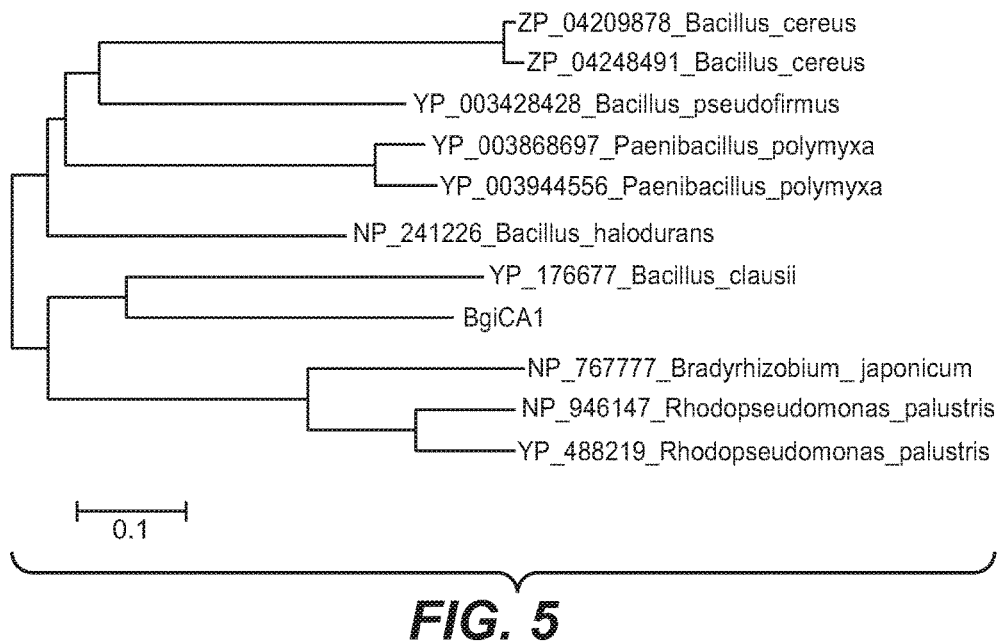
FIG. 5 provides a phylogenetic tree for Bgi CA1 and its homologs.

(SEQ ID NO:19), YP_003868697 (SEQ ID NO:20), YP_003944556 (SEQ ID NO:21), YP_176677 (SEQ ID NO:22), YP_488219 (SEQ ID NO:23), ZP_04209878 (SEQ ID NO:24), and ZP_04248491 (SEQ ID NO:25). The aligned sequences were used to prepare a phylogenetic tree using the program MEGA 5 (see, Tamura K. et al. Molecular Biology and Evolution, 2011, in press). FIG. 5 shows the phylogenic tree for Bgi CA1 and its homologs.

TABLE 1G-1

Percent Identity Shared by Bgi CA1 and Similar Sequences

| Homolog | SEQ ID NO: | % Identity (PID) |
|---|---|---|
| NP_241226 | 16 | 42 |
| NP_767777 | 17 | 40 |
| NP_946147 | 18 | 43 |
| YP_003428428 | 19 | 43 |
| YP_003868697 | 20 | 40 |
| YP_003944556 | 21 | 40 |
| YP_176677 | 22 | 51 |
| YP_488219 | 23 | 40 |
| ZP_04209878 | 24 | 42 |
| ZP_04248491 | 25 | 38 |

Example 2

A. Cloning of *Promicromonospora vindobonensis* Carbonic Anhydrase1 Pvi CA1

A carbonic anhydrase gene, Pvi CA1, was identified from the genome of *Promicromonospora vindobonensis* YIM65009 strain. The sequence of this gene is depicted in SEQ ID NO: 26. The protein encoded by the Pvi CA1 gene is depicted in SEQ ID NO: 27. The gene has an alternative start codon (GTG). At the N-terminus, the protein has a signal peptide with a length of 25 amino acids as predicted by SignalP-NN (Emanuelsson et al., *Nature Protocols*, 2: 953-971, 2007). The presence of a signal sequence suggests that Pvi CA1 is a secreted enzyme.

The nucleotide sequence of the Pvi CA1 gene isolated from *Promicromonospora vindobonensis* is set forth as SEQ ID NO: 26:

```
GTGAAGAAGCTCGCCCTGCCCACCGTCCTGCTCCTCGCCCCGTTGCTCGC
GTCCTGCGCGTCGGGCACCGCCGCCGACGGCGAGACGTCCGCACCCCCGC
CGCCCGCGACCGACGAGGTGCACTGGTCCTACGAAGGGGACACGGGCCCG
GACAACTGGGGCCAGCTCTCCGACGAGTTCGTCGAGTGCTCGATCGGCGA
GGCGCAGTCCCCCGTCGACCTGCCGGACCACGCCGACGAGACGACCACCG
AGCCCCCGACGGTCACGACGTGGCCCACCGTCGGCGAGTCGGTCGACACC
GGCCACACGATCCAGCTCGTGCCCGACGGCGACGCGTCCGAGGTCGAGTG
GCAGGACACCACGTTCGACCTCGCCCAGGTGCACTTCCACATGCCCTCGG
AGCACACGATCGAGGGTGAGGCGCTCGACGCCGAGTTCCACTTCGTCCAC
ACCACGGAGGAAGGACAGGCGCTCGTCATCGGGGTCCTCGCGCGGGAGAG
CAGCACCGAGAACGAGGCCTGGCAGCCGTTCATCGATGGTGCGGCCGAGC
CGGGCACCGAGGACCTGCCGCTCGACGTCGCCGCGATGCTACCGACGGAC
CCGACGTTCGAGGAGTACACGGGCAGCCTCACGACCCCGCCGTGCACCGA
```

-continued
```
GGGCGTCGAGTGGGTCGTCTACCACGAGCCCATCGAGCTGTCGGCGGAGC
AGATCGCCGTGCTCAGGGACGCGTACGACAACACCGCGCGCCCGACCCAG
CTCCTGGGCGACCGCGTCGTGTACGAGGGCACCATCGACGTGGAGGCGGA
GGAGGCGCAC
```

The amino acid sequence of the Pvi CA1 precursor protein is set forth as SEQ ID NO: 27. The predicted signal peptide is shown in italics.

```
MKKLALPTVLLLAPLLASCASGTAADGETSAPPPPATDEVFMSYEGDTGP
DNWGQLSDEFVECSIGEAQSPVDLPDHADETTTEPPTVTTWPTVGESVDT
GHTIQLVPDGDASEVEWQDTTFDLAQVHFHMPSEHTIEGEALDAEFHFVH
TTEEGQALVIGVLARESSTENEAWQPFIDGAAEPGTEDLPLDVAAMLPTD
PTFEEYTGSLTTPPCTEGVEWVVYHEPIELSAEQIAVLRDAYDNTARPTQ
LLGDRVVYEGTIDVEAEEAH
```

The amino acid sequence of the mature form of Pvi CA1 is set forth as SEQ ID NO: 28:

```
DGETSAPPPPATDEVHWSYEGDTGPDNWGQLSDEFVECSIGEAQSPVDLP
DHADETTTEPPTVTTWPTVGESVDTGHTIQLVPDGDASEVEWQDTTFDLA
QVHFHMPSEHTIEGEALDAEFHFVHTTEEGQALVIGVLARESSTENEAWQ
PFIDGAAEPGTEDLPLDVAAMLPTDPTFEEYTGSLTTPPCTEGVEWVVYH
EPIELSAEQIAVLRDAYDNTARPTQLLGDRVVYEGTIDVEAEEAH
```

B. Expression of *Promicromonospora vindobonensis* Carbonic Anhydrase1 (Pvi CA1)

The Pvi CA1 gene was amplified from genomic DNA of *Promicromonospora vindobonensis* by PCR. PCR was performed on a thermocycler with KOD-plus polymerase (TOYOBA) according to the instructions of the manufacturer (annealing temperature of 59° C.). The primers used were: PviCA1-Fw 5'-AGCGCTAGCC GGCCCCCCGG CACAGGCCGA CGGCGAGACG TCCGCACCCC-3' (SEQ ID NO: 29), and PviCA1-RV 5'-TCCGGATCCT TAGTGCGCCT CCTCCGCCTCCACGT-3' (SEQ ID NO: 30).

Figure 6:
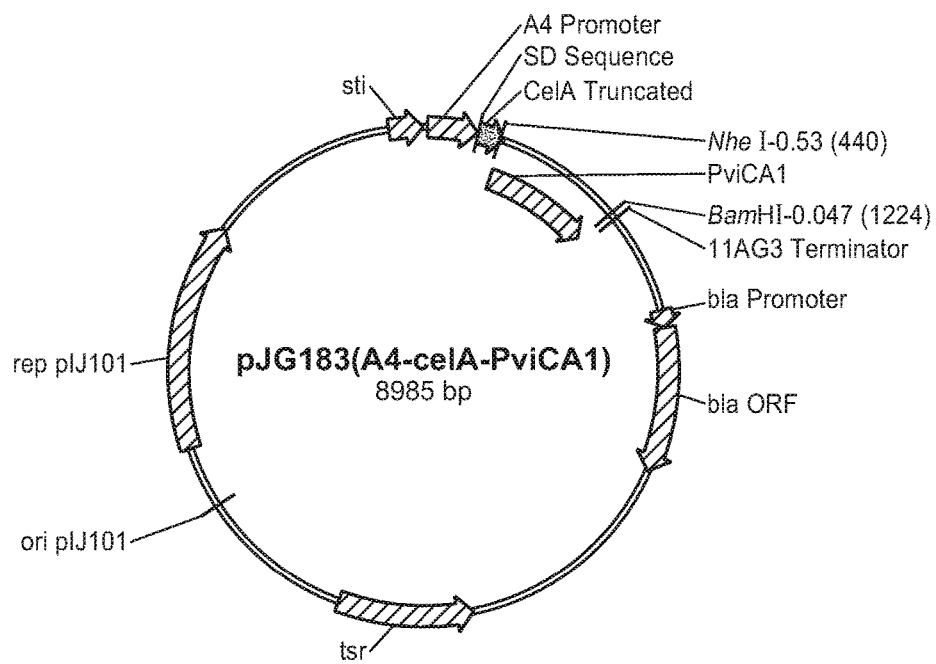
FIG. 6 provides a plasmid map of pJG183 (A4-celA-PviCA1).

The resulting PCR fragment of mature Pvi CA1 DNA was digested with NheI and BamHI, and ligated into the pKB128 vector, and then digested with the same restriction enzymes to obtain the expression plasmid pJG183 (FIG. 6). The pKB128 plasmid is a derivative of the pKB105 plasmid (as described in U.S. Patent Application Publication No. 2006/0154843) and is the source of the A4 promoter-CelA signal sequence. The ligation mixture was used to transform *E. coli* TOP 10 chemically competent cells (Invitrogen Corp.) following the manufacturer's protocol. The transformed cells were plated on Luria Agar plates supplemented with 50 ppm ampicillin and incubated overnight at 37° C. Three transformants were picked from the plate and inoculated into 5 mL Luria Broth supplemented with 50 ppm ampicillin. Cultures were grown overnight at 37° C., plasmid DNA extracted and the correct sequence of the Pvi CA1 gene was confirmed by DNA sequencing. The pJG183 plasmid was then used to transform *S. lividans* TK23 derived protoplasts (as described in U.S. Patent Application Publication No.

2006/0154843). The transformation techniques used are described in Kieser et al., *Practical Streptomyces Genetics*, The John Innes Foundation, Norwich, United Kingdom, 2000. Transformed cells were plated on R5 selection plates and incubated at 30° C. for 3 days. One clone from the *Streptomyces* transformation plate was inoculated in TSG medium in shake flasks at 28° C. for 3 days. Cultures were then transferred to a *Streptomyces* 2 Modified Medium (as described in U.S. Patent Application Publication No. 2006/0154843) and incubated for an additional 4 days at 28° C.

The TSG medium was prepared using the following ingredients: 16 g BD Difco tryptone, 4 g BD Bacto soytone, 20 g Sigma caseine (hydrolysate), and 10 g potassium phosphate, dibasic, brought to 1 L. After autoclaving, 50% glucose was added to a final concentration of 1.5%.

The R5 plates were prepared using the following ingredients: 206 g sucrose, 0.5 g $K_2SO_4$, 20.24 g $MgCl_2$, 20 g glucose, 0.2 g Difco casamino acids, 10 g Difco yeast extracts, 11.46 g TES, 4 g L-Asp, 4 mL of trace elements, 44 g Difco agar, 20 mL 5% $K_2HPO_4$, 8 mL 5 M $CaCl_2.2H_2O$ and 14 mL 1 N NaOH were added to a final volume of 1 L after autoclaving. After 20 hours, a layer of thiostrepton (50 μg/mL final concentration) was plated on the top of the plates.

The nucleotide sequence of the Pvi CA1 gene of plasmid pJG183 (A4-celA-PviCA1) is set forth as SEQ ID NO: 31:

```
GACGGCGAGACGTCCGCACCCCGCCGCCCGCGACCGACGAGGTGCACTG

GTCCTACGAAGGGGACACGGGCCCGGACAACTGGGGCCAGCTCTCCGACG

AGTTCGTCGAGTGCTCGATCGGCGAGGCGCAGTCCCCGTCGACCTGCCG

GACCACGCCGACGAGACGACCACCGAGCCCCCGACGGTCACGACGTGGCC

CACCGTCGGCGAGTCGGTCGACACCGGCCACACGATCCAGCTCGTGCCCG

ACGGCGACGCGTCCGAGGTCGAGTGGCAGGACACCACGTTCGACCTGCCC

CAGGTGCACTTCCACATGCCCTCGGAGCACACGATCGAGGGTGAGGCGCT

CGACGCCGAGTTCCACTTCGTCCACACCACGGAGGAAGGACAGGCGCTCG

TCATCGGGGTCCTCGCGCGGGAGAGCAGCACCGAGAACGAGGCCTGGCAG

CCGTTCATCGATGGTGCGGCCGAGCCGGGCACCGAGGACCTGCCGCTCGA

CGTCGCCGCGATGCTACCGACGGACCCGACGTTCGAGGAGTACACGGGCA

GCCTCACGACCCCGCCGTGCACCGAGGGCGTCGAGTGGGTCGTCTACCAC

GAGCCCATCGAGCTGTCGGCGGAGCAGATCGCCGTGCTCAGGGACGCGTA

CGACAACACCGCGCGCCCGACCCAGCTCCTGGGCGACCGCGTCGTGTACG

AGGGCACCATCGACGTGGAGGCGGAGGAGGCGCAC
```

Protein Purification of Pvi CA1

*Streptomyces lividans* cells expressing Pvi CA1 were grown in shake flasks under standard conditions. The Pvi CA1 was purified from fermentation broth using two chromatography columns: 1) an anion exchange Q sepharose column equilibrated with 20 mM Tris HCl buffer, pH 8.0, from which the protein was eluted using a linear gradient of equilibration/wash buffer to 20 mM Tris HCl, pH 8.0 buffer containing 0.5 M NaCl; 2) a Superdex 75 gel filtration column, from which the protein was eluted using 20 mM sodium phosphate, pH 7.0, containing 0.15 M NaCl. The purified protein fractions were pooled and concentrated using a 3K Amicon Ultra-15 device and the concentrated protein fraction was used in further studies.

C. Carbonic Anhydrase Activity of Pvi CA1

The carbonic anhydrase activity of purified Pvi CA1 was measured on ice in 20 mM Tris sulfate buffer (pH 8.3 at 25° C.) containing 20 mM $Na_2SO_4$. Briefly, 3 mL of chilled 20 mM Tris sulfate buffer (pH 8.3 at 25° C.) containing 20 mM $Na_2SO_4$ was added to a 50-mL polypropylene conical tube placed on ice. 20 μL of enzyme sample or buffer was added to the tubes followed by 2 mL of chilled $CO_2$ saturated water (purified and deionized using Milli-Q Integral system, Millipore). After the contents were mixed, a standardized pH meter probe was immediately inserted into the solution and the time required for the pH to drop from 8.3 to 6.3 was recorded using a stop watch. The test was repeated until at least three blank measurements (with buffer added) were within a 15-second time window and the average of three determinations ($T_{Blank,avg}$) was between 70 and 100 seconds. A standard curve was prepared using bovine carbonic anhydrase II (bCAII, Sigma C2522). The test measurements for determining activity were performed in triplicate, and $T_{enzyme,avg}$ was obtained.

One unit of activity (Wilbur-Anderson or W-A unit, Wilbur and Anderson, *Journal of Biological Chemistry* 176, 147-154, 1948) is defined as the time required for the pH of a 0.02 M Trizma buffer to drop from 8.3 to 6.3 per min at 0° C.:

Units/mL enzyme=$(T_{Blank,avg}-T_{enzyme,avg})$* DF/$(T_{enzyme,avg}*V)$ where DF=dilution factor of enzyme sample, V=volume (in mL) of enzyme used, $T_{Blank,avg}$=average time values of Blank measurements, and $T_{enzyme,avg}$=average time values of Test measurements.

Units/mg protein=(units/mL enzyme)/(mg protein/mL enzyme)

The specific activity of purified Pvi CA1 was determined to be 937±65 units/mg using the above method. Carbonic anhydrase activity of Pvi CA1 is suitable for enzyme based $CO_2$ extraction.

D. Temperature Stability of Pvi CA1

Figure 7A:
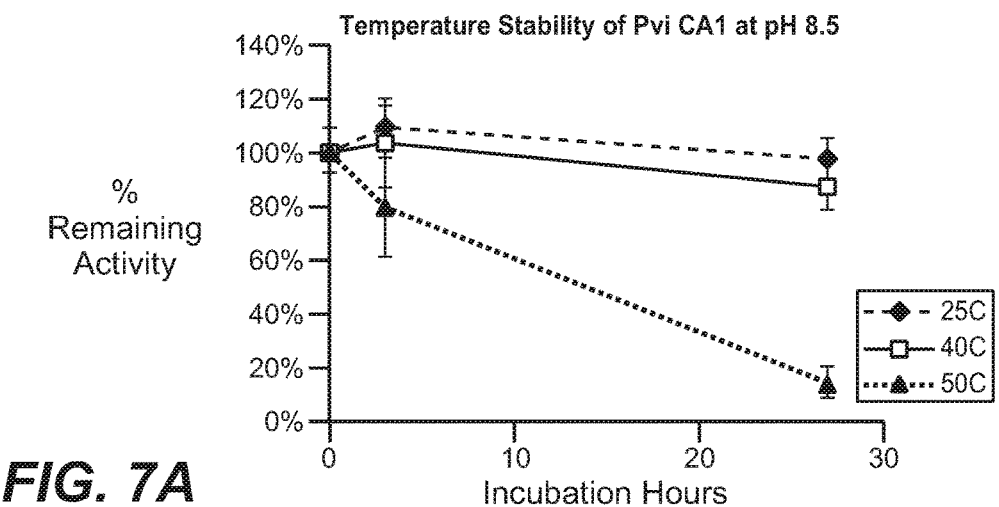
FIGS. 7A-C provide temperature stability profiles of Pvi CA1 at pH values of (A) 8.5, (B) 9.5 and (C) 10.5, respectively.
Figure 7B:
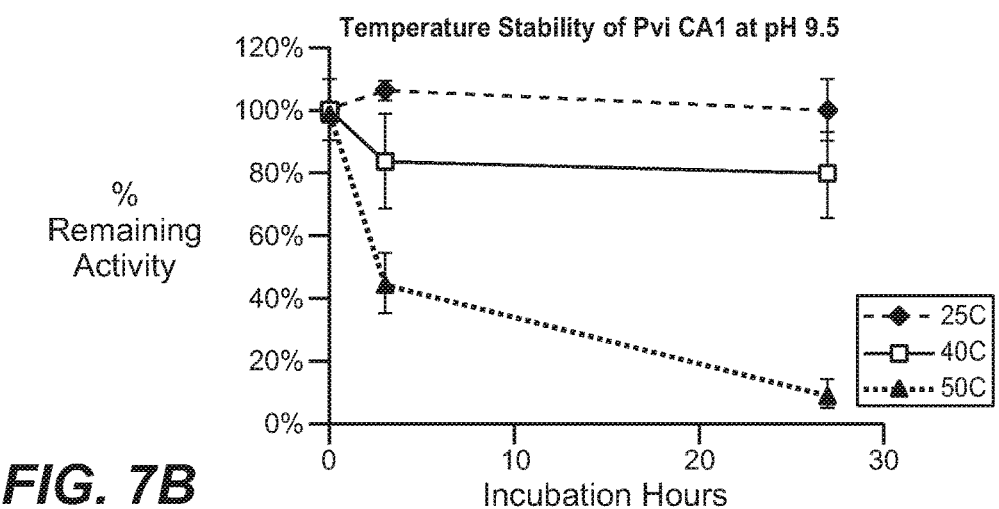
Figure 7C:
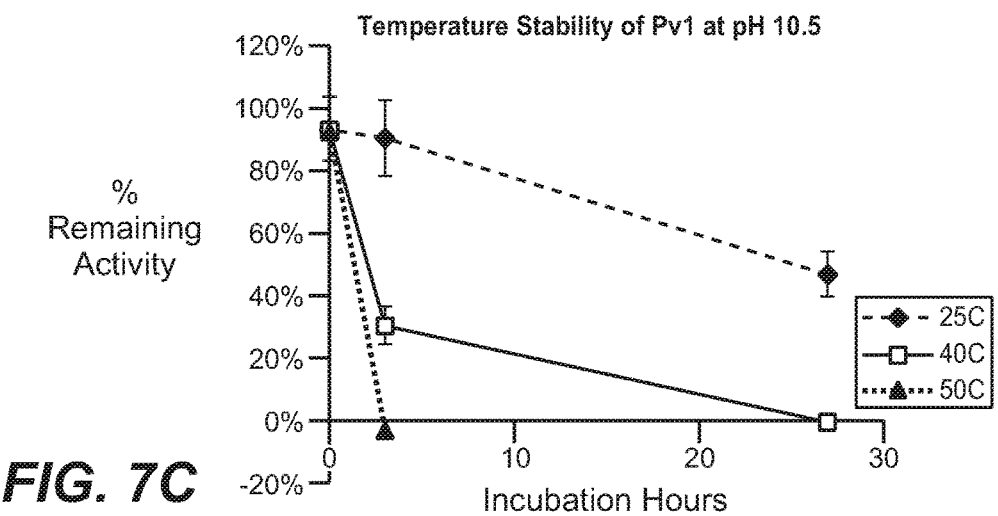

The temperature stability of Pvi CA1 was determined in 0.1 M Tris buffer, pH 8.5 (adjusted by $H_2SO_4$ at 25° C.), 0.1 M CHES buffer, pH 9.5 (adjusted by $H_2SO_4$ at 25° C.), and 0.1 M CAPS buffer, pH 10.5 (adjusted by $H_2SO_4$ at 25° C.). $Na_2SO_4$ was added to the buffer to a final concentration of 25 mM. 100 ppm of Pvi CA1 in buffer, in 20 mL final volume, was incubated in a water bath at 40° C. and 50° C. One sample was also incubated at the room temperature (25° C.). At different time points (5 minutes to 24 hours), 0.5 mL of the enzyme sample from each tube was taken and placed on ice. The specific activity of each enzyme sample was measured as described in Example 2C. The specificity activity measurements were performed in triplicates. The percent remaining activity was calculated at each time point, at each pH value. For each pH value, the activity of the sample kept at 0° C. at time 0 was defined as 100% activity. The Pvi CA1 retained 80% activity at 25° C. at pH 8.5 and pH 9.5. At 40° C., the enzyme retained more than 70% activity at pH 8.5 and pH 9.5 for 27 hrs, and 30% activity at pH 10.5 for 3 hrs. Stability of Pvi CA1 is thus suitable for enzymatic CO$_2$ sequestration processes at different pH values. As shown in FIGS. 7A-C, Pvi CA1 is stable over different pH ranges typically used for enzymatic CO$_2$ extraction, and at supra-physiological temperatures.

E. Stability of Pvi CA1 in 1 M NaHCO$_3$

Figure 8:
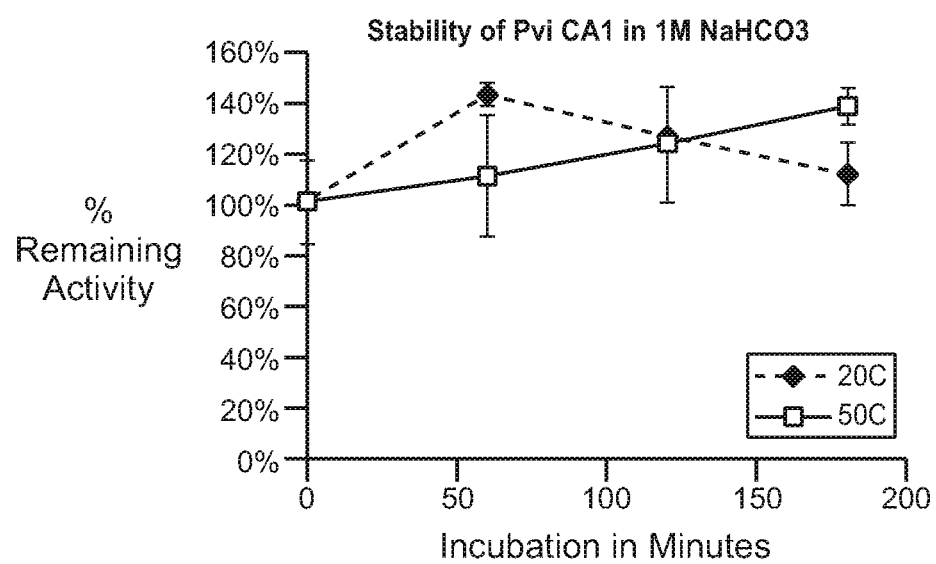
FIG. 8 provides a stability profile of Pvi CA1 in the presence of 1 M sodium bicarbonate ($NaHCO_3$).

The stability of Pvi CA1 under high ionic strength conditions was assessed. In a PCR machine, a 100 ppm solution of Pvi CA1 in 1 M NaHCO$_3$ was incubated at 20° C. and 50° C. The specific activities of the samples were measured prior to incubation as described in Example 2C. At varying time points (5 minutes to 3 hours), 100 µL samples were withdrawn, cooled on ice and their specific activity measured as described in Example 2C. The percent remaining activity was calculated for each time point. The activity of the sample kept on ice at time 0 was defined as 100% activity. FIG. 8 shows stability of Pvi CA1 in 1 M NaHCO$_3$. Pvi CA1 retains most of the activity over a 3-hr incubation period at both 20° C. and 50° C. Thus, Pvi CA1 is stable in the presence of high concentrations of NaHCO$_3$ that are encountered in enzymatic CO$_2$ extraction.

F. Heat Capacity Measurement of Pvi CA1

Excessive heat capacity curves were measured for Pvi CA1 and bovine carbonic anhydrase II (bCA II) using an ultrasensitive scanning high-throughput microcalorimeter, VP-Cap DSC (MicroCal, Inc., Northampton, Mass.). The standard procedure for differential scanning calorimetry (DSC) measurements and the theory of the technique has been described previously (Freire, *Methods Mol Biol*, 41:191-218, 1995). About 500 µL of a 0.5 mg/mL sample of each enzyme was studied. The proteins were scanned over a 35-100° C. temperature range. The same samples were then re-scanned (following cooling) to check the reversibility of the thermal unfolding process. For both carbonic anhydrases studied the thermal unfolding was irreversible. The proteins were studied in the following buffers: (1) 0.1 M Tris, pH 8.5, (2) 0.1 M CHES, pH 9.5, (3) 0.1 M CAPS, pH 10.5, and (4) 0.1 M CHES, pH 9.5+2 M NaCl. A 200° C./hr scan rate was used to minimize any artifacts that might have resulted from aggregation. The apparent thermal midpoint [T$_m$(app)] of the DSC curves was used as an indicator of the thermal stability and melting temperature for these carbonic anhydrase molecules. The melting temperature (Tm app) of each enzyme in various buffers is shown in Table 2F-1.

The T$_m$(app) values during thermal unfolding for both the carbonic anhydrase proteins showed a dependence on pH over the range of pH 8.5 to pH 10.5. Bovine carbonic anhydrase II has highest T$_m$(app) values between pH 8.5 and pH 9.5, while Pvi CA1 has the highest T$_m$(app) values at pH 8.5. The buffer of 0.1 M CHES, pH 9.5, with 2 M NaCl decreased the T$_m$(app) for bovine CA II, and increased the T$_m$(app) for Pvi CA1. For Pvi CA1, the buffer of 0.1 M CHES, pH 9.5 with 2 M NaCl increased the T$_m$(app) by about 6° C. compared to 0.1 M CHES buffer, pH 9.5 with no additives. Thus, Pvi CA1 is suitable for enzymatic CO$_2$ extraction at higher temperatures because the T$_m$ of this enzyme increases in carbonate solution and under high ionic strength conditions typical of enzymatic CO$_2$ extraction.

TABLE 2F-1

Melting Point Temperature for Pvi CA1 and bCAII

| Protein | Buffers | | | |
|---|---|---|---|---|
| | #1 0.1M Tris, pH 8.5 | #2 0.1M CHES, pH 9.5 | #3 0.1M CAPS, pH 10.5 | #4 0.1M CHES, pH 9.5 + 2M NaCl |
| Bovine CA II | 68.8 | 69.4 | 66.6 | 61.7 |
| Pvi CA1 | 70.5 | 66.9 | 62.6 | 73.7 |

T$_m$(app) was also determined for bCAII and Pvi CA1 in 1 M KHCO$_3$ with no added NaCl, at various concentrations of added NaCl, ranging from 0.1 M to 1 M (Table 2F-2). T$_m$(app) decreased for bCAII in bicarbonate solution as compared to T$_m$(app) in buffer, while T$_m$(app) increased for Pvi CA1 in bicarbonate solution, and with increased ionic strength. This increase in T$_m$(app) indicated the suitability of the enzyme Pvi CA1 for enzymatic CO$_2$ extraction, especially in the presence of high concentrations of carbonate solutions and at high ionic strength conditions. This observation of a higher Tm(app) at higher ionic strength was unexpected.

TABLE 2F-2

T$_m$(app) [° C.] of Pvi CA1 in 1M KHCO$_3$

| [Salt] (M) | bCA II | Pvi CA1 |
|---|---|---|
| 0 | 62.1 | 72.1 |
| 0.1 | 62.8 | 73.3 |
| 0.5 | 62.5 | 74.6 |
| 1 | 62.7 | 75.8 |

G. Homology Identification

Figure 10:
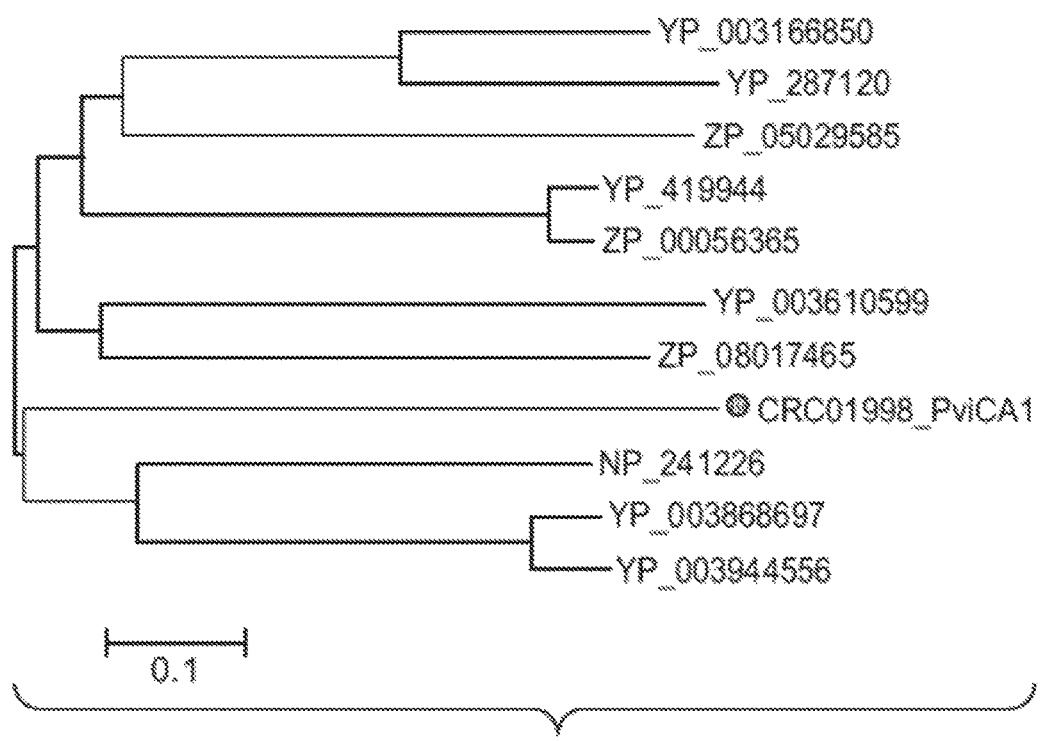
FIG. 10 provides a phylogenetic tree for Pvi CA1 and its homologs.

The Pvi CA1 mature protein sequence (245 residues) was subjected to a BLASTP search, and the top ten protein sequences were selected for sequence alignment (Vector NTI, Invitrogen). FIGs. A-D show an alignment of Pvi CA1 with similar carbonic anhydrase sequences. Table 2G-1 shows the percent identities and NCBI Accession Nos. of the aligned sequences: NP_241226 (SEQ ID NO: 16), YP_003166850 (SEQ ID NO: 32), YP_003610599 (SEQ ID NO: 33), YP_003868697 (SEQ ID NO: 20), YP_003944556 (SEQ ID NO: 21), YP_287120 (SEQ ID NO: 34), YP_419944 (SEQ ID NO: 35), ZP_00056365 (SEQ ID NO: 36), ZP_05029585 (SEQ ID NO: 37), and ZP_08017465 (SEQ ID NO: 38). The aligned sequences were used to prepare a phylogenetic tree using the program MEGA 5 (see, Tamura K. et al. Molecular Biology and Evolution, 2011, in press)). FIG. 10 shows the phylogenic tree for Pvi CA1 and its homologs.

TABLE 2G-1

Percent Identity Shared by Pvi CA1 and Similar Sequences

| Homolog | SEQ ID NO: | % IDENTITY (PID) |
|---|---|---|
| NP_241226 | 16 | 39 |
| YP_003166850 | 32 | 38 |
| YP_003610599 | 33 | 37 |
| YP_003868697 | 20 | 36 |
| YP_003944556 | 21 | 36 |

TABLE 2G-1-continued

Percent Identity Shared by Pvi CA1 and Similar Sequences

| Homolog | SEQ ID NO: | % IDENTITY (PID) |
|---|---|---|
| YP_287120 | 34 | 34 |
| YP_419944 | 35 | 39 |
| ZP_00056365 | 36 | 39 |
| ZP_05029585 | 37 | 37 |
| ZP_08017465 | 38 | 38 |

Example 3

A. Sequence of *Aspergillus terreus* Carbonic Anhydrase1 (Ate CA1)

Genomic DNA of *Aspergillus terreus* NIH2624 was purchased from Fungal Genetics Stock Center, Kansas City, Mo. (FGSC A1156). The nucleic acid sequence for the Ate CA1 gene (NCBI Reference Sequence NT_165972.1), and the amino acid sequence of the hypothetical protein encoded by the Ate CA1 gene was found in the NCBI Databases (NCBI Accession No. XP_001210252).

B. Expression of *Aspergillus terreus* Carbonic Anhydrase1 (Ate CA1)

The Ate CA1 gene was amplified from the genomic DNA of *Aspergillus terreus* NIH2624 by PCR. PCR was performed on a thermocycler with KOD-plus polymerase (TOYOBA) according to the instructions of the manufacturer, with an annealing temperature of 59° C.). Primer design was based on the sequence of the Ate CA1 genomic DNA. The following primers were used to amplify the Ate CA1 gene: AteCA1-Fw 5'-GCGGCGGCCG CACCAT-GAAG CTCACTGCTG CCGTT-3' (SEQ ID NO: 39); and AteCA1-Rv 5'-CCGGCGCGCC CTTACTAGTT GAG-GCTCTTG GCCG-3' (SEQ ID NO: 40). The forward primer contains a NotI restriction site, and the reverse primer contains an AscI restriction site.

Figure 11:
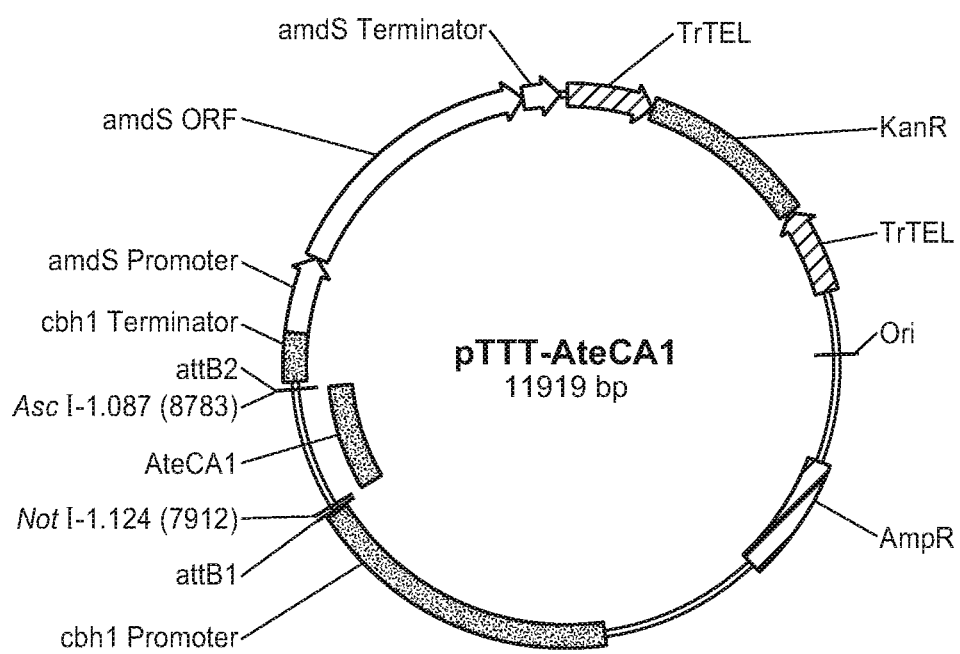
FIG. 11 provides a plasmid map of pTTT-AteCA1.

The PCR product was purified, digested with NotI and AscI, ligated into plasmid vector pTTT (derived from vector pTTT, as described in US2011/0020899A1), and digested with the same restriction enzymes to obtain pTTT-Ate CA1. The plasmid map of pTTT-Ate CA1 is shown in FIG. 11. *E. coli* TOP 10 chemically competent cells (Invitrogen Corp.) were transformed with the ligation mixture following the manufacturer's protocol. The transformed cells were plated on Luria Agar plates supplemented with 50 ppm ampicillin and incubated overnight at 37° C. Three transformants from the plates were picked, inoculated in 5 mL of Luria Broth supplemented with 50 ppm ampicillin, and grown overnight. Plasmid DNA extracted from these cultures was sent for sequence confirmation.

Following sequence confirmation, protoplasts of a quad deleted *T. reesei* strain (as described in WO 05/001036) were transformed with the expression plasmid pTTT-Ate CA1 using the PEG protoplast method (Penttila et al, *Gene*, 61:155-164, 1987). For protoplast preparation, spores were grown for about 10 hours at 24° C. in *Trichoderma* Minimal Medium MM (20 g/L glucose, 15 g/L KH$_2$PO$_4$, pH 4.5, 5 g/L (NH$_4$)2SO$_4$, 0.6 g/L MgSO$_4$×7H$_2$O, 0.6 g/L CaCl$_2$× 2H$_2$O, 1 mL of 1000× *T. reesei* Trace elements solution (175 g/L Citric Acid anhydrous, 200 g/L FeSO$_4$×7H$_2$O, 16 g/L ZnSO$_4$×7H$_2$O, 3.2 g/L CuSO$_4$, 1.4 g/L MnSO$_4$×H2O, and 0.8 g/L Boric Acid). Germinating spores were harvested by centrifugation and treated with 30 mg/mL Vinoflow FCE (Novozymes, AG Switzerland) solution for from 7 hours to overnight at 30° C. at 100 rpm to lyse the fungal cell walls. Protoplasts were washed in 0.1 M Tris HCl buffer (pH 7) containing 0.6 M sorbitol and resuspended in 10 mM Tris HCl buffer (pH 7.5) containing 1.2 M sorbitol and 10 mM calcium chloride. For PEG transformation, approximately 1 µg of DNA and 1-5×10$^7$ protoplasts in a total volume of 200 µL were treated with 2 mL of 25% PEG solution, diluted with 2 volumes of 1.2 M sorbitol/10 mM Tris, pH 7.5/10 mM CaCl$_2$ solution. Transformants were selected on a medium containing acetamide as a sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L; pH 4.25). Transformed colonies (about 50-100) appeared in about 1 week. After growth on acetamide plates, the spores were collected and reselected on acetamide plates. After 5 days, the spores were collected using 10% glycerol, and 1×10$^8$ spores were inoculated in a 250 mL shake flask with 30 ml Glucose/Sophorose defined medium for protein expression. Protein expression was confirmed by SDS-PAGE. The spore suspension was subsequently grown in a 7 L fermentor in a defined medium containing 60% glucose-sophorose feed. Glucose/Sophorose defined medium (per liter) consists of (NH$_4$)2SO$_4$ 5 g, PIPPS buffer 33 g, Casamino Acids 9 g, KH$_2$PO$_4$ 4.5 g, CaCl$_2$ (anhydrous) 1 g, MgSO$_4$.7H$_2$O 1 g, pH to 5.5 adjusted with 50% NaOH with Milli-Q H$_2$O to bring to 966.5 mL. After sterilization, the following were added: 26 mL 60% Glucose/Sophrose, and 400× *T. reesei* Trace Metals 2.5 mL.

The nucleotide sequence of the Ate CA1 gene of pTTT-Ate CA1 is set forth as SEQ ID NO: 41. (The intron sequence is underlined).

```
ATGAAGCTCACTGCTGCCGTTCTCTCCCTGGCTGTGGCCGCCTCGGCCTC

TTGCATCCGCCATGCCCGTCGGGCTGACGGCGTCGTTGAGACCAACTCCT

ATAACTACACCGAGATGGGCGGTCCGCTGAACTGGTACGGCCTGGACCCC

GAGGCCAACTCTGCCTGCGCCACGGGCAAGCACCAGTCCCCCATCGTCAT

CCACTCCGAGGACATCGACTATGTCTCCCCGGGATCCCTGAAGTTCGACA

TCCCCAAGGCCGACTACGCCAAGTTTGAGAACCTTGGGTCCGGCCTCGAG

GTCGTTCTGACCAACGGATCTCTCACTGTGGGCAACAAGAGCCTTCCCCT

GGCCCAGTTCCACTTCCATACCCCCAGCGAGCACCGCGTCAACGACGAGT

ACTATCCCATGGAGGTTCACTTTGTGTTCCAAAACAAGGGTATGCAGCGT

CCCATGCACTCTACAAGTATCAACCCTAACATCGTATAGCCAAAGACACC

GCCGTCGTCGGCTTCTTCTTCCAGCTCTCCGAGCTCGGATACTCCGTCCC

CCTGTTCGACACCATCTTCGACCACGTTCTCGAGATCGAGGAGCCTGGTG

CCTTCACCCACACCGGGGAGATGGACTTCGCCGGCCTGACCCACCACCTC

TACATGCATGGCATCTACCAGTACTCTGGCTCCCTGACCACCCCTCCCTG

CTCCGAGGACGTCGCCTGGTACCTGAGCACCGAGCCCCTGCCCCTGACCG

TCCAGGACTACAACAAGGTCAAGAAGGTGCTCAAGTACAACGCGCGCTAC

ACACAGAACGCCCTGGGCGAGGACAACCTCCTCGAGGTGGCGGCCAAGAG

CCTCAACTAG
```

The amino acid sequence of the Ate CA1 precursor is set forth as SEQ ID NO: 42. The predicted signal peptide sequence is shown in italics.

MKLTAAVLSLAVAASASCIRHARRADGVVETNSYNYTEMGGPLNWYGLDP

EANSACATGKHQSPIVIHSEDIDYVSPGSLKFDIPKADYAKFENLGSGLE

VVLTNGSLTVGNKSLPLAQFHFHTPSEHRVNDEYYPMEVHFVFQNKAKDT

AVVGFFFQLSELGYSVPLFDTIFDHVLEIEEPGAFTHTGEMDFAGLTHHL

YMHGIYQYSGSLTTPPCSEDVAWYLSTEPLPLTVQDYNKVKKVLKYNARY

TQNALGEDNLLEVAAKSLN

The amino acid sequence of the mature form of Ate CA1 is set forth as SEQ ID NO: 43.

SCIRHARRADGVVETNSYNYTEMGGPLNTNYGLDPEANSACATGKHQSPI

VIHSEDIDYVSPGSLKFDIPKADYAKFENLGSGLEVVLTNGSLTVGNKSL

PLAQFHFHTPSEHRVNDEYYPMEVHFVFQNKAKDTAVVGFFFQLSELGYS

VPLFDTIFDHVLEIEEPGAFTHTGEMDFAGLTHHLYMHGIYQYSGSLTTP

PCSEDVAWYLSTEPLPLTVQDYNKVKKVLKYNARYTQNALGEDNLLEVAA

KSLN

The nucleotide sequence of the Ate CA1 gene of pTTT-Ate CA1 without the intron sequence is set forth as SEQ ID NO: 44

```
atgaagctcactgctgccgttctctccctggctgtggccgcctcggcctc
ttgcatccgccatgcccgtcgggctgacggcgtcgttgagaccaactcct
ataactacaccgagatgggcggtccgctgaactggtacggcctggacccc
gaggccaactctgcctgcgccacgggcaagcaccagtcccccatcgtcat
ccactccgaggacatcgactatgtctccccgggatccctgaagttcgaca
tccccaaggccgactacgccaagtttgagaaccttgggtccggcctcgag
gtcgttctgaccaacggatctctcactgtgggcaacaagagccttcccct
ggcccagttccacttccataccccagcgagcaccgcgtcaacgacgagt
actatcccatggaggttcactttgtgttccaaaacaaggccaaagacacc
gccgtcgtcggcttcttcttccagctctccgagctcggatactccgtccc
cctgttcgacaccatcttcgaccacgttctcgagatcgaggagcctggtg
ccttcacccacaccggggagatggacttcgccggcctgacccaccacctc
tacatgcatggcatctaccagtactctggctccctgaccacccctccctg
ctccgaggacgtcgcctggtacctgagcaccgagcccctgccctgaccg
tccaggactacaacaaggtcaagaaggtgctcaagtacaacgcgcgctac
acacagaacgccctgggcgaggacaacctcctcgaggtggcggccaagag
cctcaactag
```

Purification of Ate CA1

Ate CA1 was purified from concentrated fermentation broth of a 7-L fermentor using three chromatography columns: 1) a phenyl sepharose column equilibrated with 20 mM Tris HCl, pH 8.0, containing 1 M ammonium sulfate, from which the protein was eluted using a linear gradient of the equilibration/wash buffer to 20 mM Tris HCl buffer, pH 8.0; 2) a DEAE sepharose column equilibrated with 20 mM Tris HCl buffer, pH 8.0, from which the protein was eluted using a linear gradient of equilibration/wash buffer to 20 mM Tris HCl buffer, pH 8.0, 0.5 M NaCl; and 3) a Superdex 75 gel filtration column, from which the protein was eluted using 20 mM sodium phosphate, pH 7.0, containing 0.15 M NaCl. The purified protein fractions were pooled and concentrated using a 3K Amicon Ultra-15 device, and the concentrated protein fraction was used in further studies.

C. Carbonic Anhydrase Activity of Ate CA1

The carbonic anhydrase activity of purified Ate CA1 was measured on ice in 20 mM Tris sulfate buffer (pH 8.3 at 25° C.) containing 20 mM $Na_2SO_4$. Briefly, 3 mL of chilled 20 mM Tris sulfate buffer (pH 8.3 at 25° C.) containing 20 mM $Na_2SO_4$ was added to a 50-mL polypropylene conical tube placed on ice. 20 µL of enzyme sample or buffer was added to the tubes followed by 2 mL of chilled $CO_2$ saturated water (purified and deionized using MilliQ Integral system, Millipore). After the contents were mixed, a standardized pH meter probe was immediately inserted into the solution and the time required for the pH to drop from 8.3 to 6.3 was recorded using a stop watch. The test was repeated until at least three blank measurements (with buffer added) were within a 15-second time window and the average of three determinations ($T_{Blank,avg}$) was between 70 and 100 seconds. A standard curve was prepared using bovine carbonic anhydrase II (bCAII, Sigma C2522). The test measurements for determining activity were performed in triplicate, and $T_{enzyme,avg}$ was obtained.

One unit of activity (Wilbur-Anderson (W-A) unit, Wilbur and Anderson, Journal of Biological Chemistry 176:147-154, 1948) is defined as the time required for the pH of a 0.02 M Trizma buffer to drop from 8.3 to 6.3 per min at 0° C.

Units/mL enzyme=$(T_{Blank,avg} - T_{enzyme,avg})$* DF/$(T_{enzyme,avg} * V)$ where DF=dilution factor of enzyme sample, V=volume (in mL) of enzyme used, $T_{Blank,avg}$=average time values of Blank measurements, and $T_{enzyme,avg}$=average time values of Test measurements.

Units/mg protein=(units/mL enzyme)/(mg protein/mL enzyme)

The specific activity of purified Ate CA1 was determined to be 1,327±285 units/mg using the above method. Thus, carbonic anhydrase activity of Ate CA1 is sufficient for enzymatic $CO_2$ sequestration processes.

D. Temperature Stability of Ate CA1

Figure 12A:
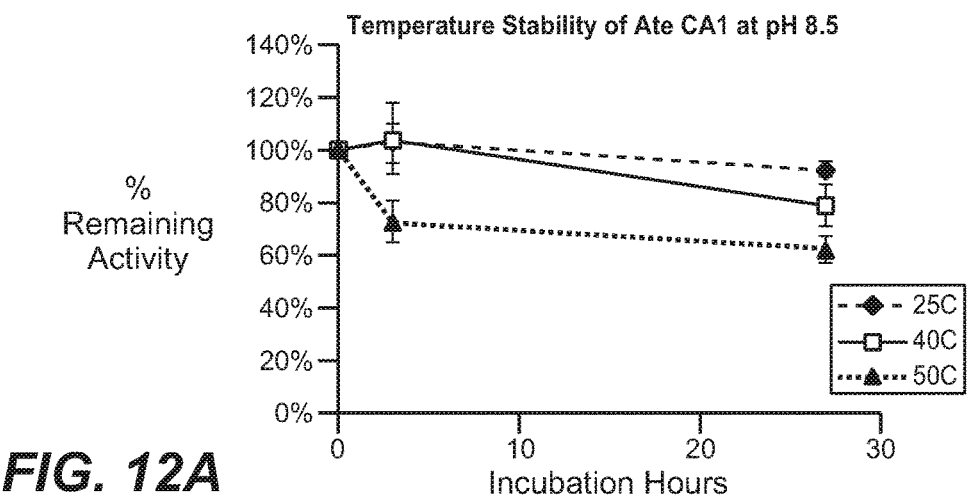
FIGS. 12A-C provide temperature stability profiles of Ate CA1 at pH values of (A) 8.5, (B) 9.5, and (C) 10.5, respectively.
Figure 12B:
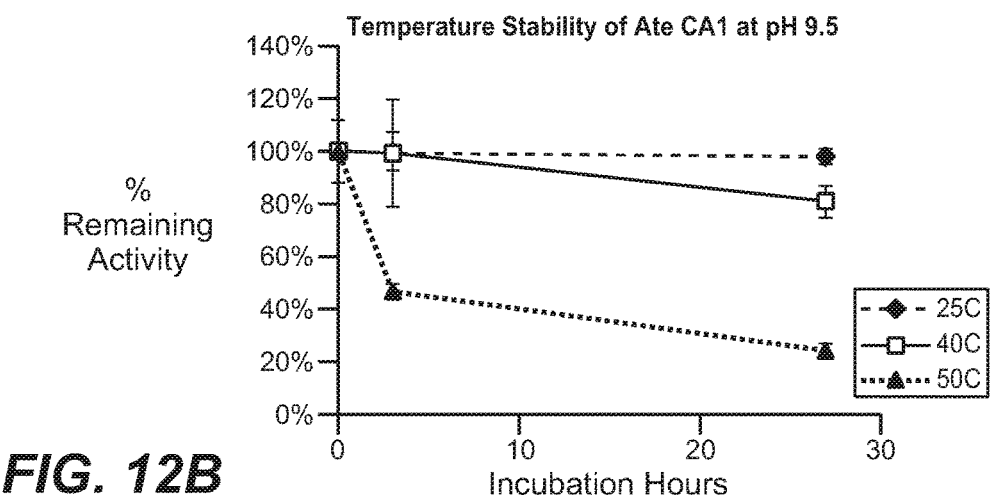
Figure 12C:
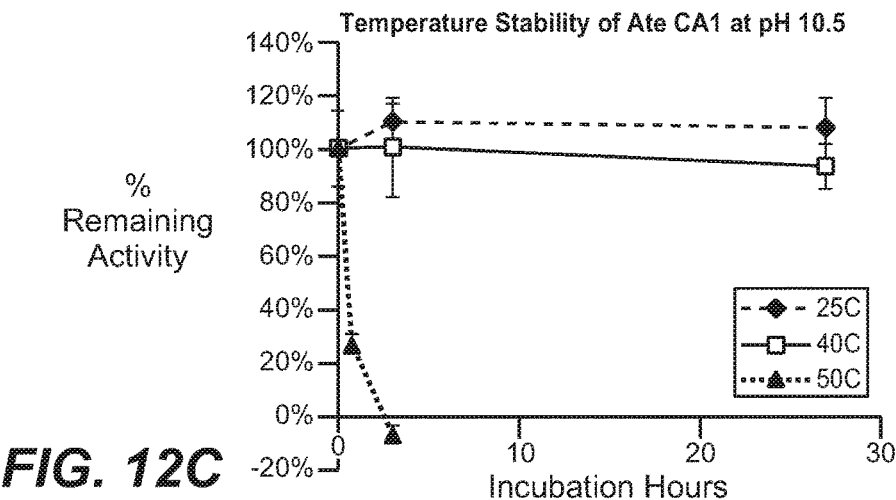

The temperature stability of Ate CA1 was determined in 0.1 M Tris buffer, pH 8.5 (adjusted with $H_2SO_4$ at 25° C.), 0.1 M CHES buffer, pH 9.5 (adjusted with $H_2SO_4$ at 25° C.), and 0.1 M CAPS buffer, pH 10.5 (adjusted with $H_2SO_4$ at 25° C.). $Na_2SO_4$ was added to the buffer to a final concentration of 25 mM. 100 ppm of Ate CA1 in buffer, in 20 mL final volume, was incubated in a water bath at 40° C. and 50° C. One sample was also incubated at room temperature (25° C.). At different time points (5 minutes to 24 hours), 0.5 mL of the enzyme sample from each tube was taken and placed on ice. The specific activity of each enzyme sample was measured as described in Example 3C. The specific activity measurements were performed in triplicates. The percent remaining activity was calculated at each time point, and at each pH value. For each pH value, the activity of the sample kept at 0° C. at time 0 was defined as 100% activity. Ate CA1 retained most of the activity under all pH conditions at 25° C. and 40° C. for 27 hrs. Also, Ate CA1 retained at least 60% activity at 50° C., pH 8.5 for 27 hrs, and retained about 50% activity at pH 9.5 for 3 hrs. As shown in FIGS. 12A-C, Ate CA1 is stable over different pH ranges typically used for enzymatic $CO_2$ extraction, and at supra-physiological temperatures.

E. Stability of Ate CA1 in 1 M $NaHCO_3$

Figure 13:
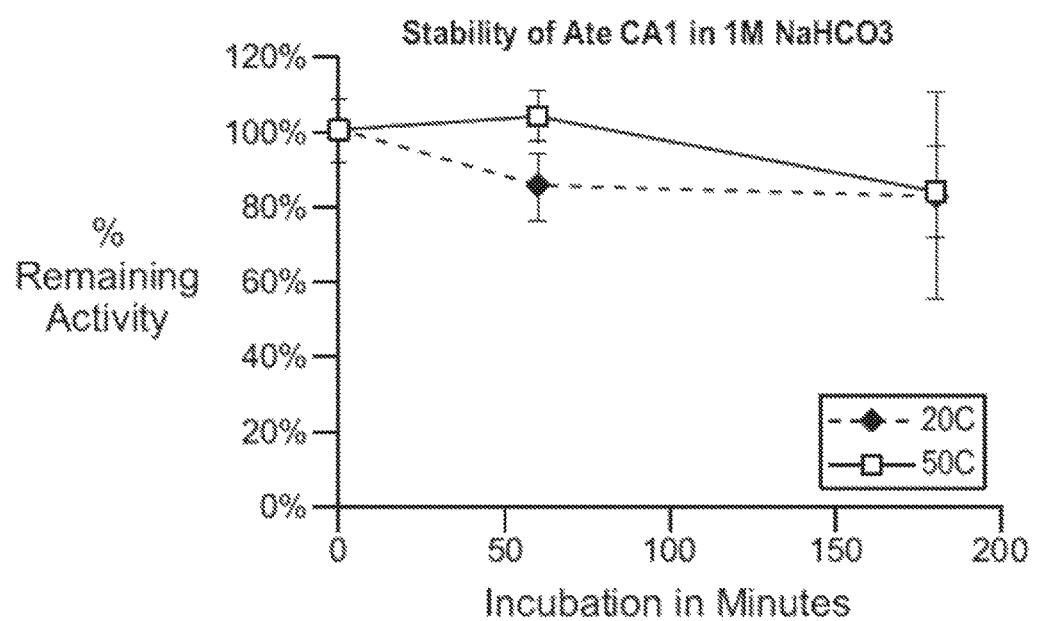
FIG. 13 provides a stability profile of Ate CA1 in the presence of 1 M sodium bicarbonate ($NaHCO_3$).

The stability of Ate CA1 under high ionic strength conditions in the presence of bicarbonate was assessed. In a PCR machine, a 100 ppm solution of Ate CA1 diluted in 1 M NaHCO$_3$ was incubated at 20° C. and 50° C. The specific activity of the sample was measured as described in Example 3C. Prior to incubation and at varying time points (5 minutes to 3 hours), 100 μL samples were withdrawn, cooled on ice and their specific activity measured in triplicate. The percent remaining activity was calculated for each time point. The activity of the sample kept on ice at time 0 was defined as 100% activity. FIG. 13 shows stability of Ate CA1 in 1 M NaHCO$_3$. Ate CA1 retains most of the activity over a 3-hr incubation period at both 20° C. and 50° C. Thus, AteCA1 is stable in the presence of high concentrations of NaHCO$_3$ that are encountered in enzymatic CO$_2$ extraction.

F. Heat Capacity Measurement of Ate CA1

Excessive heat capacity curves were measured for Ate CA1 and bovine CAII (bCAII) using an ultrasensitive scanning high-throughput microcalorimeter, VP-Cap DSC (MicroCal, Inc., Northampton, Mass.). The standard procedure for differential scanning calorimetry (DSC) measurements and the theory of the technique has been previously described (Freire, *Methods Mol Biol*, 41:191-218, 1995). About 500 μL of 0.5 mg/mL of each enzyme was studied. The proteins were scanned over a 35-100° C. temperature range. The same sample was then re-scanned (following cooling) to check the reversibility of the thermal unfolding process. For both the carbonic anhydrases studied, thermal unfolding was irreversible. The proteins were studied in the following buffers: (1) 0.1 M Tris, pH 8.5, (2) 0.1 M CHES, pH 9.5, (3) 0.1 M CAPS, pH 10.5, and (4) 0.1 M CHES, pH 9.5+2 M NaCl. A 200° C./hr scan rate was used to minimize any artifacts that might have resulted from aggregation. The apparent thermal midpoint (T$_m$(app)) of the DSC curves was used as an indicator of thermal stability. The melting points for Ate CA1 and bCAII are shown in Table 3F-1.

The thermal unfolding T$_m$(app) values for the carbonic anhydrase proteins showed a dependence on pH over the range of 8.5 to 10.5. Bovine carbonic anhydrase II has highest T$_m$(app) values between pH 8.5 and pH 9.5; Ate CA1 had the highest T$_m$(app) values at pH 8.5. The 0.1 M CHES buffer, pH 9.5 with 2 M NaCl decreased the T$_m$(app) for bCA II. For Ate CA1, the 0.1 M CHES, pH 9.5 buffer with 2 M NaCl increased the T$_m$(app) by about 7° C., as compared to the effect of 0.1 M CHES buffer, pH 9.5, with no additives. Thus, Ate CA1 is suitable for enzymatic CO$_2$ extraction at higher temperatures because the T$_m$ of this enzyme increases under high ionic strength conditions typical of enzymatic CO$_2$ extraction.

TABLE 3F-1

Melting point temperatures for Ate CA1 and bCAII

| | Buffers | | | |
|---|---|---|---|---|
| | #1 | #2 | #3 | #4 |
| Protein | 0.1M Tris, pH 8.5 | 0.1M CHES, pH 9.5 | 0.1M CAPS, pH 10.5 | 0.1M CHES, pH 9.5 + 2M NaCl |
| Bovine CA II | 68.8 | 69.4 | 66.6 | 61.7 |
| Ate CA1 | 67.8 | 63.9 | 60.8 | 71.4 |

T$_m$(app) was also determined for bCAII and Ate CA1 in 1 M KHCO$_3$ with no added NaCl, at various concentrations of added NaCl, ranging from 0.1 M to 1 M. As shown in Table 3F-2, T$_m$(app) decreased for bCAII in bicarbonate solution as compared to T$_m$(app) in buffer, while T$_m$(app) increased for Ate CA1 in bicarbonate solution, and with increased ionic strength. This increase in T$_m$(app) indicated the suitability of the enzyme Ate CA1 for enzymatic CO$_2$ extraction, especially in high ionic strength and in the presence of high concentrations of carbonate solutions. A higher Tm(app) was observed for Ate CA1 at higher bicarbonate concentrations as compared to Tm(app) at lower bicarbonate concentrations, which was unexpected.

TABLE 3F-2

T$_m$ (app) [° C.] of Ate CA1 in 1M KHCO$_3$

| [Salt] (M) | Bovine CA II | Ate CA1 |
|---|---|---|
| 0 | 62.1 | 70.4 |
| 0.1 | 62.8 | 71.8 |
| 0.5 | 62.5 | 73.1 |
| 1 | 62.7 | 74.3 |

G. Homology Identification

Figure 15:
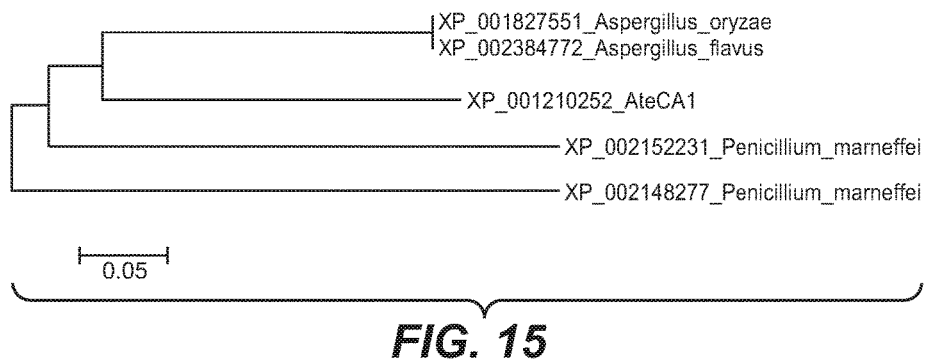
FIG. 15 provides a phylogenetic tree for Ate CA1 and its homologs.

The Ate CA1 mature protein sequence (267 residues) was subjected to a BLASTP search, and four protein sequences were identified with 50% or greater identity. FIGS. 14A-B show an alignment of Ate CA1 with similar carbonic anhydrases sequences generated with Vector NTI (Invitrogen). Table 3G-1 shows the percent identities and NCBI Accession Nos. of the aligned sequences: XP_001827551 (SEQ ID NO: 45), XP_002148277 (SEQ ID NO: 46), XP_002152231 (SEQ ID NO: 47), and XP_002384772 (SEQ ID NO: 48). The aligned sequences were used to prepare a phylogenetic tree using program MEGA 5. FIG. 15 shows the phylogenic tree for Ate CA1 and its homologs.

TABLE 3G-1

Percent Identity Shared by Ate CA1 and Similar Sequences

| Homolog | SEQ ID NO: | % IDENTITY (PID) |
|---|---|---|
| XP_001827551 | 45 | 67 |
| XP_002148277 | 46 | 55 |
| XP_002152231 | 47 | 56 |
| XP_002384772 | 48 | 67 |

Example 4

A. Sequence of *Streptomyces pristinaespiralis* Carbonic Anhydrase1 (Spr CA1)

*Streptomyces pristinaespiralis* was purchased from ATCC (ATCC Number 25486), and genomic DNA was isolated as described in Kieser et al., *Practical Streptomyces Genetics*, The John Innes Foundation, Norwich, United Kingdom (2000). The nucleic acid sequence for the Spr CA1 gene (NCBI Reference Sequence P_06907409.1), and the amino acid sequence of the hypothetical protein encoded by the Spr CA1 gene was found in the NCBI Databases (NCBI Accession No. ZP_06907409.1).

B. Expression of *Streptomyces pristinaespiralis* Carbonic Anhydrase1 (Spr CA1)

The Spr CA1 gene was identified by genome annotation and amplified from genomic DNA of *Streptomyces pristinaespiralis* by PCR. The primers were designed based on the Spr CA1 gene sequence in the public database. The primers used were: SprCA1-Fw 5'-AGCGCTAGCC GGC-CCCCCGG CACAGGCCTC CCCCGGTCCC GCGACG- GCCC-3' (SEQ ID NO: 49), and SprCA1-RV 5'-TCCG-GATCCT TATCAGGCGA CGGIGTGCACCAGC-3' (SEQ ID NO: 50).

Figure 16:
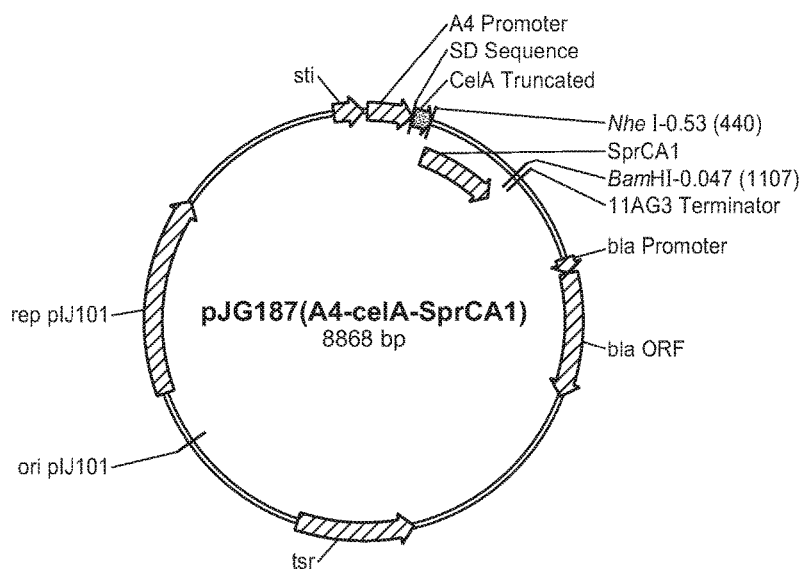
FIG. 16 provides a plasmid map of pJG187 (A4-CelA-SprCA1).

The resulting PCR fragment of mature Spr CA1 DNA was digested with NheI and BamHI and ligated into the pKB128 vector, and then digested with the same restriction enzymes to obtain the expression plasmid pJG187 (FIG. 16). The pKB128 plasmid is a derivative of the pKB105 plasmid (as described in U.S. Patent Application Publication No. 2006/0154843) and is the source of the A4 promoter-CelA signal sequence. The ligation mixture was used to transform E. coli TOP 10 chemically competent cells (Invitrogen Corp.) following the manufacturer's protocol. The transformed cells were plated on Luria Agar plates supplemented with 50 ppm ampicillin and incubated overnight at 37° C. Three transformants were picked from the plate and inoculated into 5 ml Luria Broth supplemented with 50 ppm ampicillin. Cultures were grown overnight at 37° C., plasmid DNA extracted and the correct sequence of the Spr CA1 gene was confirmed by DNA sequencing. The pJG187 plasmid was then used to transform S. lividans TK23 derived protoplasts, as described in U.S. Patent Application Publication No. 2006/0154843. The transformation techniques used are described in Kieser et al., *Practical Streptomyces Genetics*, The John Innes Foundation, Norwich, United Kingdom (2000). Transformed cells were plated on R5 selection plates and incubated at 30° C. for 3 days. One clone from the *Streptomyces* transformation plate was inoculated in TSG medium in shake flasks at 28° C. for 3 days. Cultures were then transferred to a *Streptomyces* 2 Modified Medium (as described in U.S. Pat. Application Publication No. 2006/0154843) and incubated for an additional 4 days at 28° C.

TSG medium: 16 g BD Difco tryptone, 4 g BD Bacto soytone, 20 g Sigma caseine (hydrolysate), and 10 g potassium phosphate, dibasic, brought to 1 L. After autoclaving, 50% glucose was added to a final concentration of 1.5%.

R5 plates were prepared with the following: 206 g sucrose, 0.5 g K$_2$SO$_4$, 20.24 g MgCl$_2$, 20 g glucose, 0.2 g Difco casamino acids, 10 g Difco yeast extracts, 11.46 g TES, 4 g L-Asp, 4 mL of trace elements, 44 g Difco agar, 20 mL 5% K$_2$HPO$_4$, 8 mL 5 M CaCl$_2$.2H$_2$O and 14 mL IN NaOH were added to a final volume of 1 L after autoclaving. After 20 hours, a layer of thiostrepton (50 μg/mL final concentration) was plated on the top of the plates.

The nucleotide sequence of the Spr CA1 gene of plasmid pJG187 (A4-celA-SprCA1) is set forth as SEQ ID NO: 51:

```
TCCCCCGGTCCCGCGACGGCCCGCCGCCCCCGGCCGGGCACTCCCGCGCA

GGCCCTGCGCGAGCTGGCGGCCGGCAACCGCCGCTGGCGCACCTTCCGGC

AGCAGCATCCGCACGAGAACTCGGCCGTGCGCGAGGAACTGATATCCGGT

CAGGAACCCTTCGCCGTGGTCCTCGGCTGCATCGACTCGCGGGTGCCGCC

GGAACTGGTCTTCGATCAGGGCCTCGGCGACCTGATGACCGTGCGCTCCG

CCGGTGAGGTGCTCGACGAGGCGGTCCTCGGCAGCGTCGCGTACGGGGTA

CTGGAGCTGGACATCCCCCTGGTCATGGTGCTCGGTCACCAGTCCTGCGG

AGCGGTGACGGCGGCGGTGCACGCGGAGGAGACCGGCGAGGAACTCCCCG

CCCACATCCAGTACATCGCCGACCGCATACGGCCGGCCATAGACCACTCC

CAGGAGGGCGCGGCGCGCGTCGACTCCACGATCACCCGCAATGTCCAGAT

GGTCACGCGGCTCCTCGCGCAGGAGCCCGACCTCGCGGCGAGGATCGCGG

CCGGGAAGCTCGCGGTCGTCGGCGCACGCTACGAACTGAGCTCGCAGCTG

GTGCACACCGTCGCCTGA
```

The amino acid sequence of the Spr CA1 precursor is set forth as SEQ ID NO: 52. The predicted native signal peptide is shown in italics.

```
MKNTPRTNSSVGGSRRTLLRAAVAGGALASGGLVWAGTPASASPGPATAR

RPRPGTPAQALRELAAGNRRWRTFRQQHPHENSAVREELISGQEPFAVVL

GCIDSRVPPELVFDQGLGDLMTVRSAGEVLDEAVLGSVAYGVLELDIPLV

MVLGHQSCGAVTAAVHAEETGEELPAHIQYIADRIRPAIDHSQEGAARVD

STITRNVQMVTRLLAQEPDLAARIAAGKLAVVGARYELSSQLVHTVA
```

The amino acid sequence of the mature form of Spr CA1 is set forth as SEQ ID NO: 53:

```
SPGPATARRPRPGTPAQALRELAAGNRRWRTFRQQHPHENSAVREELISG

QEPFAVVLGCIDSRVPPELVFDQGLGDLMTVRSAGEVLDEAVLGSVAYGV

LELDIPLVMVLGHQSCGAVTAAVHAEETGEELPAHIQYIADRIRPAIDHS

QEGAARVDSTITRNVQMVTRLLAQEPDLAARIAAGKLAVVGARYELSSQL

VHTVA
```

Protein Purification of Spr CA1

*Streptomyces lividans* cells expressing Spr CA1 protein were grown in shake flasks under standard conditions. The Spr CA1 protein was purified from fermentation broth using a phenyl sepharose column equilibrated with 20 mM Tris HCl buffer, pH 8.0, 1 M ammonium sulfate, from which the protein was eluted with Milli-Q water. The purified protein fractions were pooled and concentrated using a 3K Amicon Ultra-15 device and the concentrated protein fraction was used in further studies.

C. Carbonic Anhydrase Activity of Spr CA1

The carbonic anhydrase activity of purified Spr CA1 was measured on ice in 20 mM Tris sulfate buffer (pH 8.3 at 25° C.) containing 20 mM Na$_2$SO$_4$. Briefly, 3 mL of chilled 20 mM Tris sulfate buffer (pH 8.3 at 25° C.) containing 20 mM Na$_2$SO$_4$ was added to a 50-mL polypropylene conical tube placed on ice. 20 μL of enzyme sample or buffer was added to the tubes followed by 2 mL of chilled CO$_2$-saturated water (purified and deionized using Milli-Q Integral system, Millipore). After the contents were mixed, a standardized pH meter probe was immediately inserted into the solution and the time required for the pH to drop from 8.3 to 6.3 was recorded using a stop watch. The test was repeated until at least three blank measurements (with buffer added) were within a 15-second time window and the average of three determinations ($T_{Blank,avg}$) was between 70 and 100 seconds. A standard curve was prepared using bovine carbonic anhydrase II (bCAII, Sigma C2522). The test measurements for determining activity were performed in triplicate, and $T_{enzyme,avg}$ was obtained.

One unit of activity (Wilbur-Anderson or W-A unit, Wilbur and Anderson, *Journal of Biological Chemistry* 176, 147-154, 1948) is defined as the time required for the pH of a 0.02 M Trizma buffer to drop from 8.3 to 6.3 per min at 0° C.:

$$\text{Units/mL enzyme} = (T_{Blank,avg} - T_{enzyme,avg}) * DF/(T_{enzyme,avg} * V)$$

where DF=dilution factor of enzyme sample, V=volume (in mL) of enzyme used, $T_{Blank,avg}$=average time values of Blank measurements, and $T_{enzyme,avg}$=average time values of Test measurements.

Units/mg protein=(units/mL enzyme)/(mg protein/mL enzyme)

The specific activity of purified Spr CA1 was determined to be 2,433±412 units/mg using the above method. Carbonic anhydrase activity of Spr CA1 is suitable for enzyme based $CO_2$ extraction.

D. Temperature Stability of Spr CA1

Figure 17A:
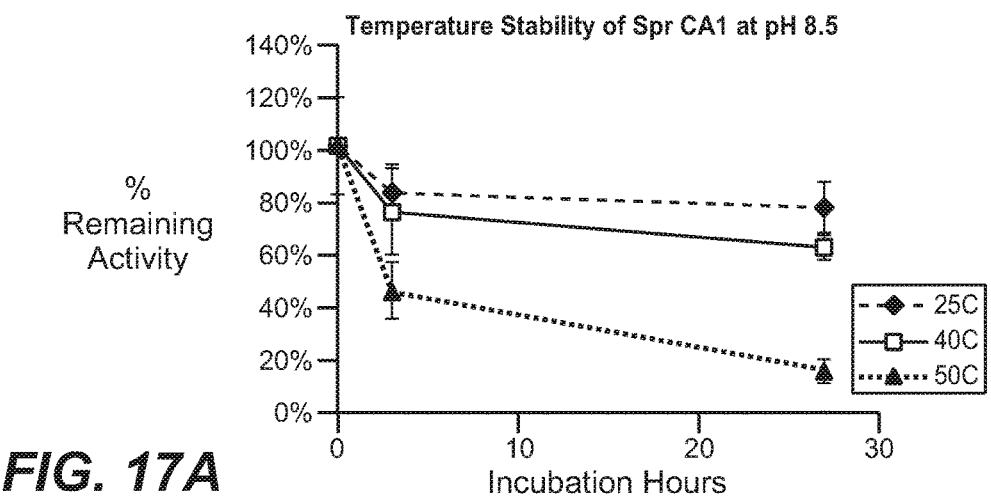
FIGS. 17A-C provide temperature stability profiles of Spr CA1 at pH values of (A) 8.5, (B) 9.5, and (C) 10.5, respectively.
Figure 17B:
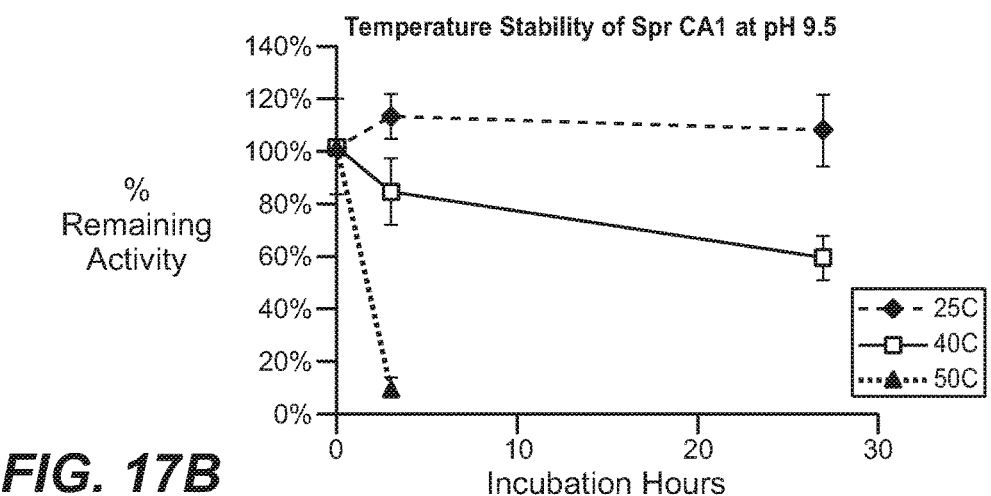
Figure 17C:
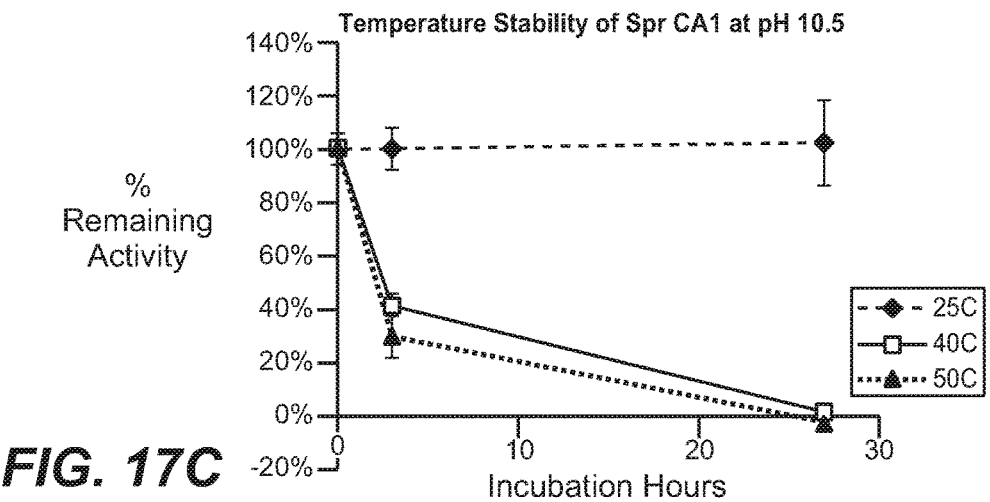

The temperature stability of Spr CA1 was determined in 0.1 M Tris buffer, pH 8.5 (adjusted by $H_2SO_4$ at 25° C.), 0.1 M CHES buffer, pH 9.5 (adjusted by $H_2SO_4$ at 25° C.), and 0.1 M CAPS buffer, pH 10.5 (adjusted by $H_2SO_4$ at 25° C.). $Na_2SO_4$ was added to the buffer to a final concentration of 25 mM. 100 ppm of Spr CA1 in 20 mL buffer was incubated in a water bath at 40° C. and 50° C. One sample was also incubated at room temperature (25° C.). At different time points (5 minutes to 72 hours), 0.5 mL of the enzyme sample from each tube was taken and placed on ice. The specific activity of the enzyme sample was measured as described in Example 4C. The specific activity measurements were performed in triplicates. The percent remaining activity was calculated at each time point, and at each pH value. For each pH value, the activity of the sample kept at 0° C. at time 0 was defined as 100% activity. The Spr CA1 retained more than 60% activity over a 27-hr incubation period between 25° C. and 40° C. at pH 8.5 and pH 9.5. As shown in FIGS. 17A-C, Spr CA1 is stable over different pH ranges typically used for enzymatic $CO_2$ extraction, and at supra-physiological temperatures.

E. Stability of Spr CA1 in 1 M $NaHCO_3$

Figure 18:
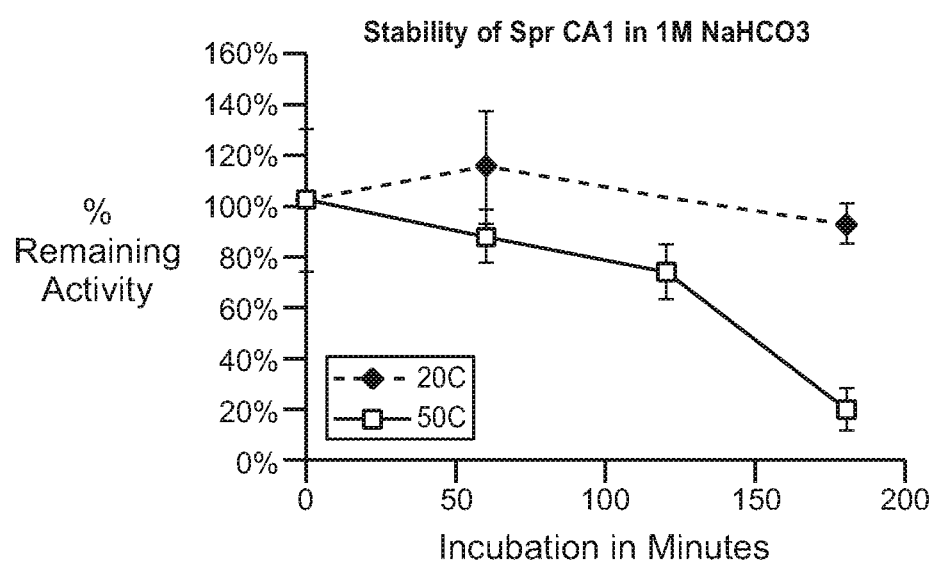
FIG. 18 provides a stability profile of Spr CA1 in the presence of 1 M sodium bicarbonate ($NaHCO_3$).

The stability of Spr CA1 under high ionic strength conditions in the presence of bicarbonate was assessed. In a PCR machine, a 100 ppm solution of Spr CA1 in 1 M $NaHCO_3$ was incubated at 20° C. and 50° C. The specific activities of the samples were measured prior to incubation as described in Example 4C. At varying time points (5 minutes to 3 hours), 100 μL samples were withdrawn, cooled on ice and their specific activity measured. The percent remaining activity was calculated for each time point. The activity of the sample kept on ice at time 0 was defined as 100% activity. FIG. 18 shows stability of Spr CA1 in 1 M $NaHCO_3$. Spr CA1 retains more than 60% of the activity over a 2-hr incubation period at both 20° C. and 50° C. Thus, Spr CA1 is stable in the presence of high concentrations of $NaHCO_3$ that are encountered in enzymatic $CO_2$ extraction.

F. Heat Capacity Measurement of Spr CA1

Excessive heat capacity curves are measured for Spr CA1 and bovine CAII (bCAII) using an ultrasensitive scanning high-throughput microcalorimeter, VP-Cap DSC (MicroCal, Inc., Northampton, Mass.). The standard procedure for differential scanning calorimetry (DSC) measurements and the theory of the technique has been previously described (Freire, *Methods Mol Biol*, 41:191-218, 1995). Approximately 500 μL of 0.5 mg/mL of each enzyme is studied. The proteins are scanned over a 35-100° C. temperature range. The same sample is then re-scanned (following cooling) to check the reversibility of the thermal unfolding process. The proteins are studied in the following buffers: (1) 0.1 M Tris, pH 8.5, (2) 0.1 M CHES, pH 9.5, (3) 0.1 M CAPS, pH 10.5, and (4) 0.1 M CHES, pH 9.5±2 M NaCl. A 200° C./hr scan rate is used to minimize any artifacts that might have resulted from aggregation. The apparent thermal midpoint ($T_m$(app)) of the DSC curves is used as an indicator of thermal stability

G. Homology Identification

Figure 20:
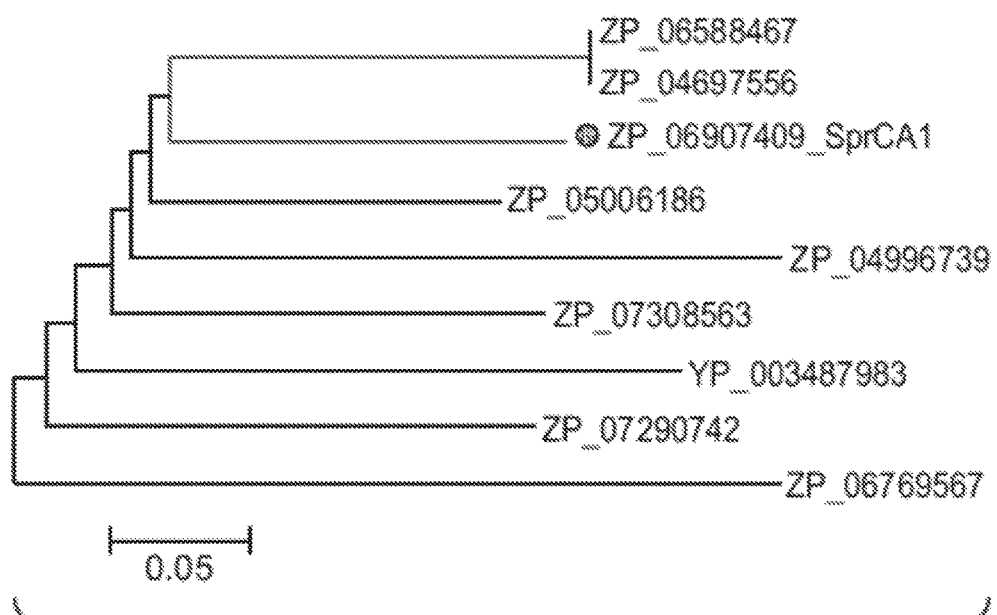
FIG. 20 provides a phylogenetic tree for Spr CA1 and its homologs.

The Spr CA1 mature protein sequence (216 residues) was subjected to a BLASTP search, and the top eight protein sequences were selected for sequence alignment (Vector NTI, Invitrogen). FIGS. 19A-B show an alignment of Spr CA1 with similar carbonic anhydrase sequences. Table 4G-1 shows the percent identities and NCBI Accession Nos. of the aligned sequences: YP_003487983 (SEQ ID NO: 54), ZP_04697556 (SEQ ID NO: 55), ZP_04996739 (SEQ ID NO: 56), ZP_05006186 (SEQ ID NO: 57), ZP_06588467 (SEQ ID NO: 58), ZP_06769567 (SEQ ID NO: 59), ZP_07290742 (SEQ ID NO: 60), and ZP_07308563 (SEQ ID NO: 61). The aligned sequences were used to prepare a phylogenetic tree using the program MEGA 5 (see, Tamura K. et al. Molecular Biology and Evolution (2011, in press). FIG. 20 shows the phylogenic tree for Spr CA1 and its homologs.

TABLE 4G-1

Percent Identity Shared by Spr CA1 and Similar Sequences

| Homolog | SEQ ID NO: | % IDENTITY (PID) |
|---|---|---|
| YP_003487983 | 54 | 61 |
| ZP_04697556 | 55 | 66 |
| ZP_04996739 | 56 | 63 |
| ZP_05006186 | 57 | 68 |
| ZP_06588467 | 58 | 69 |
| ZP_06769567 | 59 | 54 |
| ZP_07290742 | 60 | 64 |
| ZP_07308563 | 61 | 60 |

Example 5

A. Cloning of *Bacillus agaradhaerens* Carbonic Anhydrase Bag CA1

The *Bacillus agaradhaerens* strain was selected as a potential source for various enzymes, useful for industrial applications. The entire genome of the *Bacillus agaradhaerens* strain was sequenced using Illumina's next generation sequencing technology. Genomic DNA for sequencing was obtained by first growing *Bacillus agaradhaerens* on Heart Infusion agar plates (Difco) at 37° C. for 24 h. Cell material was scraped from the plates and used to prepare genomic DNA with the ZF Fungal/Bacterial DNA miniprep kit from Zymo (Cat No. D6005). This genomic DNA was used for genome sequencing and to amplify the Bag CA1 gene for expression cloning. Genome sequencing and assembly of the sequence data was performed by BaseClear (Leiden, The Netherlands). Contigs were annotated by BioXpr (Namur, Belgium). One of genes identified this way in *Bacillus agaradhaerens* encodes a carbonic anhydrase that showed homology to carbonic anhydrases of various organisms. The sequence of this gene, called the BagCA1 gene, is depicted in SEQ ID NO: 62. The protein encoded by the Bag CA1 gene is depicted in SEQ ID NO: 63. The gene has an alternative start codon (GTG). At the N-terminus, the protein has a signal peptide with a length of 39 amino acids as predicted by SignalP-NN (Emanuelsson et al., Nature Protocols, 2:953-971, 2007). The presence of a signal sequence suggests that BagCA1 is a secreted enzyme.

The nucleotide sequence of the Bag CA1 gene isolated from *Bacillus agaradhaerens* is set forth as SEQ ID NO: 62. The sequence encoding the predicted native signal peptide is shown in italics:

*GTGAAAAATGACGTCATGAAAGAAGGAACAAACATGAAAAGAAGAGTAGG*

*GTGGGGAAGCGTTGTAGTCGTTTTAGTGTCAAGTGTCGTCATAACGGCCT*

*GTTCTACAGCGCAATCAGGAGACGAAGAAGTTAACTCATTAAATGGCAGT*

GGCACTCATGAAGAGGCAATAAAAGACGAACATGAGGGGCATTGGTCATA

TACTGGAGAAACTGGACCGACGCATTGGGGATCGTTAGACGCCTCTTATG

AATTATGTGAACAAGAGCAGGAACAATCGCCGATCAACATTGAGACAGAT

GAGGTGACAACTACTGATACTCATATCAGCATCGCGTATCAACCGAGCCC

GTTTGCGATCGAAAATAACGGTCATACGATTCAAGCCAATGCCCTAACAG

AGGATAATACTATCTCGATAGAGGGTGAGAATTATCAATTAATTCAATTT

CACTTCCATGTCCCTTCTGAACATCAAAAAAATGGAGAACACTTAGACAT

GGAGCTTCATTTTGTCCATCAAAATCAAGAGGGGGAGTTGGCAGTGCTGG

GTGTCCTAATGGAAGAAGGGGAGGTGAACGACGCATTAGCAGAGCTATGG

GCTGAAATGCCACAAGAAGAGATGGATGAAACGATTGAATTAACGGATGC

TATCGATCTTAACGCATTATTGCCAAGCAGCCATGAAGGCTTTCATTATG

GTGGTTCTCTTACAACGCCTCCTTGTACTGAAGGTGTAAAATGGGTCGTC

CTCGAAAAAACAATTTCCGTCTCGCAAGAACAAATTGACACATTCGCAGA

GATCTTTCCAACCAATAATCGGCCTGTCCAACCGTGGAATGACCGGCATG

TATATGAAGTGGCTATTGAT

The amino acid sequence of the Bag CA1 precursor protein is set forth as SEQ ID NO: 63. The predicted native signal peptide is shown in italics.

*VKNDVMKEGTNMKRRVGWGSVVVVLVSSVVITACSTAQS*GDEEVNSLNGS

GTHEEAIKDEHEGHWSYTGETGPTHWGSLDASYELCEQEQEQSPINIETD

EVTTTDTHISIAYQPSPFAIENNGHTIQANALTEDNTISIEGENYQLIQF

HFHVPSEHQKNGEHLDMELHFVHQNQEGELAVLGVLMEEGEVNDALAELW

AEMPQEEMDETIELTDAIDLNALLPSSHEGFHYGGSLTTPPCTEGVKWVV

LEKTISVSQEQIDTFAEIFPTNNRPVQPWNDRHVYEVAID

The amino acid sequence of the mature form of BagCA1 is set forth as SEQ ID NO:64:

GDEEVNSLNGSGTHEEAIKDEHEGHWSYTGETGPTHWGSLDASYELCEQE

QEQSPINIETDEVTTTDTHISIAYQPSPFAIENNGHTIQANALTEDNTIS

IEGENYQLIQFHFHVPSEHQKNGEHLDMELHFVHQNQEGELAVLGVLMEE

GEVNDALAELWAEMPQEEMDETIELTDAIDLNALLPSSHEGFHYGGSLTT

PPCTEGVKWVVLEKTISVSQEQIDTFAEIFPTNNRPVQPWNDRHVYEVAI

D

B. Expression of *Bacillus agaradhaerens* Carbonic Anhydrase (Bag CA1)

The Bag CA1 gene was amplified from genomic DNA of *Bacillus agaradhaerens* by PCR. PCR was performed using a thermocycler with KOD-plus polymerase (TOYOBA) according to the instructions of the manufacturer (annealing temperature of 59° C.). The primers used were: Bag CA1-Fw 5'-GCG GCTAGC GCA GGAGACGAAGAAGT-TAACTCAT-3' (SEQ ID NO: 65), and Bag CA1-Rv 5'-TCA tta ATCAATAGCCACTTCATATACATG-3' (SEQ ID NO: 66).

Figure 21:
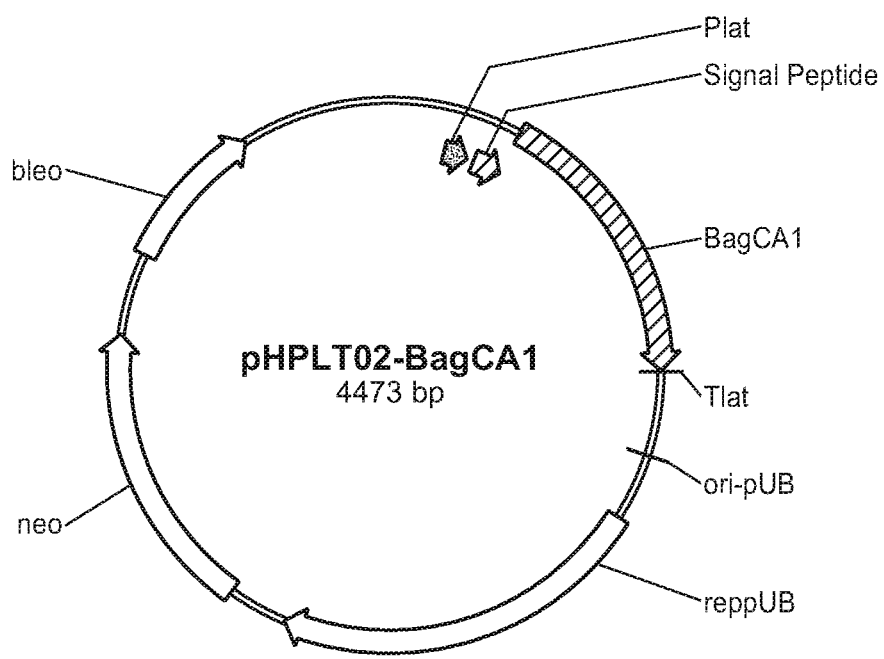
FIG. 21 provides a plasmid map of pHPLT02-BagCA1.

The resulting PCR fragment of mature Bag CA1 DNA was digested with NheI (the product from KOD-plus is blunt end) and ligated using T4 DNA ligase into pHPLT02 vector (50 ng/µL) digested with NheI and HpaI (blunt end) to obtain the expression plasmid pHPLT02-Bag CA1 (FIG. 21). The reaction conditions used for ligation were according to the instructions of the supplier (New England Biolabs, MA). The pHPLT02 vector contains the thermostable amylase LAT promoter (pLAT) and a signal peptide (SEQ ID NO: 73) from *Bacillus licheniformis* strain DSM13 for expression of Bag CA1. The vector can replicate in *B. subtilis*. The ligation mixture was amplified using a rolling circle kit (GE Healthcare Life Sciences, NJ) and *B. subtilis* cells (degUHy32, ΔnprB, Δvpr, Δepr, ΔscoC, ΔwprA, Δmpr, ΔispA, Δbpr) were transformed with the amplified ligation mixture. The transformed cells were plated on Luria Agar plates supplemented with 10 ppm kanamycin. About 50-100 colonies were obtained, 24 of which were picked and grown in 24-well plates. The sequence of Bag CA1 gene was confirmed by DNA sequencing. Selected clones from the 24 well plates were further grown in a 7 L fermentor.

The nucleotide sequence of the Bag CA1 gene in plasmid pHPLT02-Bag CA1 is set forth as SEQ ID NO: 67. The signal sequence is shown in italics:

*ATGGTCTTTAAAAAACCGAAAGTCTTTATCGCAGCGGTCATCCTGGCGCT*

*GAGCAGCTTTGCGGGAACGGCAGCTAGC*GCAGGAGACGAAGAAGTTAACT

CATTAAATGGCAGTGGCACTCATGAAGAGGCAATAAAAGACGAACATGAG

GGGCATTGGTCATATACTGGAGAAACTGGACCGACGCATTGGGGATCGTT

AGACGCCTCTTATGAATTATGTGAACAAGAGCAGGAACAATCGCCGATCA

ACATTGAGACAGATGAGGTGACAACTACTGATACTCATATCAGCATCGCG

TATCAACCGAGCCCGTTTGCGATCGAAAATAACGGTCATACGATTCAAGC

CAATGCCCTAACAGAGGATAATACTATCTCGATAGAGGGTGAGAATTATC

AATTAATTCAATTTCACTTCCATGTCCCTTCTGAACATCAAAAAAATGGA

GAACACTTAGACATGGAGCTTCATTTTGTCCATCAAAATCAAGAGGGGGA

GTTGGCAGTGCTGGGTGTCCTAATGGAAGAAGGGGAGGTGAACGACGCAT

TAGCAGAGCTATGGGCTGAAATGCCACAAGAAGAGATGGATGAAACGATT

GAATTAACGGATGCTATCGATCTTAACGCATTATTGCCAAGCAGCCATGA

AGGCTTTCATTATGGTGGTTCTCTTACAACGCCTCCTTGTACTGAAGGTG

TAAAATGGGTCGTCCTCGAAAAAACAATTTCCGTCTCGCAAGAACAAATT

GACACATTCGCAGAGATCTTTCCAACCAATAATCGGCCTGTCCAACCGTG

GAATGACCGGCATGTATATGAAGTGGCTATTGAT

The amino acid sequence of the Bag CA1 precursor protein expressed from plasmid pHPLT02-Bag CA1 is set forth as SEQ ID NO: 68. The signal sequence is shown in italics:

*MVFKKPKVFIAAVILALSSFAGTAASA*GDEEVNSLNGSGTHEEAIKDEHE

GHWSYTGETGPTHWGSLDASYELCEQEQEQSPINIETDEVTTTDTHISIA

YQPSPFAIENNGHTIQANALTEDNTISIEGENYQLIQFHFHVPSEHQKNG

EHLDMELHFVHQNQEGELAVLGVLMEEGEVNDALAELWAEMPQEEMDETI

ELTDAIDLNALLPSSHEGFHYGGSLTTPPCTEGVKWVVLEKTISVSQEQI

DTFAEIFPTNNRPVQPWNDRHVYEVAID

Several signal sequences from *Bacillus licheniformis* were used to express Bag CA1. These sequences are listed in Table 5B-1.

TABLE 5B-1

Signal sequences used to express Bag CA1

| SEQ ID | Signal Sequence (SS) |
|---|---|
| 69 | MKMWMRKALVALFTIATFGLVSPPAAASA |
| 70 | MNIKNIAKKASALTVAAALLAGGAPQASA |
| 71 | MKRKLMTLGLTAVLGSSAVLIPLKSNHASA |
| 72 | MKQQKRLYARLLPLLFALIFLLPHSAASA |
| 73 | MVFKKPKVFIAAVILALSSFAGTAASA |

Protein Purification of Bag CA1

Bag CA1 protein was purified from concentrated broth from a 7 L fermentor run using the two chromatography columns. 1) An anion exchange Q sepharose column equilibrated with 20 mM Tris-HCl pH 7.0 buffer from which the protein was eluted using a linear gradient of equilibration/wash buffer to 20 mM Tris-HCl, pH 7.0 buffer containing 0.5 M NaCl. 2) A phenyl sepharose column equilibrated with 20 mM sodium phosphate, pH 6.0, containing 1 M ammonium sulfate from which the protein was eluted in the void volume. The purified protein fractions were pooled and concentrated using a 3K Amicon Ultra-15 device and the concentrated protein fraction was used in further studies.

C. Carbonic Anhydrase Activity of Bag CA1

The carbonic anhydrase activity of purified Bag CA1 was measured in 20 mM Tris sulfate buffer (pH 8.3 at 25° C.) containing 20 mM $Na_2SO_4$. Briefly, 3 mL of chilled 20 mM Tris sulfate buffer (pH 8.3) containing 20 mM $Na_2SO_4$ was added to a 50-mL polypropylene conical tube placed on ice. Twenty (20) µL of enzyme sample or buffer was added to the tubes followed by 2 mL of chilled $CO_2$-saturated water (purified and deionized using Milli-Q Integral system, Millipore). After the contents were mixed, a standardized pH meter probe was immediately inserted into the solution and the time required for the pH to drop from 8.3 to 6.3 was recorded using a stop watch. The test was repeated until at least three blank measurements (with buffer added) were within a 15 sec time window and the average of three determinations ($T_{Blank,avg}$) was between 70-100 sec. A standard curve was prepared using bovine carbonic anhydrase II (bCAII, Sigma C2522). The test measurements for determining activity were performed in triplicate, and $T_{enzyme,avg}$ was obtained.

One unit of activity (One Wilbur-Anderson (W-A) unit, Wilbur and Anderson, *Journal of Biological Chemistry* 176, 147-154, 1948) is defined as the time required for the pH of a 0.02 M Trizma buffer to drop from 8.3 to 6.3 per min at 0° C.:

$$\text{Units/mL enzyme} = (T_{Blank,avg} - T_{enzyme,avg}) * DF / T_{enzyme,avg} * V$$

where DF=dilution factor of enzyme sample, V=volume (in mL) of enzyme used, $T_{Blank,avg}$=average time values of Blank measurements, and $T_{enzyme,avg}$=average time values of Test measurements.

Units/mL protein=units/mL enzyme/mg protein/mL enzyme

The specific activity of purified Bag CA1 was determined to be 3715±274 units/mg using the above method. Carbonic anhydrase activity of Bag CA1 is suitable for enzyme based $CO_2$ extraction.

D. Temperature Stability of Bag CA1

Figure 22A:
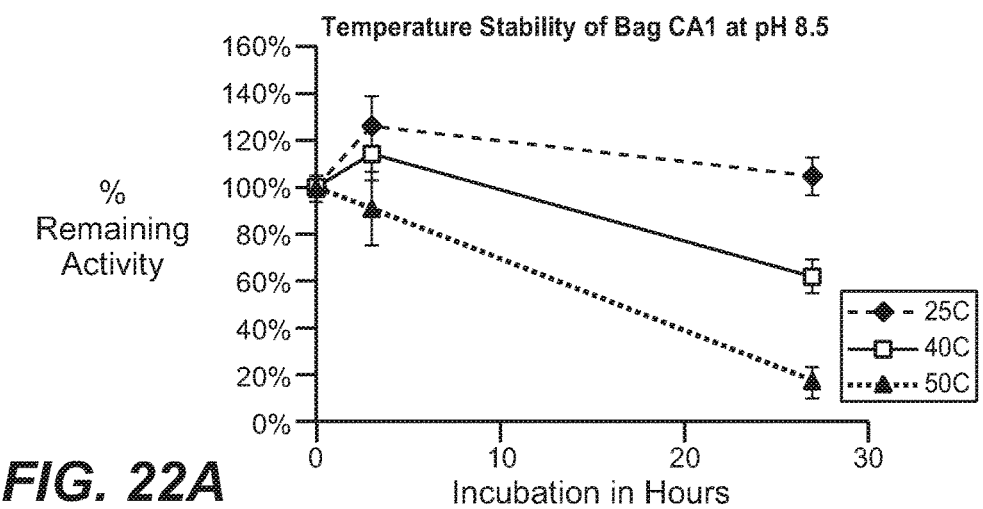
FIGS. 22A-C provide temperature stability profiles of Bag CA1 at pH values of (A) 8.5, (B) 9.5 and (C) 10.5, respectively.
Figure 22B:
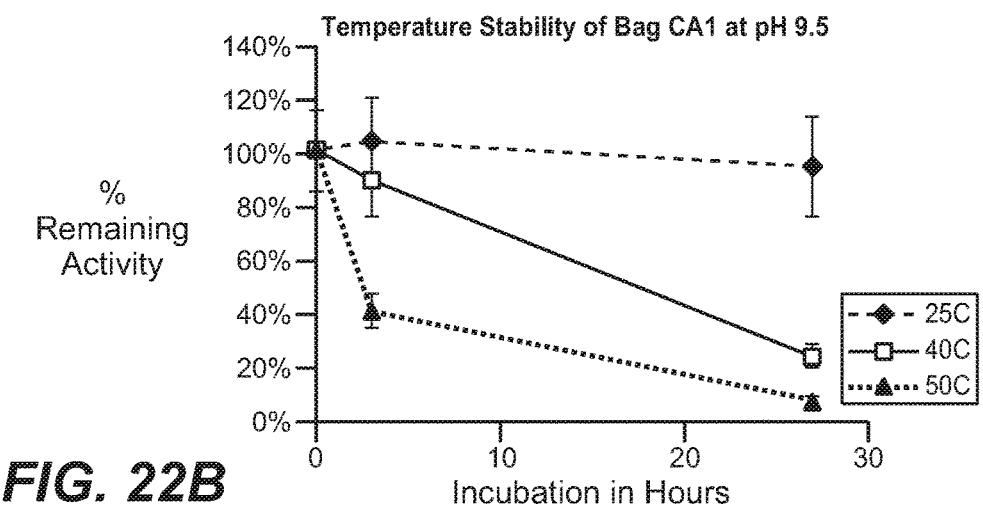
Figure 22C:
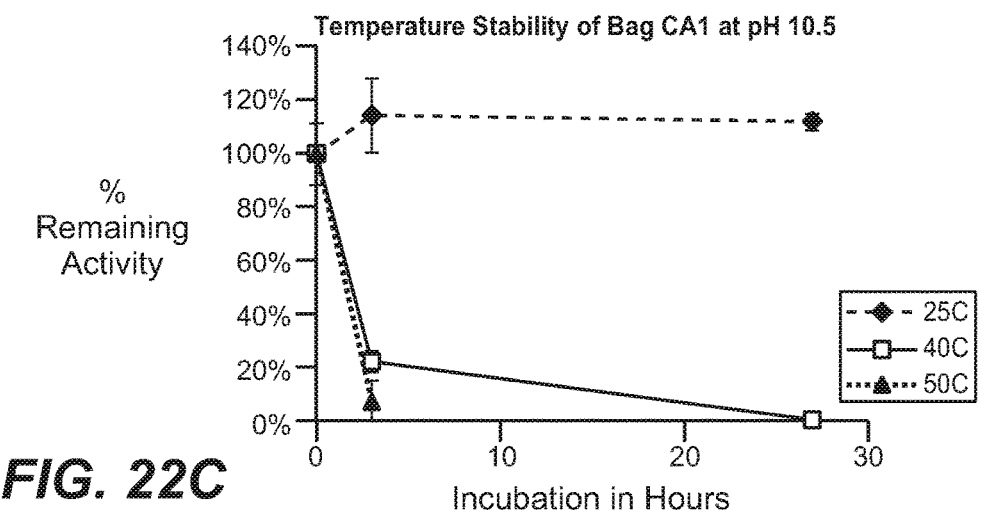

The temperature stability of Bag CA1 was determined in 0.05 M Tris buffer, pH 8.5, (adjusted using $H_2SO_4$), 0.05 M CHES buffer, pH 9.5 (adjusted using $H_2SO_4$), and 0.05 M CAPS buffer, pH 10.5 (adjusted using $H_2SO_4$). BSA at a final concentration of 1 mg/mL and $Na_2SO_4$ at a final concentration of 25 mM were added to the buffers. One hundred (100) ppm of Bag CA1 diluted in 1 M $NaHCO_3$ was incubated in a water bath at 40° C. and 50° C. One sample each was also incubated at room temperature (25° C.) and on ice (0° C.). At different time points (5 min to 24 h), 0.1 mL of the enzyme sample from each tube was taken and placed on ice. The specific activity of the enzyme sample was measured as described in Example 5C. The percent remaining activity was calculated at each time point, at each pH value. For each pH value, the activity of the sample kept at 0° C. at time 0 was defined as 100% activity. As shown in FIGS. 22A-C, Bag CA1 retained more than 90% activity over a 24 h incubation period at 25° C. for all pH ranges tested. At higher pH levels, for example, at pH 9.5, after about 2 h of incubation at 50° C., the enzyme lost nearly all of its carbonic anhydrase activity. On the other hand, it can be seen that Bag CA1 is suitably stable for in a broad pH range to allow its use in typical enzymatic $CO_2$ extraction operations, and at supra-physiological temperatures.

E. Stability of Bag CA1 in 1M $NaHCO_3$

Figure 23:
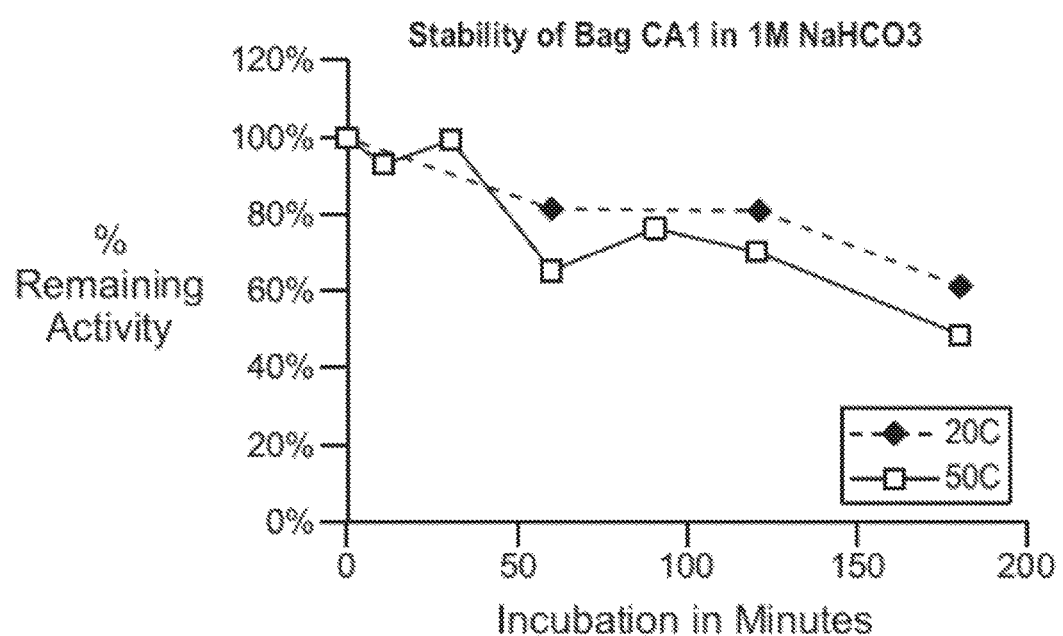
FIG. 23 provides a stability profile of Bag CA1 in the presence of 1 M sodium bicarbonate ($NaHCO_3$).

The stability of Bag CA1 was measured in 20 mM Tris sulfate buffer, pH 8.3 containing 20 mM $Na_2SO_4$ in the presence of 1 M $NaHCO_3$. One hundred (100) ppm of Bag CA1 diluted in 1 M $NaHCO_3$ was incubated at 20° C. and 50° C. in a PCR machine. The specific activity of the samples was measured prior to incubation as described in Example 5C. At varying time points (5 min to 3 h), 100 µL samples were withdrawn, cooled on ice and their specific activity measured as described in Example 5C. The percent remaining activity was calculated for each time point. The activity of the sample kept on ice at time 0 was defined as 100% activity. FIG. 23 shows stability of Bag CA1 in 1 M $NaHCO_3$. Bag CA1 retained most of the activity over a 3 h incubation period at 20° C. When incubated at 50° C., a somewhat more rapid decrease in activity was observed, however, about 45% of the initial activity remained after 3 h of incubation at this temperature.

F. Heat Capacity Measurement of Bag CA1

Excessive heat capacity curves were measured for Bag CA1 and bovine carbonic anhydrase II (bCA II) using an ultrasensitive scanning high-throughput microcalorimeter, VP-Cap DSC (MicroCal, Inc., Northampton, Mass.). The standard procedure for DSC measurements and the theory of the technique has been described previously (Freire, Differential Scanning calorimetry, *Methods Mol Biol*, 41:191-218, 1995). Approximately 500 µL of a 0.5 mg/mL sample of each enzyme was studied. The proteins were scanned over a 35-100° C. temperature range. The same samples were then re-scanned (following cooling) to check the reversibility of the thermal unfolding process. For both carbonic anhydrases studied the thermal unfolding was irreversible. The proteins were studied in the following buffers: (1) 0.1 M Tris, pH 8.5, (2) 0.1 M CHES, pH 9.5, (3) 0.1 M CAPS, pH 10.5, and (4) 0.1 M CHES, pH 9.5+2 M NaCl. A 200° C./h scan rate was used to minimize any artifacts that may result from aggregation. The apparent thermal midpoint [$T_m$(app)] of the DSC curves was used as an indicator of the thermal stability and melting points for these carbonic anhydrase molecules. The melting points of both enzymes in various buffers are shown in Table 5F-1.

The $T_m$(app) values during thermal unfolding for both the carbonic anhydrase polypeptides show a dependence on pH over the range of 8.5 to 10.5. Bovine carbonic anhydrase II has highest values between pH 8.5 and pH 9.5, while Bag CA1 has the highest values at pH 8.5. The 0.1 M CHES, pH 9.5 with 2 M NaCl buffer decreased the $T_m$(app) for bovine CA II, but increased the $T_m$(app) for Bag CA1. For Bag CA1, it was also observed that the inclusion of a carbonate buffer increased the $T_m$(app) substantially, and the 0.1M CHES, pH 9.5 with 2 M NaCl increased the $T_m$ by approximately 16° C. Moreover it has been observed that the carbonic anhydrase polypeptides had an increased melting temperature at higher ionic strength conditions, which was surprising. Thus, Bag CA1 is well suited for enzymatic $CO_2$ extraction at higher temperatures because the $T_m$ of this enzyme increases in carbonate solution and at high ionic strength conditions typical of enzymatic $CO_2$ extraction.

$T_m$(app) was also determined for bCAII, and Bag CA1 in 1M KHCO3 with and without 1M NaCl (Table 5F-2).

TABLE 5F-1

Melting Temperature for Bag CA1 and bCAII

| | Buffers | | | |
|---|---|---|---|---|
| | #1 | #2 | #3 | #4 |
| Protein | 0.1M Tris, pH 8.5 | 0.1M CHES, pH 9.5 | 0.1M CAPS, pH 10.5 | 0.1M CHES, pH 9.5 + 2M NaCl |
| Bovine CA II | 68.8 | 69.4 | 66.6 | 61.7 |
| Bag CA1 | 51 | 43.1 | 42.7 | 59.1/80.9 |

TABLE 5F-2

$T_m$(app) [° C.] of Bag CA1 in 1M KHCO3

| [Salt] (M) | bCA II | Bag CA1 |
|---|---|---|
| 0 | 62.1 | 70.3 |
| 1 | 62.7 | 80.1 |

G. Homology Identification

Figure 25:
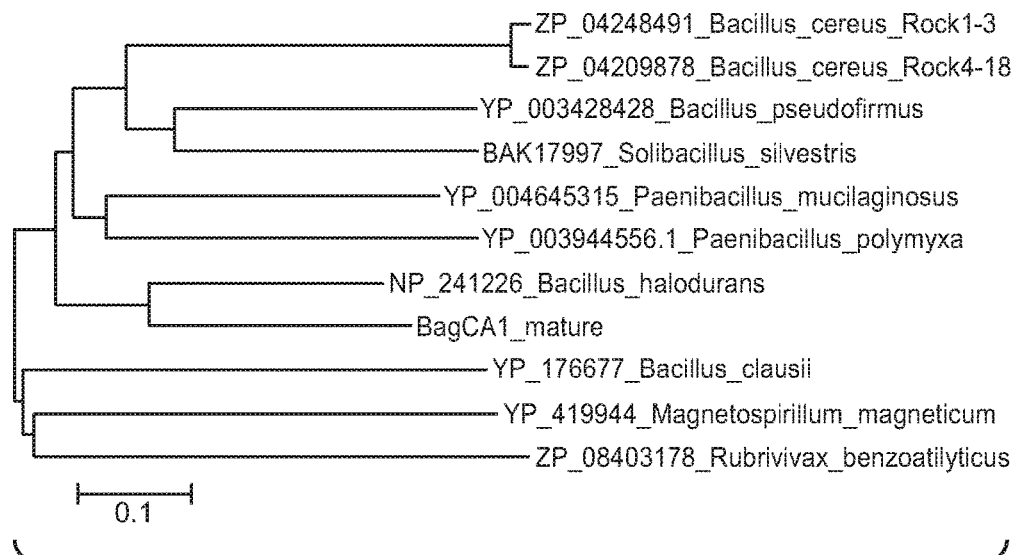
FIG. 25 provides a phylogenetic tree for Bag CA1 and its homologs.

The Bag CA1 mature protein sequence (251 residues) was subjected to a BLASTP search, and the top ten protein sequences were selected for sequence alignment (Vector NTI, Invitrogen). Table 5G-1 shows the percent identities and GENBANK Accession Nos. of the aligned sequences NP 241226 (SEQ ID NO:16), YP_004645315 (SEQ ID NO:74), ZP_04248491 (SEQ ID NO:25), YP_003428428 (SEQ ID NO:19), ZP_04209878 (SEQ ID NO:24), BAK17997 (SEQ ID NO:75), YP_176677 (SEQ ID NO:22), YP_419944 (SEQ ID NO:35), ZP_08403178 (SEQ ID NO:76), and YP_003944556 (SEQ ID NO:21). The aligned sequences were used to prepare a phylogenetic tree using the program MEGA 5 (FIGS. 24A-B). The phylogenic tree for Bag CA1 and its homologs is shown in FIG. 25.

TABLE 5G-1

Percent Identity Shared by Bag CA1 and Similar Sequences

| Homolog | SEQ ID NO: | % IDENTITY (PID) |
|---|---|---|
| NP_241226 | 16 | 64 |
| YP_004645315 | 74 | 50 |
| ZP_04248491 | 25 | 44 |
| YP_003428428 | 19 | 51 |
| ZP_04209878 | 24 | 45 |
| BAK17997 | 75 | 50 |
| YP_176677 | 22 | 48 |
| YP_419944 | 35 | 40 |
| ZP_08403178 | 76 | 41 |
| YP_003944556 | 21 | 45 |

Example 6

A. Identification and Expression of *Vibrio* sp. AND4 Carbonic Anhydrase1 (Vsp CA1)

The gene encoding a carbonic anhydrase (Vsp CA1) from *Vibrio* sp. AND4 (as determined by BLAST analysis) was synthesized by Generay (Shanghai Generay Biotech Co., Ltd). The nucleic acid sequence for the Vsp CA1 gene was determined to be at location 66128 to 66847 (*Vibrio* sp. AND4 1103602000595, whole genome shotgun sequence, NCBI Reference Sequence NZ_ABGR01000001.1) and the amino acid sequence of the protein encoded by the Vsp CA1 gene was found in the NCBI Database (NCBI Accession ZP_02194066, (/locus_tag="AND4_05779").

The nucleotide sequence of the Vsp CA1 gene synthesized is set forth as SEQ ID NO:77:

GCAAACTGGGGATACAAAGGCGATCATGGCCCGGAAAATTGGGGCGAATT

TGCATCAGAATGCGCAAAAGGCCAAAACCAAAGCCCGATTGATATCCAGT

CAGTTACGGAGGCAAAACTGGATAAACTGAATTTCGATTATGAAGGCAAA

GTTATTAGCCTGCTGAATAACGGCCATACACTGCAAACGAAACTGGAAGG

CAAAAATACGCTGATGGTTGATGGCACAGAATTCACACTGAAACAGTTTC

ATTTTCATACGCCGTCAGAAAATCATGTCAACGGCAAAGAGTATCCGCTG

GAAGCACATTTTGTGCATGCAGACAAAGCAGGCCATCTGGCAGTTGTTGC

AGTTTTCTTTAAACTTGGCGGCGAAAATCCGGAACTGGCGAAACTGCTGG

CAAATATCCCGAAAAAAGATCAAGTTGTGGCAATTAAAGTTCCGTTTGAT

GCAGATAGCCTTCTGCCGAACAATAAAGATTATTATAGATTCGACGGCAG

CCTGACAACGCCGCCGTGCAGCGAAGGCGTTAGATGGCTGGTTATCAAAG

-continued

AAACGCAGACAATCAGCCCGGAACAAGTTACAGCATTCACGAAAGCAATG

GGCCATAATAACAGACCGATTCAGCCGCTTAATTCAAGAATGATTAGAAC

ACTTCAA

Figure 26:
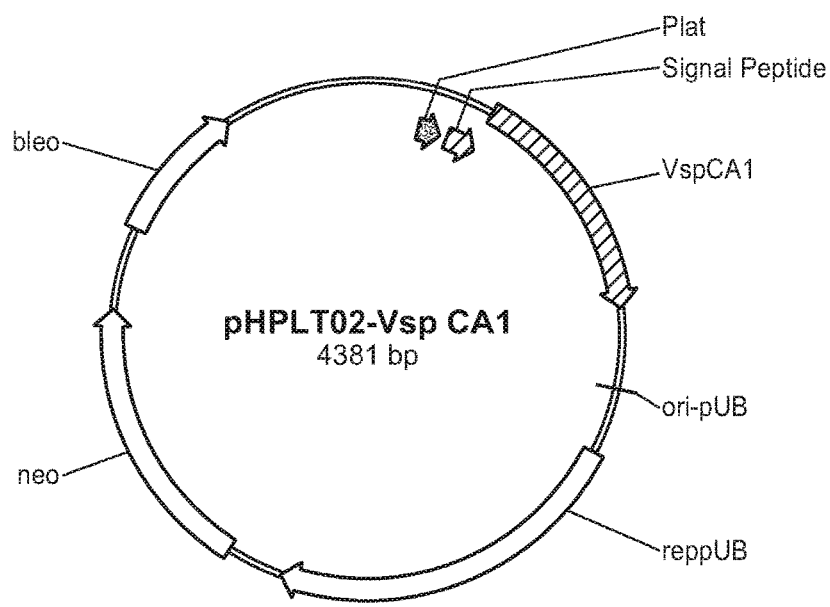
FIG. 26 provides a plasmid map of pHPLT02-Vsp CA1.

The Vsp CA1 gene was digested with NheI and HpaI and ligated using T4 DNA ligase into pHPLT02 vector (50 ng/μL) digested with the same restriction enzymes to obtain the expression plasmid pHPLT02-Vsp CA1 (FIG. 26). The reaction conditions used for ligation were according to the instructions of the supplier (New England Biolabs, MA). The pHPLT02 vector contains the thermostable amylase LAT promoter (pLAT) and a signal peptide (SEQ ID NO: 83) from *Bacillus licheniformis* strain DSM13 for expression of Vsp CA1. The vector can replicate in *B. subtilis*. The ligation mixture was amplified using a rolling circle kit (GE Healthcare Life Sciences, NJ) and *B. subtilis* cells (degUHy32, ΔnprB, Δvpr, Δepr, ΔscoC, ΔwprA, Δmpr, ΔispA, Δbpr) were transformed with the amplified ligation mixture. The transformed cells were plated on Luria Agar plates supplemented with 10 ppm kanamycin. About 50-100 colonies were obtained, 24 of which were picked and grown in 24-well plates. The sequence of Vsp CA1 gene was confirmed by DNA sequencing. Selected clones from the 24-well plates were further grown in a 7 L fermentor.

The nucleotide sequence of the Vsp CA1 gene of plasmid pHPLT02-Vsp CA1 is set forth as SEQ ID NO: 78. The signal sequence is in italics:

*ATGCTGATCAACAAAAGCAAAAAATTTTTCGTCTTTAGCTTTATCTTTGT*

*CATGATGCTGAGCCTGAGCTTTGTCAACGGCGAAGTCGCTAGCGCAGCAA*

ACTGGGGATACAAAGGCGATCATGGCCCGGAAAATTGGGGCGAATTTGCA

TCAGAATGCGCAAAAGGCCAAAACCAAAGCCCGATTGATATCCAGTCAGT

TACGGAGGCAAAACTGGATAAACTGAATTTCGATTATGAAGGCAAAGTTA

TTAGCCTGCTGAATAACGGCCATACACTGCAAACGAAACTGGAAGGCAAA

AATACGCTGATGGTTGATGGCACAGAATTCACACTGAAACAGTTTCATTT

TCATACGCCGTCAGAAAATCATGTCAACGGCAAAGAGTATCCGCTGGAAG

CACATTTTGTGCATGCAGACAAAGCAGGCCATCTGGCAGTTGTTGCAGTT

TTCTTTAAACTTGGCGGCGAAAATCCGGAACTGGCGAAACTGCTGGCAAA

TATCCCGAAAAAAGATCAAGTTGTGGCAATTAAAGTTCCGTTTGATGCAG

ATAGCCTTCTGCCGAACAATAAAGATTATTATAGATTCGACGGCAGCCTG

ACAACGCCGCCGTGCAGCGAAGGCGTTAGATGGCTGGTTATCAAAGAAAC

GCAGACAATCAGCCCGGAACAAGTTACAGCATTCACGAAAGCAATGGGCC

ATAATAACAGACCGATTCAGCCGCTTAATTCAAGAATGATTAGAACACTT

CAA

The amino acid sequence of the Vsp CA1 precursor protein expressed from plasmid pHPLT02-Vsp CA1 is set forth as SEQ ID NO: 79. The signal sequence is in italics:

*MLINKSKKFFVFSFIFVMMLSLSFVNGEVASA*ANWGYKGDHGPENWGEFA

SECAKGQNQSPIDIQSVTEAKLDKLNFDYEGKVISLLNNGHTLQTKLEGK

NTLMVDGTEFTLKQFHFHTPSENHVNGKEYPLEAHFVHADKAGHLAVVAV

FFKLGGENPELAKLLANIPKKDQVVAIKVPFDADSLLPNNKDYYRFDGSL

TTPPCSEGVRWLVIKETQTISPEQVTAFTKAMGHNNRPIQPLNSRMIRTL

Q

The amino acid sequence of the mature form of Vsp CA1 is set forth as SEQ ID NO:80:

ANWGYKGDHGPENWGEFASECAKGQNQSPIDIQSVTEAKLDKLNFDYEGK

VISLLNNGHTLQTKLEGKNTLMVDGTEFTLKQFHFHTPSENHVNGKEYPL

EAHFVHADKAGHLAVVAVFFKLGGENPELAKLLANIPKKDQVVAIKVPFD

ADSLLPNNKDYYRFDGSLTTPPCSEGVRWLVIKETQTISPEQVTAFTKAM

GHNNRPIQPLNSRMIRTLQ

Several signal sequences from *Bacillus licheniformis* were used to express Vsp CA1. These sequences are listed in Table 6A-1.

TABLE 6A-1

Signal sequences used to express Vsp CA1

| SEQ ID | Signal Sequence (SS) |
|---|---|
| NO: 81 | MKKKPLFRTFMCAALIGSLLAPVAASA |
| NO: 82 | MKNVLAVFVVLIFVLGAFGTSGPASA |
| NO: 83 | MLINKSKKFFVFSFIFVMMLSLSFVNGEVASA |

Protein Purification of Vsp CA1

Vsp CA1 protein was purified from concentrated broth from a 7 L fermentor run using the three chromatography columns. 1) An anion exchange Q sepharose column equilibrated with 20 mM Tris-HCl pH 7.0 buffer from which the protein was eluted in the void volume. 2) A phenyl sepharose column equilibrated with 20 mM sodium phosphate, pH 6.0, containing 1 M ammonium sulfate from which the protein was eluted using a linear gradient of equilibration/wash buffer to 20 mM sodium phosphate, pH 6.0. 3) A Superdex 75 gel filtration column from which the protein was eluted using 20 mM sodium phosphate, pH 7.0, containing 0.15 M NaCl. The purified protein fractions were pooled and concentrated using a 3K Amicon Ultra-15 device and the concentrated protein fraction was used in further studies.

B. Carbonic Anhydrase Activities of Vsp CA1

The carbonic anhydrase activity of purified Vsp CA1 was measured in 20 mM Tris sulfate buffer (pH 8.3 at 25° C.) containing 20 mM $Na_2SO_4$. Briefly, 3 mL of chilled 20 mM Tris sulfate buffer (pH 8.3) containing 20 mM $Na_2SO_4$ was added to a 50-mL polypropylene conical tube placed on ice. Twenty (20) μL of enzyme sample or buffer were added to the tubes followed by 2 mL of chilled $CO_2$-saturated water (purified and deionized using Milli-Q Integral system, Millipore). After the contents were mixed, a standardized pH meter probe was immediately inserted into the solution and the time required for the pH to drop from 8.3 to 6.3 was recorded using a stop watch. The test was repeated until at least three blank measurements (with buffer added) were within a 15 sec time window and the average of three determinations ($T_{Blank,avg}$) was between 70 and 100 sec. A standard curve was prepared using bovine carbonic anhydrase II (bCAII, Sigma C2522). The test measurements for determining activity were performed in triplicate, and $T_{enzyme,avg}$ was obtained.

One unit of activity (One Wilbur-Anderson (W-A) unit, Wilbur and Anderson, *Journal of Biological Chemistry* 176, 147-154, 1948) is defined as the time required for the pH of a 0.02 M Trizma buffer to drop from 8.3 to 6.3 per min at 0° C.:

Units/mL enzyme=$(T_{Blank,avg}-T_{enzyme,avg})$* DF/$T_{enzyme,avg}$*V where DF=dilution factor of enzyme sample, V=volume (in mL) of enzyme used, $T_{Blank,avg}$=average time values of Blank measurements, and $T_{enzyme,avg}$=average time values of Test measurements.

Units/mL protein=units/mL enzyme/mg protein/mL enzyme

The specific activity of purified Vsp CA1 was determined to be 10028±551 units/mg using the above method. Carbonic anhydrase activity of Vsp CA1 is suitable for enzyme based $CO_2$ extraction.

C. Temperature Stability of Vsp CA1

Figure 27A:
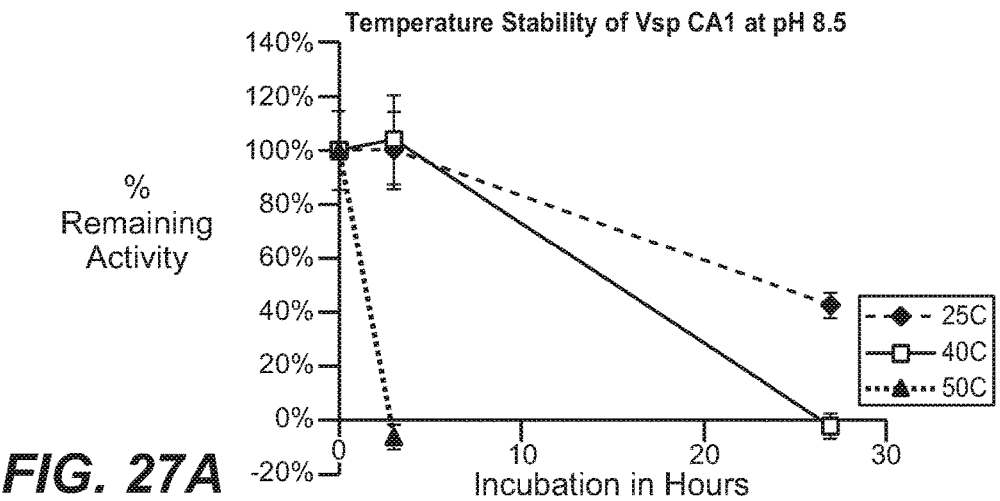
FIGS. 27A-C provide temperature stability profiles of Vsp CA1 at pH values of (A) 8.5, (B) 9.5 and (C) 10.5, respectively.
Figure 27B:
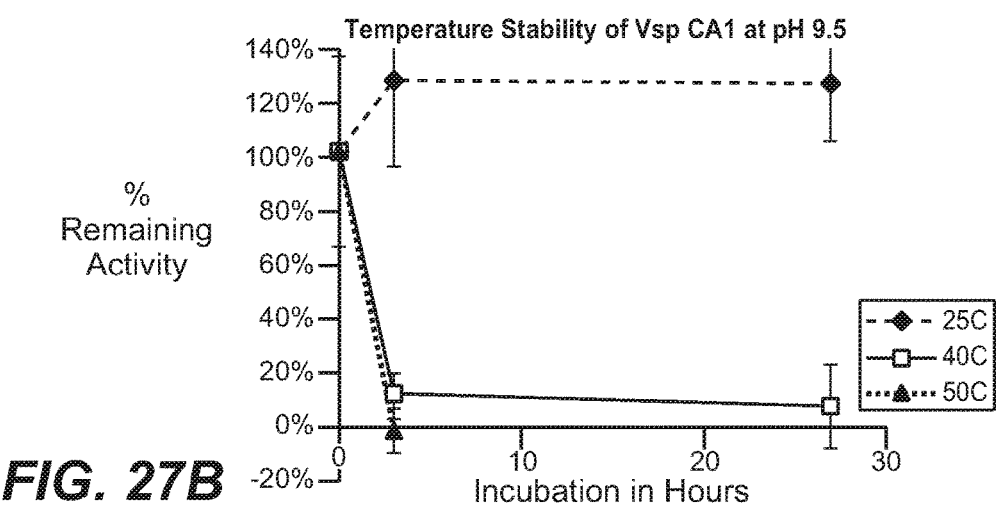
Figure 27C:
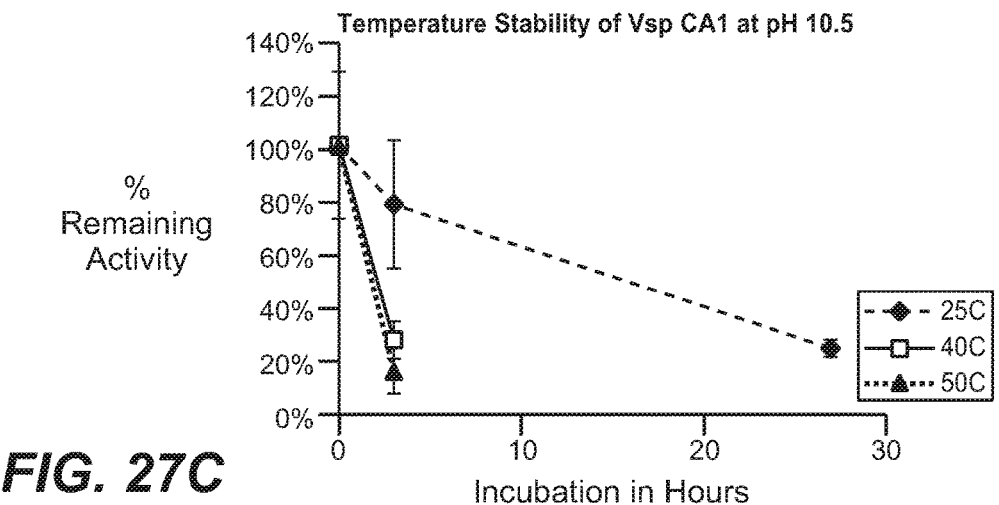

The temperature stability of Vsp CA1 was determined in 0.05 M Tris buffer, pH 8.5, (adjusted by $H_2SO_4$), 0.05 M CHES buffer, pH 9.5 (adjusted using $H_2SO_4$), and 0.05 M CAPS buffer, pH 10.5 (adjusted using $H_2SO_4$). BSA at a final concentration of 1 mg/mL and $Na_2SO_4$ at a final concentration of 25 mM were added to the buffers. One hundred (100) ppm of Vsp CA1 diluted in 1 M $NaHCO_3$ was incubated at 25° C., 40° C. and 50° C. in a PCR machine. The specific activity of the samples was measured prior to incubation as described in Example 6B. At varying time points (5 min to 24 h), 100 μL samples were withdrawn, cooled on ice and their specific activity measured as described in Example 6B. The percent remaining activity was calculated at each time point, at each pH value. For each pH value, the activity of the sample kept at 0° C. at time 0 was defined as 100% activity. As shown in FIGS. 27A-C, Vsp CA1 retained more than 50% activity over a 24 h incubation period at 25° C. for pH 8.5 and pH 9.5. The activity drop exhibited more dramatically as pH increases at the incubation of 40° C. and 50° C. At 50° C., Vsp CA1 completely lost its activity within 4 h at pH 8.5.

D. Stability of Vsp CA1 in 1M $NaHCO_3$

Figure 28:
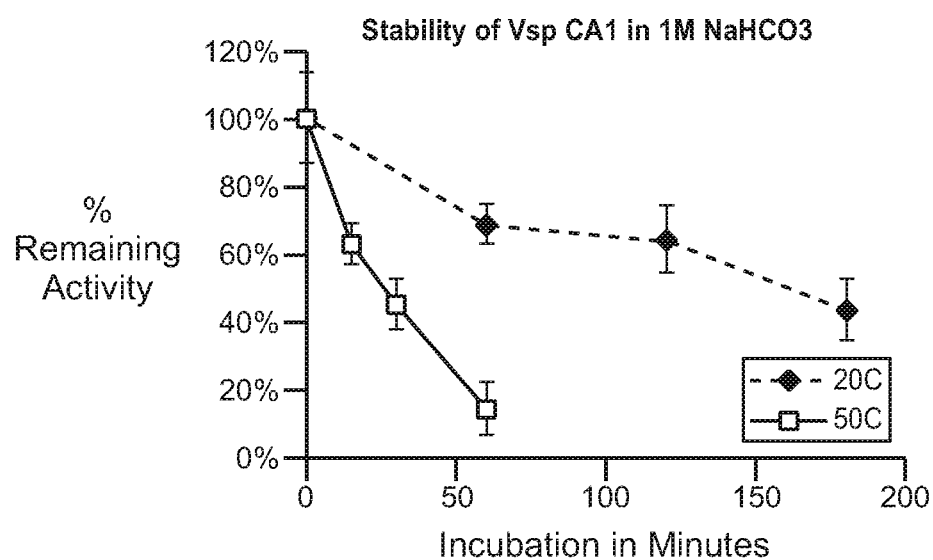
FIG. 28 provides a stability profile of Vsp CA1 in the presence of 1 M sodium bicarbonate ($NaHCO_3$).

The stability of Vsp CA1 was measured in 20 mM Tris sulfate buffer, pH 8.3, containing 20 mM $Na_2SO_4$ in the presence of 1 M $NaHCO_3$. One hundred (100) ppm of the protein was diluted in 1 M $NaHCO_3$ and incubated at 20° C. and 50° C. in a PCR machine. The specific activity of the sample was measured prior to incubation as described in Example 6B. At varying time points (5 min to 3 h), 100 μL samples were withdrawn, cooled on ice and their specific activity measured as described in Example 6B. The percent remaining activity was calculated for each time point. The activity of the sample kept on ice at time 0 was defined as 100% activity. FIG. 28 shows stability of Vsp CA1 in 1 M $NaHCO_3$. Vsp CA1 retained 50% activity over a 1 to 3 hr incubation period at 20° C. At 50° C., the activity loss was more rapid, but even at that high temperature, the enzyme retained at least 50% of its activity after about 30 min.

E. Heat Capacity Measurements of Vsp CA1

Excessive heat capacity curves were measured for Vsp CA1 and bovine carbonic anhydrase II (bCA II) using an ultrasensitive scanning high-throughput microcalorimeter, VP-Cap DSC (MicroCal, Inc., Northampton, Mass.). The standard procedure for DSC measurements and the theory of the technique has been described previously (Freire, Differential Scanning calorimetry, *Methods Mol Biol*, 41:191-218, 1995). Approximately 500 μL of a 0.5 mg/mL sample of each enzyme was studied. The proteins were scanned over a 35-100° C. temperature range. The same samples were then re-scanned (following cooling) to check the reversibility of the thermal unfolding process. For the Vsp CA1 carbonic anhydrase studied the thermal unfolding was irreversible. The proteins were studied in the following buffers: (1) 0.1 M Tris, pH 8.5, (2) 0.1 M CHES, pH 9.5, (3) 0.1 M CAPS, pH 10.5, and (4) 0.1 M CHES, pH 9.5+2 M NaCl. A 200° C./h scan rate was used to minimize any artifacts that may result from aggregation. The apparent thermal midpoint [$T_m$(app)] of the DSC curves was used as an indicator of the thermal stability and melting points for these carbonic anhydrase molecules. The melting points of both enzymes in various buffers are shown in Table 6E-1.

The $T_m$(app) values during thermal unfolding for the Vsp CA1 carbonic anhydrase protein shows a dependence on pH over the range of 8.5 to 10.5. Similar to bCAII, Vsp CA1 shows the highest values between pH 8.5 and pH 9.5. The 0.1 M CHES, pH 9.5, with 2 M NaCl buffer decreased the $T_m$(app) for bovine CA II, but did not affect the $T_m$(app) for Vsp CA1. The carbonate buffer lowered the $T_m$(app) for Vsp CA1.

$T_m$(app) was also determined for bCAII and Vsp CA1 in 1 M $KHCO_3$ with and without 1M NaCl (Table 6E-2). It was noted, surprisingly, that as the ionic strength increases, the Tm(app) of Vsp CA1 increases.

TABLE 6E-1

Melting Temperature for Vsp CA1 and bCAII Buffers

| Protein | #1 0.1M Tris, pH 8.5 | #2 0.1M CHES, pH 9.5 | #3 0.1M CAPS, pH 10.5 | #4 0.1M CHES, pH 9.5 + 2M NaCl |
|---|---|---|---|---|
| Bovine CA II | 68.8 | 69.4 | 66.6 | 61.7 |
| Vsp CA1 | 43.8/71.7 | 46/67.2 | 46.5 | 46/72.3 |

TABLE 6E-2

$T_m$(app) [° C.] of Vsp CA1 in 1M $KHCO_3$

| [Salt] (M) | bCA II | Vsp CA1 |
|---|---|---|
| 0 | 62.1 | 68.5 |
| 1 | 62.7 | 72.7 |

F. Homology Identification

Figure 29:
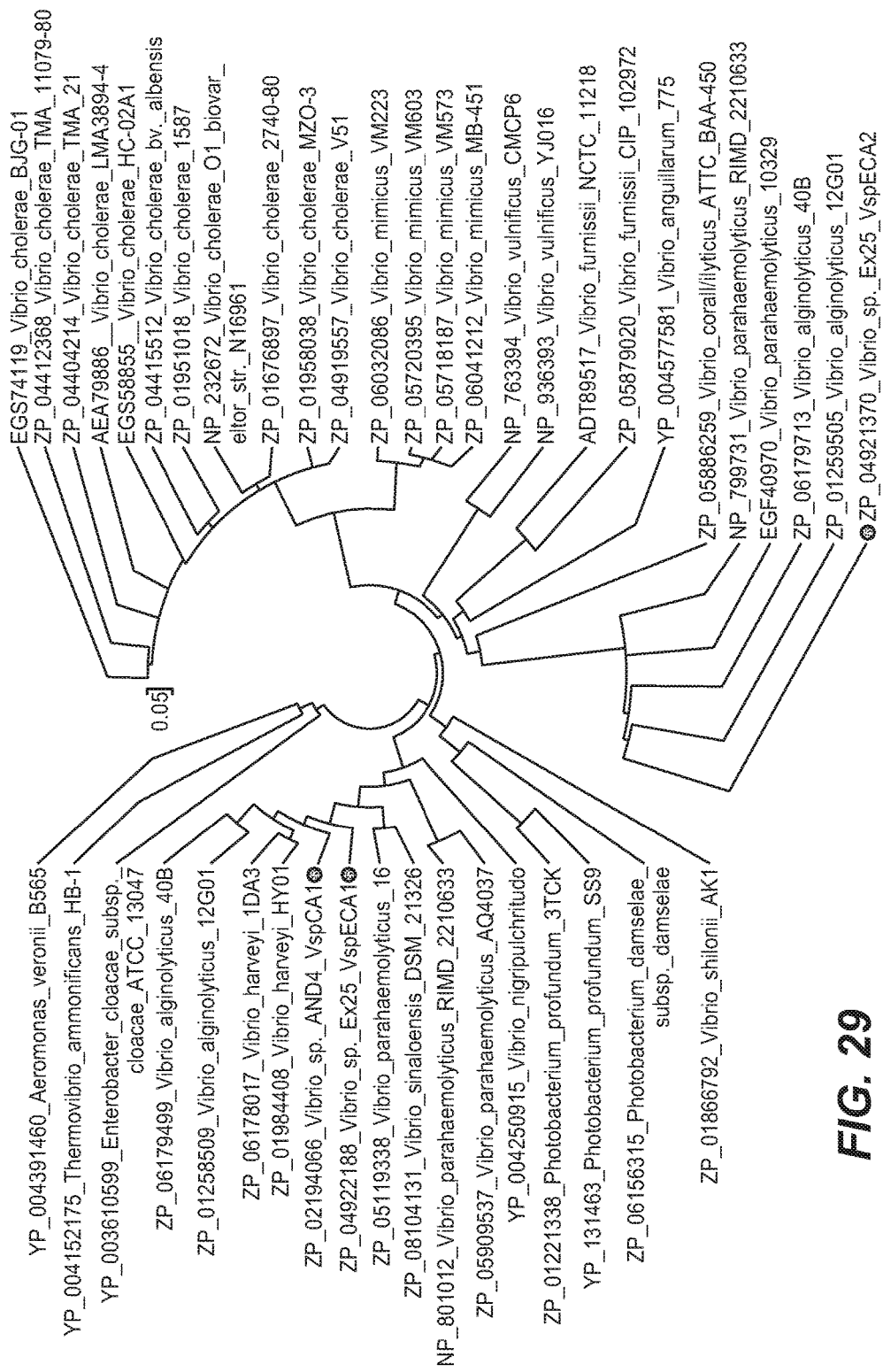
FIG. 29 provides a phylogenetic tree for Vsp CA1 and its homologs.

The Vsp CA1 mature protein sequence (219 residues) was subjected to a BLASTP search, and the resulting 43 protein sequences were selected for sequence alignment (Vector NTI, Invitrogen) and phylogenetic tree generation excluding the protein sequences with 99%400% identity with each others. Table 6F-1 shows the percent identities and NCBI Accession Nos. of the aligned sequences. The aligned sequences were used to prepare a phylogenetic tree using the program MEGA 5. FIG. 29 shows the phylogenic tree for Vsp CA1 and its homologs.

TABLE 6F-1

Percent Identity Shared by Vsp CA1 and Similar Sequences

| Homolog | SEQ ID NO: | % IDENTITY (PID) |
|---|---|---|
| ZP_02194066_Vibrio_sp._AND4_VspCA1 | 84 | 100 |
| ZP_01984408 | 85 | 86.19 |
| ZP_06178017 | 86 | 84.1 |
| ZP_01258509 | 87 | 79.08 |
| ZP_06179499 | 88 | 77.41 |
| ZP_04922188_Vibrio_sp._Ex25_VspECA1 | 89 | 77.87 |
| ZP_08104131 | 90 | 72.77 |
| ZP_05909537 | 91 | 69.62 |
| NP_801012 | 92 | 69.62 |
| ZP_05119338 | 93 | 71.43 |
| YP_004250915 | 94 | 62.96 |
| NP_763394 | 95 | 58.9 |
| NP_936393 | 96 | 58.47 |
| ZP_05886259 | 97 | 55.04 |
| EGF40970 | 98 | 53.81 |
| NP_799731 | 99 | 53.81 |
| ZP_01259505 | 100 | 53.39 |
| ZP_04921370_Vibrio_sp._Ex25_VspECA2 | 101 | 53.39 |
| ZP_06179713 | 102 | 53.39 |
| ZP_05718187 | 103 | 53.19 |
| ZP_05720395 | 104 | 52.77 |
| ZP_06032086 | 105 | 53.91 |
| YP_131463 | 106 | 56.03 |
| ADT89517 | 107 | 54.78 |
| ZP_01221338 | 108 | 55.17 |
| ZP_06041212 | 109 | 53.04 |
| YP_004577581 | 110 | 54.04 |
| ZP_01958038 | 111 | 51.91 |
| AEA79886 | 112 | 51.49 |
| ZP_04415512 | 113 | 51.91 |
| ZP_04919557 | 114 | 51.49 |
| EGS58855 | 115 | 51.06 |
| NP_232672 | 116 | 51.49 |
| EGS74119 | 117 | 51.06 |
| ZP_04404214 | 118 | 51.06 |
| ZP_06156315 | 119 | 52.97 |
| ZP_04412368 | 120 | 50.64 |
| ZP_01676897 | 121 | 51.06 |
| ZP_01951018 | 122 | 51.06 |
| ZP_01866792 | 123 | 52 |
| YP_003610599 | 33 | 50.83 |
| ZP_05879020 | 124 | 56.41 |
| YP_004152175 | 125 | 51.58 |
| YP_004391460 | 126 | 50.22 |

Example 7

A. Identification and Expression of *Vibrio* sp. Ex25 Carbonic Anhydrase1 (VspE CA1)

The amino acid sequence of a putative carbonic anhydrase (VspE CA1) from *Vibrio* sp. Ex25 was found in the NCBI Database (NCBI Accession ZP_04922188, /locus_tag="VEx25_A1217") by BLAST analysis. The location of the nucleic acid sequence for VspE CA1 gene from a *Vibrio* sp. Ex25 scf_1101759099903 genomic scaffold, whole genome shotgun sequence (NCBI Reference Sequence: NZ_DS267817.1) was found to be from 79099 to 79818. The gene encoding VspE CA1 from *Vibrio* sp. Ex25 was synthesized by Generay (Shanghai Generay Biotech Co., Ltd).

The nucleotide sequence of the VspE CA1 gene synthesized is set forth as SEQ ID NO:127:

GCATCATGGGGCTATGAAGGCTCACATGGCCCGGAACACTGGGGCGAATT

TGCAAGCGAATGCAGCAAAGGACAAAATCAGTCACCGATTAACATCGTTT

CAGCAGCGGAAGCCAAACTTGACAAACTGCAGTTCGATTACCATGGCAAG

GCGATTAGCCTGCTGAACAATGGCCATACACTGCAAACGTCACTGGAGGG

AGATAATACGCTTCTGATCGATGGCAATGCGTTCACGCTGAAACAGTTCC

ATTTCCATACGCCGAGCGAAAACCATGTGGATGGAAAAGAGTATCCGCTG

GAAGCGCATTTCGTTCATGCAGATACAACAGGCCATCTGGCAGTCGTTGC

AGTTTTCTTCCAAAGCGGCAAAGCAAATCCTGATCTGGCGAAACTTCTTG

CGAACATTCCGAGCAAGGATCAGGCAGTCGAAATTAAACTGCCGTTCGAA

GCGGATGCGCTGCTGCCGAAGGACAAAGCATATTACAGATTCAATGGCTC

ACTGACGACACCGCCGTGCTCAGAAGGCGTGAGATGGCTGGTCATGAAAG

AAGCACAGACGATCAGCCCTGAACAGATTAAAGCGTTCACGAAGGTCATG

GGCGAGAACAACAGACCGATCCAACCGCTTAATGCAAGAATGGTTCTGAT

GCAACAT

Figure 30:
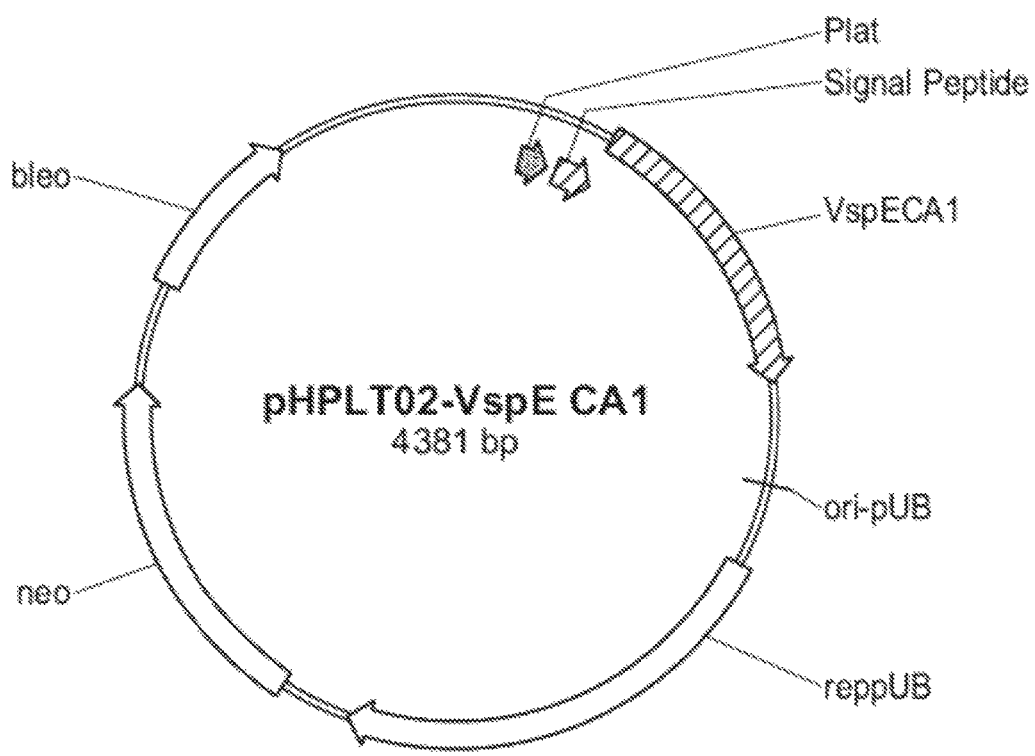
FIG. 30 provides a plasmid map of pHPLT02-VspE CA1.

The VspE CA1 gene was digested with NheI and HpaI and ligated using T4 DNA ligase into pHPLT02 vector (50 ng/μL) digested with the same restriction enzymes to obtain the expression plasmid pHPLT02-VspE CA1 (FIG. 30). The reaction conditions used for ligation were according to the instructions of the supplier (New England Biolabs, MA). The pHPLT02 vector contains the thermostable amylase LAT promoter (pLAT) and a signal peptide (SEQ ID NO: 132) from *Bacillus licheniformis* strain DSM13 for expression of VspE CA1. The vector can replicate in *B. subtilis*. The ligation mixture was amplified using a rolling circle kit (GE Healthcare Life Sciences, NJ) and *B. subtilis* cells (degUHy32, ΔnprB, Δvpr, Δepr, ΔscoC, ΔwprA, Δmpr, ΔispA, Δbpr) were transformed with the amplified ligation mixture. The transformed cells were plated on Luria Agar plates supplemented with 10 ppm kanamycin. About 50-100 colonies were obtained, 24 of which were picked and grown in 24-well plates. The sequence of VspE CA1 gene was confirmed by DNA sequencing. Selected clones from the 24-well plates were further grown in a 7 L fermentor.

The nucleotide sequence of the VspE CA1 gene of plasmid pHPLT02-VspE CA1 is set forth as SEQ ID NO: 128. The signal sequence is shown in italics:

*ATGAAACAACAAAAACGCCTGTATGCGAGACTGCTGCCGCTGCTGTTTGC*

*GCTGATCTTTCTGCTGCCGCACAGCGCAGCTAGCGC*AGCATCATGGGGCT

ATGAAGGCTCACATGGCCCGGAACACTGGGGCGAATTTGCAAGCGAATGC

AGCAAAGGACAAAATCAGTCACCGATTAACATCGTTTCAGCAGCGGAAGC

CAAACTTGACAAACTGCAGTTCGATTACCATGGCAAGGCGATTAGCCTGC

TGAACAATGGCCATACACTGCAAACGTCACTGGAGGGAGATAATACGCTT

CTGATCGATGGCAATGCGTTCACGCTGAAACAGTTCCATTTCCATACGCC

GAGCGAAAACCATGTGGATGGAAAAGAGTATCCGCTGGAAGCGCATTTCG

TTCATGCAGATACAACAGGCCATCTGGCAGTCGTTGCAGTTTTCTTCCAA

-continued
AGCGGCAAAGCAAATCCTGATCTGGCGAAACTTCTTGCGAACATTCCGAG

CAAGGATCAGGCAGTCGAAATTAAACTGCCGTTCGAAGCGGATGCGCTGC

TGCCGAAGGACAAAGCATATTACAGATTCAATGGCTCACTGACGACACCG

CCGTGCTCAGAAGGCGTGAGATGGCTGGTCATGAAAGAAGCACAGACGAT

CAGCCCTGAACAGATTAAAGCGTTCACGAAGGTCATGGGCGAGAACAACA

GACCGATCCAACCGCTTAATGCAAGAATGGTTCTGATGCAACAT

The amino acid sequence of the VspE CA1 precursor protein expressed from plasmid pHPLT02-VspE CA1 is set forth as SEQ ID NO: 129. The signal sequence is shown in italics:
MKQQKRLYARLLPLLFALIFLLPHSAASAASWGYEG-SHGPEHWGEFASECSKGQNQSPINIVSAAEAKLDK-LQFDYHGK AISLLNNGHTLQTSLEGDNTLLIDGNAF-TLKQFHFHTPSENHVDGKEYPLEAHFVHADTTGH-LAVVAVFFQSGKANPDL AKLLANIPSKDQAVEIKLP-FEADALLPKDKAYYRFNGSLTTPPCSEGVRWLVM-KEAQTISPEQIKAFTKVMGENNRPIQP LNARMV-LMQH The amino acid sequence of the mature form of VspE CA1 is set forth as SEQ ID NO:130:

ASWGYEGSHGPEHWGEFASECSKGQNQSPINIVSAAEAKLDKLQFDYHGK

AISLLNNGHTLQTSLEGDNTLLIDGNAFTLKQFHFHTPSENHVDGKEYPL

EAHFVHADTTGHLAVVAVFFQSGKANPDLAKLLANIPSKDQAVEIKLPFE

ADALLPKDKAYYRFNGSLTTPPCSEGVRWLVMKEAQTISPEQIKAFTKVM

GENNRPIQPLNARMVLMQH

Several signal sequences from *Bacillus licheniformis* were used to express VspE CA1, These sequences are listed in Table 7A-1

TABLE 7A-1

Signal sequences used to express VspE CA1

| SEQ ID | Signal Sequence (SS) |
|---|---|
| 131 | MKRHTVNLSLAMLVLGFLLSFSYASA |
| 132 | MKQQKRLYARLLPLLFALIFLLPHSAASA |

Protein Purification of VspE CA1

VspECA1 protein was purified from concentrated broth from a 7 L fermentor run using the three chromatography columns. 1) An anion exchange Q sepharose column equilibrated with 20 mM Tris-HCl, pH 8.0 buffer from which the protein was eluted in the void volume. 2) An anion exchange Q sepharose column equilibrated with 20 mM Tris-HCl, pH 8.0 buffer from which the protein was eluted using a linear gradient of equilibration/wash buffer to 20 mM Tris-HCl, pH 8.0, containing 0.25 M NaCl. 3) A Superdex 75 gel filtration column from which the protein was eluted using 20 mM sodium phosphate, pH 7.0, containing 0.15 M NaCl. The purified protein fractions were pooled and concentrated using a 3K Amicon Ultra-15 device and the concentrated protein fraction was used in further studies.

B. Carbonic Anhydrase Activities of VspE CA1

The carbonic anhydrase activity of purified VspE CA1 was measured in 20 mM Tris sulfate buffer, pH 8.3 at 25° C., containing 20 mM $Na_2SO_4$. Briefly, 3 mL of chilled 20 mM Tris sulfate buffer, pH 8.3, containing 20 mM $Na_2SO_4$ was added to a 50-mL polypropylene conical tube placed on ice. Twenty (20) µL of enzyme sample or buffer were added to the tubes followed by 2 mL of chilled $CO_2$ saturated water (purified and deionized using Milli-Q Integral system, Millipore). After the contents were mixed, a standardized pH meter probe was immediately inserted into the solution and the time required for the pH to drop from 8.3 to 6.3 was recorded using a stop watch. The test was repeated until at least three blank measurements (with buffer added) were within a 15 sec time window and the average of three determinations ($T_{Blank,avg}$) was between 70 and 100 sec. A standard curve was prepared using bovine carbonic anhydrase II (bCAII, Sigma C2522). The test measurements for determining activity were performed in triplicate, and $T_{enzyme,avg}$ was obtained.

One unit of activity (One Wilbur-Anderson (W-A) unit, Wilbur and Anderson, *Journal of Biological Chemistry* 176, 147-154, 1948) is defined as the time required for the pH of a 0.02 M Trizma buffer to drop from 8.3 to 6.3 per min at 0° C.:

$$\text{Units/mL enzyme} = (T_{Blank,avg} - T_{enzyme,avg}) * DF/T_{enzyme,avg} * V$$

where DF=dilution factor of enzyme sample, V=volume (in mL) of enzyme used, $T_{Blank,avg}$=average time values of Blank measurements, and $T_{enzyme,avg}$=average time values of Test measurements.

$$\text{Units/mL protein} = \text{units/ml enzyme/mg protein/mL enzyme}$$

The specific activity of purified VspE CA1 was determined to be 4621±431 units/mg using the above method. Carbonic anhydrase activity of VspE CA1 is suitable for enzyme based $CO_2$ extraction.

C. Stability of VspE CA1 in 1M $NaHCO_3$

Figure 31:
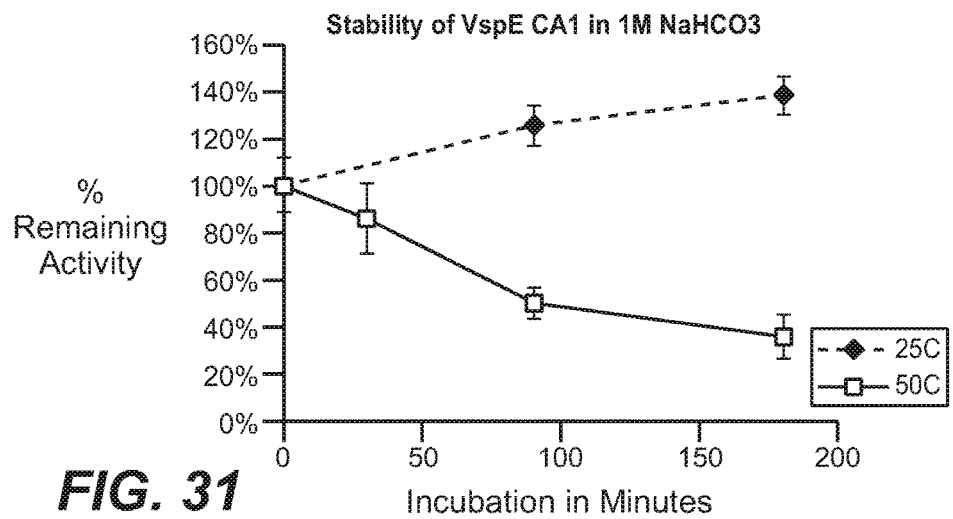
FIG. 31 provides a stability profile of VspE CA1 in the presence of 1 M sodium bicarbonate ($NaHCO_3$).

The stability of VspE CA1 was measured in 20 mM Tris sulfate buffer, pH 8.3, containing 20 mM $Na_2SO_4$ in the presence of 1 M $NaHCO_3$. One hundred (100) ppm of the protein was diluted in 1 M $NaHCO_3$ and incubated at 20° C. and 50° C. in a PCR machine. The specific activity of the sample was measured prior to incubation as described in Example 7B. At varying time points (5 min to 3 h), 100 µL samples were withdrawn, cooled on ice and their specific activity measured as described in Example 7B. The percent remaining activity was calculated for each time point. The activity of the sample kept on ice at time 0 was defined as 100% activity. FIG. 31 shows stability of VspE CA1 in 1 M $NaHCO_3$. VspE CA1 remains mostly active over a period of 3 h incubation and will likely to remain thus active well beyond this time point at 25° C. The carbonic anhydrase activity decreased more rapidly at a much higher temperature, 50° C., but much of the carbonic anhydrase activity was preserved within the first hour of incubation even at such a high temperature.

D. Heat Capacity Measurements of VspE CA1

Excessive heat capacity curves were measured for VspE CA1 and bovine carbonic anhydrase II (bCA II) using an ultrasensitive scanning high-throughput microcalorimeter, VP-Cap DSC (MicroCal, Inc., Northampton, Mass.). The standard procedure for DSC measurements and the theory of the technique has been described previously (Freire, Differential Scanning calorimetry, *Methods Mol Biol*, 41:191-218, 1995). Approximately 500 µL of a 0.5 mg/mL sample of each enzyme was studied. The proteins were scanned over a 35-100° C. temperature range. The same samples were then re-scanned (following cooling) to check the reversibility of the thermal unfolding process. For the VspE CA1 carbonic anhydrase studied the thermal unfolding was irreversible. The proteins were studied in the following buffers: (1) 0.1 M Tris, pH 8.5, (2) 0.1 M CHES, pH 9.5, (3) 0.1 M CAPS, pH 10.5, and (4) 0.1 M CHES, pH 9.5+2 M NaCl. A 200° C./h scan rate was used to minimize any artifacts that may result from aggregation. The apparent thermal midpoint [$T_m$(app)] of the DSC curves was used as an indicator of the thermal stability and melting points for these carbonic anhydrase molecules. The melting points of both enzymes in various buffers are shown in Table 7D-1.

The $T_m$(app) values during thermal unfolding for the VspE CA1 carbonic anhydrase protein shows a dependence on pH over the range of 8.5 to 10.5. Similar to bCAII, VspE CA1 shows the highest values between pH 8.5 and 9.5. The 0.1 M CHES, pH 9.5 with 2 M NaCl buffer decreased the $T_m$(app) for bovine CA II, but did not affect the $T_m$(app) for VspE CA1. The carbonate significantly increased the $T_m$(app) for VspE CA1. $T_m$(app) was also determined for bCAII and VspE CA1 in 1M KHCO$_3$ with and without 1M NaCl (Table 7D-2). It was observed that the VspE CA1 had a higher Tm(app) at 1 M salt as compared to the Tm(app) at 0 M salt.

TABLE 7D-1

Melting Temperature for VspE CA1 and bCAII Buffers

| Protein | #1 0.1M Tris, pH 8.5 | #2 0.1M CHES, pH 9.5 | #3 0.1M CAPS, pH 10.5 | #4 0.1M CHES, pH 9.5 + 2M NaCl |
|---|---|---|---|---|
| Bovine CA II | 68.8 | 69.4 | 66.6 | 61.7 |
| VspE CA1 | 49.9 | 44.9/60.9 | 44.5 | 53.4/68.8 |

TABLE 7D-2

$T_m$(app) [° C.] of VspE CA1 in 1M KHCO$_3$

| [Salt] (M) | bCA II | VspE CA1 |
|---|---|---|
| 0 | 62.1 | 49.6 |
| 1 | 62.7 | 57.9 |

Example 8

A. Identification and Expression of *Vibrio* sp. Ex25 Carbonic Anhydrase2 (VspE CA2)

The amino acid sequence of another putative carbonic anhydrase (VspE CA2) from *Vibrio* sp. Ex25 was found in the NCBI Database (NCBI Accession ZP_04921370, /locus_tag="VEx25_A0096") by BLAST analysis. The location of the nucleic acid sequence for VspE CA2 gene from a *Vibrio* sp. Ex25 scf_1101759099880 genomic scaffold, whole genome shotgun sequence (NCBI Reference Sequence: NZ_DS267810.1) was found to be from 94584 to 95303. The gene encoding VspE CA2 from *Vibrio* sp. Ex25 was synthesized by Generay (Shanghai Generay Biotech Co., Ltd).

The nucleotide sequence of the VspE CA2 gene synthesized is set forth as SEQ ID NO:133:

TCAGAGTGGGGCTATGGCAATGATAAACATGGCCCGGAACATTGGGGCGA

AATTGCAAAGGATTGCGCGACAACGAAAAACCAATCACCGATTAACATTG

ACAATCCGGCCGACGCCAAGCTGGAAGCCCTTAATCTGTCATATACAGGC

CAGGTTATTGGCCTGACGAACAATGGCCATACACTGCAAGCTCAAGTGAA

CGGCAGAAACAGCTTCACAATCGATAGCGAAACGTTTGAGCTTCAGCAGT

TTCACTTTCATACACCGAGCGAGAACCAGATCAAAGGCAGACAGTATCCG

CTTGAAGCGCACTTTGTTCATGCAAATGCCGACGGCGAACTGGCAGTGAT

TTCAGTTATGTTTGATGCAGGCGATCAGAATGCAGCACTGAGCAAGCTGA

TCAATGCAATTCCGCAGGAGAACCAAACGACGTTCTTTAAGGACACGTTT

GAGATCAACGACCTGCTGCCGAAGACGGCAAATTATTACAGATTCAACGG

CTCACTGACAACGCCGCCGTGTAGCGAAGGCGTCAGATGGTTCGTTCTGA

AAGACACACAAACACTGTCAAAGGACCAGGCAGCCAAACTGATGGAAGTT

ATGGGCCAAAATAACAGACCGCTGCAACCGCTGAATGCGAGAGTTGTGCT

TAGCAAT

Figure 32:
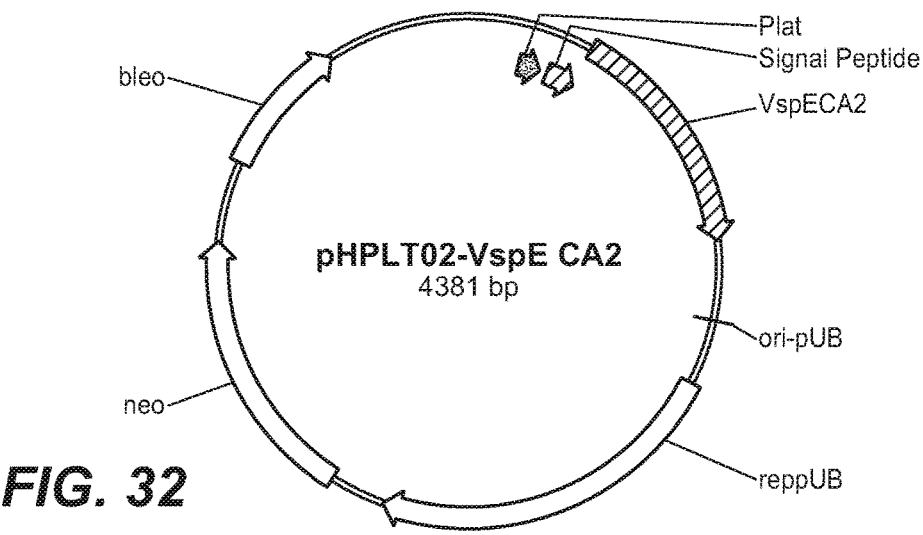
FIG. 32 provides a plasmid map of pHPLT02-VspE CA2.
Figure 33:
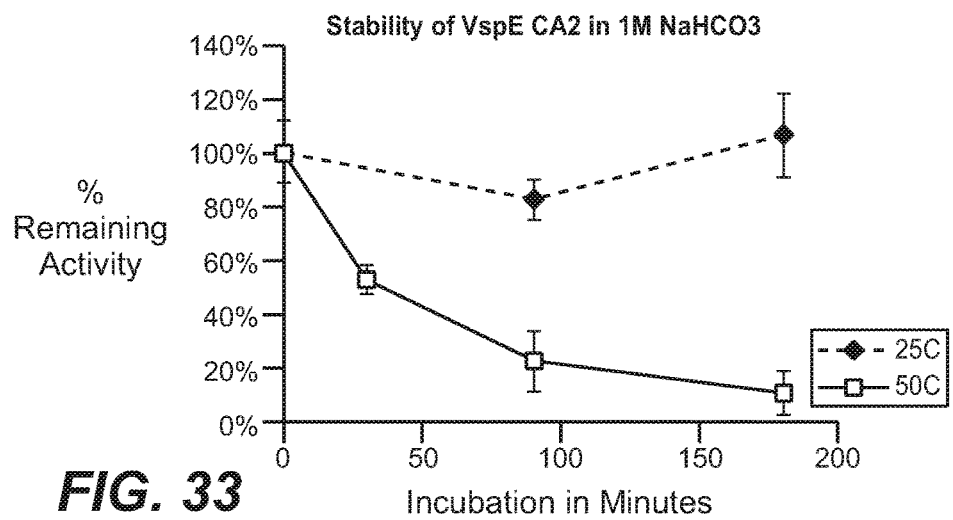
FIG. 33 provides a stability profile of VspE CA2 in the presence of 1 M sodium bicarbonate ($NaHCO_3$).

The VspE CA2 gene was digested with NheI and HpaI and ligated using T4 DNA ligase into pHPLT02 vector (50 ng/µL) digested with the same restriction enzymes to obtain the expression plasmid pHPLT02-VspE CA2 (FIG. 32). The reaction conditions used for ligation were according to the instructions of the supplier (New England Biolabs, MA). The pHPLT02 vector contains the thermostable amylase LAT promoter (pLAT) and a signal peptide from *Bacillus licheniformis* strain DSM13 (for example, one that is part of SEQ ID NO: 135) for expression of VspE CA2. The vector can replicate in *B. subtilis*. The ligation mixture was amplified using a rolling circle kit (GE Healthcare Life Sciences, NJ) and *B. subtilis* cells (degUHy32, ΔnprB, Δvpr, Δepr, ΔscoC, ΔwprA, Δmpr, ΔispA, Δbpr) were transformed with the amplified ligation mixture. The transformed cells were plated on Luria Agar plates supplemented with 10 ppm kanamycin. About 50-100 colonies were obtained, 24 of which were picked and grown in 24-well plates. The sequence of VspE CA2 gene was confirmed by DNA sequencing. Selected clones from the 24-well plates were further grown in a 7 L fermentor.

The nucleotide sequence of the VspE CA2 gene of plasmid pHPLT02-VspE CA2 is set forth as SEQ ID NO: 134. The signal sequence is shown in italics.

*ATGGTCTTTAAAAAACCGAAAGTCTTTATCGCAGCGGTCATCCTGGCGCT*

*GAGCAGCTTTGCGGGAACGGCAGCTAGCGCAT*CAGAGTGGGGCTATGGCA

ATGATAAACATGGCCCGGAACATTGGGGCGAAATTGCAAAGGATTGCGCG

ACAACGAAAAACCAATCACCGATTAACATTGACAATCCGGCCGACGCCAA

GCTGGAAGCCCTTAATCTGTCATATACAGGCCAGGTTATTGGCCTGACGA

ACAATGGCCATACACTGCAAGCTCAAGTGAACGGCAGAAACAGCTTCACA

ATCGATAGCGAAACGTTTGAGCTTCAGCAGTTTCACTTTCATACACCGAG

CGAGAACCAGATCAAAGGCAGACAGTATCCGCTTGAAGCGCACTTTGTTC

ATGCAAATGCCGACGGCGAACTGGCAGTGATTTCAGTTATGTTTGATGCA

GGCGATCAGAATGCAGCACTGAGCAAGCTGATCAATGCAATTCCGCAGGA

-continued

GAACCAAACGACGTTCTTTAAGGACACGTTTGAGATCAACGACCTGCTGC

CGAAGACGGCAAATTATTACAGATTCAACGGCTCACTGACAACGCCGCCG

TGTAGCGAAGGCGTCAGATGGTTCGTTCTGAAAGACACACAAACACTGTC

AAAGGACCAGGCAGCCAAACTGATGGAAGTTATGGGCCAAAATAACAGAC

CGCTGCAACCGCTGAATGCGAGAGTTGTGCTTAGCAAT

The amino acid sequence of the VspE CA2 precursor protein expressed from plasmid pHPLT02-VspE CA2 is set forth as SEQ ID NO: 135. The signal sequence is shown in italics.

*MVFKKPKVFIAAVILALSSFAGTAASA*SEWGYGNDKHGPEHWGEIAKDCA

TTKNQSPINIDNPADAKLEALNLSYTGQVIGLTNNGHTLQAQVNGRNSFT

IDSETFELQQFHFHTPSENQIKGRQYPLEAHFVHANADGELAVISVMFDA

GDQNAALSKLINAIPQENQTTFFKDTFEINDLLPKTANYYRFNGSLTTPP

CSEGVRWFVLKDTQTLSKDQAAKLMEVMGQNNRPLQPLNARVVLSN

The amino acid sequence of the mature form of VspE CA2 is set forth as SEQ ID NO:136:

```
SEWGYGNDKHGPEHWGEIAKDCATTKNQSPINIDNPADAKLEALNLSYTG

QVIGLTNNGHTLQAQVNGRNSFTIDSETFELQQFHFHTPSENQIKGRQYP

LEAHFVHANADGELAVISVMFDAGDQNAALSKLINAIPQENQTTFFKDTF

EINDLLPKTANYYRFNGSLTTPPCSEGVRWFVLKDTQTLSKDQAAKLMEV

MGQNNRPLQPLNARVVLSN
```

Protein Purification of VspE CA2

VspECA2 protein was purified from concentrated broth from a 7 L fermentor run using the three chromatography columns. 1) An anion exchange Q sepharose column equilibrated with 20 mM Tris-HCl, pH 8.0 buffer from which the protein was eluted using a linear gradient of equilibration/wash buffer to 20 mM Tris-HCl, pH 8.0, containing 0.25 M NaCl. 2) An anion exchange Q sepharose column equilibrated with 20 mM Tris-HCl, pH 8.0 buffer from which the protein was eluted using a linear gradient of equilibration/wash buffer to 20 mM Tris-HCl, pH 8.0, containing 0.3 M NaCl. 3) A Superdex 75 gel filtration column from which the protein was eluted using 20 mM sodium phosphate, pH 7.0, containing 0.15 M NaCl. The purified protein fractions were pooled and concentrated using a 3K Amicon Ultra-15 device and the concentrated protein fraction was used in further studies.

B. Carbonic Anhydrase Activities of VspE CA2

The carbonic anhydrase activity of purified VspE CA2 was measured in 20 mM Tris sulfate buffer (pH 8.3 at 25° C.) containing 20 mM $Na_2SO_4$. Briefly, 3 mL of chilled 20 mM Tris sulfate buffer, pH 8.3, containing 20 mM $Na_2SO_4$ was added to a 50-mL polypropylene conical tube placed on ice. Twenty (20) μL of enzyme sample or buffer were added to the tubes followed by 2 mL of chilled $CO_2$ saturated water (purified and deionized using Milli-Q Integral system, Millipore). After the contents were mixed, a standardized pH meter probe was immediately inserted into the solution and the time required for the pH to drop from 8.3 to 6.3 was recorded using a stop watch. The test was repeated until at least three blank measurements (with buffer added) were within a 15 sec time window and the average of three determinations ($T_{Blank,avg}$) was between 70 and 100 sec. A standard curve was prepared using bovine carbonic anhydrase II (bCAII, Sigma C2522). The test measurements for determining activity were performed in triplicate, and $T_{enzyme,avg}$ was obtained.

One unit of activity (One Wilbur-Anderson (W-A) unit, Wilbur and Anderson, *Journal of Biological Chemistry* 176, 147-154, 1948) is defined as the time required for the pH of a 0.02 M Trizma buffer to drop from 8.3 to 6.3 per min at 0° C.:

$$\text{Units/mL enzyme}=(T_{Blank,avg}-T_{enzyme,avg})^{*}\text{DF}/T_{enzyme,avg}{}^{*}V$$

where DF=dilution factor of enzyme sample, V=volume (in mL) of enzyme used, $T_{Blank,avg}$=average time values of Blank measurements, and $T_{enzyme,avg}$=average time values of Test measurements.

Units/ml protein=units/mL enzyme/mg protein/mL enzyme

The specific activity of purified VspE CA2 was determined to be 3189±112 units/mg using the above method. Carbonic anhydrase activity of VspE CA2 is suitable for enzyme based $CO_2$ extraction.

C. Stability of VspE CA2 in 1M $NaHCO_3$

The stability of VspE CA2 was measured in 20 mM Tris sulfate buffer, pH 8.3, containing 20 mM $Na_2SO_4$ in the presence of 1 M $NaHCO_3$. One hundred (100) ppm of the protein was diluted in 1 M $NaHCO_3$ and incubated at 20° C. and 50° C. in a PCR machine. The specific activity of the sample was measured prior to incubation as described in Example 8B. At varying time points (5 min to 3 h), 100 μL samples were withdrawn, cooled on ice and their specific activity measured as described in Example 8B. The percent remaining activity was calculated for each time point. The activity of the sample kept on ice at time 0 was defined as 100% activity. FIG. 33 shows stability of VspE CA2 in 1 M $NaHCO_3$. VspE CA2 remains mostly active over a 3 h incubation at 25° C., and can be expected to remain mostly active for an extended period of incubation. At 50° C., the loss of activity was more prominent and at a higher rate. However, at least 40% of activity remained after 30 minutes of incubation at such a high temperature, indicating a substantial thermostability in this enzyme.

D. Heat Capacity Measurements of VspE CA2

Excessive heat capacity curves were measured for VspE CA2 and bovine carbonic anhydrase II (bCA II) using an ultrasensitive scanning high-throughput microcalorimeter, VP-Cap DSC (MicroCal, Inc., Northampton, Mass.). The standard procedure for DSC measurements and the theory of the technique has been described previously (Freire, Differential Scanning calorimetry, *Methods Mol Biol,* 41:191-218, 1995). Approximately 500 μL of a 0.5 mg/mL sample of each enzyme was studied. The proteins were scanned over a 35-100° C. temperature range. The same samples were then re-scanned (following cooling) to check the reversibility of the thermal unfolding process. For the VspE CA2 carbonic anhydrase studied the thermal unfolding was irreversible. The proteins were studied in the following buffers: (1) 0.1 M Tris, pH 8.5, (2) 0.1 M CHES, pH 9.5, (3) 0.1 M CAPS, pH 10.5, and (4) 0.1 M CHES, pH 9.5+2 M NaCl. A 200° C./h scan rate was used to minimize any artifacts that may result from aggregation. The apparent thermal midpoint [$T_m$(app)] of the DSC curves was used as an indicator of the thermal stability and melting points for these carbonic anhydrase molecules. The melting points of both enzymes in various buffers are shown in Table 8D-1.

The $T_m$(app) values during thermal unfolding for the VspE CA2 carbonic anhydrase protein shows a dependence on pH over the range of 8.5 to 10.5. VspE CA2 shows the highest values at pH 8.5. The 0.1 M CHES, pH 9.5 with 2 M NaCl buffer decreased the $T_m$(app) for bovine CA II, but increased the $T_m$(app) for VspE CA2 by 7° C. The carbonate slightly increased the $T_m$(app) for VspE CA2. $T_m$(app) was also determined for bCAII and VspE CA2 in 1M KHCO$_3$ with and without 1M NaCl (Table 8D-2). Surprisingly, VspE CA2 appeared to have a higher Tm(app) at 1 M bicarbonate than at 0 M bicarbonate.

TABLE 8D-1

Melting Temperature for VspE CA2 and bCAII Buffers

| Protein | #1 | #2 | #3 | #4 |
|---|---|---|---|---|
| | 0.1M Tris, pH 8.5 | 0.1M CHES, pH 9.5 | 0.1M CAPS, pH 10.5 | 0.1M CHES, pH 9.5 + 2M NaCl |
| Bovine CA II | 68.8 | 69.4 | 66.6 | 61.7 |
| VspE CA2 | 76.8 | 72.4 | 67.3 | 76.3 |

TABLE 8D-2

$T_m$(app) [° C.] of VspE CA2 in 1M KHCO$_3$

| [Salt] (M) | bCA II | VspE CA2 |
|---|---|---|
| 0 | 62.1 | 74.1 |
| 1 | 62.7 | 79.7 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
<160> NUMBER OF SEQ ID NOS: 136

<210> SEQ ID NO 1
<211> LENGTH: 843
<212> TYPE: DNA
<213> ORGANISM: Bacillus gibsonii

<400> SEQUENCE: 1
ttgaaacgat caaatctact tattaaaacg acagtagccg ctaccattct attaactagt      60
acatcctttt tgacagaagc aatgcttgca catggaaatc acgtaagttc ctcttcttta     120
attcattcac cctatgatcg tttgactgcg aacgcgtccc atgattggtc atattctggt     180
ccaacaggtc ctgagttttg gggagagctt gactctgaat ttaaagcctg ctctaatggc     240
acgcagcaat ccccaattgc actagaccca accgatgttg gcgatgaaaa atggagcttg     300
gacctagatt atgccaaaac agagtttccc attgaaaaca atggtcatac cattcaagcc     360
aatgtggttg aaaaaaaagg acagccttcc aatcaattaa cacttggcga ctccacatat     420
gaactggttc aatttcattt tcactcaccg agtgagcata cgctagcagg agagtcttat     480
gaaatggaag tacaccttgt tcataaagat gagcaagaca atcttgctgt gttaggcgta     540
ttaatggaag aaggagaaaa aaacaaagct ttaaaagata tgtggaagaa gatgccgact     600
agtgtcggaa cttcaactaa aaccattaag ttaaatccta gtgagctggt tcctactgat     660
ctatcaactt tcaatatga cggttcgctt actacccccgc cttgctctga aggtgtgaag     720
tggagtgtga gtgactcttc aattacactc tcttcggaac agcttcaagc ttttcaagat     780
ttgtacccga ataactatcg cccaattcaa gatttagggg atcgtgaagt tggtttttcat     840 tat                                                                    843

<210> SEQ ID NO 2
<211> LENGTH: 281
<212> TYPE: PRT
<213> ORGANISM: Bacillus gibsonii

<400> SEQUENCE: 2

Met Lys Arg Ser Asn Leu Leu Ile Lys Thr Thr Val Ala Ala Thr Ile
```

```
1               5                   10                  15

Leu Leu Thr Ser Thr Ser Phe Leu Thr Glu Ala Met Leu Ala His Gly
            20                  25                  30

Asn His Val Ser Ser Ser Ser Leu Ile His Ser Pro Tyr Asp Arg Leu
        35                  40                  45

Thr Ala Asn Ala Ser His Asp Trp Ser Tyr Ser Gly Pro Thr Gly Pro
    50                  55                  60

Glu Phe Trp Gly Glu Leu Asp Ser Glu Phe Lys Ala Cys Ser Asn Gly
65                  70                  75                  80

Thr Gln Gln Ser Pro Ile Ala Leu Asp Pro Thr Asp Val Gly Asp Glu
                85                  90                  95

Lys Trp Ser Leu Asp Leu Asp Tyr Ala Lys Thr Glu Phe Ser Ile Glu
            100                 105                 110

Asn Asn Gly His Thr Ile Gln Ala Asn Val Val Glu Lys Lys Gly Gln
        115                 120                 125

Pro Ser Asn Gln Leu Thr Leu Gly Asp Ser Thr Tyr Glu Leu Val Gln
    130                 135                 140

Phe His Phe His Ser Pro Ser Glu His Thr Leu Ala Gly Glu Ser Tyr
145                 150                 155                 160

Glu Met Glu Val His Leu Val His Lys Asp Glu Gln Asp Asn Leu Ala
                165                 170                 175

Val Leu Gly Val Leu Met Glu Glu Gly Glu Lys Asn Lys Ala Leu Lys
            180                 185                 190

Asp Met Trp Lys Lys Met Pro Thr Ser Val Gly Thr Ser Thr Lys Thr
        195                 200                 205

Ile Lys Leu Asn Pro Ser Glu Leu Val Pro Thr Asp Leu Ser Thr Phe
    210                 215                 220

Gln Tyr Asp Gly Ser Leu Thr Thr Pro Pro Cys Ser Glu Gly Val Lys
225                 230                 235                 240

Trp Ser Val Ser Asp Ser Ser Ile Thr Leu Ser Ser Glu Gln Leu Gln
                245                 250                 255

Ala Phe Gln Asp Leu Tyr Pro Asn Asn Tyr Arg Pro Ile Gln Asp Leu
            260                 265                 270

Gly Asp Arg Glu Val Gly Phe His Tyr
        275                 280

<210> SEQ ID NO 3
<211> LENGTH: 252
<212> TYPE: PRT
<213> ORGANISM: Bacillus gibsonii

<400> SEQUENCE: 3

Ala His Gly Asn His Val Ser Ser Ser Ser Leu Ile His Ser Pro Tyr
1               5                   10                  15

Asp Arg Leu Thr Ala Asn Ala Ser His Asp Trp Ser Tyr Ser Gly Pro
            20                  25                  30

Thr Gly Pro Glu Phe Trp Gly Glu Leu Asp Ser Glu Phe Lys Ala Cys
        35                  40                  45

Ser Asn Gly Thr Gln Gln Ser Pro Ile Ala Leu Asp Pro Thr Asp Val
    50                  55                  60

Gly Asp Glu Lys Trp Ser Leu Asp Leu Asp Tyr Ala Lys Thr Glu Phe
65                  70                  75                  80

Ser Ile Glu Asn Asn Gly His Thr Ile Gln Ala Asn Val Val Glu Lys
                85                  90                  95
```

```
Lys Gly Gln Pro Ser Asn Gln Leu Thr Leu Gly Asp Ser Thr Tyr Glu
            100                 105                 110

Leu Val Gln Phe His Phe His Ser Pro Ser Glu His Thr Leu Ala Gly
        115                 120                 125

Glu Ser Tyr Glu Met Glu Val His Leu Val His Lys Asp Glu Gln Asp
    130                 135                 140

Asn Leu Ala Val Leu Gly Val Leu Met Glu Glu Gly Lys Asn Lys
145                 150                 155                 160

Ala Leu Lys Asp Met Trp Lys Lys Met Pro Thr Ser Val Gly Thr Ser
                165                 170                 175

Thr Lys Thr Ile Lys Leu Asn Pro Ser Glu Leu Val Pro Thr Asp Leu
            180                 185                 190

Ser Thr Phe Gln Tyr Asp Gly Ser Leu Thr Thr Pro Pro Cys Ser Glu
        195                 200                 205

Gly Val Lys Trp Ser Val Ser Asp Ser Ser Ile Thr Leu Ser Ser Glu
    210                 215                 220

Gln Leu Gln Ala Phe Gln Asp Leu Tyr Pro Asn Asn Tyr Arg Pro Ile
225                 230                 235                 240

Gln Asp Leu Gly Asp Arg Glu Val Gly Phe His Tyr
                245                 250

<210> SEQ ID NO 4
<211> LENGTH: 34
<212> TYPE: DNA
<213> ORGANISM: Artificial Sequence
<220> FEATURE:
<223> OTHER INFORMATION: synthetic primer

<400> SEQUENCE: 4
gcggctagcg cagcacatgg aaatcacgta agtt                            34

<210> SEQ ID NO 5
<211> LENGTH: 36
<212> TYPE: DNA
<213> ORGANISM: Artificial Sequence
<220> FEATURE:
<223> OTHER INFORMATION: synthetic primer

<400> SEQUENCE: 5
gcggttaact cattaataat gaaaaccaac ttcacg                          36

<210> SEQ ID NO 6
<211> LENGTH: 33
<212> TYPE: DNA
<213> ORGANISM: Artificial Sequence
<220> FEATURE:
<223> OTHER INFORMATION: synthetic primer

<400> SEQUENCE: 6
agcatacgct ggcaggagag tcttatgaaa tgg                             33

<210> SEQ ID NO 7
<211> LENGTH: 30
<212> TYPE: DNA
<213> ORGANISM: Artificial Sequence
<220> FEATURE:
<223> OTHER INFORMATION: synthetic primer

<400> SEQUENCE: 7
ctctcctgcc agcgtatgct cactcggtga                                 30
```

<210> SEQ ID NO 8
<211> LENGTH: 843
<212> TYPE: DNA
<213> ORGANISM: Artificial Sequence
<220> FEATURE:
<223> OTHER INFORMATION: synthetic sequence

<400> SEQUENCE: 8

```
atgaaaaaca tccgcaaaac ggtcatcttt gcggcaatca tcctgctggt ccatacagcg      60
gttccggcaa tcccggctag cgcagcacat ggaaatcacg taagttcctc ttctttaatt     120
cattcaccct atgatcgttt gactgcgaac gcgtcccatg attggtcata ttctggtcca     180
acaggtcctg agtttggggg agagcttgac tctgaattta agcctgctc taatggcacg      240
cagcaatccc caattgcact agacccaacc gatgttggcg atgaaaaatg gagcttggac     300
ctagattatg ccaaaacaga gttttccatt gaaaacaatg gtcataccat tcaagccaat     360
gtggttgaaa aaaaggaca gccttccaat caattaacac ttggcgactc cacatatgaa      420
ctggttcaat tcattttca ctcaccgagt gagcatacgc tggcaggaga gtcttatgaa      480
atggaagtac accttgttca taagatgag caagacaatc ttgctgtgtt aggcgtatta     540
atggaagaag gagaaaaaaa caaagcttta aaagatatgt ggaagaagat gccgactagt     600
gtcggaactt caactaaaac cattaagtta atcctagtg agctggttcc tactgatcta      660
tcaactttc aatatgacgg ttcgcttact acccgcctt gctctgaagg tgtgaagtgg      720
agtgtgagtg actcttcaat tacactctct tcggaacagc ttcaagcttt tcaagatttg     780
tacccgaata actatcgccc aattcaagat ttaggggatc gtgaagttgg ttttcattat     840
taa                                                                   843
```

<210> SEQ ID NO 9
<211> LENGTH: 280
<212> TYPE: PRT
<213> ORGANISM: Artificial Sequence
<220> FEATURE:
<223> OTHER INFORMATION: synthetic precursor protein

<400> SEQUENCE: 9

```
Met Lys Asn Ile Arg Lys Thr Val Ile Phe Ala Ala Ile Ile Leu Leu
1               5                   10                  15

Val His Thr Ala Val Pro Ala Ile Pro Ala Ser Ala Ala His Gly Asn
            20                  25                  30

His Val Ser Ser Ser Leu Ile His Ser Pro Tyr Asp Arg Leu Thr
        35                  40                  45

Ala Asn Ala Ser His Asp Trp Ser Tyr Ser Gly Pro Thr Gly Pro Glu
    50                  55                  60

Phe Trp Gly Glu Leu Asp Ser Glu Phe Lys Ala Cys Ser Asn Gly Thr
65                  70                  75                  80

Gln Gln Ser Pro Ile Ala Leu Asp Pro Thr Asp Val Gly Asp Glu Lys
                85                  90                  95

Trp Ser Leu Asp Leu Asp Tyr Ala Lys Thr Glu Phe Ser Ile Glu Asn
            100                 105                 110

Asn Gly His Thr Ile Gln Ala Asn Val Val Glu Lys Lys Gly Gln Pro
        115                 120                 125

Ser Asn Gln Leu Thr Leu Gly Asp Ser Thr Tyr Glu Leu Val Gln Phe
    130                 135                 140

His Phe His Ser Pro Ser Glu His Thr Leu Ala Gly Glu Ser Tyr Glu
145                 150                 155                 160
```

```
Met Glu Val His Leu Val His Lys Asp Glu Gln Asp Asn Leu Ala Val
                165                 170                 175
Leu Gly Val Leu Met Glu Glu Gly Glu Lys Asn Lys Ala Leu Lys Asp
            180                 185                 190
Met Trp Lys Lys Met Pro Thr Ser Val Gly Thr Ser Thr Lys Thr Ile
        195                 200                 205
Lys Leu Asn Pro Ser Glu Leu Val Pro Thr Asp Leu Ser Thr Phe Gln
    210                 215                 220
Tyr Asp Gly Ser Leu Thr Thr Pro Pro Cys Ser Glu Gly Val Lys Trp
225                 230                 235                 240
Ser Val Ser Asp Ser Ser Ile Thr Leu Ser Ser Glu Gln Leu Gln Ala
                245                 250                 255
Phe Gln Asp Leu Tyr Pro Asn Asn Tyr Arg Pro Ile Gln Asp Leu Gly
            260                 265                 270
Asp Arg Glu Val Gly Phe His Tyr
        275                 280

<210> SEQ ID NO 10
<211> LENGTH: 28
<212> TYPE: PRT
<213> ORGANISM: Bacillus licheniformis

<400> SEQUENCE: 10

Met Lys Asn Ile Arg Lys Thr Val Ile Phe Ala Ala Ile Ile Leu Leu
1               5                   10                  15
Val His Thr Ala Val Pro Ala Ile Pro Ala Ser Ala
            20                  25

<210> SEQ ID NO 11
<211> LENGTH: 24
<212> TYPE: PRT
<213> ORGANISM: Bacillus licheniformis

<400> SEQUENCE: 11

Met Ile Lys Lys Trp Ala Val His Leu Leu Phe Ser Ala Leu Val Leu
1               5                   10                  15
Leu Gly Leu Ser Gly Ala Ser Ala
            20

<210> SEQ ID NO 12
<211> LENGTH: 49
<212> TYPE: PRT
<213> ORGANISM: Bacillus licheniformis

<400> SEQUENCE: 12

Met Ala Ala Glu Lys Val Phe Ser Lys Asn Lys Ile Ile Gly Gly Lys
1               5                   10                  15
Arg Met Ser Tyr Met Lys Arg Ser Ile Ser Val Phe Ile Ala Cys Phe
            20                  25                  30
Met Val Ala Ala Leu Gly Ile Ser Gly Ile Ile Ala Pro Lys Ala Ser
        35                  40                  45
Ala

<210> SEQ ID NO 13
<211> LENGTH: 25
<212> TYPE: PRT
<213> ORGANISM: Bacillus licheniformis

<400> SEQUENCE: 13
```

```
Met Lys Lys Thr Ile Met Ser Leu Ala Ala Ala Ala Met Ser Ala
1               5                   10                  15

Thr Ala Phe Gly Ala Thr Ala Ser Ala
            20                  25

<210> SEQ ID NO 14
<211> LENGTH: 26
<212> TYPE: PRT
<213> ORGANISM: Bacillus licheniformis

<400> SEQUENCE: 14

Met Lys Lys Phe Ala Cys Val Val Ile Phe Leu Leu Leu Ala Ala Val
1               5                   10                  15

Ile Ala Gly Cys Ala Ala Asp Ala Ser Ala
            20                  25

<210> SEQ ID NO 15
<211> LENGTH: 23
<212> TYPE: PRT
<213> ORGANISM: Bacillus licheniformis

<400> SEQUENCE: 15

Met Lys Lys Arg Leu Met Ser Leu Leu Val Cys Ile Leu Val Leu Val
1               5                   10                  15

Pro Ala Ala Gly Ala Ser Ala
            20

<210> SEQ ID NO 16
<211> LENGTH: 275
<212> TYPE: PRT
<213> ORGANISM: Bacillus halodurans

<400> SEQUENCE: 16

Met Lys Lys Tyr Leu Trp Gly Lys Thr Cys Leu Val Val Ser Leu Ser
1               5                   10                  15

Val Met Val Thr Ala Cys Ser Ser Ala Pro Ser Thr Glu Pro Val Asp
            20                  25                  30

Glu Pro Ser Glu Thr His Glu Glu Thr Ser Gly Gly Ala His Glu Val
        35                  40                  45

His Trp Ser Tyr Thr Gly Asp Thr Gly Pro Glu His Trp Ala Glu Leu
    50                  55                  60

Asp Ser Glu Tyr Gly Ala Cys Ala Gln Gly Glu Gln Ser Pro Ile
65                  70                  75                  80

Asn Leu Asp Lys Ala Glu Ala Val Asp Thr Asp Thr Glu Ile Gln Val
                85                  90                  95

His Tyr Glu Pro Ser Ala Phe Thr Ile Lys Asn Asn Gly His Thr Ile
            100                 105                 110

Gln Ala Glu Thr Thr Ser Asp Gly Asn Thr Ile Glu Ile Asp Gly Lys
        115                 120                 125

Glu Tyr Thr Leu Val Gln Phe His Phe His Ile Pro Ser Glu His Glu
    130                 135                 140

Met Glu Gly Lys Asn Leu Asp Met Glu Leu His Phe Val His Lys Asn
145                 150                 155                 160

Glu Asn Asp Glu Leu Ala Val Leu Gly Val Leu Met Lys Ala Gly Glu
                165                 170                 175

Glu Asn Glu Glu Leu Ala Lys Leu Trp Ser Lys Leu Pro Ala Glu Glu
            180                 185                 190

Thr Glu Glu Asn Ile Ser Leu Asp Glu Ser Ile Asp Leu Asn Ala Leu
```

```
            195                 200                 205
Leu Pro Glu Ser Lys Glu Gly Phe His Tyr Asn Gly Ser Leu Thr Thr
    210                 215                 220

Pro Pro Cys Ser Glu Gly Val Lys Trp Thr Val Leu Ser Glu Pro Ile
225                 230                 235                 240

Thr Val Ser Gln Glu Gln Ile Asp Ala Phe Ala Glu Ile Phe Pro Asp
                245                 250                 255

Asn His Arg Pro Val Gln Pro Trp Asn Asp Arg Asp Val Tyr Asp Val
                260                 265                 270

Ile Thr Glu
        275

<210> SEQ ID NO 17
<211> LENGTH: 291
<212> TYPE: PRT
<213> ORGANISM: Bradyrhizobium japonicum

<400> SEQUENCE: 17

Met Gly Arg Lys Asp Arg Val Gly Glu Pro Ile Asn Ser Thr Arg Asp
1               5                   10                  15

Gly His Cys Asp Ser Pro Arg Leu Ser Pro Arg Leu Arg Ala His Arg
            20                  25                  30

Arg Ser Asn Ser Ser Trp Gly Asn Met Met Asn Arg Arg His Ala Leu
        35                  40                  45

Lys Ala Leu Ala Gly Leu Ala Leu Cys Pro Val Cys Lys Pro Ala Phe
    50                  55                  60

Ala Ala Glu Gly Val His Trp Ser Tyr Glu Gly Ala Gly Ala Pro Ala
65                  70                  75                  80

Lys Trp Gly Asp Leu Asp Ala Ala Asn Lys Ala Cys Ala Val Gly Leu
                85                  90                  95

Gln Gln Ser Pro Ile Asp Ile Glu Ala Thr Ile Lys Ser Gln Leu Pro
            100                 105                 110

Thr Leu Lys Leu Asn Trp Gly Lys Ser Ala Asp Thr Ile Val Asn Asn
        115                 120                 125

Gly His Thr Ile Gln Leu Asn Phe Ala Glu Gly Ser Thr Leu Thr Leu
    130                 135                 140

Gly Asp Val Lys Tyr Lys Leu Leu Gln Val His Phe His Arg Pro Ser
145                 150                 155                 160

Glu His Met Ile Gly Gly Lys Asn Phe Pro Met Glu Ala His Phe Val
                165                 170                 175

His Arg Asn Asp Ala Gly Gly Leu Ala Val Val Gly Val Leu Met Ala
            180                 185                 190

Glu Gly Lys Pro Asn Pro Ala Phe Gly Lys Ile Val Lys Thr Met Pro
        195                 200                 205

Ala Ala Asp Gly Pro Ala Val Lys Ala Asp Ala Ser Ile Asp Pro Leu
    210                 215                 220

Ala Met Leu Pro Thr Arg Leu Ser Tyr Phe Arg Tyr Pro Gly Ser Leu
225                 230                 235                 240

Thr Thr Pro Pro Cys Ser Glu Val Val Glu Trp Leu Leu Thr Thr
                245                 250                 255

Pro Ile Gln Val Ser Ala Ala Asp Val Ala Ala Phe Ala Lys Leu Tyr
            260                 265                 270

Pro Met Asn Ala Arg Pro Val Gln Lys Asp Asn Arg Arg Tyr Val Leu
        275                 280                 285
```

Arg Ser Thr
    290

<210> SEQ ID NO 18
<211> LENGTH: 252
<212> TYPE: PRT
<213> ORGANISM: Rhodopseudomonas palustris

<400> SEQUENCE: 18

Met Asp Arg Arg Asn Ile Leu Lys Ala Phe Ala Gly Leu Ala Leu Cys
1               5                   10                  15

Pro Leu Cys Ala Thr Ala Gly Ala Ala Glu Gly Ala His His Trp
            20                  25                  30

Gly Tyr Glu Gly Glu Gly Gly Pro Ala Lys Trp Gly Glu Ile Asp Pro
        35                  40                  45

Ala Asn Gln Ile Cys Ser Ile Gly Val Gln Gln Ser Pro Val Asp Ile
    50                  55                  60

Arg Ser Thr Val Ser Ala Asn Leu Phe Pro Leu Gln Val Gln Trp Ala
65                  70                  75                  80

Asp Thr Ala Asp Thr Ile Ile Asn Asn Gly His Thr Ile Gln Leu Asn
                85                  90                  95

Val Ala Glu Gly Ser Thr Leu Lys Leu Gly Gly Ala Thr Phe Lys Leu
            100                 105                 110

Val Gln Phe His Phe His Arg Pro Ser Glu His Gln Ile Asp Gly Lys
        115                 120                 125

Ser Phe Pro Met Glu Val His Phe Val His Arg Met Asp Ser Gly Thr
    130                 135                 140

Leu Gly Val Val Gly Val Leu Met Gln Glu Gly Ala Ala Asn Ala Ala
145                 150                 155                 160

Phe Ala Lys Ile Val Ala Thr Met Pro Gln Ser Glu Gly Pro Ala Val
                165                 170                 175

Lys Ala Asp Ala Gly Ile Asn Pro Asn Ala Leu Leu Pro Ala Lys Leu
            180                 185                 190

Gly Tyr Tyr Arg Tyr Glu Gly Ser Leu Thr Thr Pro Pro Cys Ser Glu
        195                 200                 205

Val Val Asp Trp Met Val Leu Thr Asp Pro Ile Thr Val Ala Ala Glu
    210                 215                 220

Asp Val Ala Ala Phe Ala Lys Leu Tyr Pro Met Asn Ala Arg Pro Val
225                 230                 235                 240

Gln Lys Asp Asn Arg Arg Phe Val Leu Gln Ser Asn
                245                 250

<210> SEQ ID NO 19
<211> LENGTH: 274
<212> TYPE: PRT
<213> ORGANISM: Bacillus pseudofirmus

<400> SEQUENCE: 19

Met Lys Arg Lys Ser Ile Tyr Leu Leu Val Ala Ala Ser Leu Ala Leu
1               5                   10                  15

Ala Ala Cys Ala Glu Gln Thr Glu Thr Ala Pro Val Glu Thr Pro Pro
            20                  25                  30

Ile Thr Asp Ser Thr Glu Pro Ser Asp Glu Thr Gln Glu Glu Ser Thr
        35                  40                  45

Glu Glu Leu Thr Glu Trp Ser Tyr Glu Gly Glu Ser Gly Pro Glu His
    50                  55                  60

```
Trp Gly His Leu His Ala Ser Tyr Ser Ala Cys Val Asp Gly Ser Glu
 65                  70                  75                  80

Gln Ser Pro Ile Asn Ile Asp Leu Ala Glu Met Glu Ala Asn Gln Gln
                 85                  90                  95

Ile Glu Glu Ile Asp Ile Gln Tyr Glu Pro Ala Ser Phe Ser Leu Val
            100                 105                 110

Asn Asn Gly His Thr Ile Gln Lys Asn Ala Val Asp Glu Asn Asn Ala
        115                 120                 125

Ile Thr Leu Asp Gly Gln Glu Tyr Gln Leu Val Gln Phe His Phe His
    130                 135                 140

Thr Pro Ser Glu His Gln Phe Asn Gly Glu His Tyr Asp Met Glu Leu
145                 150                 155                 160

His Leu Val His Gln Asp Ile Asn Gly Asn Leu Ala Val Leu Gly Val
                165                 170                 175

Met Ile Glu Glu Gly Ala Glu Asn Glu Glu Leu Ala Pro Ala Trp Gly
            180                 185                 190

Glu Leu Pro Glu Glu Glu Thr Glu Asn Glu Val Ala Leu Glu Glu Pro
        195                 200                 205

Ile Asn Leu Gln Asn Leu Leu Pro Asp Asp Gln Ser Ser Phe His Tyr
    210                 215                 220

Asn Gly Ser Leu Thr Thr Pro Pro Cys Thr Glu Gly Val Lys Trp Ile
225                 230                 235                 240

Val Phe Lys Glu Pro Ile Gln Lys Ser Ala Glu Ile Gln Ala Phe
                245                 250                 255

Gln Glu Ile Tyr Glu Glu Asn His Arg Pro Val Gln Pro Leu Asn Glu
            260                 265                 270

Arg Gly

<210> SEQ ID NO 20
<211> LENGTH: 279
<212> TYPE: PRT
<213> ORGANISM: Paenibacillus polymyxa

<400> SEQUENCE: 20

Met Lys Lys Asn Trp Lys Gly Cys Leu Phe Ser Ile Phe Ala Ile Ile
  1               5                  10                  15

Leu Val Val Ser Val Thr Gly Cys Asn Ser Gln Pro Ala Ile Ser Ser
                 20                  25                  30

Thr Pro Ser Thr Ser Ser Ser Ala Thr Asn Ala His Ala Ala Val
             35                  40                  45

Gln Lys Gly Pro His Trp Ser Tyr Glu Gly Asp Gln Gly Pro Glu His
         50                  55                  60

Trp Gly Glu Leu Glu Lys Asp Phe Val Ala Cys Gly Asn Gly His Glu
 65                  70                  75                  80

Gln Ser Pro Val Asn Ile Glu His Thr His Leu Glu Ala Ser Gln Thr
                 85                  90                  95

Arg Gln Pro Leu Gln Val His Tyr Thr Asn Thr Lys Ala Ser Ile Leu
            100                 105                 110

Asn Asn Gly His Thr Val Gln Ile Asn Val Ala Asp Ala Ser Asn Asn
        115                 120                 125

Ile Met Leu Asp Gly Thr Lys Phe Thr Leu Lys Gln Phe His Phe His
    130                 135                 140

His Pro Ser Glu His Gln Ile Asp Gly Lys Asn Ala Glu Met Glu Leu
145                 150                 155                 160
```

His Phe Val His Gln Ser Asp Asn Gly Ser Thr Ala Val Leu Gly Val
                165                 170                 175

Leu Ile Gln Ser Gly Lys Glu Asn Lys Ala Phe Asn Arg Ile Trp Ser
            180                 185                 190

Lys Leu Pro Lys Asp Asn Ser Gln Glu Ala Ala Ala Leu Asp Lys Glu
        195                 200                 205

Ile Asn Leu Ala Ala Leu Leu Pro Lys Asp Leu His Ser Val Arg Tyr
    210                 215                 220

Asn Gly Ser Leu Thr Thr Pro Pro Cys Thr Glu His Val Asn Trp Thr
225                 230                 235                 240

Val Leu Glu Gln Pro Ile Glu Met Ser Ala Asp Gln Ile Asn Gln Phe
                245                 250                 255

Ala Ala Ile Phe Pro Asp Asn His Arg Pro Val Gln Gln Leu Gly Thr
            260                 265                 270

Arg Glu Leu Thr Ala Asp Lys
        275

<210> SEQ ID NO 21
<211> LENGTH: 278
<212> TYPE: PRT
<213> ORGANISM: Paenibacillus polymyxa

<400> SEQUENCE: 21

Met Lys Lys His Trp Arg Gly Cys Leu Phe Ser Ile Phe Ser Ile Ile
1               5                   10                  15

Leu Ala Leu Ser Val Thr Gly Cys Thr Pro Ser Ala Thr Ser Ser Thr
            20                  25                  30

Thr Ser Ala Thr Ser Ser Ser Ala Asn Asn Val His Ala Val Val
            35                  40                  45

Gln Lys Ser Pro His Trp Ser Tyr Glu Gly Asp Glu Gly Pro Glu His
    50                  55                  60

Trp Gly Glu Leu Glu Lys Asp Phe Val Ala Cys Gly Asn Gly Gln Glu
65                  70                  75                  80

Gln Ser Pro Ile Asn Ile Glu His Ser His Leu Glu Ala Ser His Thr
                85                  90                  95

Gln Gln Pro Leu Gln Val His Tyr Ser Thr Thr Lys Val Ser Ile Leu
            100                 105                 110

Asn Asn Gly His Thr Val Gln Val Asn Ala Ala Ser Pro Ser Asn Asp
        115                 120                 125

Ile Val Val Asp Gly Thr Lys Phe Thr Leu Lys Gln Phe His Phe His
    130                 135                 140

His Pro Ser Glu His Gln Ile Asp Gly Lys Asn Ala Glu Met Glu Leu
145                 150                 155                 160

His Phe Val His Gln Ser Asp Thr Gly Ser Thr Ala Val Leu Gly Val
                165                 170                 175

Leu Ile Gln Ser Gly Lys Glu Asn Lys Ala Phe Asn Arg Ile Trp Ser
            180                 185                 190

Lys Leu Pro Lys Asp Ile Ser Gln Glu Ala Val Leu Asp Glu Asp Val
        195                 200                 205

Asn Leu Ala Ala Leu Leu Pro Lys Asp Leu His Ser Val Arg Tyr Asn
    210                 215                 220

Gly Ser Leu Thr Thr Pro Pro Cys Thr Glu His Val Asn Trp Thr Val
225                 230                 235                 240

Leu Glu Gln Pro Ile Glu Met Ser Ala Asp Gln Ile Lys Gln Phe Ala
                245                 250                 255

```
Ala Ile Phe Pro Asp Asn His Arg Pro Val Gln Gln Leu Gly Thr Arg
            260                 265                 270

Glu Leu Lys Ala Asp Lys
        275

<210> SEQ ID NO 22
<211> LENGTH: 263
<212> TYPE: PRT
<213> ORGANISM: Bacillus clausii

<400> SEQUENCE: 22

Met Lys Arg Ser His Leu Phe Thr Ser Ile Thr Leu Ala Ser Val Val
1               5                   10                  15

Thr Leu Ala Thr Ala Pro Ala Ala Ser Ala Ala Ser Phe Leu Ser Pro
            20                  25                  30

Leu Gln Ala Leu Lys Ala Ser Trp Ser Tyr Glu Gly Glu Thr Gly Pro
        35                  40                  45

Glu Phe Trp Gly Asp Leu Asp Glu Ala Phe Ala Ala Cys Ser Asn Gly
    50                  55                  60

Lys Glu Gln Ser Pro Ile Asn Leu Phe Tyr Asp Arg Glu Gln Thr Ser
65                  70                  75                  80

Lys Trp Asn Trp Ala Phe Ser Tyr Ser Glu Ala Ala Phe Ser Val Glu
                85                  90                  95

Asn Asn Gly His Thr Ile Gln Ala Asn Val Glu Asn Glu Asp Ala Gly
            100                 105                 110

Gly Leu Glu Ile Asn Gly Glu Ala Tyr Gln Leu Ile Gln Phe His Phe
        115                 120                 125

His Thr Pro Ser Glu His Thr Ile Glu Glu Thr Ser Phe Pro Met Glu
    130                 135                 140

Leu His Leu Val His Ala Asn His Ala Gly Asp Leu Ala Val Leu Gly
145                 150                 155                 160

Val Leu Met Glu Met Gly Asn Asp His Glu Gly Ile Glu Ala Val Trp
                165                 170                 175

Glu Val Met Pro Glu Glu Glu Gly Thr Ala Ala Tyr Ser Ile Ser Leu
            180                 185                 190

Asp Pro Asn Leu Phe Leu Pro Glu Ser Val Thr Ala Tyr Gln Tyr Asp
        195                 200                 205

Gly Ser Leu Thr Thr Pro Pro Cys Ser Glu Gly Val Lys Trp Thr Val
    210                 215                 220

Leu Asn Asp Thr Ile Ser Ile Ser Glu Thr Gln Leu Asp Ala Phe Arg
225                 230                 235                 240

Asp Ile Tyr Pro Gln Asn Tyr Arg Pro Val Gln Glu Leu Gly Asp Arg
                245                 250                 255

Glu Ile Gly Phe His Tyr His
            260

<210> SEQ ID NO 23
<211> LENGTH: 263
<212> TYPE: PRT
<213> ORGANISM: Rhodopseudomonas palustris

<400> SEQUENCE: 23

Met Glu Pro Ile Leu Ile Pro Glu His Arg Pro Met Asp Arg Arg Ala
1               5                   10                  15

Ile Leu Lys Ala Phe Ala Gly Leu Ala Leu Cys Pro Leu Cys Ala Ser
            20                  25                  30
```

```
Ala Gly Val Ala Gly Glu Gly Gly His His Trp Gly Tyr Glu Gly Asp
        35                  40                  45

Gly Gly Pro Ala Lys Trp Gly Glu Leu Asp Pro Ala Asn Gln Phe Cys
    50                  55                  60

Ser Val Gly Val Gln Gln Ser Pro Ile Asp Ile Gly Thr Thr Ile Gly
65                  70                  75                  80

Ala Asn Leu Tyr Pro Ile Glu Ile Arg Trp Ala Asp Thr Ala Asp Thr
                85                  90                  95

Ile Val Asn Asn Gly His Thr Ile Gln Leu Asn Val Ala Glu Gly Ser
            100                 105                 110

His Leu Lys Leu Gly Gly Val Thr Phe Lys Leu Val Gln Phe His Phe
        115                 120                 125

His His Pro Ser Glu His Leu Ile Asp Gly Lys Asn Phe Pro Met Glu
    130                 135                 140

Val His Phe Val His Arg Ala Asp Ser Gly Thr Leu Gly Val Val Gly
145                 150                 155                 160

Val Leu Met Gln Pro Gly Lys Ala Asn Ala Ala Phe Ser Lys Ile Val
                165                 170                 175

Ala Thr Met Pro Gln Ser Glu Gly Pro Ala Lys Lys Ala Asp Pro Ala
            180                 185                 190

Ile Asp Pro Asn Ala Leu Leu Pro Glu Thr Arg Asn Tyr Tyr Arg Tyr
        195                 200                 205

Glu Gly Ser Leu Thr Thr Pro Pro Cys Ser Glu Ile Val Asp Trp Met
    210                 215                 220

Val Leu Ala Ser Pro Ile Thr Val Ala Ala Asp Asp Ile Ala Ala Phe
225                 230                 235                 240

Ala Lys Leu Tyr Pro Met Asn Ala Arg Pro Val Gln Lys Asp Asn Arg
                245                 250                 255

Arg Phe Val Leu Gln Ser Asn
            260

<210> SEQ ID NO 24
<211> LENGTH: 243
<212> TYPE: PRT
<213> ORGANISM: Bacillus cereus

<400> SEQUENCE: 24

Met Gly Cys Asn Thr Ala Lys Gln Glu Ala Pro His Lys Gln Ser Thr
1               5                   10                  15

Lys Glu Asn Thr Gln Trp Ser Tyr Glu Gly Thr Thr Gly Pro Glu His
            20                  25                  30

Trp Gly Glu Leu Lys Pro Glu Tyr Lys Ile Cys Leu Asn Gly Gln Glu
        35                  40                  45

Gln Ser Pro Ile Asp Ile Lys Thr Glu Gln Ile Lys Ser Thr Val Asp
    50                  55                  60

Asn Asn Leu Leu Gln Ile Asn Tyr Gln Pro Ile Ser Phe Ser Ile Lys
65                  70                  75                  80

Asn Asn Gly His Ser Ile Glu Gly Lys Ala Asn Ser Ser Asp Asn Tyr
                85                  90                  95

Leu Thr Leu Gly Glu Asn Arg Tyr Thr Leu Lys Gln Phe His Phe His
            100                 105                 110

Thr Pro Ser Glu His Gln Phe Glu Gly Lys His Ala Asp Met Glu Leu
        115                 120                 125

His Leu Val His Gln Asn Asp Gln Gly Gln Leu Val Val Val Gly Ile
```

```
                130                 135                 140
Met Ile Lys Glu Gly Gln Lys Asn Glu Gly Phe Ala Ala Met Trp Gln
145                 150                 155                 160

Asn Leu Pro His Arg Lys Asn Ile Lys Ala Asp Val Gln His Thr Ile
                165                 170                 175

Asp Ile Lys Gln Ile Leu Pro Ser Asp Tyr Ser Ser Phe Arg Tyr Met
            180                 185                 190

Gly Ser Leu Thr Thr Pro Pro Cys Thr Glu Asn Val Gln Trp Ile Val
            195                 200                 205

Met Lys Gln Thr Ile Glu Met Ser Lys Lys Gln Ile Lys Val Phe His
            210                 215                 220

Lys Leu Phe Pro Thr Asn Asn Arg Pro Val Gln Pro Ile Asn Gly Arg
225                 230                 235                 240

Ala Val Leu

<210> SEQ ID NO 25
<211> LENGTH: 263
<212> TYPE: PRT
<213> ORGANISM: Bacillus cereus

<400> SEQUENCE: 25

Met Lys Gly Leu Lys Phe Val Tyr Lys Thr Pro Leu Ile Leu Thr Met
1               5                   10                  15

Ser Val Val Leu Met Gly Cys Asn Thr Ala Lys Gln Glu Ala Pro Gln
                20                  25                  30

Lys Gln Ser Thr Lys Glu Asn Thr Gln Trp Ser Tyr Lys Gly Thr Thr
            35                  40                  45

Gly Pro Glu His Trp Gly Glu Leu Lys Pro Glu Tyr Asn Met Cys Leu
        50                  55                  60

Asn Gly Gln Glu Gln Ser Pro Ile Asp Ile Lys Thr Glu Gln Ile Lys
65              70                  75                  80

Ser Thr Val Asp Asn Asn Leu Leu Gln Ile Asn Tyr Gln Pro Ile Ser
                85                  90                  95

Phe Ser Ile Lys Asn Asn Gly His Ser Ile Glu Gly Lys Ala Asn Ser
            100                 105                 110

Ser Asp Asp Tyr Leu Thr Leu Gly Glu Asn Arg Tyr Thr Leu Lys Gln
        115                 120                 125

Phe His Phe His Thr Pro Ser Glu His Gln Phe Glu Gly Lys His Ala
    130                 135                 140

Asp Met Glu Leu His Leu Val His Gln Asn Asp Gln Gly Gln Leu Ala
145                 150                 155                 160

Val Val Gly Ile Met Ile Lys Glu Gly Gln Lys Asn Glu Gly Phe Ala
                165                 170                 175

Ala Met Trp Gln Asn Leu Pro His Arg Lys Asn Ile Lys Ala Asp Val
            180                 185                 190

Gln His Thr Ile Asp Ile Lys Gln Ile Leu Pro Ser Asp His Ser Ser
        195                 200                 205

Phe Arg Tyr Met Gly Ser Leu Thr Thr Pro Pro Cys Thr Glu Asn Val
    210                 215                 220

Gln Trp Ile Val Met Lys Gln Thr Ile Glu Met Ser Lys Lys Gln Ile
225                 230                 235                 240

Lys Val Phe His Lys Leu Phe Pro Thr Asn Asn Arg Pro Val Gln Pro
                245                 250                 255

Ile Asn Gly Arg Ala Val Leu
```

<210> SEQ ID NO 26
<211> LENGTH: 810
<212> TYPE: DNA
<213> ORGANISM: Promicromonospora vindobonensis

<400> SEQUENCE: 26

```
gtgaagaagc tcgccctgcc caccgtcctg ctcctcgccc cgttgctcgc gtcctgcgcg      60
tcgggcaccg ccgccgacgg cgagacgtcc gcaccccgc cgcccgcgac cgacgaggtg     120
cactggtcct acgaagggga cacggggcccg acaactggg gccagctctc cgacgagttc     180
gtcgagtgct cgatcggcga ggcgcagtcc cccgtcgacc tgccggacca cgccgacgag     240
acgaccaccg agcccccgac ggtcacgacg tggcccaccg tcggcgagtc ggtcgacacc     300
ggccacacga tccagctcgt gcccgacggc gacgcgtccg aggtcgagtg caggacacc      360
acgttcgacc tcgcccaggt gcacttccac atgccctcgg agcacacgat cgagggtgag     420
gcgctcgacg ccgagttcca cttcgtccac accacggagg aaggacaggc gctcgtcatc     480
ggggtcctcg cgcgggagag cagcaccgag aacgaggcct ggcagccgtt catcgatggt     540
gcggccgagc cgggcaccga ggacctgccg ctcgacgtcg ccgcgatgct accgacggac     600
ccgacgttcg aggagtacac gggcagcctc acgaccccgc cgtgcaccga gggcgtcgag     660
tgggtcgtct accacgagcc catcgagctg tcggcggagc agatcgccgt gctcagggac     720
gcgtacgaca caccgcgcg cccgacccag ctcctgggcg accgcgtcgt gtacgagggc     780
accatcgacg tggaggcgga ggaggcgcac                                      810
```

<210> SEQ ID NO 27
<211> LENGTH: 270
<212> TYPE: PRT
<213> ORGANISM: Promicromonospora vindobonensis

<400> SEQUENCE: 27

Met Lys Lys Leu Ala Leu Pro Thr Val Leu Leu Leu Ala Pro Leu Leu
1               5                   10                  15

Ala Ser Cys Ala Ser Gly Thr Ala Ala Asp Gly Glu Thr Ser Ala Pro
            20                  25                  30

Pro Pro Pro Ala Thr Asp Glu Val His Trp Ser Tyr Glu Gly Asp Thr
        35                  40                  45

Gly Pro Asp Asn Trp Gly Gln Leu Ser Asp Glu Phe Val Glu Cys Ser
    50                  55                  60

Ile Gly Glu Ala Gln Ser Pro Val Asp Leu Pro Asp His Ala Asp Glu
65                  70                  75                  80

Thr Thr Thr Glu Pro Pro Thr Val Thr Thr Trp Pro Thr Val Gly Glu
                85                  90                  95

Ser Val Asp Thr Gly His Thr Ile Gln Leu Val Pro Asp Gly Asp Ala
            100                 105                 110

Ser Glu Val Glu Trp Gln Asp Thr Thr Phe Asp Leu Ala Gln Val His
        115                 120                 125

Phe His Met Pro Ser Glu His Thr Ile Glu Gly Glu Ala Leu Asp Ala
    130                 135                 140

Glu Phe His Phe Val His Thr Thr Glu Glu Gly Gln Ala Leu Val Ile
145                 150                 155                 160

Gly Val Leu Ala Arg Glu Ser Ser Thr Glu Asn Glu Ala Trp Gln Pro
                165                 170                 175

```
Phe Ile Asp Gly Ala Ala Glu Pro Gly Thr Glu Asp Leu Pro Leu Asp
            180                 185                 190

Val Ala Ala Met Leu Pro Thr Asp Pro Thr Phe Glu Glu Tyr Thr Gly
        195                 200                 205

Ser Leu Thr Thr Pro Pro Cys Thr Glu Gly Val Glu Trp Val Val Tyr
    210                 215                 220

His Glu Pro Ile Glu Leu Ser Ala Glu Gln Ile Ala Val Leu Arg Asp
225                 230                 235                 240

Ala Tyr Asp Asn Thr Ala Arg Pro Thr Gln Leu Leu Gly Asp Arg Val
                245                 250                 255

Val Tyr Glu Gly Thr Ile Asp Val Glu Ala Glu Glu Ala His
            260                 265                 270

<210> SEQ ID NO 28
<211> LENGTH: 245
<212> TYPE: PRT
<213> ORGANISM: Promicromonospora vindobonensis

<400> SEQUENCE: 28

Asp Gly Glu Thr Ser Ala Pro Pro Pro Ala Thr Asp Glu Val His
1                5                  10                  15

Trp Ser Tyr Glu Gly Asp Thr Gly Pro Asp Asn Trp Gly Gln Leu Ser
            20                  25                  30

Asp Glu Phe Val Glu Cys Ser Ile Gly Glu Ala Gln Ser Pro Val Asp
        35                  40                  45

Leu Pro Asp His Ala Asp Glu Thr Thr Thr Glu Pro Pro Thr Val Thr
    50                  55                  60

Thr Trp Pro Thr Val Gly Glu Ser Val Asp Thr Gly His Thr Ile Gln
65                  70                  75                  80

Leu Val Pro Asp Gly Asp Ala Ser Glu Val Glu Trp Gln Asp Thr Thr
                85                  90                  95

Phe Asp Leu Ala Gln Val His Phe His Met Pro Ser Glu His Thr Ile
            100                 105                 110

Glu Gly Glu Ala Leu Asp Ala Glu Phe His Phe Val His Thr Thr Glu
        115                 120                 125

Glu Gly Gln Ala Leu Val Ile Gly Val Leu Ala Arg Glu Ser Ser Thr
    130                 135                 140

Glu Asn Glu Ala Trp Gln Pro Phe Ile Asp Gly Ala Ala Glu Pro Gly
145                 150                 155                 160

Thr Glu Asp Leu Pro Leu Asp Val Ala Ala Met Leu Pro Thr Asp Pro
                165                 170                 175

Thr Phe Glu Glu Tyr Thr Gly Ser Leu Thr Thr Pro Pro Cys Thr Glu
            180                 185                 190

Gly Val Glu Trp Val Val Tyr His Glu Pro Ile Glu Leu Ser Ala Glu
        195                 200                 205

Gln Ile Ala Val Leu Arg Asp Ala Tyr Asp Asn Thr Ala Arg Pro Thr
    210                 215                 220

Gln Leu Leu Gly Asp Arg Val Val Tyr Glu Gly Thr Ile Asp Val Glu
225                 230                 235                 240

Ala Glu Glu Ala His
                245

<210> SEQ ID NO 29
<211> LENGTH: 50
<212> TYPE: DNA
<213> ORGANISM: Artificial Sequence
```

```
<220> FEATURE:
<223> OTHER INFORMATION: synthetic primer

<400> SEQUENCE: 29
agcgctagcc ggcccccccgg cacaggccga cggcgagacg tccgcacccc         50

<210> SEQ ID NO 30
<211> LENGTH: 35
<212> TYPE: DNA
<213> ORGANISM: Artificial Sequence
<220> FEATURE:
<223> OTHER INFORMATION: synthetic primer

<400> SEQUENCE: 30
tccggatcct tagtgcgcct cctccgcctc cacgt                          35

<210> SEQ ID NO 31
<211> LENGTH: 735
<212> TYPE: DNA
<213> ORGANISM: Promicromonospora vindobonensis

<400> SEQUENCE: 31
gacggcgaga cgtccgcacc cccgccgccc gcgaccgacg aggtgcactg gtcctacgaa    60
ggggacacgg gcccggacaa ctggggccag ctctccgacg agttcgtcga gtgctcgatc   120
ggcgaggcgc agtcccccgt cgacctgccg gaccacgccg acgagacgac caccgagccc   180
ccgacggtca cgacgtggcc caccgtcggc gagtcggtcg acaccggcca cacgatccag   240
ctcgtgcccg acggcgacgc gtccgaggtc gagtggcagg acaccacgtt cgacctcgcc   300
caggtgcact tccacatgcc ctcggagcac acgatcgagg gtgaggcgct cgacgccgag   360
ttccacttcg tccacaccac ggaggaagga caggcgctcg tcatcggggt cctcgcgcgg   420
gagagcagca ccgagaacga ggcctggcag ccgttcatcg atggtgcggc cgagccgggc   480
accgaggacc tgccgctcga cgtcgccgcg atgctaccga cggacccgac gttcgaggag   540
tacacgggca gcctcacgac cccgccgtgc accgagggcg tcgagtgggt cgtctaccac   600
gagcccatcg agctgtcggc ggagcagatc gccgtgctca gggacgcgta cgacaacacc   660
gcgcgcccga cccagctcct gggcgaccgc gtcgtgtacg agggcaccat cgacgtggag   720
gcggaggagg cgcac                                                    735

<210> SEQ ID NO 32
<211> LENGTH: 458
<212> TYPE: PRT
<213> ORGANISM: Candidatus accumlibacter

<400> SEQUENCE: 32

Met Ile Val Thr Thr Thr Asp Gly Thr Pro Ser Met His Pro Val Ile
1               5                   10                  15

Arg Leu Ser Ser Ala Phe Leu Val Leu Ser Leu Leu Pro Pro Gly Val
            20                  25                  30

Gly Ala Ala Trp Gln Val Ile Ser Ala Glu Pro Gly Lys Arg Val Glu
        35                  40                  45

Ile Asp Arg Ala Ser Ile Arg Lys Asp Glu Thr Gly Lys Ser Val Ala
    50                  55                  60

Gln Gly Arg Ile Val Leu Glu Lys Pro Ile Val Asp Pro Lys Thr Ser
65                  70                  75                  80

Ser Ser Tyr Arg Ile Val Glu Ala Val Asn Arg Tyr Asp Cys Ala Ser
                85                  90                  95
```

Arg Ser Tyr Ser Thr Leu Lys Arg Ser Tyr Phe Lys Asp Glu Gly Asp
            100                 105                 110

Leu Leu Arg Glu Glu Val Lys Val Gln Ile Glu Met Pro Val Arg
        115                 120                 125

Thr Gly Met Leu Asp Asp Lys Leu Leu Arg Glu Val Cys Arg Pro Lys
        130                 135                 140

Pro Gly Pro Asp Ala Ala Thr Ala Ala Ser Lys Val Ala Asp Lys Val
145                 150                 155                 160

Asn Gln Ala Ala Gly Glu Leu Arg Lys Ala Asn Glu Ala Leu Val Gln
                165                 170                 175

Lys Glu Val Lys Arg Ala Asn Leu Gln Thr Pro Asn Val Asp Lys Ala
        180                 185                 190

Glu Ala Glu Pro Arg Ser Ser Pro Ala Ala Lys Pro Thr Ala Ala Ala
        195                 200                 205

Ala Met Pro Ala Arg Val His Ser Ala Arg Pro Ala Ala Pro Arg Pro
        210                 215                 220

Gly Glu Thr Ser Pro Ala Ile Ala His Ala His Gly His Trp Ala Tyr
225                 230                 235                 240

Glu Gly Glu Gly Gly Pro Asp Asn Trp Gly Lys Leu Lys Pro Glu Tyr
                245                 250                 255

Ala Thr Cys Ala Thr Gly Lys Arg Gln Ser Pro Ile Asp Ile Arg Asp
        260                 265                 270

Gly Phe Arg Val Asp Leu Glu Pro Ile Gln Phe Val Tyr Arg Pro Ser
        275                 280                 285

Gln Phe Arg Val Val Asp Asn Gly His Thr Val Gln Val Glu Val Ser
        290                 295                 300

Gly Ser Ser Ile Ser Leu Leu Gly Arg Ser Tyr Asp Leu Thr Gln Phe
305                 310                 315                 320

His Phe His Arg Pro Ser Glu Glu Arg Val Asn Gly Lys Ala Phe Asp
                325                 330                 335

Met Val Ala His Leu Val His Arg Ala Glu Asp Gly Arg Ile Ala Val
        340                 345                 350

Val Ala Val Leu Leu Glu Lys Gly Leu Glu Asn Pro Val Ile Gln Ser
        355                 360                 365

Val Trp Asn Asn Leu Pro Leu Glu Lys Asn Glu Tyr Val Thr Pro Pro
370                 375                 380

Glu Leu Ser Ile Asp Val Ser Gln Leu Leu Pro Gln Asp His Ser Tyr
385                 390                 395                 400

Tyr Thr Tyr Met Gly Ser Leu Thr Thr Pro Pro Cys Ser Glu Gly Val
                405                 410                 415

Leu Trp Leu Val Leu Arg Gln Pro Gln Gln Ile Ser Pro Glu Gln Leu
        420                 425                 430

Ala Ile Phe Ser Arg Leu Tyr Arg Asn Asn Ala Arg Pro Val Gln Pro
        435                 440                 445

Asn Phe Ala Arg Met Ile Lys Glu Ser Arg
450                 455

<210> SEQ ID NO 33
<211> LENGTH: 243
<212> TYPE: PRT
<213> ORGANISM: Enterobacter cloacae

<400> SEQUENCE: 33

Met Lys His Ile Leu Thr Ala Ser Leu Phe Ala Leu Ser Ala Ser Val
1               5                   10                  15

```
Phe Ala Gly Ser Ala Pro His Trp Thr Tyr Glu Gly Lys Ser Gly Pro
                20                  25                  30

Glu Asn Trp Gly Glu Leu Ser Asp Glu Phe Ala Thr Cys Lys Thr Gly
            35                  40                  45

Lys Phe Gln Ser Pro Ile Asp Ile Arg Asn Ala Tyr Asn Ala Thr Leu
 50                  55                  60

Pro Pro Leu Glu Met Asn Phe His Thr Ala Ala Glu Lys Leu Val Asn
 65                  70                  75                  80

Asn Gly His Thr Leu Gln Val Thr Ala Ser Asp Glu Asp Glu Phe Arg
                85                  90                  95

Leu Asp Asp Gln Ile Phe Thr Leu Arg Gln Tyr His Phe His Thr Pro
                100                 105                 110

Ser Glu Asn Arg Ile Asn Gly Lys Ser Phe Pro Leu Glu Ala His Phe
            115                 120                 125

Val His Ala Ser Lys Glu Gly Asp Val Ala Val Leu Ala Val Met Phe
130                 135                 140

Glu Val Gly Pro Glu Asn Ser Ala Leu Asn Pro Leu Leu Ala Arg Leu
145                 150                 155                 160

Pro Lys Glu Lys Asp His Glu Ile Ser Ile Asp Lys His Leu Asp Leu
                165                 170                 175

Arg Pro Leu Phe Pro Ala Asp Leu His Tyr Tyr Arg Phe Ser Gly Ser
            180                 185                 190

Leu Thr Thr Pro Pro Cys Thr Glu Gly Leu Arg Trp Leu Val Met Lys
            195                 200                 205

Asn Thr Val Thr Leu Ser Glu Lys Gln Leu Glu Met Phe Lys Gln Ala
                210                 215                 220

Leu Glu His Ser Asn Asn Arg Pro Leu Gln Pro Leu Asn Gly Arg Val
225                 230                 235                 240

Ile Val Gln

<210> SEQ ID NO 34
<211> LENGTH: 481
<212> TYPE: PRT
<213> ORGANISM: Dechloromonas aromatica

<400> SEQUENCE: 34

Met Arg His Leu Ile Ile Ala Ser Leu Leu Ala Leu Pro Trp Ala
 1               5                  10                  15

Ala Ser Ala Ala Pro Thr Trp Gln Thr Ile Ser Ser Glu Pro Gly Lys
                20                  25                  30

Arg Ile Glu Ile Asp Arg Thr Ser Leu Lys Arg Glu Gly Ser Thr Val
            35                  40                  45

Gln Ala Gln Gly Arg Ile Val Leu Glu Lys Glu Leu Thr Asp Ala Lys
 50                  55                  60

Ser Gly Ala Gly Tyr Arg Val Ile Glu Ala Ile Thr Arg Tyr Asp Cys
 65                  70                  75                  80

Asn Thr Arg Asn Ala Asn Thr Ile Lys Arg Ile Phe Lys Lys Asn Glu
                85                  90                  95

Asn Glu Val Ile Arg Glu Glu Ile Lys Gly Ser Asp Leu Pro Val
            100                 105                 110

Arg Thr Gly Thr Leu Asp Asp Lys Val Leu Arg Glu Val Cys Arg Pro
            115                 120                 125

Pro Lys Glu Ser Pro Ala Glu Leu Ala Lys Lys Ala Asn Glu Ala Ala
130                 135                 140
```

Gly Glu Leu Lys Ala Ala Asn Asp Ala Leu Leu Lys Lys Glu Met Ala
145                 150                 155                 160

Lys Ala Glu Lys Pro Ala Thr Ile Lys Ala Ser Asp Val Pro Asp Lys
            165                 170                 175

Glu Ala Glu His Gly Ala Ile Pro Ser Ile Arg Pro Asn Leu Lys Ala
        180                 185                 190

Ala Thr Glu Ser Ala Lys Glu Thr Ala Pro Ala Pro Thr Pro Ala Ala
    195                 200                 205

Ala Pro Ala Lys Ala Val Ala Pro Ala Lys Ala Ala Thr Val Val Val
210                 215                 220

His Thr Thr Pro Ala Pro Ala Pro Lys Ala Arg Lys Pro Ala Arg Ser
225                 230                 235                 240

Glu Gly Tyr Met Leu Glu Leu Thr His Ser Glu Pro Ala Ala Gln His
                245                 250                 255

Ala Gln Ile His Trp Ala Tyr Asp Gly Ala Gly Ala Pro Glu Asn Trp
            260                 265                 270

Pro Asn Leu Asp Pro Lys Asn Lys Val Cys Ala Ile Gly Glu Arg Gln
        275                 280                 285

Ser Pro Ile Asp Ile Lys Asp Gly Ile Lys Val Asp Leu Glu Pro Ile
    290                 295                 300

Lys Phe Lys Tyr Gln Pro Ser Thr Phe Arg Ile Val Asp Asn Gly His
305                 310                 315                 320

Thr Val Gln Val Glu Val Gly Asp Gly Ser Ile Ser Leu Thr Gly Lys
                325                 330                 335

Thr Tyr Glu Leu Val Gln Phe His Phe His Arg Pro Ser Glu Glu Lys
            340                 345                 350

Val Asn Gly Gln Arg Phe Asp Met Val Val His Leu Val His Lys Ser
        355                 360                 365

Asp Asp Gly Gln Leu Ala Val Val Ala Val Leu Leu Glu Arg Gly Thr
    370                 375                 380

Glu Asn Pro Phe Ile Gln Thr Leu Trp Asn Asn Met Pro Leu Glu Lys
385                 390                 395                 400

Asn Met Ala Val Ala Pro Pro Thr Thr Thr Ile Asp Leu Asn Thr Leu
                405                 410                 415

Leu Pro Ala Thr Arg Asn Tyr Tyr Thr Tyr Met Gly Ser Leu Thr Thr
            420                 425                 430

Pro Pro Cys Ser Glu Gly Val Leu Trp Leu Val Met Lys Gln Pro Val
        435                 440                 445

Gln Val Ser Gln Asp Gln Ile Asn Ile Phe Ser Arg Leu Tyr Lys Asn
    450                 455                 460

Asn Ala Arg Pro Ile Gln Pro Ser Gly Gly Arg Leu Ile Lys Glu Gly
465                 470                 475                 480

Arg

<210> SEQ ID NO 35
<211> LENGTH: 256
<212> TYPE: PRT
<213> ORGANISM: Magnetospirillum magnetotacticum

<400> SEQUENCE: 35

Met Asp Arg Arg Ser Phe Leu Lys Gly Ala Thr Gly Ala Ala Cys Leu
1               5                   10                  15

Cys Gly Thr Cys Gly Gly Ser Ile Ala Glu Ala Val Ala Ala Glu Gly
            20                  25                  30

Ala His Trp Ala Tyr Glu Gly His Gly Gly Pro Lys Glu Trp Gly Met
         35                  40                  45

Leu Ser Pro Glu Tyr Ala Ala Cys Ser Met Gly Arg Glu Gln Ser Pro
 50                  55                  60

Val Asp Leu Thr Arg Pro Ile Ala Ala Ile Ile Gly Asp Pro Met Ala
 65                  70                  75                  80

Ala Trp Arg Pro Val Pro Leu Arg Val Gln Asn Asn Gly His Thr Ile
                 85                  90                  95

Gln Val Asp Cys Ser Gly Gly Thr Leu Met Leu Asp Gly Lys Ser
                 100                 105                 110

Tyr Asp Leu Leu Gln Phe His Phe His His Pro Ser Glu His Thr Val
             115                 120                 125

Asp Gly Ala Phe Phe Asp Met Glu Cys His Phe Val His Lys Ala Ala
         130                 135                 140

Asp Gly Gly Leu Ala Val Leu Gly Val Met Ile Ala Lys Gly Ala Ala
145                 150                 155                 160

Asn Pro Ala Leu Glu Ala Ile Trp Gln Val Met Pro Ala Lys Ala Gly
                 165                 170                 175

Glu Ala Ala Thr Ala Thr Ser Met Leu Asp Ala Ser Met Leu Leu Pro
             180                 185                 190

Lys Asp Pro Val Thr Phe Arg Tyr Ala Gly Ser Leu Thr Thr Pro Pro
         195                 200                 205

Cys Thr Glu Val Val Gln Trp Val Val Tyr Arg Gln Ala Ile Thr Ala
210                 215                 220

Ser Ala Glu Gln Leu Ala Ala Phe Ala Lys Leu Phe Pro Asn Asn Ala
225                 230                 235                 240

Arg Pro Val Gln Pro Leu Asn Arg Arg Lys Leu Leu Leu Asp Val Met
                 245                 250                 255

<210> SEQ ID NO 36
<211> LENGTH: 229
<212> TYPE: PRT
<213> ORGANISM: Magnetospirillum magnetotacticum

<400> SEQUENCE: 36

Met Ala Ser Glu Gly Ala His Trp Ala Tyr Glu Gly His Gly Gly Pro
 1               5                  10                  15

Lys Glu Trp Gly Met Leu Ser Pro Glu Tyr Ala Ala Cys Ser Met Gly
                 20                  25                  30

Arg Glu Gln Ser Pro Val Asp Leu Ser Lys Pro Ile Ala Ala Ile Ile
             35                  40                  45

Gly Asp Pro Leu Thr Ala Trp Arg Pro Ile Pro Leu Arg Val Gln Asn
         50                  55                  60

Asn Gly His Thr Ile Gln Val Asp Cys Ala Gly Gly Ser Leu Met
65                  70                  75                  80

Leu Asp Gly Lys Ser Tyr Asp Leu Leu Gln Phe His Phe His His Pro
                 85                  90                  95

Ser Glu His Thr Val Asp Gly Ala Phe Phe Asp Met Glu Cys His Phe
             100                 105                 110

Val His Lys Ala Ala Asp Gly Gly Leu Ala Val Leu Gly Val Met Ile
         115                 120                 125

Ala Lys Gly Ala Ala Asn Pro Ala Leu Glu Ala Ile Trp Gln Val Met
         130                 135                 140

Pro Ala Lys Gly Gly Glu Thr Ala Thr Gly Thr Ser Met Leu Asp Ala

```
                    145                 150                 155                 160
Ser Met Leu Leu Pro Lys Asp Pro Val Thr Phe Arg Tyr Ala Gly Ser
                165                 170                 175

Leu Thr Thr Pro Pro Cys Ser Glu Val Val Gln Trp Val Val Tyr Arg
            180                 185                 190

Gln Ala Val Thr Ala Ser Ala Glu Gln Leu Ala Ala Phe Ala Lys Leu
        195                 200                 205

Phe Pro Asn Asn Ala Arg Pro Val Gln Pro Leu Asn Arg Arg Lys Leu
210                 215                 220

Leu Leu Asp Val Met
225

<210> SEQ ID NO 37
<211> LENGTH: 255
<212> TYPE: PRT
<213> ORGANISM: Microcoleus chthonoplastes

<400> SEQUENCE: 37

Met Lys Asn Ser Thr Phe Thr Phe Ile Val Phe Val Leu Leu Ala Ser
1               5                  10                  15

Cys Leu Ile Ile Ala Pro Asn Val Lys Ser Ser Asn Thr His Ser Val
            20                  25                  30

Asp Trp Gly Tyr Ser Gly Asp Glu Ser Pro Glu Lys Trp Gly Asp Leu
        35                  40                  45

Ser Pro Glu Phe Glu Thr Cys Lys Leu Gly Lys Thr Gln Ser Pro Ile
    50                  55                  60

Asp Leu Asn Asp Met Ser Ala Ser Ser Ala Asp Ser Leu Glu Phe Thr
65                  70                  75                  80

Tyr Lys Tyr Thr Pro Tyr Lys Val Ile Asn Asn Gly His Ala Ile Glu
                85                  90                  95

Val Ala Tyr Lys Ala Gly Ser Ser Ile Lys Ile Glu Gly Lys Arg Tyr
            100                 105                 110

Glu Leu Leu Gln Phe His Phe His Ala Pro Ser Glu His Thr Ile Lys
        115                 120                 125

Gly Gly Asp Tyr Pro Met Glu Ala His Leu Val His Lys Ser Gln Asp
    130                 135                 140

Gly Gln Leu Ala Val Ile Gly Val Phe Leu Lys Glu Gly Gln Tyr Asn
145                 150                 155                 160

Pro Phe Ile Glu Thr Leu Trp Ala Asn Ile Pro Thr Gln Lys Gly Glu
                165                 170                 175

Arg Ile Val Arg Gly Val Thr Val Asn Ala Ser Ala Leu Pro Pro Lys
            180                 185                 190

Asp Lys Ser Phe Tyr His Tyr Thr Gly Ser Leu Thr Thr Pro Pro Cys
        195                 200                 205

Thr Glu Gly Val Asn Trp Tyr Val Leu Lys Gln Pro Ile Glu Ile Ser
    210                 215                 220

Ser Gln Gln Leu Ala Lys Phe Gln Ser Val Tyr Ser Gly Asn Ala Arg
225                 230                 235                 240

Pro Val Gln Pro Leu Asn Lys Arg Val Ile Lys Thr Lys Glu Met
                245                 250                 255

<210> SEQ ID NO 38
<211> LENGTH: 291
<212> TYPE: PRT
<213> ORGANISM: Lautropia mirabilis
```

<400> SEQUENCE: 38

```
Met Ile His Ile Pro Asn Leu Arg Lys Ala Ile Met His Val Lys Gln
1               5                   10                  15
Leu Leu Val Pro Leu Leu Leu Ser Gly Leu Phe Leu Ser Ser Ala Ala
            20                  25                  30
Met Ala Glu Thr Ala Gln Pro Ala Asp Ala Ala Gly Ala Ser Pro
        35                  40                  45
Gly Gln Val Pro Ala Ala Ser Ser Asp Ser Lys Pro Ala Asp Lys Pro
    50                  55                  60
Ala His Trp Ser Tyr Gly Ser Glu Gly Pro Ala Tyr Trp Gly Glu
65                  70                  75                  80
Leu Ser Ala Asp Tyr Ser Gln Cys Ser Ile Gly Arg Asn Gln Ser Pro
                85                  90                  95
Val Asp Leu Asn Gln Asp Ala Ile Arg Ser Asn Lys Asp Ala Val
            100                 105                 110
Gln Val Asp Tyr Gln Pro Met Gly Tyr Glu Leu Val Asn Asn Gly His
            115                 120                 125
Thr Leu Gln Ala Thr Pro Ala Gly Ser Gln Pro Pro Leu Gln Ile Gly
    130                 135                 140
Ser Arg Thr Phe Thr Leu Lys Gln Phe His Phe His Asp Pro Ser Glu
145                 150                 155                 160
His Thr Phe Lys Gly Arg His Phe Pro Leu Glu Leu His Leu Val His
                165                 170                 175
Gly Ala Glu Asp Gly Ala Leu Ala Val Leu Ala Val Val Phe Gln Glu
            180                 185                 190
Gly Glu Glu Asn Pro Ala Leu Ala Pro Leu Val Ala Glu Ser Leu Ser
        195                 200                 205
Lys Gly Gln Thr Arg Lys Leu Ala Glu Pro Leu Asp Ile Arg Pro Leu
    210                 215                 220
Leu Pro Lys Lys Leu Ser Tyr Phe Arg Leu Asn Gly Ser Leu Thr Thr
225                 230                 235                 240
Pro Pro Cys Ser Glu Gly Val Thr Trp Val Val Phe Ser Ser Pro Val
                245                 250                 255
Lys Ala Ser Lys Ala Gln Ile Glu Ala Leu Gly Gln Ile Met Gly Gly
            260                 265                 270
Pro Asn Asn Arg Pro Val Gln Pro Leu Asn Ala Arg Ile Leu Val Asp
        275                 280                 285
Asp Asp Arg
    290
```

<210> SEQ ID NO 39
<211> LENGTH: 35
<212> TYPE: DNA
<213> ORGANISM: Artificial Sequence
<220> FEATURE:
<223> OTHER INFORMATION: synthetic primer

<400> SEQUENCE: 39
gcggcggccg caccatgaag ctcactgctg ccgtt         35

<210> SEQ ID NO 40
<211> LENGTH: 34
<212> TYPE: DNA
<213> ORGANISM: Artificial Sequence
<220> FEATURE:
<223> OTHER INFORMATION: synthetic primer -continued

<400> SEQUENCE: 40
ccggcgcgcc cttactagtt gaggctcttg gccg                               34

<210> SEQ ID NO 41
<211> LENGTH: 860
<212> TYPE: DNA
<213> ORGANISM: Aspergillus terreus

<400> SEQUENCE: 41
atgaagctca ctgctgccgt tctctccctg gctgtggccg cctcggcctc ttgcatccgc    60
catgcccgtc gggctgacgg cgtcgttgag accaactcct ataactacac cgagatgggc   120
ggtccgctga actggtacgg cctggacccc gaggccaact ctgcctgcgc cacgggcaag   180
caccagtccc ccatcgtcat ccactccgag gacatcgact atgtctcccc gggatccctg   240
aagttcgaca tccccaaggc cgactacgcc aagtttgaga accttgggtc cggcctcgag   300
gtcgttctga ccaacggatc tctcactgtg ggcaacaaga gccttcccct ggcccagttc   360
cacttccata ccccagcga gcaccgcgtc aacgacgagt actatcccat ggaggttcac   420
tttgtgttcc aaaacaaggg tatgcagcgt cccatgcact ctacaagtat caaccctaac   480
atcgtatagc caaagacacc gccgtcgtcg gcttcttctt ccagctctcc gagctcggat   540
actccgtccc cctgttcgac accatcttcg accacgttct cgagatcgag gagcctggtg   600
ccttcaccca caccggggag atggacttcg ccggcctgac ccaccacctc tacatgcatg   660
gcatctacca gtactctggc tccctgacca ccctccctg ctccgaggac gtcgcctggt   720
acctgagcac cgagccctg cccctgaccg tccaggacta caacaaggtc aagaaggtgc   780
tcaagtacaa cgcgcgctac acacagaacg ccctgggcga ggacaacctc ctcgaggtgg   840
cggccaagag cctcaactag                                               860

<210> SEQ ID NO 42
<211> LENGTH: 269
<212> TYPE: PRT
<213> ORGANISM: Aspergillus terreus

<400> SEQUENCE: 42

Met Lys Leu Thr Ala Ala Val Leu Ser Leu Ala Val Ala Ala Ser Ala
1               5                   10                  15

Ser Cys Ile Arg His Ala Arg Arg Ala Asp Gly Val Val Glu Thr Asn
                20                  25                  30

Ser Tyr Asn Tyr Thr Glu Met Gly Gly Pro Leu Asn Trp Tyr Gly Leu
            35                  40                  45

Asp Pro Glu Ala Asn Ser Ala Cys Ala Thr Gly Lys His Gln Ser Pro
        50                  55                  60

Ile Val Ile His Ser Glu Asp Ile Asp Tyr Val Ser Pro Gly Ser Leu
65                  70                  75                  80

Lys Phe Asp Ile Pro Lys Ala Asp Tyr Ala Lys Phe Glu Asn Leu Gly
                85                  90                  95

Ser Gly Leu Glu Val Val Leu Thr Asn Gly Ser Leu Thr Val Gly Asn
            100                 105                 110

Lys Ser Leu Pro Leu Ala Gln Phe His Phe His Thr Pro Ser Glu His
        115                 120                 125

Arg Val Asn Asp Glu Tyr Tyr Pro Met Glu Val His Phe Val Phe Gln
    130                 135                 140

Asn Lys Ala Lys Asp Thr Ala Val Val Gly Phe Phe Gln Leu Ser
145                 150                 155                 160

```
Glu Leu Gly Tyr Ser Val Pro Leu Phe Asp Thr Ile Phe Asp His Val
                165                 170                 175

Leu Glu Ile Glu Glu Pro Gly Ala Phe Thr His Thr Gly Glu Met Asp
            180                 185                 190

Phe Ala Gly Leu Thr His His Leu Tyr Met His Gly Ile Tyr Gln Tyr
        195                 200                 205

Ser Gly Ser Leu Thr Thr Pro Pro Cys Ser Glu Asp Val Ala Trp Tyr
    210                 215                 220

Leu Ser Thr Glu Pro Leu Pro Leu Thr Val Gln Asp Tyr Asn Lys Val
225                 230                 235                 240

Lys Lys Val Leu Lys Tyr Asn Ala Arg Tyr Thr Gln Asn Ala Leu Gly
                245                 250                 255

Glu Asp Asn Leu Leu Glu Val Ala Ala Lys Ser Leu Asn
            260                 265

<210> SEQ ID NO 43
<211> LENGTH: 253
<212> TYPE: PRT
<213> ORGANISM: Aspergillus terreus

<400> SEQUENCE: 43

Ser Cys Ile Arg His Ala Arg Arg Ala Asp Gly Val Val Glu Thr Asn
1               5                   10                  15

Ser Tyr Asn Tyr Thr Glu Met Gly Gly Pro Leu Asn Trp Tyr Gly Leu
                20                  25                  30

Asp Pro Glu Ala Asn Ser Ala Cys Ala Thr Gly Lys His Gln Ser Pro
            35                  40                  45

Ile Val Ile His Ser Glu Asp Ile Asp Tyr Val Ser Pro Gly Ser Leu
        50                  55                  60

Lys Phe Asp Ile Pro Lys Ala Asp Tyr Ala Lys Phe Glu Asn Leu Gly
65                  70                  75                  80

Ser Gly Leu Glu Val Val Leu Thr Asn Gly Ser Leu Thr Val Gly Asn
                85                  90                  95

Lys Ser Leu Pro Leu Ala Gln Phe His Phe His Thr Pro Ser Glu His
                100                 105                 110

Arg Val Asn Asp Glu Tyr Tyr Pro Met Glu Val His Phe Val Phe Gln
            115                 120                 125

Asn Lys Ala Lys Asp Thr Ala Val Val Gly Phe Phe Phe Gln Leu Ser
        130                 135                 140

Glu Leu Gly Tyr Ser Val Pro Leu Phe Asp Thr Ile Phe Asp His Val
145                 150                 155                 160

Leu Glu Ile Glu Glu Pro Gly Ala Phe Thr His Thr Gly Glu Met Asp
                165                 170                 175

Phe Ala Gly Leu Thr His His Leu Tyr Met His Gly Ile Tyr Gln Tyr
            180                 185                 190

Ser Gly Ser Leu Thr Thr Pro Pro Cys Ser Glu Asp Val Ala Trp Tyr
        195                 200                 205

Leu Ser Thr Glu Pro Leu Pro Leu Thr Val Gln Asp Tyr Asn Lys Val
    210                 215                 220

Lys Lys Val Leu Lys Tyr Asn Ala Arg Tyr Thr Gln Asn Ala Leu Gly
225                 230                 235                 240

Glu Asp Asn Leu Leu Glu Val Ala Ala Lys Ser Leu Asn
                245                 250
```

<210> SEQ ID NO 44
<211> LENGTH: 810
<212> TYPE: DNA
<213> ORGANISM: Artificial Sequence
<220> FEATURE:
<223> OTHER INFORMATION: synthetic sequence

<400> SEQUENCE: 44

| | | | | | |
|---|---|---|---|---|---|
| atgaagctca | ctgctgccgt | tctctccctg | gctgtggccg | cctcggcctc | ttgcatccgc | 60 |
| catgcccgtc | gggctgacgg | cgtcgttgag | accaactcct | ataactacac | cgagatgggc | 120 |
| ggtccgctga | actggtacgg | cctggacccc | gaggccaact | ctgcctgcgc | acgggcaag | 180 |
| caccagtccc | ccatcgtcat | ccactccgag | gacatcgact | atgtctcccc | gggatccctg | 240 |
| aagttcgaca | tccccaaggc | cgactacgcc | aagtttgaga | ccttgggtc | cggcctcgag | 300 |
| gtcgttctga | ccaacggatc | tctcactgtg | ggcaacaaga | ccttcccct | ggcccagttc | 360 |
| cacttccata | ccccagcga | gcaccgcgtc | aacgacgagt | actatcccat | ggaggttcac | 420 |
| tttgtgttcc | aaaacaaggc | caaagacacc | gccgtcgtcg | gcttcttctt | ccagctctcc | 480 |
| gagctcggat | actccgtccc | cctgttcgac | accatcttcg | accacgttct | cgagatcgag | 540 |
| gagcctggtg | ccttcaccca | caccggggag | atggacttcg | ccggcctgac | ccaccacctc | 600 |
| tacatgcatg | gcatctacca | gtactctggc | tccctgacca | cccctccctg | ctccgaggac | 660 |
| gtcgcctggt | acctgagcac | cgagcccctg | cccctgaccg | tccaggacta | caacaaggtc | 720 |
| aagaaggtgc | tcaagtacaa | cgcgcgctac | acacagaacg | ccctgggcga | ggacaacctc | 780 |
| ctcgaggtgg | cggccaagag | cctcaactag | | | | 810 |

<210> SEQ ID NO 45
<211> LENGTH: 274
<212> TYPE: PRT
<213> ORGANISM: Aspergillus oryza

<400> SEQUENCE: 45

Met Lys Phe Ala Thr Thr Leu Leu Pro Leu Leu Ala Gly Ala Ser Ala
1               5                   10                  15

Phe Cys Ile His Ser Pro Val Met Arg Arg Ala Ala Gly Gly Leu Asp
            20                  25                  30

Asp Ala Asn Lys Phe Asn Tyr Thr Gly Leu Gly Gly Pro Leu Asn Trp
        35                  40                  45

Tyr Gly Leu Asp Glu Ala Asn Glu Ala Cys Ala Lys Gly Lys His Gln
    50                  55                  60

Ser Pro Ile Val Ile Asp Ser Ala Ala Ile Asp Tyr Ala Ala Ser Gly
65                  70                  75                  80

Ser Leu Lys Leu Asp Leu Pro Leu Ala Asp Gly Ser Lys Leu Glu Asn
                85                  90                  95

Leu Gly Phe Gly Leu Gln Val Thr Leu Thr Asn Gly Ser Leu Thr Ala
            100                 105                 110

Asn Ser Lys Thr Tyr Thr Leu Ala Gln Phe His Phe His Thr Pro Ser
        115                 120                 125

Glu His His Val Asn Glu Glu His Phe Pro Met Glu Val His Phe Val
    130                 135                 140

Phe Gln Thr Ala Ala Lys Glu Thr Ala Val Val Gly Phe Phe Gln
145                 150                 155                 160

Leu Ser Glu Val Gly Asp Ser Val Pro Leu Phe Asp Ser Val Phe Ala
                165                 170                 175

Pro Ile Asp Asn Ile Pro Asp Ala Gly Thr Ser Thr Thr Thr Gly Gln

```
              180             185             190
Leu Asp Phe Gly Gly Leu Leu Asp His Phe Asn Arg His Gly Val Tyr
            195             200             205

Gln Tyr Thr Gly Ser Leu Thr Thr Pro Pro Cys Thr Glu Val Met
    210             215             220

Trp Asn Leu Ser Thr Glu Pro Leu Pro Leu Thr Val Gln Gly Tyr Asn
225             230             235             240

Lys Val Lys Lys Ile Ile Lys Tyr Asn Ala Arg Tyr Thr Gln Asn Ala
                245             250             255

Leu Gly Gln Asp Asn Leu Leu Glu Val Ala Ala Gln Lys Leu Asn Ser
            260             265             270

Ile Arg

<210> SEQ ID NO 46
<211> LENGTH: 277
<212> TYPE: PRT
<213> ORGANISM: Penicillium marneffei

<400> SEQUENCE: 46

Met Met Lys Leu Ser Ser Leu Leu Phe Phe Ala Leu Pro Ala Ala Ala
1               5               10              15

Ala His Ile His Ala Arg Ala Ala His Gly Val Ile Asp Thr Asn Pro
            20              25              30

Phe Asn Tyr Thr Gly Leu Gly Gly Pro Leu Asn Trp Tyr Gly Leu Asn
        35              40              45

Lys Thr Ala Asn Glu Ala Cys Ala Lys Gly Met Arg Gln Ser Pro Ile
    50              55              60

Asn Ile Asp Thr His Thr Ile Glu Tyr Ala Thr Gly Ser Val Asn
65              70              75              80

Phe Asn Ile Ser Asn Val Ala Ser Ala Lys Phe Glu Asn Ser Gly Phe
                85              90              95

Gly Leu Glu Val Leu Met Thr Asn Gly Ser Leu Val Val Asn Asn Ile
            100             105             110

Thr Tyr Tyr Leu Asp Asn Phe His Phe His Thr Pro Ser Glu His Arg
        115             120             125

Val Asp Glu Glu Tyr Phe Pro Met Glu Cys His Phe Gly Phe Val Ser
    130             135             140

Asp Asp Tyr Lys Ile Ala Val Val Gly Phe Phe Met Glu Ile Ser Arg
145             150             155             160

Phe Gly Tyr Thr Thr Pro Leu Leu Asp Ser Val Phe Ala Arg Leu Asp
                165             170             175

Asp Ile Thr Lys Pro Gly Thr Phe Thr Lys Thr Gly Pro Leu Asp Phe
            180             185             190

Ser Gly Leu Ile Ser His Phe Asn Lys Tyr Gly Val Tyr Thr Tyr Ser
        195             200             205

Gly Ser Leu Thr Thr Pro Pro Cys Thr Glu Gly Val Ser Trp Phe Ile
    210             215             220

Ser Thr Glu Pro Leu Trp Ile Asn Val Gln Gln Ser Gln Ala Val Lys
225             230             235             240

Lys Val Ile Arg Tyr Asn Ala Arg Tyr Thr Gln Asn Asn Leu Gly Glu
                245             250             255

Pro Asn Leu Leu Val Val Ala Ala Lys Ala Phe Asp Cys Asn Val Ser
            260             265             270

Ser Ser Met Trp Ser
```

-continued

275

<210> SEQ ID NO 47
<211> LENGTH: 273
<212> TYPE: PRT
<213> ORGANISM: Penicillium marneffei

<400> SEQUENCE: 47

Met Asp Phe Ala Leu Ala Phe Val Ser Leu Ile Thr Ala Ala Ser Ala
1               5                   10                  15

Ser Cys Ile Tyr Gly Thr Ser Leu Met Pro Arg Ala Ala Glu Gly Val
            20                  25                  30

Val Asp Ile Leu Ser Phe Asn Tyr Thr Ala Thr Gly Gly Pro Leu Asn
        35                  40                  45

Trp His Leu Leu Asn Thr Thr Ala Asn Asn Ala Cys Ala Thr Gly Lys
    50                  55                  60

Asn Gln Ser Pro Val Asp Ile Val Met Glu Gly Ile Thr Tyr Ala Ile
65                  70                  75                  80

Pro Gly Ser Val Lys Leu Asp Ile Pro Cys Ala Gly Val Glu Leu
                85                  90                  95

Glu Asn Leu Asn Asn Val Val Glu Val Val Ala Asn Asn Gly Thr Leu
            100                 105                 110

Thr Thr Pro Glu Ser Ile Tyr Lys Leu Ala Gln Phe His Phe His Thr
        115                 120                 125

Pro Ser Glu His Arg Val Asn Glu Glu Tyr Phe Pro Met Glu Ala His
    130                 135                 140

Phe Val Phe Glu Asn Glu Ala Ser Gln Ile Ala Val Ala Ala Phe Leu
145                 150                 155                 160

Phe Gln Leu Ser Glu Ser Gly Ala Ser Asn Pro Leu Phe Asp Ser Val
                165                 170                 175

Phe Ala His Leu Asp Asp Ile Thr Thr Pro Gly Thr Phe Thr Lys Thr
            180                 185                 190

Gly Pro Leu Asp Phe Thr Thr Val Asn Gln His Phe Ser Asn His Gly
        195                 200                 205

Ile Phe Gln Tyr Ser Gly Ser Leu Thr Thr Pro Cys Ser Glu Gly
    210                 215                 220

Leu Ser Trp Tyr Ile Ser Thr Glu Pro Met Pro Leu Asn Val Gln Thr
225                 230                 235                 240

Tyr Asn Lys Val Lys Lys Val Val Lys Phe Asn Ala Arg Tyr Thr Gln
                245                 250                 255

Asn Thr Leu Gly Gln Asn Asn Leu Leu Glu Leu Ala Ala Thr Pro Ser
            260                 265                 270

Gly

<210> SEQ ID NO 48
<211> LENGTH: 291
<212> TYPE: PRT
<213> ORGANISM: Aspergillus flavus

<400> SEQUENCE: 48

Met Trp Leu Pro Cys Phe Gln Pro Ile Ile Phe Phe Arg Cys Ser Ser
1               5                   10                  15

Val Met Lys Phe Ala Thr Thr Leu Leu Pro Leu Leu Ala Gly Ala Ser
            20                  25                  30

Ala Phe Cys Ile His Ser Pro Val Met Arg Arg Ala Ala Gly Gly Leu
        35                  40                  45

```
Asp Asp Ala Asn Lys Phe Asn Tyr Thr Gly Leu Gly Gly Pro Leu Asn
 50                  55                  60

Trp Tyr Gly Leu Asp Glu Ala Asn Glu Ala Cys Ala Lys Gly Lys His
 65                  70                  75                  80

Gln Ser Pro Ile Val Ile Asp Ser Ala Ala Ile Asp Tyr Ala Ala Ser
                 85                  90                  95

Gly Ser Leu Lys Leu Asp Leu Pro Leu Ala Asp Gly Ser Lys Leu Glu
            100                 105                 110

Asn Leu Gly Phe Gly Leu Gln Val Thr Leu Thr Asn Gly Ser Leu Thr
            115                 120                 125

Ala Asn Ser Lys Thr Tyr Thr Leu Ala Gln Phe His Phe His Thr Pro
        130                 135                 140

Ser Glu His His Val Asn Glu Glu His Phe Pro Met Glu Val His Phe
145                 150                 155                 160

Val Phe Gln Thr Ala Ala Lys Glu Thr Ala Val Val Gly Phe Phe Phe
                165                 170                 175

Gln Leu Ser Glu Val Gly Asp Ser Val Pro Leu Phe Asp Ser Val Phe
            180                 185                 190

Ala Pro Ile Asp Asn Ile Pro Asp Ala Gly Thr Ser Thr Thr Thr Gly
            195                 200                 205

Gln Leu Asp Phe Gly Gly Leu Leu Asp His Phe Asn Arg His Gly Val
        210                 215                 220

Tyr Gln Tyr Thr Gly Ser Leu Thr Thr Pro Pro Cys Thr Glu Glu Val
225                 230                 235                 240

Met Trp Asn Leu Ser Thr Glu Pro Leu Pro Leu Thr Val Gln Gly Tyr
                245                 250                 255

Asn Lys Val Lys Lys Ile Ile Lys Tyr Asn Ala Arg Tyr Thr Gln Asn
            260                 265                 270

Ala Leu Gly Gln Asp Asn Leu Leu Glu Val Ala Ala Gln Lys Leu Asn
        275                 280                 285

Ser Ile Arg
    290

<210> SEQ ID NO 49
<211> LENGTH: 50
<212> TYPE: DNA
<213> ORGANISM: Artificial Sequence
<220> FEATURE:
<223> OTHER INFORMATION: synthetic primer

<400> SEQUENCE: 49
agcgctagcc ggcccccccgg cacaggcctc ccccggtccc gcgacggccc         50

<210> SEQ ID NO 50
<211> LENGTH: 34
<212> TYPE: DNA
<213> ORGANISM: Artificial Sequence
<220> FEATURE:
<223> OTHER INFORMATION: synthetic primer

<400> SEQUENCE: 50
tccggatcct tatcaggcga cggtgtgcac cagc                           34

<210> SEQ ID NO 51
<211> LENGTH: 618
<212> TYPE: DNA
<213> ORGANISM: Streptomyces pristinaespiralis
```

```
<400> SEQUENCE: 51
tcccccggtc cgcgacggc cgccgcccc cggccgggca ctcccgcgca ggccctgcgc    60
gagctggcgg ccggcaaccg ccgctggcgc accttccggc agcagcatcc gcacgagaac   120
tcggccgtgc gcgaggaact gatatccggt caggaaccct cgccgtggt cctcggctgc   180 atcgactcgc gggtgccgcc ggaactggtc ttcgatcagg gcctcggcga cctgatgacc   240
gtgcgctccg ccggtgaggt gctcgacgag gcggtcctcg gcagcgtcgc gtacggggta   300
ctggagctgg acatccccct ggtcatggtg ctcggtcacc agtcctgcgg agcggtgacg   360
gcggcggtgc acgcggagga gaccggcgag gaactcccg cccacatcca gtacatcgcc   420
gaccgcatac ggccggccat agaccactcc caggagggcg cggcgcgcgt cgactccacg   480
atcacccgca atgtccagat ggtcacgcgg ctcctcgcgc aggagcccga cctcgcggcg   540
aggatcgcgg ccgggaagct cgcggtcgtc ggcgcacgct acgaactgag ctcgcagctg   600
gtgcacaccg tcgcctga                                                618

<210> SEQ ID NO 52
<211> LENGTH: 247
<212> TYPE: PRT
<213> ORGANISM: Streptomyces pristinaespiralis

<400> SEQUENCE: 52

Met Lys Asn Thr Pro Arg Thr Asn Ser Ser Val Gly Gly Ser Arg Arg
1               5                   10                  15

Thr Leu Leu Arg Ala Ala Val Ala Gly Gly Ala Leu Ala Ser Gly Gly
            20                  25                  30

Leu Val Trp Ala Gly Thr Pro Ala Ser Ala Ser Pro Gly Pro Ala Thr
        35                  40                  45

Ala Arg Arg Pro Arg Pro Gly Thr Pro Ala Gln Ala Leu Arg Glu Leu
    50                  55                  60

Ala Ala Gly Asn Arg Arg Trp Arg Thr Phe Arg Gln Gln His Pro His
65                  70                  75                  80

Glu Asn Ser Ala Val Arg Glu Glu Leu Ile Ser Gly Gln Glu Pro Phe
                85                  90                  95

Ala Val Val Leu Gly Cys Ile Asp Ser Arg Val Pro Pro Glu Leu Val
            100                 105                 110

Phe Asp Gln Gly Leu Gly Asp Leu Met Thr Val Arg Ser Ala Gly Glu
        115                 120                 125

Val Leu Asp Glu Ala Val Leu Gly Ser Val Ala Tyr Gly Val Leu Glu
    130                 135                 140

Leu Asp Ile Pro Leu Val Met Val Leu Gly His Gln Ser Cys Gly Ala
145                 150                 155                 160

Val Thr Ala Ala Val His Ala Glu Glu Thr Gly Glu Glu Leu Pro Ala
                165                 170                 175

His Ile Gln Tyr Ile Ala Asp Arg Ile Arg Pro Ala Ile Asp His Ser
            180                 185                 190

Gln Glu Gly Ala Ala Arg Val Asp Ser Thr Ile Thr Arg Asn Val Gln
        195                 200                 205

Met Val Thr Arg Leu Leu Ala Gln Glu Pro Asp Leu Ala Ala Arg Ile
    210                 215                 220

Ala Ala Gly Lys Leu Ala Val Val Gly Ala Arg Tyr Glu Leu Ser Ser
225                 230                 235                 240

Gln Leu Val His Thr Val Ala
                245
```

-continued

```
<210> SEQ ID NO 53
<211> LENGTH: 205
<212> TYPE: PRT
<213> ORGANISM: Streptomyces pristinaespiralis

<400> SEQUENCE: 53

Ser Pro Gly Pro Ala Thr Ala Arg Arg Pro Arg Pro Gly Thr Pro Ala
1               5                   10                  15

Gln Ala Leu Arg Glu Leu Ala Ala Gly Asn Arg Arg Trp Arg Thr Phe
            20                  25                  30

Arg Gln Gln His Pro His Glu Asn Ser Ala Val Arg Glu Glu Leu Ile
        35                  40                  45

Ser Gly Gln Glu Pro Phe Ala Val Val Leu Gly Cys Ile Asp Ser Arg
    50                  55                  60

Val Pro Pro Glu Leu Val Phe Asp Gln Gly Leu Gly Asp Leu Met Thr
65                  70                  75                  80

Val Arg Ser Ala Gly Glu Val Leu Asp Glu Ala Val Leu Gly Ser Val
                85                  90                  95

Ala Tyr Gly Val Leu Glu Leu Asp Ile Pro Leu Val Met Val Leu Gly
            100                 105                 110

His Gln Ser Cys Gly Ala Val Thr Ala Ala Val His Ala Glu Glu Thr
        115                 120                 125

Gly Glu Glu Leu Pro Ala His Ile Gln Tyr Ile Ala Asp Arg Ile Arg
    130                 135                 140

Pro Ala Ile Asp His Ser Gln Glu Gly Ala Ala Arg Val Asp Ser Thr
145                 150                 155                 160

Ile Thr Arg Asn Val Gln Met Val Thr Arg Leu Leu Ala Gln Glu Pro
                165                 170                 175

Asp Leu Ala Ala Arg Ile Ala Ala Gly Lys Leu Ala Val Val Gly Ala
            180                 185                 190

Arg Tyr Glu Leu Ser Ser Gln Leu Val His Thr Val Ala
        195                 200                 205

<210> SEQ ID NO 54
<211> LENGTH: 271
<212> TYPE: PRT
<213> ORGANISM: Streptomyces scabiei

<400> SEQUENCE: 54

Met Asn Leu Asp Ala Ala Pro His Ser Gly Asp Thr Ala Glu Ala Thr
1               5                   10                  15

Ala Gly Gly Ala Asp Ala Pro Ile Ser Pro Ala Gln Pro Arg Gly Arg
            20                  25                  30

Arg Ser Leu Leu Arg Ala Ala Leu Ala Gly Thr Ala Val Val Gly Gly
        35                  40                  45

Gly Leu Ala Val Gly Ala Phe Pro Ala Asn Ala Glu Ser Val Ser Arg
    50                  55                  60

Ser Thr Pro Ala His Gln Thr Pro Pro Ala His Lys Arg Pro Thr Thr
65                  70                  75                  80

Ala Glu Glu Ala Leu Lys Glu Leu Ser Gln Gly Asn Arg Arg Trp Arg
                85                  90                  95

Thr Leu His Glu Gln His Pro Asp Glu Gly Tyr Ala Leu Arg Lys Ala
            100                 105                 110

Leu Thr Thr Gly Gln Gln Pro Phe Ala Leu Val Leu Gly Cys Ile Asp
        115                 120                 125
```

```
Ser Arg Val Pro Pro Glu Leu Val Phe Asp Gln Gly Leu Gly Asp Leu
    130                 135                 140

Met Thr Val Arg Ser Ala Gly Glu Val Leu Asp Gln Ser Val Leu Gly
145                 150                 155                 160

Ser Val Lys Tyr Gly Val Leu Glu Leu Asn Ile Pro Leu Val Val Val
                165                 170                 175

Leu Gly His Gln Ser Cys Gly Ala Val Lys Ala Ala Val Ala Val Asp
                180                 185                 190

Glu Ser Gly Glu Glu Leu Pro Ser Gly Ile Gln Tyr Ile Ala Asp Glu
            195                 200                 205

Ile Ala Pro Ala Ile Asp His Ser Val Thr Gly Asp Ala Arg Val Ala
    210                 215                 220

Ala Thr Ile Asp Ala Asn Val Arg Leu Val Arg Ser Lys Val Val Ala
225                 230                 235                 240

Asp Pro Asp Val Ala Ala Arg Leu Lys Ala Gly Lys Val Ala Val Val
                245                 250                 255

Gly Ala Arg Tyr Asp Leu Thr Thr Gln Arg Val His Leu Leu Lys
                260                 265                 270

<210> SEQ ID NO 55
<211> LENGTH: 240
<212> TYPE: PRT
<213> ORGANISM: Streptomyces roseosporus

<400> SEQUENCE: 55

Met Arg Ile Thr Arg Thr Pro Arg Thr Ala Pro Thr Thr Arg Arg Thr
1               5                   10                  15

Leu Leu Arg Ala Ser Ala Ala Thr Ala Ala Ala Gly Val Leu Ala Ala
                20                  25                  30

Gly Ser Ser Pro Val Gly Ala Ala Pro Arg Thr Arg Pro Ala Ser Ala
            35                  40                  45

Ala Arg Pro Ala Thr Pro Ala Ala Leu Lys Glu Leu Ala Ala Gly
    50                  55                  60

Asn Arg Arg Trp Arg Thr Leu His Gln Arg His Pro His Glu Thr Ala
65                  70                  75                  80

Gly Val Arg Ser Ala Leu Val Ser Gly Gln Ser Pro Phe Ala Leu Ile
                85                  90                  95

Leu Gly Cys Ile Asp Ser Arg Val Pro Pro Glu Leu Val Phe Asp Gln
                100                 105                 110

Gly Leu Gly Asp Leu Met Thr Val Arg Ser Ala Gly Glu Val Leu Asp
            115                 120                 125

Glu Ala Val Leu Gly Ser Ile Gly Tyr Gly Val Leu Glu Leu Gly Ile
    130                 135                 140

Pro Leu Val Val Val Leu Gly His Gln Ser Cys Gly Ala Val His Ala
145                 150                 155                 160

Glu Glu Thr Gly Glu Ser Leu Pro Ala His Ile Gln Tyr Val Ala Glu
                165                 170                 175

Gln Ile Arg Pro Ala Ile Val His Gly Gln His Gly Asp Ala Arg Val
            180                 185                 190

Asp Ala Thr Val Ser Ala Gln Val Arg Leu Val Arg Ser Arg Leu Ala
    195                 200                 205

Arg Glu Thr Asp Leu Ala Ser Lys Val Ala Gly Glu Leu Ala Ile
    210                 215                 220

Val Gly Ala Arg Tyr Glu Leu Ser Thr Glu Leu Val His Arg Val Gly
```

```
                 225                 230                 235                 240

<210> SEQ ID NO 56
<211> LENGTH: 213
<212> TYPE: PRT
<213> ORGANISM: Streptomyces sp. Mg1

<400> SEQUENCE: 56

Met Val Ser Gly Ser Ser Ala Val Ser Thr Arg Ser Asp Gly Val
1               5                   10                  15

Arg Arg Arg Pro Val Thr Pro Glu Gly Ala Trp Ala Glu Leu Ala Ala
                20                  25                  30

Gly Asn Gly Arg Trp Arg Thr Leu Arg Glu Arg His Pro Asp Glu Ser
            35                  40                  45

Ala Gly Leu Arg Arg Glu Leu Val Gly Gly Gln His Pro Phe Ala Val
        50                  55                  60

Val Leu Gly Cys Val Asp Ser Arg Val Pro Pro Glu Leu Val Phe Asp
65                  70                  75                  80

Gln Gly Leu Gly Asp Leu Leu Thr Val Arg Ser Ala Gly Glu Val Leu
                85                  90                  95

Asp Glu Ala Val Val Gly Ser Val Ala Tyr Gly Val Leu Glu Leu Gly
            100                 105                 110

Ile Pro Leu Val Val Leu Gly His Gln Ala Cys Gly Ala Val Ala
        115                 120                 125

Ala Ala Val His Ala Glu Thr Gly His Gly Glu Leu Pro Gly Pro Leu
130                 135                 140

Arg Tyr Leu Ala Gly Gln Ile Arg Pro Ser Ile Asp Arg Thr Leu Arg
                145                 150                 155                 160

Gly Asp Ala Cys Val Asp Ala Ala Val Thr Ala Asn Val Arg Arg Val
            165                 170                 175

Ala Ala Arg Leu Ala Ala Gln Ala Glu Met Ala Gly Arg Ile Ala Ala
        180                 185                 190

Gly Lys Leu Ala Val Val Gly Ala Arg Tyr Glu Leu Ala Gly Gln Trp
    195                 200                 205

Val His Gln Val Gly
        210

<210> SEQ ID NO 57
<211> LENGTH: 252
<212> TYPE: PRT
<213> ORGANISM: Streptomyces clavuligerus

<400> SEQUENCE: 57

Met Thr Phe Pro Ser Glu Arg His Ala Ala Gly Gly Ala Thr Pro Ala
1               5                   10                  15

Pro Val Ser Arg Pro Arg Arg Gly Leu Leu Arg Ala Ala Ile Ile Gly
                20                  25                  30

Ser Thr Val Thr Ala Gly Ala Trp Ala Leu Gly Gly Pro Ala Ala Ser
            35                  40                  45

Ala Val Pro Arg Thr Ser Thr Gly Pro Arg Pro Ala Thr Pro Glu Ala
        50                  55                  60

Ala Leu Arg Glu Leu His Ala Gly Asn Gln Arg Trp Arg Thr Phe His
65                  70                  75                  80

Glu Gln His Pro His Glu Thr His Thr Ile Arg Arg Glu Ala Val Ser
                85                  90                  95

Gly Gln His Pro Phe Ala Val Val Leu Gly Cys Ile Asp Ser Arg Val
```

```
                    100                 105                 110
Pro Pro Glu Leu Val Phe Asp Gln Gly Leu Gly Asp Leu Leu Thr Val
                115                 120                 125

Arg Ser Ala Gly Gln Val Leu Asp Glu Ala Val Leu Gly Ser Val Ala
            130                 135                 140

Tyr Gly Val Leu Glu Leu Asp Ile Pro Leu Val Val Leu Gly His
145                 150                 155                 160

Gln Ser Cys Gly Ala Val Ala Ala Val His Ala Asp Glu Thr Gly
                165                 170                 175

Ala Glu Leu Pro Ala His Ile Gln Tyr Ile Ala Ala Glu Ile Arg Pro
            180                 185                 190

Ala Ile Asp Arg Ser Val Gln Gly Asp Ala Arg Ile Asp Ala Thr Val
            195                 200                 205

Ser Ala Gln Val Arg Arg Val Arg Ser Arg Leu Ala Ala Glu Pro Asp
        210                 215                 220

Leu Ala Pro Arg Ile Ala Ala Gly Arg Leu Ala Ile Thr Gly Ala Arg
225                 230                 235                 240

Tyr Glu Leu Thr Ser Gln Leu Val His Gln Leu Ala
                245                 250

<210> SEQ ID NO 58
<211> LENGTH: 212
<212> TYPE: PRT
<213> ORGANISM: Streptomyces roseosporus

<400> SEQUENCE: 58

Met Leu Ala Ala Gly Ser Ser Pro Val Gly Ala Ala Pro Arg Thr Arg
1               5                   10                  15

Pro Ala Ser Ala Ala Arg Pro Thr Pro Ala Ala Leu Lys Glu
            20                  25                  30

Leu Ala Ala Gly Asn Arg Arg Trp Arg Thr Leu His Gln Arg His Pro
            35                  40                  45

His Glu Thr Ala Gly Val Arg Ser Ala Leu Val Ser Gly Gln Ser Pro
50                  55                  60

Phe Ala Leu Ile Leu Gly Cys Ile Asp Ser Arg Val Pro Pro Glu Leu
65                  70                  75                  80

Val Phe Asp Gln Gly Leu Gly Asp Leu Met Thr Val Arg Ser Ala Gly
                85                  90                  95

Glu Val Leu Asp Glu Ala Val Leu Gly Ser Ile Gly Tyr Gly Val Leu
            100                 105                 110

Glu Leu Gly Ile Pro Leu Val Val Leu Gly His Gln Ser Cys Gly
        115                 120                 125

Ala Val His Ala Glu Glu Thr Gly Glu Ser Leu Pro Ala His Ile Gln
        130                 135                 140

Tyr Val Ala Glu Gln Ile Arg Pro Ala Ile Val His Gly Gln His Gly
145                 150                 155                 160

Asp Ala Arg Val Asp Ala Thr Val Ser Ala Gln Val Arg Leu Val Arg
                165                 170                 175

Ser Arg Leu Ala Arg Glu Thr Asp Leu Ala Ser Lys Val Ala Ala Gly
            180                 185                 190

Glu Leu Ala Ile Val Gly Ala Arg Tyr Glu Leu Ser Thr Glu Leu Val
        195                 200                 205

His Arg Val Gly
    210
```

```
<210> SEQ ID NO 59
<211> LENGTH: 263
<212> TYPE: PRT
<213> ORGANISM: Streptomyces clavuligerus

<400> SEQUENCE: 59

Met Thr Val Asn Val Glu Gln Asn Arg Leu Glu Glu Asn Val Thr Val
1               5                   10                  15

Ala Ala Ser His Gly Thr Leu Arg Arg Ser Met Leu Arg Ala Ala Val
            20                  25                  30

Gly Gly Ala Ser Ala Leu Gly Ala Leu Gly Val Leu Gly Ser Gly Thr
        35                  40                  45

Ala Thr Ala Ala Ser Pro Leu His Thr Pro Ser Pro Ala Ser Ser
    50                  55                  60

Pro Pro Thr Arg Pro Val Arg Thr Pro Arg Ala Ala Leu Gln Ala Leu
65                  70                  75                  80

Leu Asp Gly Asn Arg Arg Trp Arg Thr Ser Thr Gln Arg His Pro Asn
                85                  90                  95

Glu Asp Pro Ala Ala Arg Arg Ala Ile Ala Gly Gln Ala Pro Phe
            100                 105                 110

Ala Val Val Leu Gly Cys Ile Asp Ser Arg Val Pro Pro Glu His Val
        115                 120                 125

Phe Asp Gln Gly Leu Gly Asp Leu Leu Thr Pro Arg Ser Ala Gly Gln
    130                 135                 140

Val Leu Asp Glu Ser Val Ile Gly Ser Val Glu Tyr Gly Val Val Ala
145                 150                 155                 160

Leu Arg Ile Pro Leu Val Val Leu Gly His Gln Ser Cys Gly Ala
                165                 170                 175

Val Lys Ser Ala Ile Glu Ile Glu Gln Thr Gly Glu Gln Leu Pro Gly
            180                 185                 190

Ser Ile Gln Tyr Ile Ala Glu Arg Ile Trp Pro Ala Ile Asp Gln Thr
        195                 200                 205

Gln Gln Gly Asp Ala Arg Leu Asn Ala Thr Thr Asp Ala Asn Ala Leu
    210                 215                 220

Met Ile Arg Asp Gln Leu Ala Ala Leu Pro Thr Leu Ala Thr Arg Ile
225                 230                 235                 240

Ala Ala Gly Gln Leu Ser Val Val Ser Ala Arg Tyr Glu Leu Thr Asp
                245                 250                 255

Gln Ser Val Arg Leu Leu Pro
            260

<210> SEQ ID NO 60
<211> LENGTH: 261
<212> TYPE: PRT
<213> ORGANISM: Streptomyces sp.

<400> SEQUENCE: 60

Met Leu Ser Asn Ile Arg Pro Ser Asn Val Ser Pro Glu Val Ala Ala
1               5                   10                  15

Pro Asn Thr Ala Ala Arg Gly Ala Asp Ser Pro Ser Arg Arg Thr Leu
            20                  25                  30

Leu Arg Thr Ala Val Ala Gly Thr Ala Thr Ala Gly Ser Val Leu Ala
        35                  40                  45

Leu Gly Ser Ala Phe Pro Ala Ser Ala Thr Pro Pro Ala Pro Thr Thr
    50                  55                  60
```

Gly Ser Arg Pro Thr Thr Pro Glu Gln Ala Leu Arg Glu Leu Ala Ala
65                  70                  75                  80

Gly Asn Arg Arg Trp Arg Thr Tyr Arg Gln Glu His Pro His Glu Ser
                85                  90                  95

Pro Ser Thr Arg Leu Arg Leu Ala Lys Gly Gln Asn Pro Phe Ala Val
            100                 105                 110

Val Leu Gly Cys Val Asp Ser Arg Val Pro Pro Glu Leu Val Phe Asp
        115                 120                 125

Gln Gly Leu Gly Asp Leu Leu Thr Val Arg Ser Ala Gly Glu Val Leu
    130                 135                 140

Asp Glu Ala Val Leu Gly Ser Ile Ala Tyr Gly Val Leu Glu Leu Lys
145                 150                 155                 160

Ile Pro Leu Val Leu Val Leu Gly His Gln Ser Cys Gly Ala Val Gly
                165                 170                 175

Ala Ala Val His Ala Asp Glu Thr Gly Glu Arg Leu Pro Ala His Ile
            180                 185                 190

Gln Tyr Leu Ala Asp Gln Ile Asn Pro Ala Ile Asp Arg Thr Arg His
        195                 200                 205

Gly Asp Ala Arg Val Arg Ala Thr Ile Asp Ala His Ala Arg Ser Thr
210                 215                 220

Arg Asp Arg Leu Ala Ala Glu Pro Asp Leu Ala Arg Ala Val Ser Ala
225                 230                 235                 240

Gly Lys Leu Ala Val Ala Ala Arg Tyr Asp Leu His Asp Gln Arg
                245                 250                 255

Val Ser Thr Leu Asn
            260

<210> SEQ ID NO 61
<211> LENGTH: 260
<212> TYPE: PRT
<213> ORGANISM: Streptomyces viridochromogene

<400> SEQUENCE: 61

Met Asn Ser His Thr Thr Ser His Arg Gly Ser Gly Pro Glu Pro His
1               5                   10                  15

Ser Phe Ala Gly Ser Arg Pro Thr Pro Gly Gly Thr Val Arg Arg Thr
            20                  25                  30

Leu Leu Arg Thr Ala Leu Thr Gly Ala Ala Leu Gly Ala Gly Phe
        35                  40                  45

Ala Ala Ala Pro Gln Ala Thr Ala Thr Thr Ser Ala Pro Gly Thr Pro
    50                  55                  60

Pro Arg Pro Gly Thr Pro Asp Glu Ala Leu Arg Glu Leu Ala Glu Gly
65                  70                  75                  80

Asn Arg Arg Trp Arg Ala Tyr Arg Glu Arg His Pro His Glu Asp Pro
                85                  90                  95

Ala Leu Arg Arg Thr Leu Ala Thr Ala Gln His Pro Phe Ala Val Val
            100                 105                 110

Leu Gly Cys Ile Asp Ser Arg Val Pro Pro Glu Leu Val Phe Asp Gln
        115                 120                 125

Gly Leu Gly Asp Leu Met Thr Val Arg Thr Ala Gly Glu Val Leu Asp
    130                 135                 140

Glu Ala Val Leu Gly Ser Val Ala Tyr Gly Val Leu Glu Leu Ala Ile
145                 150                 155                 160

Pro Leu Val Val Val Leu Gly His Gln Ser Cys Gly Ala Val Arg Ala
                165                 170                 175

```
Ala Val Gln Ala Glu Gln Ser Gly Glu Arg Leu Pro Ala His Met Gln
            180                 185                 190

Tyr Leu Val Asp Gln Ile Gly Pro Ala Ile Asp His Gly Val Asp Gly
        195                 200                 205

Asp Ala Arg Ile Asp Ala Thr Val Ser Ala Asn Val Arg Leu Val Arg
    210                 215                 220

Ser Arg Leu Ala Ala Glu Pro Glu Leu Ala Ala Arg Val Ala Asp Gly
225                 230                 235                 240

Arg Leu Ala Ile Val Gly Ala Arg Tyr Glu Leu Thr Thr Gln Thr Val
                245                 250                 255

His Arg Val Ala
            260

<210> SEQ ID NO 62
<211> LENGTH: 870
<212> TYPE: DNA
<213> ORGANISM: Bacillus agaradhaerens

<400> SEQUENCE: 62
gtgaaaaatg acgtcatgaa agaaggaaca aacatgaaaa gaagagtagg gtggggaagc      60
gttgtagtcg tttagtgtc aagtgtcgtc ataacggcct gttctacagc gcaatcagga     120
gacgaagaag ttaactcatt aaatggcagt ggcactcatg aagaggcaat aaaagacgaa     180 catgagggc attggtcata tactggagaa actggaccga cgcattgggg atcgttagac     240
gcctcttatg aattatgtga acaagagcag gaacaatcgc cgatcaacat tgagacagat     300
gaggtgacaa ctactgatac tcatatcagc atcgcgtatc aaccgagccc gtttgcgatc     360
gaaaataacg gtcatacgat tcaagccaat gccctaacag aggataatac tatctcgata     420
gagggtgaga attatcaatt aattcaattt cacttccatg tcccttctga acatcaaaaa     480
aatggagaac acttagacat ggagcttcat tttgtccatc aaaatcaaga gggggagttg     540
gcagtgctgg gtgtcctaat ggaagaaggg gaggtgaacg acgcattagc agagctatgg     600
gctgaaatgc cacaagaaga gatggatgaa acgattgaat taacggatgc tatcgatctt     660
aacgcattat tgccaagcag ccatgaaggc tttcattatg gtggttctct tacaacgcct     720
ccttgtactg aaggtgtaaa atgggtcgtc ctcgaaaaaa caatttccgt ctcgcaagaa     780
caaattgaca cattcgcaga gatctttcca accaataatc ggcctgtcca accgtggaat     840
gaccggcatg tatatgaagt ggctattgat                                     870

<210> SEQ ID NO 63
<211> LENGTH: 290
<212> TYPE: PRT
<213> ORGANISM: Bacillus agaradhaerens

<400> SEQUENCE: 63

Val Lys Asn Asp Val Met Lys Glu Gly Thr Asn Met Lys Arg Arg Val
1               5                  10                  15

Gly Trp Gly Ser Val Val Val Leu Val Ser Ser Val Val Ile Thr
            20                  25                  30

Ala Cys Ser Thr Ala Gln Ser Gly Asp Glu Glu Val Asn Ser Leu Asn
        35                  40                  45

Gly Ser Gly Thr His Glu Glu Ala Ile Lys Asp Glu His Glu Gly His
    50                  55                  60

Trp Ser Tyr Thr Gly Glu Thr Gly Pro Thr His Trp Gly Ser Leu Asp
65                  70                  75                  80
```

Ala Ser Tyr Glu Leu Cys Glu Gln Glu Gln Ser Pro Ile Asn
                85                  90                  95

Ile Glu Thr Asp Glu Val Thr Thr Thr Asp Thr His Ile Ser Ile Ala
            100                 105                 110

Tyr Gln Pro Ser Pro Phe Ala Ile Glu Asn Asn Gly His Thr Ile Gln
        115                 120                 125

Ala Asn Ala Leu Thr Glu Asp Asn Thr Ile Ser Ile Glu Gly Glu Asn
130                 135                 140

Tyr Gln Leu Ile Gln Phe His Phe His Val Pro Ser Glu His Gln Lys
145                 150                 155                 160

Asn Gly Glu His Leu Asp Met Glu Leu His Phe Val His Gln Asn Gln
                165                 170                 175

Glu Gly Glu Leu Ala Val Leu Gly Val Leu Met Glu Glu Gly Glu Val
            180                 185                 190

Asn Asp Ala Leu Ala Glu Leu Trp Ala Glu Met Pro Gln Glu Glu Met
        195                 200                 205

Asp Glu Thr Ile Glu Leu Thr Asp Ala Ile Asp Leu Asn Ala Leu Leu
210                 215                 220

Pro Ser Ser His Glu Gly Phe His Tyr Gly Gly Ser Leu Thr Thr Pro
225                 230                 235                 240

Pro Cys Thr Glu Gly Val Lys Trp Val Leu Glu Lys Thr Ile Ser
                245                 250                 255

Val Ser Gln Glu Gln Ile Asp Thr Phe Ala Glu Ile Phe Pro Thr Asn
            260                 265                 270

Asn Arg Pro Val Gln Pro Trp Asn Asp Arg His Val Tyr Glu Val Ala
        275                 280                 285

Ile Asp
    290

<210> SEQ ID NO 64
<211> LENGTH: 251
<212> TYPE: PRT
<213> ORGANISM: Bacillus agaradhaerens

<400> SEQUENCE: 64

Gly Asp Glu Glu Val Asn Ser Leu Asn Gly Ser Gly Thr His Glu Glu
1               5                   10                  15

Ala Ile Lys Asp Glu His Glu Gly His Trp Ser Tyr Thr Gly Glu Thr
            20                  25                  30

Gly Pro Thr His Trp Gly Ser Leu Asp Ala Ser Tyr Glu Leu Cys Glu
        35                  40                  45

Gln Glu Gln Glu Gln Ser Pro Ile Asn Ile Glu Thr Asp Glu Val Thr
    50                  55                  60

Thr Thr Asp Thr His Ile Ser Ile Ala Tyr Gln Pro Ser Pro Phe Ala
65                  70                  75                  80

Ile Glu Asn Asn Gly His Thr Ile Gln Ala Asn Ala Leu Thr Glu Asp
                85                  90                  95

Asn Thr Ile Ser Ile Glu Gly Glu Asn Tyr Gln Leu Ile Gln Phe His
            100                 105                 110

Phe His Val Pro Ser Glu His Gln Lys Asn Gly Glu His Leu Asp Met
        115                 120                 125

Glu Leu His Phe Val His Gln Asn Gln Glu Gly Glu Leu Ala Val Leu
    130                 135                 140

Gly Val Leu Met Glu Glu Gly Glu Val Asn Asp Ala Leu Ala Glu Leu

```
                145                 150                 155                 160
Trp Ala Glu Met Pro Gln Glu Met Asp Glu Thr Ile Glu Leu Thr
                165                 170                 175
Asp Ala Ile Asp Leu Asn Ala Leu Leu Pro Ser Ser His Glu Gly Phe
                180                 185                 190
His Tyr Gly Gly Ser Leu Thr Thr Pro Pro Cys Thr Glu Gly Val Lys
                195                 200                 205
Trp Val Val Leu Glu Lys Thr Ile Ser Val Ser Gln Glu Gln Ile Asp
        210                 215                 220
Thr Phe Ala Glu Ile Phe Pro Thr Asn Asn Arg Pro Val Gln Pro Trp
225                 230                 235                 240
Asn Asp Arg His Val Tyr Glu Val Ala Ile Asp
                245                 250

<210> SEQ ID NO 65
<211> LENGTH: 34
<212> TYPE: DNA
<213> ORGANISM: Artificial Sequence
<220> FEATURE:
<223> OTHER INFORMATION: synthetic primer

<400> SEQUENCE: 65
gcggctagcg caggagacga agaagttaac tcat                              34

<210> SEQ ID NO 66
<211> LENGTH: 30
<212> TYPE: DNA
<213> ORGANISM: Artificial Sequence
<220> FEATURE:
<223> OTHER INFORMATION: synthetic primer

<400> SEQUENCE: 66
tcattaatca atagccactt catatacatg                                   30

<210> SEQ ID NO 67
<211> LENGTH: 834
<212> TYPE: DNA
<213> ORGANISM: Artificial Sequence
<220> FEATURE:
<223> OTHER INFORMATION: synthetic sequence

<400> SEQUENCE: 67
atggtcttta aaaaccgaa agtctttatc gcagcggtca tcctggcgct gagcagcttt    60 gcggaacgg cagctagcgc aggagacgaa gaagttaact cattaaatgg cagtggcact   120
catgaagagg caataaaaga cgaacatgag gggcattggt catatactgg agaaactgga   180
ccgacgcatt ggggatcgtt agacgcctct tatgaattat gtgaacaaga gcaggaacaa   240
tcgccgatca acattgagac agatgaggtg acaactactg atactcatat cagcatcgcg   300
tatcaaccga gcccgtttgc gatcgaaaat aacggtcata cgattcaagc caatgcccta   360
acagaggata atactatctc gatagagggt gagaattatc aattaattca atttcacttc   420
catgtcccct ctgaacatca aaaaaatgga gaacacttag acatggagct tcattttgtc   480
catcaaaatc aagagggga gttggcagtg ctgggtgtcc taatgaaga aggggaggtg    540 aacgacgcat tagcagagct atgggctgaa atgccacaag aagagatgga tgaaacgatt   600
gaattaacgg atgctatcga tcttaacgca ttattgccaa gcagccatga aggctttcat   660
tatggtggtt ctcttacaac gcctcctgt actgaaggtg taaatgggt cgtcctcgaa    720 aaaacaattt ccgtctcgca agaacaaatt gacacattcg cagagatctt ccaaccaat    780
```
aatcggcctg tccaaccgtg gaatgaccgg catgtatatg aagtggctat tgat 834

<210> SEQ ID NO 68
<211> LENGTH: 278
<212> TYPE: PRT
<213> ORGANISM: Artificial Sequence
<220> FEATURE:
<223> OTHER INFORMATION: synthetic precursor protein

<400> SEQUENCE: 68

```
Met Val Phe Lys Lys Pro Lys Val Phe Ile Ala Ala Val Ile Leu Ala
1               5                   10                  15

Leu Ser Ser Phe Ala Gly Thr Ala Ala Ser Ala Gly Asp Glu Val
            20                  25                  30

Asn Ser Leu Asn Gly Ser Gly Thr His Glu Glu Ala Ile Lys Asp Glu
        35                  40                  45

His Glu Gly His Trp Ser Tyr Thr Gly Glu Thr Gly Pro Thr His Trp
    50                  55                  60

Gly Ser Leu Asp Ala Ser Tyr Glu Leu Cys Glu Gln Glu Gln Glu Gln
65                  70                  75                  80

Ser Pro Ile Asn Ile Glu Thr Asp Glu Val Thr Thr Thr Asp Thr His
                85                  90                  95

Ile Ser Ile Ala Tyr Gln Pro Ser Pro Phe Ala Ile Glu Asn Asn Gly
            100                 105                 110

His Thr Ile Gln Ala Asn Ala Leu Thr Glu Asp Asn Thr Ile Ser Ile
        115                 120                 125

Glu Gly Glu Asn Tyr Gln Leu Ile Gln Phe His Phe His Val Pro Ser
    130                 135                 140

Glu His Gln Lys Asn Gly Glu His Leu Asp Met Glu Leu His Phe Val
145                 150                 155                 160

His Gln Asn Gln Glu Gly Glu Leu Ala Val Leu Gly Val Leu Met Glu
                165                 170                 175

Glu Gly Glu Val Asn Asp Ala Leu Ala Glu Leu Trp Ala Glu Met Pro
            180                 185                 190

Gln Glu Glu Met Asp Glu Thr Ile Glu Leu Thr Asp Ala Ile Asp Leu
        195                 200                 205

Asn Ala Leu Leu Pro Ser Ser His Glu Gly Phe His Tyr Gly Gly Ser
    210                 215                 220

Leu Thr Thr Pro Pro Cys Thr Glu Gly Val Lys Trp Val Val Leu Glu
225                 230                 235                 240

Lys Thr Ile Ser Val Ser Gln Glu Gln Ile Asp Thr Phe Ala Glu Ile
                245                 250                 255

Phe Pro Thr Asn Asn Arg Pro Val Gln Pro Trp Asn Ser Arg His Val
            260                 265                 270

Tyr Glu Val Ala Ile Asp
        275
```

<210> SEQ ID NO 69
<211> LENGTH: 29
<212> TYPE: PRT
<213> ORGANISM: Bacillus licheniformis

<400> SEQUENCE: 69

```
Met Lys Met Trp Met Arg Lys Ala Leu Val Ala Leu Phe Thr Ile Ala
1               5                   10                  15

Thr Phe Gly Leu Val Ser Pro Pro Ala Ala Ala Ser Ala
```

<210> SEQ ID NO 70
<211> LENGTH: 29
<212> TYPE: PRT
<213> ORGANISM: Bacillus licheniformis

<400> SEQUENCE: 70

Met Asn Ile Lys Asn Ile Ala Lys Lys Ala Ser Ala Leu Thr Val Ala
1               5                   10                  15

Ala Ala Leu Leu Ala Gly Gly Ala Pro Gln Ala Ser Ala
            20                  25

<210> SEQ ID NO 71
<211> LENGTH: 30
<212> TYPE: PRT
<213> ORGANISM: Bacillus licheniformis

<400> SEQUENCE: 71

Met Lys Arg Lys Leu Met Thr Leu Gly Leu Thr Ala Val Leu Gly Ser
1               5                   10                  15

Ser Ala Val Leu Ile Pro Leu Lys Ser Asn His Ala Ser Ala
            20                  25                  30

<210> SEQ ID NO 72
<211> LENGTH: 29
<212> TYPE: PRT
<213> ORGANISM: Bacillus licheniformis

<400> SEQUENCE: 72

Met Lys Gln Gln Lys Arg Leu Tyr Ala Arg Leu Leu Pro Leu Leu Phe
1               5                   10                  15

Ala Leu Ile Phe Leu Leu Pro His Ser Ala Ala Ser Ala
            20                  25

<210> SEQ ID NO 73
<211> LENGTH: 27
<212> TYPE: PRT
<213> ORGANISM: Bacillus licheniformis

<400> SEQUENCE: 73

Met Val Phe Lys Lys Pro Lys Val Phe Ile Ala Ala Val Ile Leu Ala
1               5                   10                  15

Leu Ser Ser Phe Ala Gly Thr Ala Ala Ser Ala
            20                  25

<210> SEQ ID NO 74
<211> LENGTH: 211
<212> TYPE: PRT
<213> ORGANISM: Paenibacillus mucilaginosus

<400> SEQUENCE: 74

Asp Gln Thr Phe Ala Ala Cys Ala Asn Gly Thr Glu Gln Ser Pro Val
1               5                   10                  15

Asp Ile Glu Leu Thr Gln Thr Lys Val Asp Lys Thr Ala Val Gln Val
            20                  25                  30

Glu Leu His Tyr Gln Pro Ser Ala Phe Thr Leu Met Asn Asn Gly His
                35                  40                  45

Thr Ile Gln Ala Asn Ala Ala Ala Gly Asn Gly Asn Thr Ile Thr Val
            50                  55                  60

Asp Gly Thr Asp Tyr Thr Leu Ala Gln Met His Phe His His Pro Ser

```
                65                  70                  75                  80
Glu Asn Gln Ile Asn Gly Lys Asn Phe Glu Met Glu Gly His Leu Val
                    85                  90                  95

His Lys Asn Lys Asp Gly Gly Leu Ala Val Val Gly Phe Leu Met Thr
                100                 105                 110

Ala Gly Lys Glu Asn Lys Pro Leu Ala Glu Met Trp Ser Lys Leu Pro
                115                 120                 125

Lys Gln Glu Thr Lys Glu Asp Val Lys Leu Glu Gln Pro Val Asp Leu
                130                 135                 140

Pro Gly Leu Val Pro Ser Thr Ala His Ala Phe Arg Tyr Glu Gly Ser
145                 150                 155                 160

Leu Thr Thr Pro Pro Cys Ser Glu His Val Lys Trp Ile Val Leu Ala
                165                 170                 175

Asp Pro Ile Glu Val Ser Lys Glu Gln Ile Glu Ala Phe Ala Ala Ile
                180                 185                 190

Phe Pro Asp Asn His Arg Pro Val Gln Pro Leu Asn Gln Arg Thr Val
                195                 200                 205

Val Ser Asn
210

<210> SEQ ID NO 75
<211> LENGTH: 196
<212> TYPE: PRT
<213> ORGANISM: Solibacillus silvestris

<400> SEQUENCE: 75

Asn Val Glu Phe Pro Glu Val Lys Ala Asp Gly Asn Leu Lys Gly Asn
1               5                   10                  15

Glu Ile His Tyr Glu Pro Thr Pro Tyr Thr Leu Glu Asn Asn Gly His
                20                  25                  30

Thr Ile Gln Ala Asn Ala Thr Thr Glu Ser Asn His Ile Ile Ile Glu
                35                  40                  45

Asp Asn Glu Tyr Lys Leu Ser Gln Phe His Phe His Thr Pro Ser Glu
                50                  55                  60

His Gln Phe Asn Gly Gln Asn Tyr Asp Met Glu Leu His Leu Val His
65                  70                  75                  80

Ser Asp Lys Asp Gly Lys Leu Ala Val Ile Gly Leu Met Ile Gln Glu
                85                  90                  95

Gly Asn Glu Asn Lys Gln Phe Ala Ser Met Trp Asn Glu Leu Pro Thr
                100                 105                 110

Asp Lys Thr Ala Lys Gly Asn Ser Glu Lys His Ile Ile Asp Leu Gln
                115                 120                 125

Ala Leu Leu Pro Glu Asn Glu Thr Thr Phe Gln Tyr Ala Gly Ser Leu
                130                 135                 140

Thr Thr Pro Pro Cys Thr Glu Glu Val Gln Trp Ile Val Phe Glu Gln
145                 150                 155                 160

Pro Ile Glu Met Ser Lys Ala Gln Ile Lys Ala Phe Gln Lys Ile Phe
                165                 170                 175

Pro Asp Asn His Arg Pro Val Gln Pro Ile Asn Glu Arg Glu Ile Asn
                180                 185                 190

Lys Ser Gly Glu
195

<210> SEQ ID NO 76
<211> LENGTH: 246
```

```
<212> TYPE: PRT
<213> ORGANISM: Rurivivax benzoatilyticus

<400> SEQUENCE: 76

Pro Gly Asp Ala Pro Ala Ala Arg Lys Pro Ala Pro Arg Pro Arg Pro
1               5                   10                  15

Glu Pro Val Pro Ala Pro Glu Ile His Trp Asn Tyr Thr Gly Glu Gly
            20                  25                  30

Gly Pro Ala Arg Trp Gly Ala Leu Arg Pro Glu Phe Gly Leu Cys Ala
        35                  40                  45

Arg Gly Gln Arg Gln Ser Pro Ile Asp Ile Arg Gly Gly Ile Ala Val
    50                  55                  60

Asp Leu Glu Glu Ile Val Phe Asp Tyr Arg Pro Ala Gly Phe Ala Val
65                  70                  75                  80

Leu Asp Asn Gly His Thr Val Gln Val Asn Val Gly Pro Gly Asn Val
                85                  90                  95

Ile Ala Val Gly Gly Arg Arg Tyr Glu Leu Gln Gln Phe His Phe His
            100                 105                 110

Arg Pro Ser Glu Glu Arg Ile Asp Gly Arg Gln Ser Glu Met Val Ala
        115                 120                 125

His Leu Val His Arg Asp Pro Glu Gly Arg Leu Ala Val Val Ala Val
    130                 135                 140

Leu Leu Gln Arg Gly Glu Glu Gln Pro Val Val Gln Ser Val Trp Asn
145                 150                 155                 160

Asn Leu Pro Leu Glu Lys His Asp Glu Ala Arg Ala Ser Gly Ala Ile
                165                 170                 175

Asp Leu Ala Gln Leu Leu Pro Ala Asp Arg Gly Tyr Tyr Thr Tyr Met
            180                 185                 190

Gly Ser Leu Thr Thr Pro Pro Cys Thr Glu Gly Val Leu Trp Ile Val
        195                 200                 205

Met Arg Gln Pro Val Ala Val Ser Gly Glu Ile Asp Ile Phe Ala
    210                 215                 220

Arg Leu Tyr Pro Met Asn Ala Arg Pro Val Gln Pro Ser Ser Gly Arg
225                 230                 235                 240

Leu Ile Lys Gln Ser Arg
                245

<210> SEQ ID NO 77
<211> LENGTH: 657
<212> TYPE: DNA
<213> ORGANISM: Artificial Sequence
<220> FEATURE:
<223> OTHER INFORMATION: synthesized sequence

<400> SEQUENCE: 77
gcaaactggg gatacaaagg cgatcatggc ccggaaaatt ggggcgaatt tgcatcagaa      60
tgcgcaaaag gccaaaacca aagcccgatt gatatccagt cagttacgga ggcaaaactg    120
gataaactga atttcgatta tgaaggcaaa gttattagcc tgctgaataa cggccataca    180
ctgcaaacga aactggaagg caaaaatacg ctgatggttg atggcacaga attcacactg    240
aaacagtttc attttcatac gccgtcagaa aatcatgtca acggcaaaga gtatccgctg    300
gaagcacatt ttgtgcatgc agacaaagca ggccatctgg cagttgttgc agttttcttt    360
aaacttggcg gcgaaaatcc ggaactggcg aaactgctgg caaatatccc gaaaaaagat    420
caagttgtgg caattaaagt tccgtttgat gcagatagcc ttctgccgaa caataaagat    480
```

-continued

```
tattatagat tcgacggcag cctgacaacg ccgccgtgca gcgaaggcgt tagatggctg    540
gttatcaaag aaacgcagac aatcagcccg gaacaagtta cagcattcac gaaagcaatg    600
ggccataata acagaccgat tcagccgctt aattcaagaa tgattagaac acttcaa      657
```

<210> SEQ ID NO 78
<211> LENGTH: 753
<212> TYPE: DNA
<213> ORGANISM: Artificial Sequence
<220> FEATURE:
<223> OTHER INFORMATION: synthetic sequence

<400> SEQUENCE: 78

```
atgctgatca acaaaagcaa aaattttttc gtctttagct ttatctttgt catgatgctg     60
agcctgagct tgtcaacgg cgaagtcgct agcgcagcaa actggggata caaaggcgat    120
catggcccgg aaaattgggg cgaatttgca tcagaatgcg caaaaggcca aaaccaaagc    180
ccgattgata tccagtcagt tacggaggca aaactggata aactgaattt cgattatgaa    240
ggcaaagtta ttagcctgct gaataacggc catacactgc aaacgaaact ggaaggcaaa    300
aatacgctga tggttgatgg cacagaattc acactgaaac agtttcattt tcatacgccg    360
tcagaaaatc atgtcaacgg caaagagtat ccgctggaag cacattttgt gcatgcagac    420
aaagcaggcc atctggcagt tgttgcagtt ttctttaaac ttggcggcga aatccggaa    480 ctggcgaaac tgctggcaaa tatcccgaaa aagatcaag ttgtggcaat taagttccg    540 tttgatgcag atagccttct gccgaacaat aaagattatt atagattcga cggcagcctg    600
acaacgccgc cgtgcagcga aggcgttaga tggctggtta tcaaagaaac gcagacaatc    660
agcccggaac aagttacagc attcacgaaa gcaatgggcc ataataacag accgattcag    720
ccgcttaatt caagaatgat tagaacactt caa                                  753
```

<210> SEQ ID NO 79
<211> LENGTH: 251
<212> TYPE: PRT
<213> ORGANISM: Artificial Sequence
<220> FEATURE:
<223> OTHER INFORMATION: synthetic sequence

<400> SEQUENCE: 79

```
Met Leu Ile Asn Lys Ser Lys Lys Phe Phe Val Phe Ser Phe Ile Phe
1               5                   10                  15

Val Met Met Leu Ser Leu Ser Phe Val Asn Gly Glu Val Ala Ser Ala
            20                  25                  30

Ala Asn Trp Gly Tyr Lys Gly Asp His Gly Pro Glu Asn Trp Gly Glu
        35                  40                  45

Phe Ala Ser Glu Cys Ala Lys Gly Gln Asn Gln Ser Pro Ile Asp Ile
    50                  55                  60

Gln Ser Val Thr Glu Ala Lys Leu Asp Lys Leu Asn Phe Asp Tyr Glu
65                  70                  75                  80

Gly Lys Val Ile Ser Leu Leu Asn Asn Gly His Thr Leu Gln Thr Lys
                85                  90                  95

Leu Glu Gly Lys Asn Thr Leu Met Val Asp Gly Thr Glu Phe Thr Leu
            100                 105                 110

Lys Gln Phe His Phe His Thr Pro Ser Glu Asn His Val Asn Gly Lys
        115                 120                 125

Glu Tyr Pro Leu Glu Ala His Phe Val His Ala Asp Lys Ala Gly His
    130                 135                 140
```

```
Leu Ala Val Val Ala Val Phe Phe Lys Leu Gly Gly Glu Asn Pro Glu
145                 150                 155                 160

Leu Ala Lys Leu Leu Ala Asn Ile Pro Lys Lys Asp Gln Val Val Ala
                165                 170                 175

Ile Lys Val Pro Phe Asp Ala Asp Ser Leu Leu Pro Asn Asn Lys Asp
            180                 185                 190

Tyr Tyr Arg Phe Asp Gly Ser Leu Thr Thr Pro Pro Cys Ser Glu Gly
        195                 200                 205

Val Arg Trp Leu Val Ile Lys Glu Thr Gln Thr Ile Ser Pro Glu Gln
    210                 215                 220

Val Thr Ala Phe Thr Lys Ala Met Gly His Asn Asn Arg Pro Ile Gln
225                 230                 235                 240

Pro Leu Asn Ser Arg Met Ile Arg Thr Leu Gln
                245                 250
```

<210> SEQ ID NO 80
<211> LENGTH: 219
<212> TYPE: PRT
<213> ORGANISM: Vibrio sp. AND4

<400> SEQUENCE: 80

```
Ala Asn Trp Gly Tyr Lys Gly Asp His Gly Pro Glu Asn Trp Gly Glu
1               5                   10                  15

Phe Ala Ser Glu Cys Ala Lys Gly Gln Asn Gln Ser Pro Ile Asp Ile
                20                  25                  30

Gln Ser Val Thr Glu Ala Lys Leu Asp Lys Leu Asn Phe Asp Tyr Glu
            35                  40                  45

Gly Lys Val Ile Ser Leu Leu Asn Asn Gly His Thr Leu Gln Thr Lys
        50                  55                  60

Leu Glu Gly Lys Asn Thr Leu Met Val Asp Gly Thr Glu Phe Thr Leu
65                  70                  75                  80

Lys Gln Phe His Phe His Thr Pro Ser Glu Asn His Val Asn Gly Lys
                85                  90                  95

Glu Tyr Pro Leu Glu Ala His Phe Val His Ala Asp Lys Ala Gly His
                100                 105                 110

Leu Ala Val Val Ala Val Phe Phe Lys Leu Gly Gly Glu Asn Pro Glu
            115                 120                 125

Leu Ala Lys Leu Leu Ala Asn Ile Pro Lys Lys Asp Gln Val Val Ala
        130                 135                 140

Ile Lys Val Pro Phe Asp Ala Asp Ser Leu Leu Pro Asn Asn Lys Asp
145                 150                 155                 160

Tyr Tyr Arg Phe Asp Gly Ser Leu Thr Thr Pro Pro Cys Ser Glu Gly
                165                 170                 175

Val Arg Trp Leu Val Ile Lys Glu Thr Gln Thr Ile Ser Pro Glu Gln
                180                 185                 190

Val Thr Ala Phe Thr Lys Ala Met Gly His Asn Asn Arg Pro Ile Gln
            195                 200                 205

Pro Leu Asn Ser Arg Met Ile Arg Thr Leu Gln
        210                 215
```

<210> SEQ ID NO 81
<211> LENGTH: 27
<212> TYPE: PRT
<213> ORGANISM: Bacillus licheniformis

<400> SEQUENCE: 81

Met Lys Lys Lys Pro Leu Phe Arg Thr Phe Met Cys Ala Ala Leu Ile
1               5                   10                  15

Gly Ser Leu Leu Ala Pro Val Ala Ala Ser Ala
            20                  25

<210> SEQ ID NO 82
<211> LENGTH: 26
<212> TYPE: PRT
<213> ORGANISM: Bacillus licheniformis

<400> SEQUENCE: 82

Met Lys Asn Val Leu Ala Val Phe Val Val Leu Ile Phe Val Leu Gly
1               5                   10                  15

Ala Phe Gly Thr Ser Gly Pro Ala Ser Ala
            20                  25

<210> SEQ ID NO 83
<211> LENGTH: 32
<212> TYPE: PRT
<213> ORGANISM: Bacillus licheniformis

<400> SEQUENCE: 83

Met Leu Ile Asn Lys Ser Lys Lys Phe Phe Val Phe Ser Phe Ile Phe
1               5                   10                  15

Val Met Met Leu Ser Leu Ser Phe Val Asn Gly Glu Val Ala Ser Ala
            20                  25                  30

<210> SEQ ID NO 84
<211> LENGTH: 239
<212> TYPE: PRT
<213> ORGANISM: Vibrio sp. AND4

<400> SEQUENCE: 84

Met Ser Lys Ser Leu Val Ala Leu Gly Leu Thr Leu Val Phe Ala Ser
1               5                   10                  15

Ser Val Asn Ala Ala Asn Trp Gly Tyr Lys Gly Asp His Gly Pro Glu
            20                  25                  30

Asn Trp Gly Glu Phe Ala Ser Glu Cys Ala Lys Gly Gln Asn Gln Ser
        35                  40                  45

Pro Ile Asp Ile Gln Ser Val Thr Glu Ala Lys Leu Asp Lys Leu Asn
    50                  55                  60

Phe Asp Tyr Glu Gly Lys Val Ile Ser Leu Leu Asn Asn Gly His Thr
65                  70                  75                  80

Leu Gln Thr Lys Leu Glu Gly Lys Asn Thr Leu Met Val Asp Gly Thr
                85                  90                  95

Glu Phe Thr Leu Lys Gln Phe His Phe His Thr Pro Ser Glu Asn His
            100                 105                 110

Val Asn Gly Lys Glu Tyr Pro Leu Glu Ala His Phe Val His Ala Asp
        115                 120                 125

Lys Ala Gly His Leu Ala Val Val Ala Val Phe Phe Lys Leu Gly Gly
    130                 135                 140

Glu Asn Pro Glu Leu Ala Lys Leu Leu Ala Asn Ile Pro Lys Lys Asp
145                 150                 155                 160

Gln Val Val Ala Ile Lys Val Pro Phe Asp Ala Asp Ser Leu Leu Pro
                165                 170                 175

Asn Asn Lys Asp Tyr Tyr Arg Phe Asp Gly Ser Leu Thr Thr Pro Pro
            180                 185                 190

Cys Ser Glu Gly Val Arg Trp Leu Val Ile Lys Glu Thr Gln Thr Ile

```
                195                 200                 205
Ser Pro Glu Gln Val Thr Ala Phe Thr Lys Ala Met Gly His Asn Asn
    210                 215                 220

Arg Pro Ile Gln Pro Leu Asn Ser Arg Met Ile Arg Thr Leu Gln
225                 230                 235
```

<210> SEQ ID NO 85
<211> LENGTH: 241
<212> TYPE: PRT
<213> ORGANISM: Vibrio harvei

<400> SEQUENCE: 85

```
Met Lys Met Arg Lys Ser Leu Thr Ala Leu Gly Leu Ala Leu Val Phe
1               5                   10                  15

Ala Gly Ser Ala Asn Ala Ala Asn Trp Gly Tyr Glu Gly Glu His Gly
                20                  25                  30

Pro Ala Asn Trp Gly Glu Phe Ala Ser Glu Cys Ala Lys Gly Gln Asn
            35                  40                  45

Gln Ser Pro Ile Asp Ile Gln Ser Thr Thr Glu Ala Lys Leu Asp Lys
        50                  55                  60

Leu Asn Phe Asp Tyr Glu Gly Lys Val Met Ser Leu Asn Asn Gly
65                  70                  75                  80

His Thr Leu Gln Thr Ser Leu Glu Gly Asn Asn Thr Leu Thr Val Asp
                85                  90                  95

Gly Lys Glu Phe Thr Leu Lys Gln Phe His Phe His Thr Pro Ser Glu
            100                 105                 110

Asn His Val Asp Gly Lys Glu Tyr Pro Leu Glu Ala His Phe Val His
        115                 120                 125

Ala Asp Lys Ala Gly His Leu Ala Val Val Ala Val Phe Phe Lys Leu
    130                 135                 140

Gly Asp Ala Asn Pro Asp Leu Ala Lys Leu Leu Ala Asn Val Pro Asn
145                 150                 155                 160

Lys Asp Gln Asp Val Ala Ile Lys Val Pro Phe Asp Ala Asp Ala Leu
                165                 170                 175

Ile Pro Ser Asp Lys Glu Tyr Tyr Arg Phe Asn Gly Ser Leu Thr Thr
            180                 185                 190

Pro Pro Cys Ser Glu Gly Val Arg Trp Leu Val Ile Lys Glu Thr Gln
        195                 200                 205

Thr Ile Ser Pro Glu Gln Val Lys Ala Phe Ala Lys Ala Met Gly His
    210                 215                 220

Asn Asn Arg Pro Ile Gln Pro Leu Asn Ala Arg Met Ile Leu Ala Gln
225                 230                 235                 240

Gln
```

<210> SEQ ID NO 86
<211> LENGTH: 241
<212> TYPE: PRT
<213> ORGANISM: Vibrio harveyi

<400> SEQUENCE: 86

```
Met Lys Met Arg Lys Ser Leu Thr Ala Leu Gly Leu Ala Leu Val Phe
1               5                   10                  15

Ala Gly Ser Ala Asn Ala Ala Asn Trp Gly Tyr Glu Gly Glu His Gly
                20                  25                  30

Pro Ala Asn Trp Gly Glu Phe Ala Ser Glu Cys Ala Lys Gly Gln Asn
            35                  40                  45
```

```
Gln Ser Pro Ile Asn Ile Glu Ser Thr Thr Glu Ala Lys Leu Glu Lys
    50                  55                  60

Leu Asp Phe Asp Tyr Glu Gly Lys Ala Ile Ser Leu Leu Asn Asn Gly
65                  70                  75                  80

His Thr Leu Gln Thr Ser Leu Glu Gly Lys Asn Thr Leu Thr Ile Asp
                85                  90                  95

Gly Lys Glu Phe Thr Leu Lys Gln Phe His Phe His Thr Pro Ser Glu
            100                 105                 110

Asn His Val Asp Gly Lys Glu Tyr Pro Leu Glu Ala His Phe Val His
        115                 120                 125

Ala Asp Lys Val Gly His Leu Ala Val Val Ala Val Phe Phe Lys Leu
    130                 135                 140

Gly Asp Ala Asn Pro Asp Leu Ala Lys Leu Leu Ala Asn Ile Pro Thr
145                 150                 155                 160

Lys Asp Gln Asp Val Ala Ile Lys Val Pro Phe Asp Ala Asp Ala Leu
                165                 170                 175

Ile Pro Ser Asp Lys Asp Tyr Tyr Arg Phe Asn Gly Ser Leu Thr Thr
            180                 185                 190

Pro Pro Cys Ser Glu Gly Val Arg Trp Leu Val Ile Lys Glu Thr Gln
        195                 200                 205

Thr Ile Ser Pro Glu Gln Val Lys Glu Phe Ala Lys Ala Met Gly Gln
210                 215                 220

Asn Asn Arg Pro Ile Gln Pro Leu Asn Ala Arg Met Ile Leu Ala Gln
225                 230                 235                 240

Gln
```

<210> SEQ ID NO 87
<211> LENGTH: 239
<212> TYPE: PRT
<213> ORGANISM: Vibrio alginolyticus

<400> SEQUENCE: 87

```
Met Lys Lys Ser Leu Thr Thr Leu Gly Leu Ala Leu Val Phe Thr Gly
1               5                   10                  15

Thr Ala Tyr Ala Ala Ser Trp Gly Tyr Glu Gly Asn His Gly Pro Ala
                20                  25                  30

His Trp Gly Glu Phe Ala Ser Glu Cys Ala Lys Gly Gln Asn Gln Ser
            35                  40                  45

Pro Ile Asn Ile Glu Ser Ala Thr Glu Ala Lys Leu Glu Lys Leu Asn
    50                  55                  60

Phe Asp Tyr Glu Gly Lys Ala Ile Ser Leu Leu Asn Asn Gly His Thr
65                  70                  75                  80

Leu Gln Thr Gly Leu Glu Gly Lys Asn Thr Leu Thr Ile Asp Gly Lys
                85                  90                  95

Glu Phe Thr Leu Lys Gln Phe His Phe His Thr Pro Ser Glu Asn His
            100                 105                 110

Val Asp Gly Lys Glu Tyr Pro Leu Glu Ala His Phe Val His Ala Asp
        115                 120                 125

Lys Val Gly His Leu Ala Val Val Ala Val Phe Phe Lys Leu Gly Asp
    130                 135                 140

Ala Asn Pro Asp Leu Ala Lys Met Leu Ala Asn Ile Pro Thr Lys Asp
145                 150                 155                 160

Gln Asp Val Thr Ile Lys Val Pro Phe Asp Ala Asp Ala Leu Ile Pro
                165                 170                 175
```

```
Ser Asp Lys Asp Tyr Tyr Arg Phe Asn Gly Ser Leu Thr Thr Pro Pro
        180                 185                 190

Cys Ser Glu Gly Val Arg Trp Leu Val Met Lys Glu Ala Gln Thr Ile
        195                 200                 205

Ser Pro Glu Gln Ile Lys Ser Phe Ser Glu Val Met Gly Lys Asn Asn
        210                 215                 220

Arg Pro Ile Gln Pro Leu Asn Ala Arg Met Val Leu Thr Gln Gln
225                 230                 235

<210> SEQ ID NO 88
<211> LENGTH: 240
<212> TYPE: PRT
<213> ORGANISM: Vibrio alginolyticus

<400> SEQUENCE: 88

Met Met Lys Lys Ser Leu Thr Thr Leu Gly Leu Ala Leu Val Phe Thr
1               5                   10                  15

Gly Thr Ala Tyr Ala Ala Ser Trp Gly Tyr Glu Gly Asn His Gly Pro
            20                  25                  30

Ala His Trp Gly Glu Phe Ala Ser Glu Cys Ala Lys Gly Gln Asn Gln
        35                  40                  45

Ser Pro Ile Asn Ile Glu Ser Ala Thr Glu Ala Lys Leu Glu Lys Leu
    50                  55                  60

Asn Phe Asp Tyr Glu Gly Lys Ala Ile Ser Leu Leu Asn Asn Gly His
65                  70                  75                  80

Thr Leu Gln Thr Gly Leu Glu Gly Lys Asn Thr Leu Thr Ile Asp Gly
                85                  90                  95

Lys Glu Phe Met Leu Lys Gln Phe His Phe His Thr Pro Ser Glu Asn
            100                 105                 110

His Val Asp Gly Lys Glu Tyr Pro Leu Glu Val His Phe Val His Ala
        115                 120                 125

Asp Lys Val Gly His Leu Ala Val Val Ala Val Phe Phe Lys Leu Gly
    130                 135                 140

Asp Ala Asn Pro Asp Leu Ala Lys Met Leu Ala Asn Thr Pro Thr Lys
145                 150                 155                 160

Asp Gln Asp Val Thr Ile Lys Val Pro Phe Asp Ala Asp Ala Leu Ile
                165                 170                 175

Pro Ser Asp Lys Asp Tyr Tyr Arg Phe Asn Gly Ser Leu Thr Thr Pro
            180                 185                 190

Pro Cys Ser Glu Gly Val Arg Trp Phe Val Met Lys Glu Ala Gln Thr
        195                 200                 205

Ile Ser Pro Glu Gln Ile Lys Ser Phe Ser Glu Val Met Gly Lys Asn
    210                 215                 220

Asn Arg Pro Ile Gln Pro Leu Asn Ala Arg Met Val Leu Thr Gln Gln
225                 230                 235                 240

<210> SEQ ID NO 89
<211> LENGTH: 239
<212> TYPE: PRT
<213> ORGANISM: Vibrio sp. Ex25

<400> SEQUENCE: 89

Met Lys Lys Ser Leu Ala Ala Leu Gly Leu Ala Leu Val Phe Thr Gly
1               5                   10                  15

Thr Ala Tyr Ala Ala Ser Trp Gly Tyr Glu Gly Ser His Gly Pro Glu
            20                  25                  30
```

His Trp Gly Glu Phe Ala Ser Glu Cys Ser Lys Gly Gln Asn Gln Ser
            35                  40                  45

Pro Ile Asn Ile Val Ser Ala Glu Ala Lys Leu Asp Lys Leu Gln
 50                  55                  60

Phe Asp Tyr His Gly Lys Ala Ile Ser Leu Leu Asn Asn Gly His Thr
 65                  70                  75                  80

Leu Gln Thr Ser Leu Glu Gly Asp Asn Thr Leu Leu Ile Asp Gly Asn
                85                  90                  95

Ala Phe Thr Leu Lys Gln Phe His Phe His Thr Pro Ser Glu Asn His
                100                 105                 110

Val Asp Gly Lys Glu Tyr Pro Leu Glu Ala His Phe Val His Ala Asp
                115                 120                 125

Thr Thr Gly His Leu Ala Val Val Ala Val Phe Phe Gln Ser Gly Lys
            130                 135                 140

Ala Asn Pro Asp Leu Ala Lys Leu Leu Ala Asn Ile Pro Ser Lys Asp
145                 150                 155                 160

Gln Ala Val Glu Ile Lys Leu Pro Phe Glu Ala Asp Ala Leu Leu Pro
                165                 170                 175

Lys Asp Lys Ala Tyr Tyr Arg Phe Asn Gly Ser Leu Thr Thr Pro Pro
                180                 185                 190

Cys Ser Glu Gly Val Arg Trp Leu Val Met Lys Glu Ala Gln Thr Ile
                195                 200                 205

Ser Pro Glu Gln Ile Lys Ala Phe Thr Lys Val Met Gly Glu Asn Asn
                210                 215                 220

Arg Pro Ile Gln Pro Leu Asn Ala Arg Met Val Leu Met Gln His
225                 230                 235

<210> SEQ ID NO 90
<211> LENGTH: 238
<212> TYPE: PRT
<213> ORGANISM: Vibrio sinaloensis

<400> SEQUENCE: 90

Met Lys Arg Thr Ile Met Ala Phe Thr Leu Thr Met Ala Leu Ala Ser
 1               5                  10                  15

Ser Val Asn Ala Ala Asp Trp Gly Tyr Lys Gly Glu His Gly Pro Glu
                20                  25                  30

His Trp Gly Asp Phe Ala Ser Glu Cys Ala Ser Gly Val Asn Gln Ser
            35                  40                  45

Pro Ile Asn Ile Glu Ser Ala Thr Asp Ala Ser Leu Ser Lys Leu Gln
 50                  55                  60

Phe Asp Tyr Gln Gly Lys Val Ile Ser Leu Leu Asn Asn Gly His Thr
 65                  70                  75                  80

Leu Gln Thr Ser Leu Glu Gly Asn Asn Thr Leu Thr Val Asp Gly Lys
                85                  90                  95

Val Phe Ser Leu Lys Gln Phe His Phe His Thr Pro Ser Glu Asn His
                100                 105                 110

Val Asp Gly Lys Glu Tyr Pro Leu Glu Ala His Phe Val His Ala Asp
                115                 120                 125

Lys Ala Gly His Leu Ala Val Val Ala Val Phe Phe Glu Leu Gly Lys
            130                 135                 140

Ala Asn Pro Asp Leu Ala Gln Leu Leu Ala Thr Val Pro Ser Ala Asn
145                 150                 155                 160

Ser Asp Val Ala Ile Lys Ile Pro Phe Asp Ala Asp Ala Leu Leu Thr

```
                165                 170                 175
Asn Thr Asn Asp Tyr Tyr Arg Phe Asn Gly Ser Leu Thr Thr Pro Pro
                180                 185                 190

Cys Ser Glu Gly Val Arg Trp Leu Val Leu Lys Ala Pro Gln Thr Val
            195                 200                 205

Ser Ala Glu Gln Val Lys Leu Phe Asn Gln Ala Met Gly Asn Asn Asn
        210                 215                 220

Arg Pro Leu Gln Ser Leu Asn Ala Arg Ile Val Thr Gln Ser
225                 230                 235

<210> SEQ ID NO 91
<211> LENGTH: 238
<212> TYPE: PRT
<213> ORGANISM: Vibrio parahaemolyticus

<400> SEQUENCE: 91

Met Lys Lys Ser Leu Thr Ala Ile Gly Leu Ser Leu Val Phe Val Gly
1               5                   10                  15

Ser Ala Asn Ala Ala Asn Trp Gly Tyr Glu Gly Ser His Gly Pro Glu
            20                  25                  30

His Trp Gly Glu Phe Ala Ser Glu Cys Ala Gln Gly Lys Asn Gln Ser
        35                  40                  45

Pro Ile Asp Ile His Ser Ala Thr Gln Ala Glu Leu Ala Lys Leu Gln
    50                  55                  60

Leu Asp Tyr Gln Gly Lys Val Val Ala Leu Thr Asn Asn Gly His Thr
65                  70                  75                  80

Leu Gln Thr Ser Ile Glu Gly Glu Asn Val Leu Thr Ile Asp Gly Lys
                85                  90                  95

Ala Phe Ala Leu Lys Gln Phe His Phe His Thr Pro Ser Glu Asn His
            100                 105                 110

Val Asp Gly Lys Ser Tyr Pro Leu Glu Ala His Tyr Val His Ala Asp
        115                 120                 125

Glu Gln Gly Asn Leu Ala Val Val Ala Val Phe Phe Glu Gln Gly Lys
    130                 135                 140

Ala Asn Pro Ala Leu Ala Asn Leu Leu Glu Asn Val Pro Glu Arg Asp
145                 150                 155                 160

Gln Asn Val Ala Ile Arg Ala Pro Phe Asp Ala Asn Ala Leu Ile Pro
                165                 170                 175

Ser Asp Lys Asp Tyr Tyr Arg Phe Asn Gly Ser Leu Thr Thr Pro Pro
            180                 185                 190

Cys Ser Glu Gly Val Arg Trp Leu Val Ile Lys Asp Pro Gln Ser Ile
        195                 200                 205

Ser Ala Glu Gln Ile Ala Gln Phe Glu His Val Met Gly Glu Asn Asn
    210                 215                 220

Arg Pro Val Gln Pro Leu Asn Ala Arg Met Val Leu Thr Lys
225                 230                 235

<210> SEQ ID NO 92
<211> LENGTH: 238
<212> TYPE: PRT
<213> ORGANISM: Vibrio parahaemolyticus

<400> SEQUENCE: 92

Met Lys Lys Ser Leu Thr Ala Ile Gly Leu Ser Leu Val Phe Val Gly
1               5                   10                  15

Ser Ala Asn Ala Ala Asn Trp Gly Tyr Glu Gly Ser His Gly Pro Glu
```

```
                 20                  25                  30
His Trp Gly Glu Phe Ala Ser Glu Cys Ala Gln Gly Lys Asn Gln Ser
             35                  40                  45

Pro Ile Asp Ile His Ser Ala Thr Gln Ala Glu Leu Ala Lys Leu Gln
 50                  55                  60

Leu Asp Tyr Gln Gly Lys Val Val Ala Leu Thr Asn Asn Gly His Thr
 65                  70                  75                  80

Leu Gln Thr Ser Ile Glu Gly Glu Asn Val Leu Thr Ile Asp Ser Lys
                 85                  90                  95

Ala Phe Thr Leu Lys Gln Phe His Phe His Thr Pro Ser Glu Asn His
             100                 105                 110

Val Asp Gly Lys Ser Tyr Pro Leu Glu Ala His Tyr Val His Ala Asp
             115                 120                 125

Glu Gln Gly Asn Leu Ala Val Val Ala Val Phe Glu Gln Gly Lys
             130                 135                 140

Ala Asn Pro Ala Leu Ala Asn Leu Leu Glu Asn Val Pro Glu Arg Asp
145                 150                 155                 160

Gln Asn Val Ala Ile Arg Ala Pro Phe Asp Ala Asn Ala Leu Ile Pro
                 165                 170                 175

Ser Asp Lys Asp Tyr Tyr Arg Phe Asn Gly Ser Leu Thr Thr Pro Pro
             180                 185                 190

Cys Ser Glu Gly Val Arg Trp Leu Val Ile Lys Asp Pro Gln Ser Ile
             195                 200                 205

Ser Ala Glu Gln Ile Ala Gln Phe Glu His Val Met Gly Glu Asn Asn
             210                 215                 220

Arg Pro Val Gln Pro Leu Asn Ala Arg Met Val Leu Thr Lys
225                 230                 235

<210> SEQ ID NO 93
<211> LENGTH: 225
<212> TYPE: PRT
<213> ORGANISM: Vibrio parahaemolyticus

<400> SEQUENCE: 93

Met Ser Asn Ala Asn Ala Ala Gln Trp Gly Tyr Glu Gly Gln His Gly
 1               5                  10                  15

Pro Ser His Trp Gly Glu Phe Ala Ser Glu Cys Ala Asn Gly Val Asn
             20                  25                  30

Gln Ser Pro Ile Asn Ile Glu Ser Ala Thr Glu Ala Lys Leu Glu Lys
             35                  40                  45

Leu Ser Phe Asp Tyr Gln Gly Gln Val Val Ser Leu Leu Asn Asn Ser
 50                  55                  60

His Thr Leu Gln Thr Gln Leu Glu Gly Ile Asn Thr Leu Ala Ile Asp
 65                  70                  75                  80

Gly Lys Ser Phe Thr Leu Lys Gln Phe His Phe His Thr Pro Ser Glu
                 85                  90                  95

Asn His Val Asp Gly Lys Glu Tyr Pro Leu Glu Ala His Phe Val His
             100                 105                 110

Ala Asp Lys Ala Gly His Leu Ala Val Val Ala Val Phe Phe Glu Leu
             115                 120                 125

Gly Glu Asp Asn Ser Glu Leu Ala Lys Leu Leu Asp Asn Ile Pro Glu
             130                 135                 140

Lys Gly Ala Asp Ser Pro Ile Asp Val Pro Phe Asn Ala Ser Ala Leu
145                 150                 155                 160
```

```
Leu Ser Asp Thr Asn Asp Tyr Tyr Arg Phe Ser Gly Ser Leu Thr Thr
                165                 170                 175

Pro Pro Cys Ser Glu Gly Val Arg Trp Leu Val Leu Lys Thr Pro Gln
            180                 185                 190

Thr Val Ser Ala Lys Gln Ala Ala Leu Phe Asn Lys Ile Met Gly Asn
        195                 200                 205

Asn Asn Arg Pro Leu Gln Lys Leu Asn Ala Arg Leu Ile Thr Gln Thr
    210                 215                 220

Gln
225

<210> SEQ ID NO 94
<211> LENGTH: 239
<212> TYPE: PRT
<213> ORGANISM: Vibrio nigripulchritudo

<400> SEQUENCE: 94

Met Lys Met Gln Cys Met Ala Leu Gly Leu Leu Ala Leu Thr Gly
1               5                   10                  15

Pro Ala Gln Ala Ser Thr Trp Gly Tyr Glu Gly Gln Gln Gly Pro Ala
            20                  25                  30

His Trp Gly Lys Val Ala Lys Glu Cys Ser Thr Gly Gln Asn Gln Ser
        35                  40                  45

Pro Val Asn Ile Ala Ser Thr Thr Lys Ala Lys Leu Gly Gln Leu Gln
    50                  55                  60

Phe Asp Tyr Gln Gly Arg Ala Ile Ala Ile Leu Asn Asn Gly His Thr
65                  70                  75                  80

Leu Gln Thr Thr Leu Glu Gly Arg Asn Thr Leu Thr Ile Asp Gly Lys
                85                  90                  95

Arg Phe Lys Leu Lys Gln Phe His Phe His Thr Pro Ser Glu Asn Gln
            100                 105                 110

Val Asp Gly Lys Val Tyr Pro Met Glu Ala His Leu Val His Ala Asp
        115                 120                 125

Lys Met Gly His Leu Ala Val Val Ala Val Phe Phe Thr Leu Gly Gln
    130                 135                 140

Glu Asn Pro Asn Leu Ala Ala Leu Leu Lys Asn Val Pro Gly Ser Glu
145                 150                 155                 160

Gln Arg Met Pro Ile Ser Glu Pro Ile Glu Thr Gly Ser Leu Leu Pro
                165                 170                 175

Ala Ser Arg Asp Tyr Tyr Arg Phe Asn Gly Ser Leu Thr Thr Pro Pro
            180                 185                 190

Cys Ser Glu Gly Val Arg Trp Ile Val Met Lys Asp Pro Leu Val Met
        195                 200                 205

Ser Arg Ala Gln Leu Gln Leu Phe Met Gln Ala Met Gly Ser Asn Ser
    210                 215                 220

Arg Pro Val Gln Pro Val Asn Ala Arg Leu Ile Leu Ala Gln His
225                 230                 235

<210> SEQ ID NO 95
<211> LENGTH: 240
<212> TYPE: PRT
<213> ORGANISM: Vibrio vulnificus

<400> SEQUENCE: 95

Met Lys Lys Thr Val Ile Ala Val Leu Ala Thr Gly Leu Thr Ala
1               5                   10                  15
```

```
Met Gly Cys His Ala Ala Glu Trp Gly Tyr Glu Gly Lys His Gly Pro
            20                  25                  30

Glu His Trp Gly Glu Ile Ala Lys Glu Cys Ala Met Gly Lys Asn Gln
        35                  40                  45

Ser Pro Ile Asp Ile Arg Gln Pro Thr Gln Ala Asp Leu Lys Gly Leu
 50                  55                  60

Asp Leu His Tyr Ser Gly Gln Val Ile Ala Leu Ser Asn Asn Gly His
65                   70                  75                  80

Thr Leu Gln Gly Ser Leu Ser Gly Glu Asn Val Leu Asp Ile Asp Gly
                85                  90                  95

Lys Ser Phe Glu Leu Lys Gln Phe His Phe His Thr Pro Ser Glu Asn
            100                 105                 110

Leu Ile Gln Gly Lys Gln Tyr Pro Leu Glu Ala His Phe Val His Ala
        115                 120                 125

Asp Lys Ala Gly Asn Leu Ala Val Val Ala Val Met Phe Glu Ser Gly
130                 135                 140

Ser Gln Asn Gln Ala Leu Asn Ser Leu Ile Ala Lys Val Pro Lys Ala
145                 150                 155                 160

Gly Glu Glu Val Lys Leu Ala Gln Ala Phe Asp Val Asn Asp Leu Ile
                165                 170                 175

Pro Ala His Ser Glu Tyr Tyr Arg Phe Asn Gly Ser Leu Thr Thr Pro
            180                 185                 190

Pro Cys Ser Glu Gly Val Arg Trp Leu Val Ile Lys Glu Ala Ser Glu
        195                 200                 205

Leu Ser Pro Thr Gln Thr His Val Leu Met Ala Met Gly Gln Asn
210                 215                 220

Asn Arg Pro Val Gln Pro Leu Asn Ala Arg Val Val Leu Ser Lys Glu
225                 230                 235                 240

<210> SEQ ID NO 96
<211> LENGTH: 257
<212> TYPE: PRT
<213> ORGANISM: Vibrio vulnificus

<400> SEQUENCE: 96

Met Ile Thr Met Ala Arg Phe Tyr Lys Thr Gln Arg Lys Gln Gly Lys
1               5                   10                  15

Arg Met Lys Lys Thr Val Ile Ala Ala Val Leu Ala Thr Gly Leu Thr
            20                  25                  30

Ala Met Gly Cys His Ala Ala Glu Trp Gly Tyr Glu Gly Lys His Gly
        35                  40                  45

Pro Glu His Trp Gly Glu Ile Ala Lys Glu Cys Ala Met Gly Lys Asn
 50                  55                  60

Gln Ser Pro Ile Asp Ile Arg Gln Pro Thr Gln Ala Asp Leu Lys Gly
65                  70                  75                  80

Leu Asp Leu His Tyr Ser Gly Gln Val Ile Ala Leu Ser Asn Asn Gly
                85                  90                  95

His Thr Leu Gln Gly Ser Leu Ser Gly Glu Asn Val Leu Asp Ile Asp
            100                 105                 110

Gly Lys Ser Phe Glu Leu Lys Gln Phe His Phe His Thr Pro Ser Glu
        115                 120                 125

Asn Leu Ile Gln Gly Lys Gln Tyr Pro Leu Glu Ala His Phe Val His
130                 135                 140

Ala Asp Lys Ala Gly Asn Leu Ala Val Val Ala Val Met Phe Glu Ser
145                 150                 155                 160
```

```
Gly Ser Gln Asn Gln Ala Leu Asn Ser Leu Ile Ala Lys Val Pro Lys
                165                 170                 175

Ala Gly Glu Glu Val Lys Leu Ala Gln Ala Phe Asp Val Asn Asp Leu
            180                 185                 190

Ile Pro Ala His Ala Glu Tyr Tyr Arg Phe Asn Gly Ser Leu Thr Thr
        195                 200                 205

Pro Pro Cys Ser Glu Gly Val Arg Trp Phe Val Ile Lys Glu Ala Ser
    210                 215                 220

Glu Leu Ser Pro Thr Gln Thr His Val Leu Met Gln Ala Met Gly Glu
225                 230                 235                 240

Asn Asn Arg Pro Val Gln Pro Leu Asn Ala Arg Val Val Leu Ser Lys
                245                 250                 255

Glu

<210> SEQ ID NO 97
<211> LENGTH: 240
<212> TYPE: PRT
<213> ORGANISM: Vibrio coralliilyticus

<400> SEQUENCE: 97

Met Lys Lys Thr Phe Ile Ala Ala Ser Leu Met Ile Ala Met Ala Gly
1               5                   10                  15

Thr Val Gln Ala Ala Glu Trp Gly Tyr Lys Gly Asp Lys Gly Pro Glu
            20                  25                  30

His Trp Gly Asp Val Ala Lys Glu Cys Ala Thr Gly Lys Asn Gln Ser
        35                  40                  45

Pro Ile Asp Ile Lys Asp Val Val Asp Ala Glu Leu Met Pro Leu Asn
    50                  55                  60

Ile Glu Tyr Gln Gly Met Val Thr Gly Leu Thr Asn Asn Gly His Thr
65                  70                  75                  80

Leu Gln Ala Val Val Glu Gly Asn Asn Ala Val Thr Val Asp Gly Val
                85                  90                  95

Glu Phe Asn Leu Ala Gln Phe His Phe His Thr Pro Ser Glu Asn His
            100                 105                 110

Ile Arg Gly Gln Asn Phe Pro Leu Glu Ala His Phe Val Asn Ala Asp
        115                 120                 125

Lys Asp Gly Asn Leu Ala Val Val Ala Val Met Tyr Asn Ala Ala Pro
    130                 135                 140

Gly Glu Asn Asn Gln Ile Thr Gln Leu Thr Ala Thr Met Pro Glu Pro
145                 150                 155                 160

Gly Glu Thr Val Arg Leu Gln Thr Pro Phe Ala Val Lys Asp Met Leu
                165                 170                 175

Pro Ala Thr Gly Glu Tyr Tyr Arg Phe Asn Gly Ser Leu Thr Thr Pro
            180                 185                 190

Pro Cys Ser Glu Gly Val Arg Trp Phe Val Leu Lys Ser Ala Gln Thr
        195                 200                 205

Leu Thr Thr Glu Gln Ala Lys Gln Met Gln Met Val Met Gly Asn Asn
    210                 215                 220

Asn Arg Pro Ile Gln Lys Gln Asn Ala Arg Val Val Leu Thr Asn Asp
225                 230                 235                 240

<210> SEQ ID NO 98
<211> LENGTH: 239
<212> TYPE: PRT
<213> ORGANISM: Vibrio parahaemolyticus
```

<400> SEQUENCE: 98

```
Met Asn Lys Thr Leu Leu Ala Phe Ser Leu Ser Leu Leu Thr Leu Ser
1               5                   10                  15

Ala Ala Gln Ala Ser Glu Trp Gly Tyr Gly Asn Asp Lys His Gly Pro
            20                  25                  30

Glu His Trp Gly Glu Ile Ala Lys Asp Cys Ala Thr Thr Lys Asn Gln
        35                  40                  45

Ser Pro Ile Asn Ile Asp Asn Pro Ala Asn Ala Lys Leu Glu Ala Leu
    50                  55                  60

Asn Leu Ser Tyr Thr Gly Gln Val Ile Gly Leu Thr Asn Asn Gly His
65                  70                  75                  80

Thr Leu Gln Ala Gln Val Asn Gly Arg Asn Ser Phe Thr Ile Asp Gly
                85                  90                  95

Glu Thr Phe Glu Leu Gln Gln Phe His Phe His Thr Pro Ser Glu Asn
            100                 105                 110

Gln Ile Lys Gly Arg Gln Tyr Pro Leu Glu Ala His Phe Val His Ala
        115                 120                 125

Asn Glu Asp Gly Glu Leu Ala Val Ile Ser Val Met Phe Asp Ala Gly
130                 135                 140

Asp Gln Asn Ala Ala Leu Ser Lys Leu Ile Asn Ala Ile Pro Gln Glu
145                 150                 155                 160

Asn Gln Thr Thr Phe Phe Lys Asp Thr Phe Glu Ile Asn Asp Leu Leu
                165                 170                 175

Pro Lys Thr Ala Asn Tyr Tyr Arg Phe Asn Gly Ser Leu Thr Thr Pro
            180                 185                 190

Pro Cys Ser Glu Gly Val Arg Trp Phe Val Leu Lys Asp Thr Gln Thr
        195                 200                 205

Leu Ser Lys Asp Gln Ala Ala Lys Leu Met Glu Val Met Gly Gln Asn
    210                 215                 220

Asn Arg Pro Leu Gln Pro Leu Asn Ala Arg Val Val Leu Ser Asn
225                 230                 235
```

<210> SEQ ID NO 99
<211> LENGTH: 239
<212> TYPE: PRT
<213> ORGANISM: Vibrio parahaemolyticus

<400> SEQUENCE: 99

```
Met Asn Lys Thr Leu Leu Ala Phe Ser Leu Ser Leu Leu Thr Leu Ser
1               5                   10                  15

Ala Ala Gln Ala Ser Glu Trp Gly Tyr Gly Asn Asp Lys His Gly Pro
            20                  25                  30

Glu His Trp Gly Glu Ile Ala Lys Asp Cys Ala Thr Thr Lys Asn Gln
        35                  40                  45

Ser Pro Ile Asn Ile Glu Asn Pro Ala Asp Ala Lys Leu Glu Ala Leu
    50                  55                  60

Asn Pro Ser Tyr Thr Gly Gln Val Ile Gly Leu Thr Asn Asn Gly His
65                  70                  75                  80

Thr Leu Gln Ala Gln Val Asn Gly Arg Asn Ser Phe Thr Ile Asp Gly
                85                  90                  95

Glu Thr Phe Glu Leu Gln Gln Phe His Phe His Thr Pro Ser Glu Asn
            100                 105                 110

Gln Ile Lys Gly Arg Gln Tyr Pro Leu Glu Ala His Phe Val His Ala
        115                 120                 125
```

Asn Glu Asp Gly Glu Leu Ala Val Ile Ser Val Met Phe Asp Ala Gly
            130                 135                 140

Asp Gln Asn Ala Ala Leu Ser Lys Leu Ile Asn Ala Ile Pro Gln Glu
145                 150                 155                 160

Asn Gln Thr Thr Phe Phe Lys Asp Thr Phe Glu Ile Asn Asp Leu Leu
                165                 170                 175

Pro Lys Thr Ala Asn Tyr Tyr Arg Phe Asn Gly Ser Leu Thr Thr Pro
            180                 185                 190

Pro Cys Ser Glu Gly Val Arg Trp Phe Val Leu Lys Asp Thr Gln Thr
            195                 200                 205

Leu Ser Lys Asp Gln Ala Ala Lys Leu Met Glu Val Met Gly Gln Asn
            210                 215                 220

Asn Arg Pro Leu Gln Pro Leu Asn Ala Arg Val Val Leu Ser Asn
225                 230                 235

<210> SEQ ID NO 100
<211> LENGTH: 239
<212> TYPE: PRT
<213> ORGANISM: Vibrio alginolyticus

<400> SEQUENCE: 100

Met Asn Lys Thr Leu Leu Ala Phe Ser Leu Ser Leu Leu Thr Leu Ser
1               5                   10                  15

Ala Ala Gln Ala Ser Glu Trp Gly Tyr Gly Asn Asp Lys His Gly Pro
            20                  25                  30

Glu His Trp Gly Lys Ile Ala Lys Asp Cys Ala Thr Thr Lys Asn Gln
        35                  40                  45

Ser Pro Ile Asn Ile Asp Asn Pro Ala Asp Ala Lys Leu Glu Ala Leu
50                  55                  60

Asn Leu Ser Tyr Thr Gly Gln Val Ile Gly Leu Thr Asn Asn Gly His
65                  70                  75                  80

Thr Leu Gln Ala Gln Val Asn Gly Arg Asn Ser Phe Thr Ile Asp Gly
            85                  90                  95

Glu Thr Phe Glu Leu Gln Gln Phe His Phe His Thr Pro Ser Glu Asn
            100                 105                 110

Gln Ile Lys Gly Arg Gln Tyr Pro Leu Glu Ala His Phe Val His Ala
        115                 120                 125

Asn Ala Asp Gly Glu Leu Ala Val Ile Ser Val Met Phe Asp Ala Gly
            130                 135                 140

Asp Gln Asn Ala Ala Leu Ser Lys Leu Ile Asn Ala Ile Pro Gln Glu
145                 150                 155                 160

Asn Gln Thr Thr Phe Phe Lys Asp Thr Phe Glu Ile Asn Asp Leu Leu
                165                 170                 175

Pro Lys Thr Ala Asn Tyr Tyr Arg Phe Asn Gly Ser Leu Thr Thr Pro
            180                 185                 190

Pro Cys Ser Glu Gly Val Arg Trp Phe Val Leu Lys Asp Thr Gln Thr
            195                 200                 205

Leu Ser Lys Asp Gln Ala Ala Lys Leu Met Glu Val Met Gly Gln Asn
            210                 215                 220

Asn Arg Pro Leu Gln Pro Leu Asn Ala Arg Val Val Leu Ser Asn
225                 230                 235

<210> SEQ ID NO 101
<211> LENGTH: 239
<212> TYPE: PRT

<213> ORGANISM: Vibrio sp. Ex25

<400> SEQUENCE: 101

Met Asn Lys Thr Leu Leu Ala Phe Ser Leu Ser Leu Leu Thr Leu Ser
1               5                   10                  15

Ala Ala Gln Ala Ser Glu Trp Gly Tyr Gly Asn Asp Lys His Gly Pro
            20                  25                  30

Glu His Trp Gly Glu Ile Ala Lys Asp Cys Ala Thr Thr Lys Asn Gln
        35                  40                  45

Ser Pro Ile Asn Ile Asp Asn Pro Ala Asp Ala Lys Leu Glu Ala Leu
    50                  55                  60

Asn Leu Ser Tyr Thr Gly Gln Val Ile Gly Leu Thr Asn Asn Gly His
65                  70                  75                  80

Thr Leu Gln Ala Gln Val Asn Gly Arg Asn Ser Phe Thr Ile Asp Ser
                85                  90                  95

Glu Thr Phe Glu Leu Gln Gln Phe His Phe His Thr Pro Ser Glu Asn
            100                 105                 110

Gln Ile Lys Gly Arg Gln Tyr Pro Leu Glu Ala His Phe Val His Ala
        115                 120                 125

Asn Ala Asp Gly Glu Leu Ala Val Ile Ser Val Met Phe Asp Ala Gly
    130                 135                 140

Asp Gln Asn Ala Ala Leu Ser Lys Leu Ile Asn Ala Ile Pro Gln Glu
145                 150                 155                 160

Asn Gln Thr Thr Phe Phe Lys Asp Thr Phe Glu Ile Asn Asp Leu Leu
                165                 170                 175

Pro Lys Thr Ala Asn Tyr Tyr Arg Phe Asn Gly Ser Leu Thr Thr Pro
            180                 185                 190

Pro Cys Ser Glu Gly Val Arg Trp Phe Val Leu Lys Asp Thr Gln Thr
        195                 200                 205

Leu Ser Lys Asp Gln Ala Ala Lys Leu Met Glu Val Met Gly Gln Asn
    210                 215                 220

Asn Arg Pro Leu Gln Pro Leu Asn Ala Arg Val Val Leu Ser Asn
225                 230                 235

<210> SEQ ID NO 102
<211> LENGTH: 239
<212> TYPE: PRT
<213> ORGANISM: Vibrio alginolyticus

<400> SEQUENCE: 102

Met Asn Lys Thr Leu Leu Ala Phe Ser Leu Ser Leu Leu Thr Leu Ser
1               5                   10                  15

Ala Ala Gln Ala Ser Glu Trp Gly Tyr Gly Asn Tyr Lys His Gly Pro
            20                  25                  30

Glu His Trp Gly Glu Ile Ala Lys Asp Cys Ala Thr Thr Lys Asn Gln
        35                  40                  45

Ser Pro Ile Asn Ile Asp Asn Pro Ala Asp Ala Lys Leu Glu Ala Leu
    50                  55                  60

Asn Leu Ser Tyr Thr Gly Gln Val Ile Gly Leu Thr Asn Asn Gly His
65                  70                  75                  80

Thr Leu Gln Ala Gln Val Asn Gly Arg Asn Ser Phe Thr Ile Asp Gly
                85                  90                  95

Glu Thr Phe Glu Leu Gln Gln Phe His Phe His Thr Pro Ser Glu Asn
            100                 105                 110

Gln Ile Lys Gly Arg Gln Tyr Pro Leu Glu Ala His Phe Val His Ala

```
              115                 120                 125
Asn Ala Asp Gly Glu Leu Ala Val Ile Ser Val Met Phe Asp Ala Gly
    130                 135                 140

Asp Gln Asn Ala Ala Leu Ser Lys Leu Ile Asn Ala Ile Pro Gln Glu
145                 150                 155                 160

Asn Gln Thr Thr Phe Lys Asp Thr Phe Glu Ile Asn Asp Leu Leu
                165                 170                 175

Pro Lys Thr Ala Asn Tyr Tyr Arg Phe Asn Gly Ser Leu Thr Thr Pro
            180                 185                 190

Pro Cys Ser Glu Gly Val Arg Trp Phe Val Leu Lys Asp Thr Gln Thr
        195                 200                 205

Leu Ser Lys Ala Gln Ala Ala Lys Leu Met Glu Val Met Gly Gln Asn
    210                 215                 220

Asn Arg Pro Leu Gln Pro Leu Asn Ala Arg Val Val Leu Ser Asn
225                 230                 235

<210> SEQ ID NO 103
<211> LENGTH: 239
<212> TYPE: PRT
<213> ORGANISM: Vibrio mimicus

<400> SEQUENCE: 103

Met Lys Arg Met Thr Leu Ala Leu Ala Val Thr Ala Cys Val Gly Phe
1               5                   10                  15

Gly Ala Gln Ala Ser Glu Trp Gly Tyr Glu Gly Glu His Gly Pro Asp
            20                  25                  30

His Trp Gly Lys Ile Ala Pro Leu Cys Ala Glu Gly Lys Asn Gln Ser
        35                  40                  45

Pro Ile Asp Val Thr Gln Ser Val Glu Ala Glu Leu Pro Pro Phe Ala
    50                  55                  60

Leu Asn Tyr Gln Gly Gln Val Ile Gly Leu Leu Asn Asn Gly His Thr
65                  70                  75                  80

Leu Gln Ala Glu Val Ser Gly Asn Asn Gln Leu Gln Val Asp Gly Asn
                85                  90                  95

Thr Phe Gln Leu Lys Gln Phe His Leu His Thr Pro Ser Glu Asn Leu
            100                 105                 110

Leu Asn Gly Lys Gln Phe Pro Leu Glu Ala His Phe Val His Ala Asp
        115                 120                 125

Glu Gln Gly Asn Leu Ala Val Val Ala Val Met Tyr Glu Val Gly Ser
    130                 135                 140

Glu Asn Pro Met Leu Ser Ser Leu Thr Ala Asn Met Pro Ser Lys Gly
145                 150                 155                 160

Ser Lys Val Glu Leu Val His Ser Leu Pro Leu Asp Lys Trp Ile Pro
                165                 170                 175

Ala Ser Lys Asn Tyr Tyr Arg Phe Asn Gly Ser Leu Thr Thr Pro Pro
            180                 185                 190

Cys Ser Glu Gly Val Arg Trp Ile Val Leu Asn Glu Pro Ser Val Leu
        195                 200                 205

Ser Glu Gln Gln Glu Gln Gly Leu Ile Ser Val Met Gly His Asn Asn
    210                 215                 220

Arg Pro Val Gln Pro His Asn Ala Arg Leu Val Val Ser Ala Asp
225                 230                 235

<210> SEQ ID NO 104
<211> LENGTH: 239
```

```
<212> TYPE: PRT
<213> ORGANISM: Vibrio mimicus

<400> SEQUENCE: 104

Met Lys Arg Met Thr Leu Ala Leu Ala Val Thr Ala Cys Val Gly Phe
1               5                   10                  15

Gly Ala Gln Ala Ser Glu Trp Gly Tyr Glu Gly Glu His Gly Pro Asp
            20                  25                  30

His Trp Gly Lys Ile Ala Pro Leu Cys Ala Glu Gly Lys Asn Gln Ser
        35                  40                  45

Pro Ile Asp Val Thr Gln Ser Val Glu Ala Asp Leu Pro Pro Phe Ala
    50                  55                  60

Leu Asn Tyr Gln Gly Gln Val Val Gly Leu Leu Asn Asn Gly His Thr
65                  70                  75                  80

Leu Gln Ala Glu Val Arg Gly Asn Asn Gln Leu Gln Val Asp Gly Asn
                85                  90                  95

Thr Phe Gln Leu Lys Gln Phe His Leu His Thr Pro Ser Glu Asn Leu
            100                 105                 110

Leu Asn Gly Lys Gln Phe Pro Leu Glu Ala His Phe Val His Ala Asp
        115                 120                 125

Glu Gln Gly Asn Leu Ala Val Val Ala Val Met Tyr Glu Val Gly Ser
    130                 135                 140

Glu Asn Pro Met Leu Ser Ser Leu Thr Ala Asn Met Pro Ser Lys Gly
145                 150                 155                 160

Ser Lys Val Glu Leu Val His Ser Leu Pro Leu Asp Lys Trp Ile Pro
                165                 170                 175

Ala Ser Lys Asn Tyr Tyr Arg Phe Asn Gly Ser Leu Thr Thr Pro Pro
            180                 185                 190

Cys Ser Glu Gly Val Arg Trp Ile Val Leu Asn Glu Pro Ser Val Leu
        195                 200                 205

Ser Glu Gln Gln Glu Gln Gly Leu Ile Ser Val Met Gly His Asn Asn
    210                 215                 220

Arg Pro Val Gln Pro His Asn Ala Arg Leu Val Val Ser Ala Asp
225                 230                 235

<210> SEQ ID NO 105
<211> LENGTH: 236
<212> TYPE: PRT
<213> ORGANISM: Vibrio mimicus

<400> SEQUENCE: 105

Met Thr Leu Ala Leu Ala Val Thr Ala Cys Val Gly Phe Gly Ala Gln
1               5                   10                  15

Ala Ser Glu Trp Gly Tyr Glu Gly Glu His Gly Pro Glu His Trp Gly
            20                  25                  30

Lys Ile Ala Pro Leu Cys Ala Glu Gly Lys Asn Gln Ser Pro Ile Asp
        35                  40                  45

Val Thr Gln Ser Val Glu Ala Asp Leu Pro Pro Phe Ala Leu Asn Tyr
    50                  55                  60

Gln Gly Gln Val Val Gly Leu Leu Asn Asn Gly His Thr Leu Gln Ala
65                  70                  75                  80

Glu Val Ser Gly Asn Asn Gln Leu Gln Val Asp Gly Asn Thr Phe Gln
                85                  90                  95

Leu Lys Gln Phe His Leu His Thr Pro Ser Glu Asn Leu Leu Asn Gly
            100                 105                 110
```

```
Lys Gln Phe Pro Leu Glu Ala His Phe Val His Ala Asp Glu Gln Gly
            115                 120                 125

Asn Leu Ala Val Val Ala Val Met Tyr Glu Val Gly Ser Glu Asn Pro
        130                 135                 140

Met Leu Ser Ser Leu Thr Ala Asn Met Pro Ser Lys Gly Ser Lys Val
145                 150                 155                 160

Glu Leu Ala His Thr Leu Pro Leu Asp Lys Trp Ile Pro Ala Ser Lys
                165                 170                 175

Asn Tyr Tyr Arg Phe Asn Gly Ser Leu Thr Thr Pro Pro Cys Ser Glu
                180                 185                 190

Gly Val Arg Trp Ile Val Leu Asn Glu Pro Ser Val Leu Ser Glu Gln
            195                 200                 205

Gln Glu Gln Gly Leu Ile Ser Val Met Gly His Asn Asn Arg Pro Val
        210                 215                 220

Gln Pro His Asn Ala Arg Leu Val Val Ser Ala Asp
225                 230                 235
```

<210> SEQ ID NO 106
<211> LENGTH: 241
<212> TYPE: PRT
<213> ORGANISM: Photobacterium profundum

<400> SEQUENCE: 106

```
Met Lys Thr Arg Thr Leu His Val Leu Ala Phe Ala Met Val Thr Thr
1               5                   10                  15

Trp Ala Thr Thr Ser Tyr Ala Ala Glu Trp Ser Tyr Thr Gly Glu His
            20                  25                  30

Gly Thr Glu His Trp Gly Asp Ser Phe Ala Thr Cys Ala Glu Gly Val
        35                  40                  45

Asn Gln Thr Pro Ile Asp Ile Asn Gln Thr Thr Gln Ala Glu Leu Ala
    50                  55                  60

Pro Leu His Leu Asp Tyr Glu Gly Gln Val Thr Glu Leu Val Asn Asn
65                  70                  75                  80

Gly His Thr Ile Gln Ala Asn Leu Thr Gly Lys Asn Thr Leu Thr Val
                85                  90                  95

Asp Gly Lys Thr Phe Glu Leu Lys Gln Phe His Phe His Thr Pro Ser
            100                 105                 110

Glu Asn Tyr Leu Lys Gly Lys Gln Tyr Pro Leu Glu Ala His Phe Val
        115                 120                 125

His Ala Thr Asp Lys Gly Glu Leu Ala Val Val Ala Val Met Phe Asp
    130                 135                 140

Phe Gly Pro Arg Ser Asn Asn Glu Leu Thr Thr Leu Leu Ala Ser Ile
145                 150                 155                 160

Pro Ser Lys Gly Gln Thr Val Glu Leu Lys Glu Ala Leu Asn Pro Ala
                165                 170                 175

Asp Leu Leu Pro Arg Asp Arg Glu Tyr Tyr Arg Phe Asn Gly Ser Leu
            180                 185                 190

Thr Thr Pro Pro Cys Ser Glu Gly Val Arg Trp Phe Val Met Gln Glu
        195                 200                 205

Pro Gln Thr Ser Ser Lys Ala Gln Thr Glu Lys Leu Gln Ala Val Met
    210                 215                 220

Gly Asn Asn Ala Arg Pro Leu Gln Pro Leu Asn Ala Arg Leu Ile Leu
225                 230                 235                 240

Glu
```

<210> SEQ ID NO 107
<211> LENGTH: 238
<212> TYPE: PRT
<213> ORGANISM: Vibrio furnissii

<400> SEQUENCE: 107

```
Met Lys Thr Leu Gly Leu Ala Met Ala Val Ser Ala Leu Cys Ala Val
1               5                   10                  15

Asn Ala His Ala Ser Glu Trp Gly Tyr Glu Gly Glu His Gly Pro Ala
            20                  25                  30

His Trp Gly Asn Val Ser Ser Val Cys Ala Ala Gly Val Asn Gln Ser
        35                  40                  45

Pro Ile Asp Ile Lys Gln Thr Val Ser Ala Lys Leu Ala Pro Leu Thr
50                  55                  60

Val His Tyr Ala Gly Thr Val Thr Ala Leu Thr Asn Asn Gly His Thr
65                  70                  75                  80

Leu Gln Ala Ser Val Ser Gly Asp Asn Thr Leu Thr Val Asp Gly Lys
                85                  90                  95

Thr Phe Thr Leu Gln Gln Phe His Phe His Thr Pro Ser Glu Asn Leu
            100                 105                 110

Ile Asn Thr His Gln Tyr Pro Met Glu Ala His Phe Val Asn Ala Asp
        115                 120                 125

Ala Gln Gly His Leu Ala Val Leu Ala Val Met Phe Glu Val Gly Glu
    130                 135                 140

Ala Asn Thr Ala Leu Asn Gln Leu Thr Ala Thr Leu Pro Lys Pro Gly
145                 150                 155                 160

Gln Ser Gln Pro Leu Ser Thr Thr Phe Ser Val Gly Asp Leu Leu Pro
                165                 170                 175

Gln Ala Ser Asp Tyr Tyr Arg Phe Asn Gly Ser Leu Thr Thr Pro Pro
            180                 185                 190

Cys Ser Glu Gly Val Arg Trp Leu Val Leu Lys Gln Pro Gln Val Leu
        195                 200                 205

Ser Ala Gln Gln Glu Ala Val Leu Thr Thr His Met Gly His Asn Asn
    210                 215                 220

Arg Pro Ile Gln Pro His His Ala Arg Val Ile Leu Ser Asn
225                 230                 235
```

<210> SEQ ID NO 108
<211> LENGTH: 241
<212> TYPE: PRT
<213> ORGANISM: Photobacterium profundum

<400> SEQUENCE: 108

```
Met Lys Lys Arg Thr Leu His Ile Leu Ala Phe Ala Met Met Thr Thr
1               5                   10                  15

Trp Ala Thr Thr Ser Tyr Ala Ala Glu Trp Ser Tyr Thr Gly Glu His
            20                  25                  30

Gly Ala Glu His Trp Gly Glu Ser Phe Ala Thr Cys Gly Glu Gly Val
        35                  40                  45

Asn Gln Thr Pro Ile Asp Ile Asn Gln Thr Thr Gln Ala Glu Leu Thr
50                  55                  60

Pro Leu His Leu Asp Tyr Glu Gly Gln Val Thr Glu Leu Val Asn Asn
65                  70                  75                  80

Gly His Thr Ile Gln Ala Asn Leu Thr Gly Lys Asn Thr Leu Thr Val
                85                  90                  95
```

```
Asp Gly Lys Thr Phe Glu Leu Lys Gln Phe His Phe His Thr Pro Ser
            100                 105                 110

Glu Asn Tyr Leu Lys Gly Lys Gln Tyr Pro Leu Glu Ala His Phe Val
            115                 120                 125

His Ala Thr Asp Lys Gly Glu Leu Ala Val Val Ala Val Met Phe Asp
            130                 135                 140

Val Gly Pro Arg Ser Asn Asn Glu Leu Thr Thr Leu Leu Gly Ser Ile
145                 150                 155                 160

Pro Asp Asp Gly Gln Lys Val Glu Leu Lys Glu Ser Leu Asn Pro Ala
                165                 170                 175

Asp Leu Leu Pro Arg Asp Arg Glu Tyr Tyr Arg Phe Asn Gly Ser Leu
            180                 185                 190

Thr Thr Pro Pro Cys Ser Glu Gly Val Arg Trp Phe Val Met Gln Glu
            195                 200                 205

Pro Gln Thr Ser Ser Lys Ala Gln Thr Glu Lys Leu Gln Glu Val Met
            210                 215                 220

Gly Asn Asn Ser Arg Pro Leu Gln Pro Leu Asn Ala Arg Leu Ile Leu
225                 230                 235                 240

Glu

<210> SEQ ID NO 109
<211> LENGTH: 236
<212> TYPE: PRT
<213> ORGANISM: Vibrio mimicus

<400> SEQUENCE: 109

Met Thr Leu Ala Leu Ala Val Thr Ala Cys Val Gly Phe Gly Ala Gln
1               5                   10                  15

Ala Ser Glu Trp Gly Tyr Glu Gly Glu His Gly Pro Asp His Trp Gly
            20                  25                  30

Lys Ile Ala Pro Leu Cys Ala Glu Gly Lys Asn Gln Ser Pro Ile Asp
        35                  40                  45

Val Thr Gln Ser Val Glu Ala Asp Leu Pro Pro Phe Ala Leu Asn Tyr
    50                  55                  60

Gln Gly Gln Val Val Gly Leu Leu Asn Asn Gly His Thr Leu Gln Ala
65                  70                  75                  80

Glu Val Ser Gly Asn Asn Gln Leu Gln Val Asp Gly Asn Thr Phe Gln
                85                  90                  95

Leu Lys Gln Phe His Leu His Thr Pro Ser Glu Asn Leu Leu Asn Gly
            100                 105                 110

Lys Gln Phe Pro Leu Glu Ala His Phe Val His Ala Asp Glu Gln Gly
            115                 120                 125

Asn Leu Ala Val Val Ala Val Met Tyr Glu Val Gly Ser Glu Asn Ser
        130                 135                 140

Met Leu Ser Ser Leu Thr Ala Asn Met Pro Ser Lys Gly Ser Lys Val
145                 150                 155                 160

Glu Leu Val His Ser Leu Pro Leu Asp Lys Trp Ile Pro Ala Ser Lys
                165                 170                 175

Asn Tyr Tyr Arg Phe Asn Gly Ser Leu Thr Thr Pro Pro Cys Ser Glu
            180                 185                 190

Gly Val Arg Trp Ile Val Leu Asn Glu Pro Ser Val Leu Ser Glu Gln
            195                 200                 205

Gln Glu Gln Gly Leu Ile Ser Val Met Gly His Asn Asn Arg Pro Val
            210                 215                 220
```

Gln Pro His Asn Ala Arg Leu Val Val Ser Ala Asp
225                 230                 235

<210> SEQ ID NO 110
<211> LENGTH: 239
<212> TYPE: PRT
<213> ORGANISM: Vibrio anguillarum

<400> SEQUENCE: 110

Met Lys Lys Gln Leu Leu Thr Leu Ala Ile Ser Val Cys Phe Thr Tyr
1               5                   10                  15

Val Ala Gln Ala Asn Glu Trp Gly Tyr Glu Gly Glu Arg Gly Pro Glu
                20                  25                  30

His Trp Gly His Val Ser Lys Ile Cys Glu Met Gly Lys Asn Gln Ser
            35                  40                  45

Pro Ile Asp Ile Asn Gly Leu Val Glu Ala Asp Leu Lys Ser Leu Asp
        50                  55                  60

Ile His Tyr Ser Gly Val Val Gly Ala Leu Thr Asn Asn Gly His Thr
65                  70                  75                  80

Leu Gln Ala Ser Val Ser Gly Lys Asn Thr Leu Val Val Asp Gly Thr
                85                  90                  95

Glu Phe Glu Leu Lys Gln Phe His Phe His Thr Pro Ser Glu Asn Leu
            100                 105                 110

Ile Lys Gly His Gln Ser Pro Leu Glu Ala His Phe Val His Ala Asp
        115                 120                 125

Ala Ala Gly Asn Leu Ala Val Leu Ala Val Met Phe Glu Thr Gly Ala
    130                 135                 140

Gln Asn Glu Pro Leu Ala Gln Leu Thr Ala Glu Leu Pro Lys Val Gly
145                 150                 155                 160

Ala Ser Val Pro Leu Ala Lys Glu Leu Ala Val Gln Ser Leu Leu Pro
                165                 170                 175

Lys Leu Asp Glu Tyr Tyr Arg Phe Asn Gly Ser Leu Thr Thr Pro Pro
            180                 185                 190

Cys Ser Glu Gly Val Arg Trp Phe Val Val Lys Gln Pro Lys Ser Leu
        195                 200                 205

Ser Gln Gln Gln Ser Ala Ala Leu His Ser Val Met Gly Asn Asn Asn
    210                 215                 220

Arg Pro Ile Gln Ala His Asn Ala Arg Leu Val Leu Glu Lys Glu
225                 230                 235

<210> SEQ ID NO 111
<211> LENGTH: 239
<212> TYPE: PRT
<213> ORGANISM: Vibrio cholerae

<400> SEQUENCE: 111

Met Lys Lys Thr Thr Trp Val Leu Ala Met Ala Ala Ser Met Ser Phe
1               5                   10                  15

Gly Val Gln Ala Ser Glu Trp Gly Tyr Glu Gly Glu His Ala Pro Glu
                20                  25                  30

His Trp Gly Lys Val Ala Ser Leu Cys Ala Glu Gly Lys Asn Gln Ser
            35                  40                  45

Pro Ile Asp Val Ala Gln Ser Val Glu Ala Asp Leu Gln Pro Phe Thr
        50                  55                  60

Leu Asn Tyr Gln Gly Gln Val Val Gly Leu Leu Asn Asn Gly His Thr
65                  70                  75                  80

```
Leu Gln Ala Ile Val Ser Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Lys Gln Phe Pro Leu Glu Ala His Phe Val His Ala Asp
            115                 120                 125

Glu Gln Gly Asn Leu Ala Val Val Ala Val Met Tyr Gln Val Gly Ala
            130                 135                 140

Glu Asn Pro Leu Leu Lys Ala Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Leu
            195                 200                 205

Ser Asn Gln Gln Glu Gln Gln Leu Ser Ala Val Met Gly His Asn Asn
            210                 215                 220

Arg Pro Val Gln Pro His Asn Ala Arg Leu Val Leu Gln Ala Asp
225                 230                 235

<210> SEQ ID NO 112
<211> LENGTH: 239
<212> TYPE: PRT
<213> ORGANISM: Vibrio cholerae

<400> SEQUENCE: 112

Met Lys Lys Thr Thr Trp Val Leu Ala Met Ala Ala Ser Met Ser Phe
1               5                   10                  15

Gly Val Gln Ala Ser Glu Trp Gly Tyr Glu Gly Glu His Ala Pro Glu
            20                  25                  30

His Trp Gly Lys Val Ala Pro Leu Cys Ala Glu Gly Lys Asn Gln Ser
        35                  40                  45

Pro Ile Asp Val Ser Gln Ser Val Glu Ala Asp Leu Gln Pro Phe Thr
    50                  55                  60

Leu Asn Tyr Gln Gly Gln Val Val Gly Leu Leu Asn Asn Gly His Thr
65                  70                  75                  80

Leu Gln Ala Ile Val Ser Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Lys Gln Phe Pro Leu Glu Ala His Phe Val His Ala Asp
            115                 120                 125

Glu Gln Gly Asn Leu Ala Val Val Ala Val Met Tyr Gln Val Gly Ser
            130                 135                 140

Glu Asn Pro Leu Leu Lys Ala Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Val
            195                 200                 205

Ser Asn Gln Gln Glu Gln Gln Leu Ser Ala Val Met Gly His Asn Asn
            210                 215                 220
```

Arg Pro Val Gln Pro His Asn Ala Arg Leu Val Leu Gln Ala Asp
225                 230                 235

<210> SEQ ID NO 113
<211> LENGTH: 239
<212> TYPE: PRT
<213> ORGANISM: Vibrio cholerae

<400> SEQUENCE: 113

Met Lys Lys Thr Thr Trp Val Leu Ala Met Ala Ala Ser Met Ser Phe
1               5                   10                  15

Gly Val Gln Ala Ser Glu Trp Gly Tyr Glu Gly Glu His Ala Pro Glu
                20                  25                  30

His Trp Gly Lys Val Ala Pro Leu Cys Ala Glu Gly Lys Asn Gln Ser
            35                  40                  45

Pro Ile Asp Val Ala Gln Ser Val Glu Ala Asp Leu Gln Pro Phe Thr
        50                  55                  60

Leu Asn Tyr Gln Gly Gln Val Val Gly Leu Leu Asn Asn Gly His Thr
65                  70                  75                  80

Leu Gln Ala Ile Val Ser Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Lys Gln Phe Pro Leu Glu Ala His Phe Val His Ala Asp
        115                 120                 125

Glu Gln Gly Asn Leu Ala Val Val Ala Val Met Tyr Gln Val Gly Ser
130                 135                 140

Glu Asn Pro Leu Leu Lys Ala Leu Thr Ala Asp Ile Pro Ile Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Val
        195                 200                 205

Ser Asn Gln Gln Glu Gln Leu Ser Ala Val Met Gly His Asn Asn
210                 215                 220

Arg Pro Val Gln Pro His Asn Ala Arg Leu Val Leu Gln Ala Asp
225                 230                 235

<210> SEQ ID NO 114
<211> LENGTH: 239
<212> TYPE: PRT
<213> ORGANISM: Vibrio cholerae

<400> SEQUENCE: 114

Met Lys Lys Thr Thr Trp Val Leu Ala Met Ala Ala Ser Met Ser Phe
1               5                   10                  15

Gly Val Gln Ala Ser Glu Trp Gly Tyr Glu Gly Glu His Ala Pro Glu
                20                  25                  30

His Trp Gly Lys Val Ala Pro Leu Cys Ala Glu Gly Lys Asn Gln Ser
            35                  40                  45

Pro Ile Asp Val Ala Gln Ser Val Glu Ala Asp Leu Gln Pro Phe Thr
        50                  55                  60

Leu Asn Tyr Gln Gly Gln Val Val Gly Leu Leu Asn Asn Gly His Thr
65                  70                  75                  80

Leu Gln Ala Ile Val Ser Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Lys Gln Phe Pro Leu Glu Ala His Phe Val His Ala Asp
        115                 120                 125

Glu Gln Gly Asn Leu Ala Val Val Ala Val Met Tyr Gln Val Gly Ser
    130                 135                 140

Glu Asn Pro Leu Leu Lys Ala Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Leu
        195                 200                 205

Ser Asn Gln Gln Glu Gln Gln Leu Ser Ala Val Met Gly His Asn Asn
    210                 215                 220

Arg Pro Val Gln Pro His Asn Ala Arg Leu Val Leu Gln Ala Asp
225                 230                 235

<210> SEQ ID NO 115
<211> LENGTH: 239
<212> TYPE: PRT
<213> ORGANISM: Vibrio cholerae

<400> SEQUENCE: 115

Met Lys Lys Thr Thr Trp Val Leu Ala Met Ala Ala Ser Met Ser Phe
1               5                   10                  15

Gly Val Gln Ala Ser Glu Trp Gly Tyr Glu Gly Glu His Ala Pro Glu
            20                  25                  30

His Trp Gly Lys Val Ala Pro Leu Cys Ala Glu Gly Lys Asn Gln Ser
        35                  40                  45

Pro Ile Asp Val Ala Gln Ser Val Glu Ala Asp Leu Gln Pro Phe Thr
    50                  55                  60

Leu Asn Tyr Gln Gly Gln Val Val Gly Leu Leu Asn Asn Gly His Thr
65                  70                  75                  80

Leu Gln Ala Ile Val Ser Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Arg Gln Phe Pro Leu Glu Ala His Phe Val His Ala Asp
        115                 120                 125

Glu Gln Gly Asn Leu Ala Val Val Ala Val Met Tyr Gln Val Gly Ser
    130                 135                 140

Glu Asn Pro Leu Leu Lys Ala Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Val
        195                 200                 205

Ser Asn Gln Gln Glu Gln Gln Leu Ser Ala Val Met Gly His Asn Asn

```
                210                 215                 220
Arg Pro Val Gln Pro His Asn Ala Arg Leu Val Leu Gln Ala Asp
225                 230                 235

<210> SEQ ID NO 116
<211> LENGTH: 239
<212> TYPE: PRT
<213> ORGANISM: Vibrio cholerae

<400> SEQUENCE: 116

Met Lys Lys Thr Thr Trp Val Leu Ala Met Ala Ser Met Ser Phe
1               5                   10                  15

Gly Val Gln Ala Ser Glu Trp Gly Tyr Glu Gly Glu His Ala Pro Glu
                20                  25                  30

His Trp Gly Lys Val Ala Pro Leu Cys Ala Glu Gly Lys Asn Gln Ser
            35                  40                  45

Pro Ile Asp Val Ala Gln Ser Val Glu Ala Asp Leu Gln Pro Phe Thr
        50                  55                  60

Leu Asn Tyr Gln Gly Gln Val Val Gly Leu Leu Asn Asn Gly His Thr
65                  70                  75                  80

Leu Gln Ala Ile Val Arg Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Lys Gln Phe Pro Leu Glu Ala His Phe Val His Ala Asp
        115                 120                 125

Glu Gln Gly Asn Leu Ala Val Val Ala Val Met Tyr Gln Val Gly Ser
    130                 135                 140

Glu Asn Pro Leu Leu Lys Val Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Leu
        195                 200                 205

Ser Asn Gln Gln Glu Gln Leu Ser Ala Val Met Gly His Asn Asn
    210                 215                 220

Arg Pro Val Gln Pro His Asn Ala Arg Leu Val Leu Gln Ala Asp
225                 230                 235

<210> SEQ ID NO 117
<211> LENGTH: 239
<212> TYPE: PRT
<213> ORGANISM: Vibrio cholerae

<400> SEQUENCE: 117

Met Lys Lys Thr Thr Trp Val Leu Ala Met Ala Ser Met Ser Phe
1               5                   10                  15

Gly Val Gln Ala Ser Glu Trp Gly Tyr Glu Gly Glu His Ala Pro Glu
                20                  25                  30

His Trp Gly Lys Val Ala Pro Leu Cys Ala Glu Gly Lys Asn Gln Ser
            35                  40                  45

Pro Ile Asp Val Ala Gln Ser Val Glu Ala Asp Leu Gln Pro Phe Thr
        50                  55                  60

Leu Asn Tyr Gln Gly Gln Val Val Gly Leu Leu Asn Asn Gly His Thr
```

```
                65                  70                  75                  80
Leu Gln Ala Ile Val Ser Gly Asn Asn Pro Leu Gln Ile Asp Gly Lys
                    85                  90                  95

Thr Phe Gln Leu Lys Gln Phe His Phe His Thr Pro Ser Glu Asn Leu
                100                 105                 110

Leu Lys Gly Lys Gln Phe Pro Leu Glu Ala His Phe Val His Ala Asp
                115                 120                 125

Glu Gln Gly Asn Leu Ala Val Val Ala Val Met Tyr Gln Val Gly Ser
            130                 135                 140

Glu Ser Pro Leu Leu Lys Ala Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Val
            195                 200                 205

Ser Asn Gln Gln Glu Gln Leu Ser Ala Val Met Gly His Asn Asn
    210                 215                 220

Arg Pro Val Gln Pro His Asn Ala Arg Leu Val Leu Gln Ala Asp
225                 230                 235
```

<210> SEQ ID NO 118
<211> LENGTH: 239
<212> TYPE: PRT
<213> ORGANISM: Vibrio cholerae

<400> SEQUENCE: 118

```
Met Lys Lys Thr Thr Trp Val Leu Ala Met Ala Ala Ser Met Ser Phe
1               5                   10                  15

Gly Val Gln Ala Ser Glu Trp Gly Tyr Glu Gly Glu His Ala Pro Glu
                20                  25                  30

His Trp Gly Lys Val Ala Pro Leu Cys Val Glu Gly Lys Asn Gln Ser
            35                  40                  45

Pro Ile Asp Val Ala Gln Ser Val Glu Ala Asp Leu Gln Pro Phe Thr
        50                  55                  60

Leu Asn Tyr Gln Gly Gln Val Val Gly Leu Leu Asn Asn Gly His Thr
65                  70                  75                  80

Leu Gln Ala Ile Val Ser Gly Asn Asn Pro Leu Gln Ile Asp Gly Lys
                    85                  90                  95

Thr Phe Gln Leu Lys Gln Phe His Phe His Thr Pro Ser Glu Asn Leu
                100                 105                 110

Leu Lys Gly Lys Gln Phe Pro Leu Glu Ala His Phe Val His Ala Asp
                115                 120                 125

Glu Gln Gly Asn Leu Ala Val Val Ala Val Met Tyr Gln Val Gly Ser
            130                 135                 140

Glu Asn Pro Leu Leu Lys Ala Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Val
            195                 200                 205
```

Ser Asn Gln Gln Glu Gln Gln Leu Ser Ala Val Met Gly His Asn Asn
210                 215                 220

Arg Pro Val Gln Pro His Asn Ala Arg Leu Val Leu Gln Ala Asp
225                 230                 235

<210> SEQ ID NO 119
<211> LENGTH: 242
<212> TYPE: PRT
<213> ORGANISM: Photobacterium damselae

<400> SEQUENCE: 119

Met Lys Lys Ile Thr Ala Ser Ala Thr Cys Leu Ser Leu Ala Leu Leu
1               5                   10                  15

Phe Ala Gly Gln Val Gln Ala Glu Gly Trp Gly Tyr Gly Glu Ala Asn
                20                  25                  30

Gly Pro Glu His Trp Gly Glu Val Ala Pro Leu Cys Ala Thr Gly Val
            35                  40                  45

Asn Gln Ser Pro Ile Asn Ile Thr Lys Ala Thr Gln Ala Asn Leu Leu
    50                  55                  60

Pro Leu Arg Ile Asp Tyr Gln Gly Lys Val Thr Gln Leu Val Asn Asn
65                  70                  75                  80

Gly His Thr Ile Glu Ala Leu Val Ser Gly Lys Asn Asp Val Ile Ile
                85                  90                  95

Asn Gly Asp Thr Tyr His Leu Lys Gln Phe His Phe His Thr Pro Ser
            100                 105                 110

Glu Asn Leu Ile Asp Gly Lys Gln Tyr Pro Leu Glu Ala His Phe Val
        115                 120                 125

Asn Ala Asp Asp Lys Gly Lys Leu Ala Val Ile Ser Val Met Phe Glu
    130                 135                 140

Ile Gly Pro Arg Ala Asn Ser Asp Leu Asp Ala Leu Leu Asn Glu Ile
145                 150                 155                 160

Pro Glu Lys Gly Gln Thr Ile Glu Ile Lys Gln Asp Leu Thr Pro Gly
                165                 170                 175

Ala Leu Leu Pro Arg Asp Arg Glu Tyr Tyr Gln Phe Asn Gly Ser Leu
            180                 185                 190

Thr Thr Pro Pro Cys Thr Glu Gly Val Arg Trp Tyr Val Met Gln Glu
        195                 200                 205

His Gln Thr Ser Ser Lys Glu Gln Thr Glu Met Leu His Ala Val Met
    210                 215                 220

Gly Asn Asn Asn Arg Pro Thr Gln Pro Leu Asn Ala Arg Val Ile Leu
225                 230                 235                 240

Asp Glu

<210> SEQ ID NO 120
<211> LENGTH: 239
<212> TYPE: PRT
<213> ORGANISM: Vibrio cholerae

<400> SEQUENCE: 120

Met Lys Lys Thr Thr Trp Val Leu Ala Met Ala Ala Ser Met Ser Phe
1               5                   10                  15

Gly Val Gln Ala Ser Glu Trp Gly Tyr Glu Gly Glu His Ala Pro Glu
                20                  25                  30

His Trp Gly Lys Val Ala Pro Leu Cys Thr Glu Gly Lys Asn Gln Ser
            35                  40                  45

Pro Ile Asp Val Ala Gln Ser Val Glu Ala Asp Leu Gln Pro Phe Thr

Leu Asn Tyr Gln Gly Gln Val Val Gly Leu Leu Asn Asn Gly His Thr
65                  70                  75                  80

Leu Gln Ala Ile Val Ser Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Lys Gln Phe Pro Leu Glu Ala His Phe Val His Ala Asp
            115                 120                 125

Glu Gln Gly Asn Leu Ala Val Val Ala Val Met Tyr Gln Val Gly Ser
            130                 135                 140

Glu Ser Pro Leu Leu Lys Ala Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Leu
            195                 200                 205

Ser Asn Gln Gln Glu Gln Gln Leu Ser Ala Val Met Gly His Asn Asn
            210                 215                 220

Arg Pro Val Gln Pro His Asn Ala Arg Leu Val Leu Gln Ala Asp
225                 230                 235

<210> SEQ ID NO 121
<211> LENGTH: 239
<212> TYPE: PRT
<213> ORGANISM: Vibrio cholerae

<400> SEQUENCE: 121

Met Lys Lys Thr Thr Trp Val Leu Ala Met Val Ala Ser Met Ser Phe
1               5                   10                  15

Gly Val Gln Ala Ser Glu Trp Gly Tyr Glu Gly Gly His Ala Pro Glu
            20                  25                  30

His Trp Gly Lys Val Ala Pro Leu Cys Ala Glu Gly Lys Asn Gln Ser
            35                  40                  45

Pro Ile Asp Val Ala Gln Ser Val Glu Ala Asp Leu Gln Pro Phe Thr
        50                  55                  60

Leu Asn Tyr Gln Gly Gln Val Val Gly Leu Leu Asn Asn Gly His Thr
65                  70                  75                  80

Leu Gln Ala Ile Val Arg Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Lys Gln Phe Pro Leu Glu Ala His Phe Val His Ala Asp
            115                 120                 125

Glu Gln Gly Asn Leu Ala Val Val Ala Val Met Tyr Gln Val Gly Ser
            130                 135                 140

Glu Asn Pro Leu Leu Lys Val Leu Thr Ala Asp Met Pro Thr Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

```
Cys Ser Glu Gly Val Arg Trp Ile Val Leu Lys Glu Pro Ala His Val
            195                 200                 205

Ser Asn Gln Gln Glu Gln Gln Leu Ser Ala Val Met Gly His Asn Asn
        210                 215                 220

Arg Pro Val Gln Leu His Asn Ala Arg Leu Val Leu Gln Ala Asp
225                 230                 235

<210> SEQ ID NO 122
<211> LENGTH: 239
<212> TYPE: PRT
<213> ORGANISM: Vibrio cholerae

<400> SEQUENCE: 122

Met Lys Lys Thr Thr Trp Val Leu Ala Met Ala Ala Ser Met Ser Phe
1               5                   10                  15

Gly Val Gln Ala Ser Glu Trp Gly Tyr Glu Gly Glu His Ala Pro Glu
            20                  25                  30

His Trp Gly Lys Val Ala Pro Leu Cys Ala Glu Gly Lys Asn Gln Ser
        35                  40                  45

Pro Ile Asp Val Ala Gln Ser Val Glu Ala Asp Leu Gln Pro Phe Thr
    50                  55                  60

Leu Asn Tyr Gln Gly Gln Val Val Gly Leu Leu Asn Asn Gly His Thr
65                  70                  75                  80

Leu Gln Ala Ile Val Ser Gly Asn Asn Pro Leu Gln Ile Asp Gly Lys
                85                  90                  95

Thr Phe Gln Leu Lys Gln Phe His Phe His Thr Pro Ser Glu Asn Leu
            100                 105                 110

Leu Lys Gly Lys Gln Phe Pro Leu Glu Ala His Phe Val His Ala Asp
        115                 120                 125

Glu Gln Gly Asn Leu Ala Val Val Ala Val Met Tyr Gln Val Gly Ser
    130                 135                 140

Glu Asn Pro Leu Leu Lys Ala Leu Thr Ala Asp Met Pro Ile Lys Gly
145                 150                 155                 160

Asn Ser Thr Gln Leu Thr Gln Gly Ile Pro Leu Ala Asp Trp Ile Pro
                165                 170                 175

Glu Ser Lys His Tyr Tyr Arg Phe Asn Gly Ser Leu Thr Thr Pro Pro
            180                 185                 190

Cys Ser Glu Gly Val Arg Trp Ile Val Leu Lys Glu Pro Ala His Val
        195                 200                 205

Ser Asn Gln Gln Glu Gln Gln Leu Ser Ala Val Met Gly His Asn Asn
    210                 215                 220

Arg Pro Val Gln Leu His Asn Ala Arg Leu Val Leu Gln Ala Asp
225                 230                 235

<210> SEQ ID NO 123
<211> LENGTH: 243
<212> TYPE: PRT
<213> ORGANISM: Vibrio shilonii

<400> SEQUENCE: 123

Met Lys Asn Lys Ile Thr Leu Ala Leu Thr Leu Thr Ser Leu Leu Pro
1               5                   10                  15

Phe Ser Gln Gly Val Val Ala Gln Ser Trp Gly Tyr Gly Ala Asp Asn
            20                  25                  30

Gly Pro Ala His Trp Gly Ser Phe Ser Ser Thr Cys Ser Gln Gly Lys
        35                  40                  45
```

Asn Gln Ser Pro Ile Asp Ile Glu Thr Gln Ser Leu Thr Ala Ala Glu
 50                  55                  60

Met Thr Pro Leu Glu Phe Asp Tyr Ser Gly Ser Ile Gly Asn Val Val
 65                  70                  75                  80

Asn Asn Gly His Thr Ile Gln Ile Asn Val Ala Gly Ser Asn Thr Leu
                 85                  90                  95

Lys Leu Asp Gln Gln Thr Phe Thr Leu Lys Gln Phe His Phe His Thr
            100                 105                 110

Pro Ser Glu Asn Thr Ile Asn Gly Lys His Ala Pro Leu Glu Ala His
        115                 120                 125

Phe Val His Ala Asn Asp Asn Gly Glu Leu Ala Val Val Ala Val Met
130                 135                 140

Tyr Asp Ile Gly Lys Arg Glu Asp Ser Thr Leu Ser Ala Leu Leu Asn
145                 150                 155                 160

Thr Leu Pro Ala Asn Gly Gln Ser Ile Lys Val Glu Ser Asp Val Lys
                165                 170                 175

Leu Lys Ser Leu Leu Pro Arg Val His Ser Tyr Tyr Arg Tyr Asn Gly
            180                 185                 190

Ser Leu Thr Thr Pro Pro Cys Ser Glu Gly Val Arg Trp Ile Val Leu
        195                 200                 205

Thr Asp Pro Gln Phe Ile Glu Gln Ala Pro Leu Asp Asn Leu Ser Asp
210                 215                 220

Thr Met Gly Asn Asn Ala Arg Pro Ile Gln Pro His Asn Ala Arg Leu
225                 230                 235                 240

Ile Leu Lys

<210> SEQ ID NO 124
<211> LENGTH: 199
<212> TYPE: PRT
<213> ORGANISM: Vibrio furnissii

<400> SEQUENCE: 124

Met Cys Ala Ala Gly Val Asn Gln Ser Pro Ile Asn Ile Lys Gln Thr
 1               5                  10                  15

Val Ser Ala Lys Leu Ala Pro Leu Thr Val His Tyr Ala Gly Thr Val
                 20                  25                  30

Thr Ala Leu Thr Asn Asn Gly His Thr Leu Gln Ala Ser Val Ser Gly
             35                  40                  45

Asp Asn Thr Leu Thr Val Asp Gly Lys Thr Phe Thr Leu Gln Gln Phe
 50                  55                  60

His Phe His Thr Pro Ser Glu Asn Leu Ile Asn Thr His Gln Tyr Pro
 65                  70                  75                  80

Met Glu Ala His Phe Val Asn Ala Asp Ala Gln Gly Asn Leu Ala Val
                 85                  90                  95

Leu Ala Val Met Phe Glu Val Gly Glu Ala Asn Thr Ala Leu Asn Gln
            100                 105                 110

Leu Thr Ala Thr Leu Pro Lys Pro Gly Gln Ser Gln Pro Leu Ser Ala
        115                 120                 125

Thr Phe Ser Val Gly Glu Leu Leu Pro Gln Thr Val Asp Tyr Tyr Arg
130                 135                 140

Phe Asn Gly Ser Leu Thr Thr Pro Pro Cys Thr Glu Gly Val Arg Trp
145                 150                 155                 160

Leu Val Leu Lys Gln Pro Gln Val Leu Ser Ala Gln Gln Glu Ala Val
                165                 170                 175

```
Leu Thr Thr His Met Gly His Asn Asn Arg Pro Ile Gln Pro His His
            180                 185                 190

Ala Arg Val Ile Leu Ser Lys
            195

<210> SEQ ID NO 125
<211> LENGTH: 247
<212> TYPE: PRT
<213> ORGANISM: Thermovibrio ammonificans

<400> SEQUENCE: 125

Met Lys Arg Val Leu Val Thr Leu Gly Ala Val Ala Ala Leu Ala Thr
1               5                   10                  15

Gly Ala Val Ala Gly Gly Ala His Trp Gly Tyr Ser Gly Ser Ile
            20                  25                  30

Gly Pro Glu His Trp Gly Asp Leu Ser Pro Glu Tyr Leu Met Cys Lys
        35                  40                  45

Ile Gly Lys Asn Gln Ser Pro Ile Asp Ile Asn Ser Ala Asp Ala Val
50                  55                  60

Lys Ala Cys Leu Ala Pro Val Ser Val Tyr Tyr Val Ser Asp Ala Lys
65                  70                  75                  80

Tyr Val Val Asn Asn Gly His Thr Ile Lys Val Val Met Gly Gly Arg
                85                  90                  95

Gly Tyr Val Val Asp Gly Lys Arg Phe Tyr Leu Lys Gln Phe His
            100                 105                 110

Phe His Ala Pro Ser Glu His Thr Val Asn Gly Lys His Tyr Pro Phe
        115                 120                 125

Glu Ala His Phe Val His Leu Asp Lys Asn Gly Asn Ile Thr Val Leu
    130                 135                 140

Gly Val Phe Phe Lys Val Gly Lys Glu Asn Pro Glu Leu Glu Lys Val
145                 150                 155                 160

Trp Arg Val Met Pro Glu Glu Pro Gly Gln Lys Arg His Leu Thr Ala
                165                 170                 175

Arg Ile Asp Pro Glu Lys Leu Leu Pro Glu Asn Arg Asp Tyr Tyr Arg
            180                 185                 190

Tyr Ser Gly Ser Leu Thr Thr Pro Pro Cys Ser Glu Gly Val Arg Trp
        195                 200                 205

Ile Val Phe Lys Glu Pro Val Glu Met Ser Arg Glu Gln Leu Glu Lys
    210                 215                 220

Phe Arg Lys Val Met Gly Phe Asp Asn Asn Arg Pro Val Gln Pro Leu
225                 230                 235                 240

Asn Ala Arg Lys Val Met Lys
            245

<210> SEQ ID NO 126
<211> LENGTH: 241
<212> TYPE: PRT
<213> ORGANISM: Aeromonas veronii

<400> SEQUENCE: 126

Met Arg Lys Ser Leu Leu Ala Cys Ser Leu Leu Cys Pro Val Val
1               5                   10                  15

Phe Ala Ala Thr Pro His Trp Glu Tyr Ser Gly Glu Ala Gly Pro Ala
            20                  25                  30

His Trp Ala Lys Leu Thr Pro Glu Phe Gly Gln Cys Ala Gly Ser Asn
        35                  40                  45
```

Gln Ser Pro Val Asp Leu Ser Gly Leu Val Glu Ala Lys Leu Ala Pro
            50                  55                  60

Leu Val Leu His Tyr Lys Ala Gly Gly Asn Thr Val Val Asn Asn Gly
 65                  70                  75                  80

His Thr Val Gln Val Gly Tyr Ala Pro Gly Ser Thr Leu Gln Leu Asp
                85                  90                  95

Gly Thr Arg Phe Glu Leu Lys Gln Phe His Phe His Ala Pro Ser Glu
            100                 105                 110

Asn Leu Ile Glu Gly Lys Ser Tyr Pro Leu Gly His Leu Val His
            115                 120                 125

Val Ser Asp Lys Gly Glu Ile Ala Val Ala Val Met Phe Glu Ala
            130                 135                 140

Gly Lys Ala Asn Pro Ala Leu Ala Ala Trp Gly Glu Leu Pro Ala
145                 150                 155                 160

Lys Val Gly Glu Thr Gln Ala Leu Lys Ala Pro Leu Ser Ala Glu Gln
                165                 170                 175

Leu Leu Pro Glu Asn Arg Asp Tyr Tyr Arg Phe Ser Gly Ser Leu Thr
            180                 185                 190

Thr Pro Pro Cys Ser Glu Gly Val Arg Trp Leu Val Met Lys Gln Pro
            195                 200                 205

Val Glu Val Ser Gln Ala Gln Ile Asp Ala Phe Lys Ala Val Met His
    210                 215                 220

His Pro Asn Asn Arg Pro Val Gln Pro Leu Asn Gly Arg Val Val Leu
225                 230                 235                 240

Gln

<210> SEQ ID NO 127
<211> LENGTH: 657
<212> TYPE: DNA
<213> ORGANISM: Artificial Sequence
<220> FEATURE:
<223> OTHER INFORMATION: synthesized sequence

<400> SEQUENCE: 127

```
gcatcatggg gctatgaagg ctcacatggc ccggaacact ggggcgaatt tgcaagcgaa      60
tgcagcaaag acaaaatca gtcaccgatt aacatcgttt cagcagcgga agccaaactt     120
gacaaactgc agttcgatta ccatggcaag gcgattagcc tgctgaacaa tggcccataca   180
ctgcaaacgt cactggaggg agataatacg cttctgatcg atggcaatgc gttcacgctg    240
aaacagttcc atttccatac gccgagcgaa aaccatgtgg atggaaaaga gtatccgctg    300
gaagcgcatt tcgttcatgc agatacaaca ggccatctgg cagtcgttgc agttttcttc    360
caaagcggca agcaaatcc tgatctggcg aaacttcttg cgaacattcc gagcaaggat     420
caggcagtcg aaattaaact gccgttcgaa gcggatgcgc tgctgccgaa ggacaaagca    480
tattacagat tcaatggctc actgacgaca ccgccgtgct cagaaggcgt gagatggctg    540
gtcatgaaag aagcacagac gatcagccct gaacagatta aagcgttcac gaaggtcatg    600
ggcgagaaca acagaccgat ccaaccgctt aatgcaagaa tggttctgat gcaacat      657
```

<210> SEQ ID NO 128
<211> LENGTH: 744
<212> TYPE: DNA
<213> ORGANISM: Artificial Sequence
<220> FEATURE:
<223> OTHER INFORMATION: synthetic sequence

<400> SEQUENCE: 128

```
atgaaacaac aaaaacgcct gtatgcgaga ctgctgccgc tgctgtttgc gctgatcttt      60
ctgctgccgc acagcgcagc tagcgcagca tcatggggct atgaaggctc acatggcccg     120
gaacactggg gcgaatttgc aagcgaatgc agcaaaggac aaaatcagtc accgattaac     180
atcgtttcag cagcggaagc caaacttgac aaactgcagt tcgattacca tggcaaggcg     240
attagcctgc tgaacaatgg ccatacactg caaacgtcac tggagggaga taatacgctt     300
ctgatcgatg gcaatgcgtt cacgctgaaa cagttccatt tccatacgcc gagcgaaaac     360
catgtggatg gaaaagagta tccgctggaa gcgcatttcg ttcatgcaga tacaacaggc     420
catctggcag tcgttgcagt tttcttccaa agcggcaaag caaatcctga tctggcgaaa     480
cttcttgcga acattccgag caaggatcag gcagtcgaaa ttaaactgcc gttcgaagcg     540
gatgcgctgc tgccgaagga caaagcatat tacagattca atggctcact gacgacaccg     600
ccgtgctcag aaggcgtgag atggctggtc atgaaagaag cacagacgat cagccctgaa     660
cagattaaag cgttcacgaa ggtcatgggc gagaacaaca gaccgatcca accgcttaat     720
gcaagaatgg ttctgatgca acat                                            744
```

<210> SEQ ID NO 129
<211> LENGTH: 248
<212> TYPE: PRT
<213> ORGANISM: Artificial Sequence
<220> FEATURE:
<223> OTHER INFORMATION: synthetic sequence

<400> SEQUENCE: 129

```
Met Lys Gln Gln Lys Arg Leu Tyr Ala Arg Leu Leu Pro Leu Leu Phe
 1               5                  10                  15

Ala Leu Ile Phe Leu Leu Pro His Ser Ala Ala Ser Ala Ala Ser Trp
            20                  25                  30

Gly Tyr Glu Gly Ser His Gly Pro Glu His Trp Gly Glu Phe Ala Ser
        35                  40                  45

Glu Cys Ser Lys Gly Gln Asn Gln Ser Pro Ile Asn Ile Val Ser Ala
    50                  55                  60

Ala Glu Ala Lys Leu Asp Lys Leu Gln Phe Asp Tyr His Gly Lys Ala
65                  70                  75                  80

Ile Ser Leu Leu Asn Asn Gly His Thr Leu Gln Thr Ser Leu Glu Gly
                85                  90                  95

Asp Asn Thr Leu Leu Ile Asp Gly Asn Ala Phe Thr Leu Lys Gln Phe
            100                 105                 110

His Phe His Thr Pro Ser Glu Asn His Val Asp Gly Lys Glu Tyr Pro
        115                 120                 125

Leu Glu Ala His Phe Val His Ala Asp Thr Thr Gly His Leu Ala Val
    130                 135                 140

Val Ala Val Phe Phe Gln Ser Gly Lys Ala Asn Pro Asp Leu Ala Lys
145                 150                 155                 160

Leu Leu Ala Asn Ile Pro Ser Lys Asp Gln Ala Val Glu Ile Lys Leu
                165                 170                 175

Pro Phe Glu Ala Asp Ala Leu Leu Pro Lys Asp Lys Ala Tyr Tyr Arg
            180                 185                 190

Phe Asn Gly Ser Leu Thr Thr Pro Pro Cys Ser Glu Gly Val Arg Trp
        195                 200                 205

Leu Val Met Lys Glu Ala Gln Thr Ile Ser Pro Glu Gln Ile Lys Ala
    210                 215                 220
```

Phe Thr Lys Val Met Gly Glu Asn Asn Arg Pro Ile Gln Pro Leu Asn
225                 230                 235                 240

Ala Arg Met Val Leu Met Gln His
                245

<210> SEQ ID NO 130
<211> LENGTH: 219
<212> TYPE: PRT
<213> ORGANISM: Vibrio sp. Ex25

<400> SEQUENCE: 130

Ala Ser Trp Gly Tyr Glu Gly Ser His Gly Pro Glu His Trp Gly Glu
1               5                   10                  15

Phe Ala Ser Glu Cys Ser Lys Gly Gln Asn Gln Ser Pro Ile Asn Ile
                20                  25                  30

Val Ser Ala Ala Glu Ala Lys Leu Asp Lys Leu Gln Phe Asp Tyr His
            35                  40                  45

Gly Lys Ala Ile Ser Leu Leu Asn Asn Gly His Thr Leu Gln Thr Ser
    50                  55                  60

Leu Glu Gly Asp Asn Thr Leu Leu Ile Asp Gly Asn Ala Phe Thr Leu
65                  70                  75                  80

Lys Gln Phe His Phe His Thr Pro Ser Glu Asn His Val Asp Gly Lys
                85                  90                  95

Glu Tyr Pro Leu Glu Ala His Phe Val His Ala Asp Thr Thr Gly His
            100                 105                 110

Leu Ala Val Val Ala Val Phe Phe Gln Ser Gly Lys Ala Asn Pro Asp
        115                 120                 125

Leu Ala Lys Leu Leu Ala Asn Ile Pro Ser Lys Asp Gln Ala Val Glu
130                 135                 140

Ile Lys Leu Pro Phe Glu Ala Asp Ala Leu Leu Pro Lys Asp Lys Ala
145                 150                 155                 160

Tyr Tyr Arg Phe Asn Gly Ser Leu Thr Thr Pro Pro Cys Ser Glu Gly
                165                 170                 175

Val Arg Trp Leu Val Met Lys Glu Ala Gln Thr Ile Ser Pro Glu Gln
            180                 185                 190

Ile Lys Ala Phe Thr Lys Val Met Gly Glu Asn Asn Arg Pro Ile Gln
        195                 200                 205

Pro Leu Asn Ala Arg Met Val Leu Met Gln His
    210                 215

<210> SEQ ID NO 131
<211> LENGTH: 26
<212> TYPE: PRT
<213> ORGANISM: Bacillus licheniformis

<400> SEQUENCE: 131

Met Lys Arg His Thr Val Asn Leu Ser Leu Ala Met Leu Val Leu Gly
1               5                   10                  15

Phe Leu Leu Ser Phe Ser Tyr Ala Ser Ala
                20                  25

<210> SEQ ID NO 132
<211> LENGTH: 29
<212> TYPE: PRT
<213> ORGANISM: Bacillus licheniformis

<400> SEQUENCE: 132

Met Lys Gln Gln Lys Arg Leu Tyr Ala Arg Leu Leu Pro Leu Leu Phe

```
 1               5                  10                 15
Ala Leu Ile Phe Leu Leu Pro His Ser Ala Ala Ser Ala
                20                 25
```

<210> SEQ ID NO 133
<211> LENGTH: 657
<212> TYPE: DNA
<213> ORGANISM: Artificial Sequence
<220> FEATURE:
<223> OTHER INFORMATION: synthesized sequence

<400> SEQUENCE: 133

| | | | | | |
|---|---|---|---|---|---|
| tcagagtggg | gctatggcaa | tgataaacat | ggcccggaac | attggggcga | aattgcaaag | 60 |
| gattgcgcga | caacgaaaaa | ccaatcaccg | attaacattg | acaatccggc | cgacgccaag | 120 |
| ctggaagccc | ttaatctgtc | atatacaggc | caggttattg | gcctgacgaa | caatggccat | 180 |
| acactgcaag | ctcaagtgaa | cggcagaaac | agcttcacaa | tcgatagcga | aacgtttgag | 240 |
| cttcagcagt | ttcactttca | taccgagcg | agaaccaga | tcaaaggcag | acagtatccg | 300 |
| cttgaagcgc | actttgttca | tgcaaatgcc | gacggcgaac | tggcagtgat | ttcagttatg | 360 |
| tttgatgcag | gcgatcagaa | tgcagcactg | agcaagctga | tcaatgcaat | tccgcaggag | 420 |
| aaccaaacga | cgttctttaa | ggacacgttt | gagatcaacg | acctgctgcc | gaagacggca | 480 |
| aattattaca | gattcaacgg | ctcactgaca | acgccgccgt | gtagcgaagg | cgtcagatgg | 540 |
| ttcgttctga | agacacaca | aacactgtca | aaggaccagg | cagccaaact | gatggaagtt | 600 |
| atgggccaaa | ataacagacc | gctgcaaccg | ctgaatgcga | gagttgtgct | tagcaat | 657 |

<210> SEQ ID NO 134
<211> LENGTH: 738
<212> TYPE: DNA
<213> ORGANISM: Artificial Sequence
<220> FEATURE:
<223> OTHER INFORMATION: synthetic sequence

<400> SEQUENCE: 134

| | | | | | |
|---|---|---|---|---|---|
| atggtcttta | aaaaccgaa | agtctttatc | gcagcggtca | tcctggcgct | gagcagcttt | 60 |
| gcgggaacgg | cagctagcgc | atcagagtgg | ggctatggca | atgataaaca | tggcccggaa | 120 |
| cattggggcg | aaattgcaaa | ggattgcgcg | acaacgaaaa | accaatcacc | gattaacatt | 180 |
| gacaatccgg | ccgacgccaa | gctggaagcc | cttaatctgt | catatacagg | ccaggttatt | 240 |
| ggcctgacga | caatggcca | tacactgcaa | gctcaagtga | acggcagaaa | cagcttcaca | 300 |
| atcgatagcg | aaacgtttga | gcttcagcag | tttcactttc | ataccgagcg | agaaccag | 360 |
| atcaaaggca | gacagtatcc | gcttgaagcg | cactttgttc | atgcaaatgc | cgacggcgaa | 420 |
| ctggcagtga | tttcagttat | gtttgatgca | ggcgatcaga | atgcagcact | gagcaagctg | 480 |
| atcaatgcaa | ttccgcagga | gaaccaaacg | acgttcttta | aggacacgtt | tgagatcaac | 540 |
| gacctgctgc | cgaagacggc | aaattattac | agattcaacg | gctcactgac | aacgccgccg | 600 |
| tgtagcgaag | gcgtcagatg | gttcgttctg | aaagacacac | aaacactgtc | aaaggaccag | 660 |
| gcagccaaac | tgatggaagt | tatgggccaa | aataacagac | cgctgcaacc | gctgaatgcg | 720 |
| agagttgtgc | ttagcaat | | | | | 738 |

<210> SEQ ID NO 135
<211> LENGTH: 246
<212> TYPE: PRT
<213> ORGANISM: Artificial Sequence
<220> FEATURE:

<223> OTHER INFORMATION: synthetic sequence

<400> SEQUENCE: 135

Met Val Phe Lys Lys Pro Lys Val Phe Ile Ala Ala Val Ile Leu Ala
1               5                   10                  15

Leu Ser Ser Phe Ala Gly Thr Ala Ala Ser Ala Ser Glu Trp Gly Tyr
            20                  25                  30

Gly Asn Asp Lys His Gly Pro Glu His Trp Gly Glu Ile Ala Lys Asp
        35                  40                  45

Cys Ala Thr Thr Lys Asn Gln Ser Pro Ile Asn Ile Asp Asn Pro Ala
    50                  55                  60

Asp Ala Lys Leu Glu Ala Leu Asn Leu Ser Tyr Thr Gly Gln Val Ile
65                  70                  75                  80

Gly Leu Thr Asn Asn Gly His Thr Leu Gln Ala Gln Val Asn Gly Arg
                85                  90                  95

Asn Ser Phe Thr Ile Asp Ser Glu Thr Phe Glu Leu Gln Gln Phe His
            100                 105                 110

Phe His Thr Pro Ser Glu Asn Gln Ile Lys Gly Arg Gln Tyr Pro Leu
        115                 120                 125

Glu Ala His Phe Val His Ala Asn Ala Asp Gly Glu Leu Ala Val Ile
    130                 135                 140

Ser Val Met Phe Asp Ala Gly Asp Gln Asn Ala Ala Leu Ser Lys Leu
145                 150                 155                 160

Ile Asn Ala Ile Pro Gln Glu Asn Gln Thr Thr Phe Phe Lys Asp Thr
                165                 170                 175

Phe Glu Ile Asn Asp Leu Leu Pro Lys Thr Ala Asn Tyr Tyr Arg Phe
            180                 185                 190

Asn Gly Ser Leu Thr Thr Pro Pro Cys Ser Glu Gly Val Arg Trp Phe
        195                 200                 205

Val Leu Lys Asp Thr Gln Thr Leu Ser Lys Asp Gln Ala Ala Lys Leu
    210                 215                 220

Met Glu Val Met Gly Gln Asn Asn Arg Pro Leu Gln Pro Leu Asn Ala
225                 230                 235                 240

Arg Val Val Leu Ser Asn
                245

<210> SEQ ID NO 136
<211> LENGTH: 219
<212> TYPE: PRT
<213> ORGANISM: Vibrio sp. Ex25

<400> SEQUENCE: 136

Ser Glu Trp Gly Tyr Gly Asn Asp Lys His Gly Pro Glu His Trp Gly
1               5                   10                  15

Glu Ile Ala Lys Asp Cys Ala Thr Thr Lys Asn Gln Ser Pro Ile Asn
            20                  25                  30

Ile Asp Asn Pro Ala Asp Ala Lys Leu Glu Ala Leu Asn Leu Ser Tyr
        35                  40                  45

Thr Gly Gln Val Ile Gly Leu Thr Asn Asn Gly His Thr Leu Gln Ala
    50                  55                  60

Gln Val Asn Gly Arg Asn Ser Phe Thr Ile Asp Ser Glu Thr Phe Glu
65                  70                  75                  80

Leu Gln Gln Phe His Phe His Thr Pro Ser Glu Asn Gln Ile Lys Gly
                85                  90                  95

Arg Gln Tyr Pro Leu Glu Ala His Phe Val His Ala Asn Ala Asp Gly

-continued

```
                100                 105                 110
Glu Leu Ala Val Ile Ser Val Met Phe Asp Ala Gly Asp Gln Asn Ala
            115                 120             125

Ala Leu Ser Lys Leu Ile Asn Ala Ile Pro Gln Glu Asn Gln Thr Thr
        130                 135             140

Phe Phe Lys Asp Thr Phe Glu Ile Asn Asp Leu Leu Pro Lys Thr Ala
145             150                 155                 160

Asn Tyr Tyr Arg Phe Asn Gly Ser Leu Thr Thr Pro Pro Cys Ser Glu
                165             170                 175

Gly Val Arg Trp Phe Val Leu Lys Asp Thr Gln Thr Leu Ser Lys Asp
            180             185             190

Gln Ala Ala Lys Leu Met Glu Val Met Gly Gln Asn Asn Arg Pro Leu
        195             200             205

Gln Pro Leu Asn Ala Arg Val Val Leu Ser Asn
    210             215
```

We claim:

1. A composition comprising a recombinant polypeptide that comprises an amino acid sequence having carbonic anhydrase activity, wherein said amino acid sequence has high thermostability and/or melting temperature under high ionic strength conditions, and wherein said amino acid sequence is at least 90% identical to the amino acid sequence of SEQ ID NO:28.

2. The composition of claim 1, wherein the amino acid sequence is at least 95% identical to the amino acid sequence of SEQ ID NO:28.

3. The composition of claim 1, wherein the polypeptide retains greater than 70% of the carbonic anhydrase activity when incubated for 5 or more hours at a pH of 8.5 to 9.5.

4. The composition of claim 1, wherein the polypeptide retains at least 80% of the carbonic anhydrase activity when incubated for about 24 hours at a temperature of about 25° C.

5. The composition of claim 1, wherein the polypeptide retains at least 90% of the carbonic anhydrase activity when incubated for about 24 hours at a temperature of about 40° C.

6. The composition of claim 1, wherein the polypeptide retains at least 40% of the carbonic anhydrase activity when incubated for about 3 hours at a temperature of about 50° C.

7. The composition of claim 1, wherein the polypeptide retains at least 25% of the carbonic anhydrase activity when incubated for about 3 hours at a temperature of about 40° C.

8. The composition of claim 1, wherein the polypeptide retains at least 50% of the carbonic anhydrase activity when incubated for 1 to 3 hours at a temperature of from 20° C. to 50° C. under high ionic strength conditions.

9. The composition of claim 1, wherein the high ionic strength conditions comprise 1 M bicarbonate.

10. The composition of claim 1, wherein the polypeptide has a melting temperature that is elevated in the presence of 1 M to 2 M bicarbonate.

11. The composition of claim 1, further comprising carbon dioxide.

12. The composition of claim 11, wherein the recombinant polypeptide is immobilized, preferably wherein the recombinant polypeptide is immobilized on a polymer, a membrane, a matrix, a micellar material, a wafer, a solid support, or a micro-particle.

13. The composition of claim 1, wherein the composition further comprises supernatant of a cell culture medium.

14. A method for extracting carbon dioxide from a carbon dioxide-containing medium, comprising: contacting the carbon dioxide-containing medium with the composition of claim 1 to yield a medium reduced in carbon dioxide.

15. The method of claim 14, wherein the carbon dioxide-containing medium is selected from the group consisting of a gas, a liquid, and a multi-phase mixture.

16. The method of claim 14, wherein the carbon dioxide-containing medium is a gas selected from the group consisting of a flue gas, a raw natural gas, a syngas, a hydrogen gas, and a biogas.

17. The method of claim 14, wherein the carbon dioxide-containing medium is a by-product of combustion or fermentation.

18. A method for regulating pH of a medium containing one or both of $CO_2$ and bicarbonate, comprising: contacting the medium with the composition of claim 1 to yield a medium with an altered pH.

* * * * *